(12) United States Patent
Kim et al.

(10) Patent No.: US 10,851,380 B2
(45) Date of Patent: *Dec. 1, 2020

(54) METHODS FOR CLEAVING A TARGET DNA USING A GUIDE RNA SPECIFIC FOR THE TARGET DNA AND CAS PROTEIN-ENCODING NUCLEIC ACID OR CAS PROTEIN

(71) Applicant: TOOLGEN INCORPORATED, Seoul (KR)

(72) Inventors: Jin-Soo Kim, Seoul (KR); Seung Woo Cho, Seoul (KR); Sojung Kim, Seoul (KR)

(73) Assignee: TOOLGEN INCORPORATED, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/685,568

(22) Filed: Apr. 13, 2015

(65) Prior Publication Data

US 2015/0322457 A1 Nov. 12, 2015

Related U.S. Application Data

(63) Continuation of application No. PCT/KR2013/009488, filed on Oct. 23, 2013.

(60) Provisional application No. 61/837,481, filed on Jun. 20, 2013, provisional application No. 61/803,599, filed on Mar. 20, 2013, provisional application No. 61/717,324, filed on Oct. 23, 2012.

(51) Int. Cl.
| | |
|---|---|
| *C12N 15/85* | (2006.01) |
| *C12N 15/52* | (2006.01) |
| *C12N 15/90* | (2006.01) |
| *C12N 9/22* | (2006.01) |
| *C12N 15/82* | (2006.01) |
| *C12N 15/10* | (2006.01) |
| *C12N 15/63* | (2006.01) |
| *C12N 15/11* | (2006.01) |
| *C12N 9/16* | (2006.01) |

(52) U.S. Cl.
CPC ............ *C12N 15/52* (2013.01); *C12N 9/16* (2013.01); *C12N 9/22* (2013.01); *C12N 15/102* (2013.01); *C12N 15/111* (2013.01); *C12N 15/63* (2013.01); *C12N 15/8216* (2013.01); *C12N 15/85* (2013.01); *C12N 15/907* (2013.01); *C12Y 301/21* (2013.01); *C12N 2310/10* (2013.01); *C12N 2310/20* (2017.05); *C12N 2310/531* (2013.01)

(58) Field of Classification Search
None
See application file for complete search history.

(56) References Cited

U.S. PATENT DOCUMENTS

| | | |
|---|---|---|
| 5,766,900 A | 6/1998 | Shillito et al. |
| 5,767,367 A | 6/1998 | Dudits et al. |
| 8,697,359 B1 | 4/2014 | Zhang |
| 8,771,495 B2 | 7/2014 | Paneccasio, Jr. et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Le Cong et al. |
| 8,883,233 B2 | 11/2014 | Gillessen et al. |
| 8,889,356 B2 | 11/2014 | Zhang et al. |
| 8,889,418 B2 | 11/2014 | Zhang et al. |
| 8,889,559 B2 | 11/2014 | Trapp et al. |
| 8,895,308 B1 | 11/2014 | Zhang et al. |
| 8,906,616 B2 | 12/2014 | Zhang et al. |
| 8,932,814 B2 | 1/2015 | Le Cong et al. |
| 8,945,839 B2 | 2/2015 | Zhang et al. |
| 8,993,233 B2 | 3/2015 | Zhang et al. |
| 8,999,641 B2 | 4/2015 | Zhang et al. |
| 9,023,649 B2 | 5/2015 | Mali et al. |
| 9,260,723 B2 | 2/2016 | Mali et al. |
| 9,637,739 B2 | 5/2017 | Siksnys et al. |
| 2005/0220796 A1 | 10/2005 | Dynan et al. |
| 2010/0076057 A1† | 3/2010 | Sontheimer |
| 2014/0068797 A1* | 3/2014 | Doudna ............... C12N 15/102 800/18 |
| 2014/0090113 A1 | 3/2014 | Cogan et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0189896 A1 | 7/2014 | Zhang et al. |

(Continued)

FOREIGN PATENT DOCUMENTS

| | | |
|---|---|---|
| AU | 733057 B2 | 5/2001 |
| CN | 102358902 A | 2/2012 |

(Continued)

OTHER PUBLICATIONS

Jinek et al A Programmable Dual-RNA-Guided DNA Endonuclease in Adaptive Bacterial Immunity (Science vol. 337, published online Jun. 28, 2012).*

(Continued)

*Primary Examiner* — Catherine S Hibbert
(74) *Attorney, Agent, or Firm* — Jones Day

(57) ABSTRACT

The present invention relates to targeted genome editing in eukaryotic cells or organisms. More particularly, the present invention relates to a composition for cleaving a target DNA in eukaryotic cells or organisms comprising a guide RNA specific for the target DNA and Cas protein-encoding nucleic acid or Cas protein, and use thereof.

10 Claims, 61 Drawing Sheets

Specification includes a Sequence Listing.

(56) References Cited

U.S. PATENT DOCUMENTS

| | | |
|---|---|---|
| 2014/0242664 A1 | 8/2014 | Zhang et al. |
| 2014/0242699 A1 | 8/2014 | Zhang et al. |
| 2014/0273230 A1 | 9/2014 | Chen et al. |
| 2014/0273233 A1 | 9/2014 | Chen et al. |
| 2014/0310830 A1 | 10/2014 | Zhang et al. |
| 2014/0342456 A1 | 11/2014 | Mali et al. |
| 2014/0357530 A1 | 12/2014 | Zhang et al. |
| 2015/0020223 A1 | 1/2015 | Zhang et al. |
| 2015/0031134 A1 | 1/2015 | Zhang et al. |
| 2015/0045546 A1 | 2/2015 | Siksnys et al. |
| 2015/0050699 A1 | 2/2015 | Siksnys et al. |
| 2015/0067921 A1 | 3/2015 | Cogan et al. |
| 2015/0079681 A1 | 3/2015 | Zhang et al. |
| 2015/0184139 A1 | 7/2015 | Zhang et al. |
| 2015/0203872 A1 | 7/2015 | Zhang et al. |
| 2015/0225734 A1 | 8/2015 | Voytas et al. |
| 2015/0232833 A1 | 8/2015 | Mali et al. |
| 2015/0232882 A1 | 8/2015 | Zhang et al. |
| 2015/0240261 A1 | 8/2015 | Siksnys et al. |
| 2015/0247150 A1 | 9/2015 | Zhang et al. |
| 2015/0259704 A1 | 9/2015 | Church et al. |
| 2015/0291961 A1 | 10/2015 | Siksnys et al. |
| 2015/0291965 A1 | 10/2015 | Zhang et al. |
| 2015/0356239 A1 | 12/2015 | Zhang et al. |
| 2016/0002670 A1 | 1/2016 | Church et al. |
| 2016/0017366 A1 | 1/2016 | Chen et al. |
| 2016/0032274 A1 | 2/2016 | Church et al. |
| 2016/0046961 A1 | 2/2016 | Jinek et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0115488 A1 | 4/2016 | Zhang et al. |
| 2016/0115489 A1 | 4/2016 | Zhang et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0153004 A1 | 6/2016 | Zhang et al. |
| 2016/0153005 A1 | 6/2016 | Zhang et al. |
| 2016/0153006 A1 | 6/2016 | Zhang et al. |
| 2016/0160210 A1 | 6/2016 | Mali et al. |
| 2016/0168594 A1 | 6/2016 | Zhang et al. |
| 2016/0175462 A1 | 6/2016 | Zhang et al. |
| 2016/0186213 A1 | 6/2016 | Zhang et al. |

FOREIGN PATENT DOCUMENTS

| | | |
|---|---|---|
| JP | H1080274 A | 3/1998 |
| JP | 2001503971 A | 3/2001 |
| JP | 2002538842 A | 11/2002 |
| JP | 2005006578 A | 1/2005 |
| JP | 2009505663 A | 2/2009 |
| JP | 2012508002 A | 4/2012 |
| KR | 1020150016588 A | 2/1916 |
| KR | 1020150023670 A | 3/2015 |
| KR | 1020150056539 A | 5/2015 |
| WO | WO 1998010084 A1 | 3/1998 |
| WO | WO 2000055378 A1 | 9/2000 |
| WO | WO 2007025195 A1 | 3/2007 |
| WO | WO 2008/108989 A2 | 12/2008 |
| WO | WO 2010052341 A1 | 5/2010 |
| WO | 2010/076939 A1 | 7/2010 |
| WO | WO 2010076939 A1 | 7/2010 |
| WO | WO 2011056186 A1 | 5/2011 |
| WO | WO 2011130346 A1 | 10/2011 |
| WO | 2011/146121 A1 | 11/2011 |
| WO | WO 2012012738 A1 | 1/2012 |
| WO | 2013/098244 A1 | 7/2013 |
| WO | 2013/141680 A1 | 9/2013 |
| WO | WO 2013/142578 | 9/2013 |
| WO | 2013/176772 A1 | 11/2013 |
| WO | WO 2013176772 A1 | 11/2013 |
| WO | 2014/022702 A2 | 2/2014 |
| WO | WO 2014/065596 | 5/2014 |
| WO | 2014/089290 A1 | 6/2014 |
| WO | 2014/093622 A2 | 6/2014 |
| WO | 2014/093655 A2 | 6/2014 |
| WO | 2014/093661 A2 | 6/2014 |
| WO | 2014/099744 A1 | 6/2014 |
| WO | 2014/099750 A2 | 6/2014 |
| WO | WO 2014/093595 | 6/2014 |
| WO | WO 2014/093635 | 6/2014 |
| WO | WO 2014/093655 A2 | 6/2014 |
| WO | WO 2014/093694 | 6/2014 |
| WO | WO 2014/093701 | 6/2014 |
| WO | WO 2014/093709 | 6/2014 |
| WO | WO 2014/093712 | 6/2014 |
| WO | WO 2014/093718 | 6/2014 |
| WO | WO 2014089290 A1 | 6/2014 |
| WO | WO 2014093661 A2 | 6/2014 |
| WO | WO 2014093661 A9 | 6/2014 |
| WO | WO 2014144155 A1 | 9/2014 |
| WO | WO 2014197568 A2 | 12/2014 |
| WO | WO 2014204725 A1 | 12/2014 |
| WO | WO 2015026883 A1 | 2/2015 |

OTHER PUBLICATIONS

Chiu et al in Engineered GFP as a viral reporter in plants (Curr. Biol. vol. 6, No. 3, pp. 325-330).*

Gustafsson et al., Codon bias and heterologous protein expression (Trends in Biotech vol. 22, No. 7, pp. 346-353).*

Chen et al "Transfection and expression of plasmid DNA in plant cells by an arginine-rich intracellular delivery peptide without protoplast preparation" (FEBS Letters 581, 2007, pp. 1891-1897).*

Miller et al., Nat. Biotechnol. 29, 143 (2011.*

Urnov et al ("Genome editing with engineered zinc finger nucleases" Nature vol. 11, Sep. 2010, pp. 636-646). (Year: 2010).*

Miller et al (Nat. Biotechnol. 29, 143; 2011). (Year: 2011).*

0000 (Year: XXXX).*

Anonymous, Third Party Observation dated Sep. 18, 2015, Application No. EP13849670.8 (Publication No. EP 2 912 175 A1) filed Oct. 23, 2015.

Office Action dated Sep. 1, 2015 for Australian Application No. 2013335451, 3 pages.

Extended European Search Report dated Nov. 9, 2015 for European Application No. 13849670.8, 10 pages.

Letter of Notice of Opposition dated Nov. 10, 2015 for European Patent No. EP2771468 (application No. EP 13818570.7) granted on Feb. 11, 2015, 57 pages.

Chang et al., "Genome editing with RNA-guided Cas9 nuclease in Zebrafish embryos", Cell Research, 2013, vol. 23, No. 4, pp. 465-472 and Supplementary Materials.

Bassett et al., "Highly Efficient Targeted Mutagenesis of *Drosophila* with the CRISPR/Cas9 System", Cell Reports, Jul. 11, 2013, vol. 4, No. 1, pp. 220-228 and Supplementary Table.

Kondo et al., "Highly Improved Gene Targeting by Germline-Specific Cas9 Expression in *Drosophila*" Genetics, Nov. 2013, vol. 195, No. 3, pp. 715-721.

Sebo et al., "A simplified and efficient germline-specific CRISPR/Cas9 system for *Drosophila* genomic engineering" Fly, 2014, vol. 8, No. 1 pp. 52-57.

Primo et al., "Lentiviral vectors for cutaneous RNA managing", Experimental Dermatology, 2011, vol. 21, No. 3, pp. 162-170.

Yi et al., "Current Advances in Retroviral Gene Therapy", Current Gene Therapy, 2011, vol. 11, No. 3, pp. 162-170.

Sung et al., "Mouse genetics: Catalogue and scissors", BMB Reports, Nov. 23, 2012, vol. 45, No. 12, pp. 686-692.

Japanese Office Action dated Nov. 24, 2015 for Japanese Patent Application No. 2015-538033, pp. 1-10 (with English Translation).

Hwang et al., "Efficient in Vivo Genome Editing Using RNA-Guided Nucleases", Nat Biotechnol., Mar. 2013, vol. 31, No. 3, Supplementary material,18 pages.

Mali et al., "RNA-Guided Human Genome Engineering via Cas9", Science, Feb. 15, 2013, vol. 339, No. 612, Supplementary material, 36 pages.

Gilbert et al., "CRISPR-Mediated Modular RNA-Guided Regulation of Transcription in Eukaryotes", Cell, Jul. 18, 2013, vol. 154, No. 2, Supplementary Table, 2 pages.

(56) References Cited

OTHER PUBLICATIONS

DiCarlo, "Genome engineering in *Saccharomyces cerevisiae* using CRISPR-Cas systems", Nucleic Acids Research, 2013, vol. 41, No. 7, Supplementary material, 5 pages.
Yang et al., "One-Step Generation of Mice Carrying Reporter and Conditional Alleles by CRISPR/Cas-Mediated Genome Engineering" Cell, Sep. 12, 2013, vol. 154, No. 6, pp. 1370-1379, Supplementary Tables, 4 pages.
Wang et al., "One-Step Generation of Mice Carrying Mutations in Multiple Genes by CRISPR/Cas-Mediated Genome Engineering", 2013, Cell, vol. 153, Supplementary Tables, 3 pages.
Letter of Notice of Opposition dated Jan. 8, 2016 for European Patent No. EP2784162 (application No. EP 14170383.5) granted on Apr. 8, 2015, 54 pages.
Fleck et al., "Modifications of the *E.coli* Lac repressor for expression in eukaryotic cells: effects of nuclear signal sequences on protein activity and nuclear accumulation", Nucleic Acids Research, 1992, vol. 20, No. 7, pp. 1785-1791.
Fisher-Fantuzzi & Vesco, "Cell-Dependent Efficiency of Reiterated Nuclear Signals in a Mutant Simian Virus 40 Oncoprotein Targeted to the Nucleus", Mol. Cell Biol, 1988, vol. 8, No. 12, pp. 5495-5503.
Au et al., "Characterization of a baculovirus nuclear localization signal domain in the late expression factor 3 protein", Virology, 2008, vol. 385, pp. 209-217.
Greensan et al., "Two Nuclear Location Signals in the Influenza Virus NS1 Nonstructural Protein", J. Virol, 1988, vol. 62, No. 8, pp. 3020-3026.
Imagawa et al., "Two nuclear localization signals are required for nuclear translocation of nuclear factor 1-A", FEBS lett, 2000, vol. 484, pp. 118-124.
Luo et al., "Multiple Nuclear Localization Sequences Allow Modulation of 5-Lipoxygenase Nuclear Import", Traffic, 2004, vol. 5, pp. 847-854, Oct. 31, 2016.
Morin et al., "Nuclear Localization of the Adenovirus DNA-Binding Protein: Requirement for Two Signals and Complementation during Viral Infection", 1989, Mol. Cell Biol, vol. 9, No. 10, pp. 4372-4380.
Nagarajan et al., "A Hierarchy of Nuclear Localization Signals X Complex Subunits and MHC Class II Governs the Import of the Regulatory Factor Expression", J. Immunol, 2004, vol. 173, No. 1, pp. 410-419.
Chan et al., "Characterization of the Kinetochore Binding Domain of CENP-E Reveals Interactions with the Kinetochore Proteins CENP-F and hBUBR1", J. Cell Biol, 1988, vol. 143, No. 1, pp. 49-63.
Rodrigues et al., "Red Fluorescent Protein (DsRed) as a Reporter in *Saccharomyces cerevisiae*", J. Bact., 2001, vol. 183, No. 12, pp. 3791-3794.
Los et al., "Halotag Technology: Cell Imaging and Protein Analysis", Cell Notes, 2006, vol. 14, pp. 10-14.
PShooter™ Vector user guide, Invitrogen by Life Technologies, revision date Mar. 29, 2012, 36 pages.
Singer and Verma, "Applications of Lentiviral Vectors for shRNA Delivery and Transgenesis", Curr Gene Ther., 2008, vol. 8, No. 6, pp. 483-488, 36 pages.
Chiu et al., "Engineered GFP as a viral reporter in plants", Current Biology, Feb. 2, 1996, vol. 6, No. 3, pp. 325-330.
Office Action dated Nov. 17, 2015, U.S. Appl. No. 14/685,510, filed Apr. 13, 2015, pp. 1-16.
Porteus, M & Carroll, D., "Gene targeting using zinc finger nucleases", Nature Biotechnology, published online Aug. 8, 2005, 23(8): 967-972.
Qi, et al., "RNA Processing Enables Predictable Programming of Gene Expression," Nature Biotechnology, 2012, vol. 30(10), pp. 1002-1007 (including Supplementary Information).
Raymond, C.S. and Soriano, P., "High-Efficiency FLP and •C31 Site-Specific Recombination in Mammalian Cells," PLoS One, Jan. 2007, 1:e162, pp. 1-4.

Rand et al., "Argonaute2 Cleaves the Anti-Guide Strand of siRNA during RISC Activation", Cell, Nov. 18, 2005, 123:621-629.
Rebar et al., "Induction of angiogenesis in a mouse model using engineered transcription factors", Nature Medicine, Dec. 2002, 6(12):1427-1432.
Regalado, A., "Who Owns the Biggest Biotech Discovery of the Century?", MIT Technology Review, Dec. 4, 2014, http://www.technologyreview.com/featuredstory/532796/who-owns-the-biggest-biotech-discovery-of-the-century/, pp. 1-4.
Dr. A. Maschio, Response to EPO Communication dated Dec. 31, 2014, European Application No. 13824232.6, pp. 1-7.
Sanders, R. "Cheap and easy technique to snip DNA could revolutionize gene therapy," UC Berkeley News Center, Jan. 7, 2013, http://newscenter.berkeley.edu/2013/01/07/cheap-and-easy-technique-to-snip-dna-could-revolutionize-gene-therapy/, pp. 1-3.
Sanders, R. "New DNA-editing technology spawns bold UC Initiative," UC Berkeley News Center, Mar. 18, 2014, http://newscenter.berkeley.edu/2014/03/18/new-dna-editing-technology-spawns-bold-uc-initiative/, pp. 1-3.
Schramm, L and Hernandez, N., "Recruitment of RNA polymerase III to its target promoters", Genes Dev., 2002, 16:2593-2620.
Shanks, P., "CRISPR Opportunities . . . For What? And For Whom?", BioPolitical Times, Dec. 4, 2014, http://www.biopoliticaltimes.org/article.php?id=8235, pp. 1-2.
Shen et al., "Generation of gene-modified mice via Cas9/RNA-mediated gene targeting", Cell Research, 2013, 23:720-723, published online Apr. 2, 2013.
Singer, O. and Verma I. M., "Applications of Lentiviral Vectors for shRNA Delivery and Transgenesis", Curr. Gene Ther., Dec. 2008, 8(6):483-488 and Figures (3 pages).
Tolia, N. and Joshua-Tor, L., "Slicer and the Argonautes", Nature Chemical Biology, Jan. 2007, published online Dec. 15, 2006, 3(1), 36-43.
Urnov et al., "Highly efficient endogenous human gene correction using designed zinc-finger nucleases", Nature, Jun. 2005, 435(2):646-651.
Fuqiang Chen et al., "Methods and Reagents for Modifying Genomes Using RNA-Guided Endonucleases", U.S. Appl. No. 61/734,256, filed Dec. 6, 2012.
Martin Jinek et al., "Methods and Compositions for RNA-Directed Site-Specific DNA Modification", U.S. Appl. No. 61/652,086, filed May 25, 2012.
Jennifer A. Doudna et al., "Methods and Compositions for RNA-Directed Target DNA Modification and for RNA-Directed Modulation of Transcription", U.S. Appl. No. 13/842,859 USPTO Papers, filed Mar. 15, 2013.
Van Der Dost, J., "New Tool for Genome Surgery," Science, Feb. 15, 2013, 339(6121):768-770.
Wiedenheft et al., "RNA-Guided Genetic Silencing Systems in Bacteria and Archaea," Nature, 2012, 482:331-338.
Dr. A. Maschio, Response to EPO Communication dated Jan. 5, 2015, European Application No. 13824232.6, pp. 1-2.
Notice of Allowance and Fees Due dated Feb. 4, 2015, U.S. Appl. No. 14/226,274, filed Mar. 26, 2014, pp. 1-22.
Anonymous, PCT Third Party Observation dated Feb. 19, 2015, International Application No. PCT/KR2013/009488 filed Oct. 23, 2013, pp. 1-5.
PCT International Search Report dated Jan. 27, 2014, International Application No. PCT/KR2013/009488 filed Oct. 23, 2013, pp. 1-5.
Giedrius Gasiunas et al., "Cas9-crRNA ribonucleoprotein complex mediates specific DNA cleavage for adaptive immunity in bacteria", PNAS, Sep. 2012, vol. 109, No. 39, pp. 2579-2586.
Seung Woo Cho et al., "Targeted genome engineering in human cells with the Cas9 RNA-guided endonuclease", Nature Biotechnology, Mar. 2013, vol. 31, No. 3, pp. 230-232.
Prashant Mali et al., "RNA-Guided Human Genome Engineering via Cas9", Science, Feb. 2013, vol. 339, pp. 823-826 and Supplementary Material (36 pages).
Woong Y. Hwang et al., "Efficient genome editing in zebrafish using a CRISPR-Cas system", Nature Biotechnology, Jan. 2013, vol. 31, No. 3, pp. 1-3.
Martin Jinek et al., "RNA-programmed genome editing in human cells", eLife, 2013, 2:e00471, pp. 1-9.

(56) References Cited

OTHER PUBLICATIONS

Marin Jinek et al., "A Programmable Dual-RNA-Guided DNA Endonuclease in Adaptive Bacterial Immunity", Science, vol. 337, Aug. 2012, pp. 816-821 and Supplementary Materials (37 pages).
Rimantas Sapranauskas et al., "The *Streptococcus thermophilus* CRISPR/Cas system provides immunity in *Escherichia coli*", Nucleic Acids Research, vol. 39, No. 21, Aug. 2011, pp. 9275-9282 and Supplementary Materials (10 pages).
Patrick D. Hsu et al., "DNA targeting specificity of RNA-guided Cas9 nucleases", Nature Biotechnology, vol. 31, No. 9, Sep. 2013, pp. 827-834.
James E. Dicarlo et al., "Genome engineering in *Saccharomyces cerevisiae* using CRISPR-Cas systems", Nucleic Acids Research, vol. 41, No. 7, Jan. 2013, pp. 4336-4343.
David Bikard et al., "Programmable repression and activation of bacterial gene expression using an engineered CRISPR-Cas system", Nucleic Acids Research, vol. 41, No. 15, Jun. 2013, pp. 7429-7437.
Krzysztof Chylinski et al., "The tracrRNA and Cas9 families of type II CRISPR-Cas immunity systems", RNA Biology, vol. 10, No. 5, May 2013, pp. 727-737.
Thomas J. Cradick et al., "CRISPR/Cas 9 systems targeting B-globin and CCR5 genes have substantial off-target activity", Nucleic Acids Research, vol. 41, No. 20, Aug. 2013, pp. 9584-9592.
Ari E. Friedland et al., "Heritable genome editing in C. elegans via a CRISPR-Cas 9 system", Nat Methods, vol. 10, No. 8, Aug. 2013, pp. 1-12.
Philippe Horvath et al., "RNA-guided genome editing a la carte", Cell Research, vol. 23, Mar. 2013, pp. 733-734.
Le Cong et al., "Multiplex Genome Engineering Using CRISPR/Cas Systems", Science, vol. 339, No. 6121, Feb. 2013, pp. 1-9 and Supplementary Materials (28 pages).
Wenyan Jiang et al., "CRISPR-assisted editing of bacterial genomes", Nature Biotechnology, vol. 31, No. 3, Mar. 2013, pp. 1-22.
Tautvydas Karvelis et al., "crRNA and tracrRNA guide Cas9-mediated DNA interference in *Streptococcus thermophilus*", RNA Biology, vol. 10, No. 5, May 2013, pp. 841-851.
David J. Segal, "Genome engineering: Bacteria herald a new era of gene editing", eLife, vol. 2, e00563, 2013, pp. 1-3.
Prashant Mali et al., "CAS9 transcriptional activators for target specificity screening and paired nickases for cooperative genome engineering", Nature Biotechnology, vol. 31, Aug. 2013, pp. 1-8.
Pablo Perez-Pinera et al., "RNA-guided gene activation by CRISPR-Cas9-based transcription factors", Nat Methods, vol. 10, No. 10, Oct. 2013, pp. 1-11.
Lei S. Qi et al., "Repurposing CRISPR as an RNA-Guided Platform for Sequence-Specific Control of Gene Expression", Cell., vol. 152, No. 5, Feb. 2013, pp. 1-22.
Haoyi Wang et al., "One-Step Generation of Mice Carrying Mutations in Multiple Genes by CRISPR/Cas-Mediated Genome Engineering", Cell., vol. 153, No. 4, May 2013, pp. 1-17.
Zhongsheng Yu et al., "Highly Efficient Genome Modifications Mediated by CRISPR/Cas9 in *Drosophila*", Genetics, vol. 195, Sep. 2013, pp. 289-291.
Ryan M. Walsh et al., "A variant CRISPR-Cas9 system adds versatility to genome engineering", PNAS, vol. 110, No. 39, Sep. 2013, pp. 15514-15515.
Andreas et al., "Enhanced efficiency through nuclear localization signal fusion on phage •C31-integrase: activity comparison with Cre and FLPe recombinase in mammalian cells", Nucleic Acids Research, 2002, 30(11):2299-2306.
Barrangou, R., RNA-Mediated Programmable DNA Cleavage, Nature Biotechnology, Sep. 10, 2012, 30(9):836-838.
Bassett, A.R. and Liu, J.-L., "CRISPR/Cas9 and Genome Editing in *Drosophila*," Journal of Genetics and Genomics, 2014, vol. 41, pp. 7-19 (including supplementary materials).
Boch J. and Bonas U., "Xanthomonas AvrBs3 Family-Type III Effectors: Discovery and Function", Annu. Rev. Phytopathol. 2010, 48:419-436, first published online May 10, 2010.

Brouns, S.J.J., "A Swiss Army Kinfe of Immuity", Science, 2012, vol. 337, pp. 808-809.
Carrol, D., "A CRISPR Approach to Gene Targeting," Molecular Therapy, Sep. 2012, 20(9):1658-1660.
Cermak et al., "Efficient design and assembly of custom TALEN and other TAL effector-based constructs for DNA targeting", Nucleic Acids Research, 2011, 39(12) e82, 11 pages, first published online Apr. 14, 2011.
Christian et al. "Targeting DNA Double-Strand Breaks with TAL Effector Nucleases", Genetics, Oct. 2010, 186:757-761 and 2S1-8S1.
Communication forwarding Declaration of Feng Zhang and Declaration of Feng Zhang filed in U.S. Appl. No. 14/266,274 dated Nov. 21, 2014.
Decision on Petition issued Jun. 17, 2013 in U.S. Appl. No. 13/842,859 (3 pages).
Deltcheva et al., "CRISPR RNA maturation by trans-encoded small RNA and host factor RNase III", Nature, Mar. 31, 2011, 471(7340):602-607 and Supplementary Information (71 pages).
Dingwall et al., "A polypeptide domain that specifies migration of nucleoplasm into the nucleus", Cell, Sep. 1982, 30(2):449-458, abstract only.
Doudna, J., "The CRISPR Revolution," Catalyst Magazine, College of Chemistry, University of California, Berkeley, Jul. 9, 2014, pp. 1-4.
Garneau et al., "The CRISPR/Cas bacterial immune system cleaves bacteriophage and plasmid DNA", Nature, Nov. 4, 2010, vol. 468:67-71.
Goldfarb et al., "Synthetic peptides as nuclear localization signals", Nature, Aug. 14, 1986, 322: 641-644.
Gustafsson et al., "Codon bias and heterologous protein expression", Trends in Biotechnology, 2004, 22(7), 346-353.
Lambowitz et al., "Group II Introns: Mobile Ribozymes that invade DNA," Cold Spring Har. Perspect. Biol., 2011, 3:a003616, pp. 1-19.
Li et al., "Modularly Assembled Designer TAL Effector Nucleases for Targeted Gene Knockout and Gene Replacement in Eukaryotes," Nucleci Acids Rsearch, 2011, vol. 39(14), pp. 6315-6325.
Mali et al., "Cas9 as a Versatile Tool for Engineering Biology," Nature Methods, 2013, vol. 10(10), pp. 957-963.
Miller et al., "A TALE nuclease architecture for efficient genome editing", Nature Biotechnology, Feb. 2011, 29 (2):143-148 and online methods 2 pages.
Nakamura et al., "Codon usage tabulated from international DNA sequence databases: status for the year 2000", Nucleic Acids Research, 2000, 28(1):292.
Patterson et al., "Codon optimization of bacterial luciferase (lux) for expression in mammalian cells", J. Ind. Microbiol. Biotechnol., published online Mar. 11, 2005, 32:115-123.
Petition under 37 C.F.R. § 1.183 to Suspend the Rules in Order to Permit Joint Representation in a Patent Application, Filing Receipt (exhibit to Petition), Declaration of Emmanuelle Charpentier accompanying Petition (exhibit to Petition) filed in U.S. Appl. No. 13/842,859, filed Jun. 11, 2013 (9 pages).
Melissa Pandika, "Jennifer Doudna, CRISPR Code Killer", www.ozy.com/rising-stars-and-provocateurs/jennifer-doudna-crispr-code-killer/4690, Jan. 7, 2014, pp. 1-6.
Baker, 2014, "Gene editing at CRISPR speed", Nat Biotechnol, 32(4):309-312.
Barrangou et al., 2007, "CRISPR provides acquired resistance against viruses in prokaryotes", Science, 315(5819):1709-1712.
Bikard et al., 2012, "CRISPR interference can prevent natural transformation and virulence acquisition during in vivo bacterial infection", Cell Host & Microbe, 12:177-186.
Brothers et al., 2003, "Unexpected effects of epitope and chimeric tags on gonadotropin-releasing hormone receptors: implications for understanding the molecular etiology of hypogonadotropic hypogonadism", J Clin Endocrin Metabol, 88(12):6107-6112.
Brzostek-Racine et al., 2011, "The DNA damage response induces IFN", J Immunol, 187:5336-5345.
Chuan et al., 2008, "High-level expression of soluble viral structural protein in *Escherichia coli*", J Biotech, 134:64-71.
Close et al., 2012, "Expression of non-native genes in a surrogate host organism", Retrieved from the Internet: ww.intechopen.com.

(56) References Cited

OTHER PUBLICATIONS

Coppoolse et al., 2003, "Cre recombinase expression can result in phenotypic aberrations in plants", Plant Mol Biol, 51:563-579.
Deveau et al, 2008, "Phage Response to CRISPR-Encoded Resistance in *Streptococcus thermophilus*", J Bacteriol, 190(4):1390-1400.
Edgar and Qimron, 2010, "The *Escherichia coli* CRISPR system protects from λ lysogenization, lysogens, and prophage induction", J Bacteriol, 192(23):6291-6294.
Elbashir et al., 2001, "Duplexes of 21±nucleotide RNAs mediate RNA interference in cultured mammalian cells", Nature, 411:494-498.
Ellis, 2001, "Macromolecular crowding: obvious but underappreciated", Trends in Biochem Sci, 26(10):597-604.
Fraley et al., 1983, "Expression of bacterial genes in plant cells", Proc Natl Acad Sci USA, 80:4803-4807.
Goren et al., 2012, "The bacterial CRISPR/Cas system as analog of the mammalian adaptive immune system", RNA Biol, 9(5):549-554.
Görlich and Kutay, 1999, "Transport between the cell nucleus and the cytoplasm", Annu Rev Cell Dev Biol, 15:607-660.
Hatfull, 2008, "Bacteriophage genomics", Curr Opin Microbiol, 11(5):447-453.
Heidmann and Lehner, 2001, "Reduction of Cre recombinase toxicity in proliferating *Drosophila* cells by estrogen-dependent activity regulation", Dev Genes Evol, 211:458-465.
Hocine et al., 2010, "RNA processing export", Cold Spring Harb Perspect Biol, 2:a000752.
Karpala et al., 2005, "Immune responses to dsRNA: implications for gene silencing technologies", Immun Cell Biol, 83:211-216.
Kim et al., 2009, "Targeted genome editing in human cells with zinc finger nucleases constructed via modular assembly", Genome Research, 19:1279-1288.
Komar, 2008, "A pause for thought along the co-translational folding pathway", Trends Biotechnol Sci, 34(1):16-24.
Koonin, 2009, "Evolution of genome architecture", Int J Biochem Cell Biol, 41(2):298-306.
Lander et al., 2001, "Initial sequencing and analysis of the human genome", Nature, 409:860-921.
Lechardeur et al., 1999, "Metabolic instability of plasmid DNA in the cytosol: a potential barrier to gene transfer", Gene Therapy, 6:482-497.
Link and Breaker, 2009, "Engineering ligand-responsive gene-control elements: lessons learned from natural riboswitches", Gene Therapy, 16:1189-1201.
Loonstra et al., 2001, "Growth inhibition and DNA damage induced by Cre recombinase in mammalian cells", Proc Natl Acad Sci USA, 98(16):9209-9214.
Mastroianni et al., 2008, "Group II intron-based gene targeting reactions in eukaryotes", PLoS One, 3(9):e3121, 15 pages.
Mazzara et al., 2011, "Maturation events leading to transfer RNA and ribosomal RNA", Cell Biology, 3:439-545.
McCall and Bender, 1996, "Probes for chromatin accessibility in the *Drosophila* bithorax complex respond differently to Polycomb-mediated repression", EMBO J, 15(3):569-580.
McShan et al., 2008, "Genome sequence of a nephritogenic and highly transformable M49 strain of *Streptococcus pyogenes*", J Bacteriol, 190(23):7773-7785.
Minton, 2006, "How can biochemical reactions within cells differ from those in test tubes", J Cell Sci, 119:2863-2869.
Mussolino et al., 2011, "A novel TALE nuclease scaffold enables high genome editing activity in combination with low toxicity", Nucl Acids Res, 39(21):9283-9293.
Ogawa, 2011, "Rational design of artificial riboswitches based on ligand-dependent modulation of internal ribosome entry in wheat germ extract and their applications as label-free biosensors", RNA, 17:478-488.
Pattanayak et al., 2011, "Revealing off-target cleavage specificities of zinc finger nucleases by in vitro selection", Nat Methods, 8(9):765-770.

Perez-Rodriguez, 2010, "Elucidating a novel mechanism of DNA silencing caused by envelope stress in *Escherichia coli*", Dissertation and Abstract first available to the public on Jun. 17, 2010.
Romani and Maguire, 2002, "Hormonal regulation of Mg2+ transport and homeostasis in eukaryotic cells", BioMetals, 15:271-283.
Sanders et al., 1994, "Use of a macromolecular crowding agent to dissect interactions and define functions in transcriptional activation by a DNA-tracking protein: bacteriophage T4 gene 45 protein and late transcription", Proc Natl Acad Sci USA, 91:7703-7707.
Sauer and Henderson, 1988, "Site-specific DNA recombination in mammalian cells by the Cre recombinase of bacteriophage P1", Proc Natl Acad Sci USA, 85:5166-5170.
Schmidt et al., 2000, "Illegitimate Cre-dependent chromosome rearrangements in transgenic mouse spermatids", Proc Natl Acad USA, 97(25):13702-13707.
Schultz et al., 2004, "The interferon system of non-mammalian vertebrates" Dev Comp Immunol, 28:499-508.
Seamon et al., 2002, "Inserting a nuclear targeting signal into a replication-competent moloney murine leukemia virus affects viral export and is not sufficient for cell cycle-independent infection", J Virol, 76(16):8475-8484.
Silverman and Mirsky, 1973, "Accessibility of DNA in chromatin to DNA polymerase and RNA polymerase", Proc Natl Acad Sci USA, 70(5):1326-1330.
Singapore Written Opinion of Singapore application No. 11201503059X, dated Mar. 18, 2016.
Staynov, 2000, "Inserting a nuclear targeting signal into a replication-competent moloney murine leukemia virus affects viral export and is not sufficient for cell cycle-independent infection", Nucl Acids Res, 28(16):3092-3099.
Third Party Submission Under 37 C.F.R. §1.290 of U.S. Appl. No. 14/438,098, filed Apr. 6, 2016.
Third Party Submission Under 37 C.F.R. §1.290 of U.S. Appl. No. 14/685,510, filed Jun. 2, 2016.
Turner et al., 1996, "Carboxyl-terminal vesicular stomatitis virus g protein-tagged intestinal nal-dependent glucose cotransporter (SGLT1)", J Biol Chem, 271(13):7738-7744.
Walker et al., 1994, "The roles of magnesium in biotechnology", Crit Rev Biotechnol, 14(4):311-354.
Wirtz et al., 1998, "Regulated processive transcription of chromatin by T7 RNA polymerase in *Trypanosoma brucei*", Nucl Acids Res, 26(20):4626-4634.
Zaret and Carroll, 2011, "Pioneer transcription factors: establishing competence for gene expression", Genes & Development, 25:2227-2241.
Chen, B. et al. Dynamic imaging of genomic loci in living human cells by an optimized CRISPR/Cas system. Cell 155, 1479-1491 (2013).
Gilbert, L. A. et al. CRISPR-Mediated Modular RNA-Guided Regulation of Transcription in Eukaryotes. Cell 154, 442-451 (2013).
Ran, F. A. et al. Double nicking by RNA-guided CRISPR cas9 for enhanced genome editing specificity. Cell 154, 1380-1389 (2013).
Yang, H. et al. One-Step Generation of Mice Carrying Reporter and Conditional Alleles by CRISPR / Cas-Mediated Genome Engineering. Cell 154, 1370-1379 (2013).
Sung, Y. H. et al. Highly efficient gene knockout in mice and zebrafish with RNA-guided endonucleases. Genome Res (2013). 1-8. doi:10.1101/gr.163394.113.
Maresca, M. et al. Obligate ligation-gated recombination (ObLiGaRe): Custom-designed nuclease-mediated targeted integration through nonhomologous end joining. Genome Res. 23, 539-546 (2013).
Fu, Y. et al. High-frequency off-target mutagenesis induced by CRISPR-Cas nucleases in human cells. Nat. Biotechnol. 31, 822-826 (2013).
Jiang, W. et al. RNA-guided editing of bacterial genomes using CRISPR-Cas systems. Nat. Biotechnol. 31, 233-239 (2013).
Pattanayak, V. et al. High-throughput profiling of off-target DNA cleavage reveals RNA-programmed Cas9 nuclease specificity. Nat. Biotechnol. 31, 839-843 (2013).
Shalem, O. et al. Genome-Scale CRISPR-Cas9 Knockout Screening in Humen Cells. Science. 3, 1-7 (2013).

(56) References Cited

OTHER PUBLICATIONS

Dickinson, D. J. et al. Engineering the Caenorhabditis elegans genome using Cas9-triggered homologous recombination. Nat. Methods 10, 1028-1034 (2013).
Esvelt, K. M. et al. Orthogonal Cas9 proteins for RNA-guided gene regulation and editing. Nat. Methods 10, 1116-1121 (2013).
Maeder, M. L. et al. CRISPR RNA-guided activation of endogenous human genes. Nat. Methods 10, 977-979 (2013).
Larson, M. H. et al. CRISPR interference (CRISPRi) for sequence-specific control of gene expression. Nat. Protoc. 8, 2180-2196 (2013).
Ran, F. A. et al. Genome engineering using the CRISPR-Cas9 system. Nat. Protoc. 8, 2281-2308 (2013).
Pennisi, E. The CRISPR Craze. Science. 341, 833-836 (2013).
Wang, T. et al. Genetic Screens in Human Cells Using the CRISPR / Cas9 System. Science. 343, 1-8 (2013). doi:10.1126/science.1246981.
Third Party Submission dated Sep. 5, 2014, U.S. Appl. No. 13/842,859, filed Mar. 15, 2013, pp. 1-72.
Third Party Submissions dated Jan. 16, 2015, U.S. Appl. No. 13/842,859, filed Mar. 15, 2013, pp. 1-40.
Third Party Submissions dated Dec. 22, 2014, U.S. Appl. No. 14/104,977, filed Dec. 12, 2013, pp. 1-56.
Mussolino, C. & Cathomen, T. RNA guides genome engineering. Nat. Biotechnol. 31, 208-209 (2013).
Carroll, D. Staying on target with CRISPR-Cas. Nat. Biotechnol. 31, 807-809 (2013).
Burgess, D. J. Technology: Characterizing CRISPR off-target effects. Nat. Rev. Genet. 15, 5 (2013).
Cain, C. CRISPR genome editing. SciBX Sc. Exch. 1-3 (2013). doi:10.1038/scibx.2013.77.
Anonymous, Third Party Observation dated Jul. 18, 2014, Application No. PCT/US2013/033106 filed Mar. 20, 2013 (7 pages).
Anonymous, Third Party Observation dated Sep. 24, 2014, Application No. PCT/US2013/032589 filed Mar. 15, 2013 (8 pages).
Anonymous, Third Party Observations dated Sep. 8, 2014, European Application No. EP20130824232 (Publication No. EP2764103) filed Dec. 12, 2013, pp. 1-48.
Anonymous, Third Party Observations dated Sep. 22, 2014, European Application No. EP20130824232 (Publication No. EP2764103) filed Dec. 12, 2013, pp. 1-19.
Anonymous, Third Party Observations dated Oct. 22, 2014, European Application No. EP20130824232 (Publication No. EP2764103) filed Dec. 12, 2013, pp. 1-8.
Anonymous, Third Party Observation dated Nov. 7, 2014, Application No. EP20130824232 (Publication No. EP2764103) filed Dec. 12, 2013 (7 pages).
Anonymous, Third Party Observation dated Feb. 16, 2015 Application No. EP20130824232 (Publication No. EP2764103) filed Dec. 12, 2013 (12 pages).
Anonymous, Third Party Observation dated Mar. 25, 2015, Application No. EP20130824232 (Publication No. EP2764103) filed Dec. 12, 2013 (7 pages).
Anonymous, Third Party Observations dated Jan. 6, 2015, Application No. EP20130793997 (Publication No. EP2800811) filed Mar. 15, 2013, (50 pages).
Anonymous, Third Party Observation dated Feb. 3, 2015, Application No. EP20130793997 (Publication No. EP2800811) filed Mar. 15, 2013, (3 pages).
Anonymous, Third Party Observation dated Feb. 5, 2015, Application No. EP20130793997 (Publication No. EP2800811) filed Mar. 15, 2013, (2 pages).
Li et al, "Heritable gene targeting in the mouse and rat using a CRISPR-Cas system" Nature Biotechnology, 2013, vol. 31, No. 8, pp. 681-683 and Supplementary Information.
Li et al, "Simultaneous generation and germline transmission of multiple gene mutations in rat using CRISPR-Cas systems", Nature Biotechnology, 2013, vol. 31, No. 8, pp. 684-686 and Supplementary Information.

Statement of Grounds and Particulars in Support of Opposition [Fisher], dated Mar. 15, 2017, for Opposition of Australian Patent Application No. 2013335451 accepted on Aug. 24, 2016, and Cited Documents D1-10.
Statement of Grounds and Particulars [JH Corp], dated Mar. 15, 2017, for Opposition of Australian Patent Application No. 2013335451 accepted on Aug. 24, 2016, and Cited Documents D1-5.
Anonymous, Third Party Observation dated Jan. 9, 2017, European Application No. EP13849670.8 (Publication No. EP 2 912 175 A1) filed Oct. 23, 2015.
U.S. Appl. No. 61/652,086, filed May 25, 2012, Jinek at al.
U.S. Appl. No. 61/716,256, filed Oct. 19, 2013, Jinek at al.
U.S. Appl. No. 61/736,527, filed Dec. 12, 2012, Zhang.
U.S. Appl. No. 61/757,640, filed Jan. 28, 2013, Jinek at al.
U.S. Appl. No. 61/765,576, filed Feb. 15, 2013, Lim et al.
U.S. Appl. No. 61/803,599, filed Mar. 20, 2013, Kim et al.
U.S. Appl. No. 61/837,481, filed Jun. 20, 2013, Cho et al.
Barrangou, R., 2012, "RNA-mediated programmable DNA cleavage", Nature Biotechnology, 30(9):836-838.
Bassett and Liu, 2014, "CRISPR/Cas9 and genome editing in *Drosophilia*", Journal of Genetics and Genomics, 41:7-19 including supplementary materials.
Baum et al., 2010, "Preference of RIG-I for short viral RNA molecules in infected cells revealed by next-generation sequencing", PNAS, 107(37):16303-16308.
Bogerd et al., 2010, "A mammalian herpesvirus uses non-canonical expression and processing mechanisms to generate viral microRNAs", Molecular Cell, 37:135-142.
Brummelkamp et al., 2002, "A system for stable expression of short interfering RNAs in mammalian cells", Science, 296:550-553.
Carey et al., 2009, "Dignam and roeder nuclear extract preparation", Cold Spring Harb Protoc, 4(12):1-4.
Carlson et al., 2012, "Cell-free protein synthesis: applications come of age", Biotechnology Advances, 30:1185-1194.
Carroll, 2011, "Genome engineering with zinc-finger nucleases", Genetics, 188:773-782.
Carroll, 2012, "A CRISPR approach to gene targeting", Molecular Therapy, 20(9):1658-60.
Chen et al., 2007, "Transfection and expression of plasmid DNA in plant cells by an arginine-rich intracellular delivery peptide without protoplast preparation", FEBS Letters, 581:1891-1897.
Chiu et al., 1996, "Engineered GFP as a viral reporter in plants", Curr Biol, 6(3):325-330.
Close et al., 2012, "Expression of non-native genes in a surrogate host organism", Genetic Engineering—Basics, New Applications and Responsibilities, Prof. Hugo A. Barrera-Saldana (Ed.), InTech.
Cohen et al., 2011, "The emerging race to cure HIV infections", Science, 332(6031):784-789.
Collins et al., 2010, "Cytosol as battleground: ubiquitin as a weapon for both host and pathogen", Trends in Cell Biology, 20(4):205-213.
Cong et al., 2013, "Multiplex genome engineering using CRISPR/Cas systems", Science, 339(819):819-823.
Coppoolse et al., 2003, "Cre recombinase expression can result in phenotypic abberations in plants", Plant Molecular Biology, 51:263-279.
Doudna, 2014, "The CRISPR Revolution", Catalyst Magazine, Jul. 9, 2014.
Ellis, 2001, "Macromolecular crowding: obvious but underappreciated", Trends in Biochemical Sciences, 26(10):597-604.
Fu et al., 2013, "High-frequency off-target mutagenesis induced by CRISPR-Cas nucleases in human cells", Nat Biotech, 31(9):822-826.
Gabriel et al., 2012, "An unbiased genome-wide analysis of zinc-finger nuclease specificity", Nat Biotechnol, 29(9):816-823.
Goldberg, 2003, "Protein degradation and protection against misfolded or damaged proteins", Nature, 426:895-899.
Gonzalez et al, 2010, "Modular system for the construction of zinc-finger libraries and proteins", Nature Protocols, 5(4):791-810.
Gottwein et al., 2011, "Viral microRNA targetome of KSHV-infected primary effusion lymphoma cell lines", Cell Host & Microbe, 10:515-526.
Gustafsson et al., 2004, "Codon bias and heterologous protein expression", Trends in Biotech, 22(7):346-353.

(56) References Cited

OTHER PUBLICATIONS

Hatfull, G., 2008, "Bacteriophage Genomics", Curr Opin Microbiol., 11(5):447-453.
Heidmann and Lehner, 2001, "Reduction of Cre recombinase toxicity in proliferating *Drosophilia* cells by estrogen-dependent activity regulation", Dev Genes Evol, 211:458-468.
Hocine et al., 2010, "RNA processing and export", Cold Spring Harbor Perspectives in Biology, retrieved from the internet at http://cshperspectives.cship.org/ on Jun. 13, 2016.
Houseley et al., 2009, The many pathways of RNA degradation, Cell, 136:763-776.
Hsu et al., 2013, "DNA targeting specificity of RNA-guided Cas9 mucleases", Nature Biotechnology, doi: 10.1038/nbt.2647.
Jenuwein et al., 1993, "The immunoglobulin μ enhancer core establishes local factor access in nuclear chromatin independent of transcriptional stimulation", Genes & Development, 7:2016-2032.
Jiang et al, 2011, "Structural basis of RNA recognition and activation by innate immune receptor RIG-I", Nature, 479:423-429.
Jinek et al., 2012, "A programmable dual-RNA-guided DNA endonuclease in adaptive bacterial immunity", Science, 337(6096):816-821.
Jinek et al., 2013, "RNA-programmed genome editing in human cells", eLife, 2:00471.
Karpala et al., 2005, "Immune responses to dsRNA: Implications for gene silencing technologies", Immunology and Cell Biology, 83:211-216.
Kennedy et al., 2014, "Inactivation of the human papillomavirus E6 or E7 gene in cervical carcinoma cells using a bacterial CRISPR/Cas RNA-guided endonuclease", Journal of Virology, 88:11965-11972.
Kim et al., 2011, "Surrogate reporters for enrichment of cells with nuclease-induced mutations", Nat Methods, 8:941-943.
Kim et al., 2012, "Precision genome engineering with programmable DNA-nicking enzymes", Genome Res, 22:1327-1333.
Komar, 2008, "A pause for thought along the co-translational folding pathway", Trends in Biochemical Sciences, 34(1):16-24.
Koseki et al., 1999, "Factors governing the activity in vivo of ribozymes transcribed by RNA polymerase III", J Virol, 73(3):1868-1877.
Kosugi et al., 2009, "Six classes of nuclear localization signals specific to different binding grooves of importin α", The Journal of Biological Chemistry, 284(1):478-485.
Lambowitz et al., 2011, "Group II introns: mobile ribozymes that invade DNA", Cold Spring Perspect Biol, 3:a003616 pp. 1-19.
Lander, 2001, "Initial sequencing and analysis of the human genome", Nature, 409:860-921.
Lee et al., 2010, "Targeted chromosomal deletions in human cells using zinc finger nucleases", Genome Res, 20:81-89.
Lee et al., 2012, "Targeted chromosomal duplications and inversions in the human genome using zinc finger nucleases", Genome Res, 22:539-548.
Link et al. 2009, "Engineering ligand-responsive gene-control elements: lessons learned from natural riboswitches", Gene Therapy, 16:1189-1201.
Liu et al., 2008, "Sequence space coverage, entropy of genomes and the potential to detect non-human DNA samples", BMC Genomics, 9(509):1-17.
Loonstra et al., 2001, "Growth inhibition and DNA damage induced by Cre recombinase in mammalian cells", PNAS, 98(16):9209-9214.
Mali et al, 2013, "CAS9 transcriptional activators for target specificity screening and paired nickases for cooperative genome engineering", Nature Biotechnology, doi:10.1038/ntb.2675.
Mali et al., 2013, "RNA-guided human genome engineering via Cas9", Science, 339(823):823-826.
Maraia et al., 2001, "La protein and the trafficking of nascent RNA polymerase III transcripts", J Cell Biology, 153(4):F13-F17.
Maraia et al., 2002, "La protein and its associated small nuclear and nucleolar precursor RNAs", Gene Expression, 10:41-57.
Mastroianni et al., 2008, "Group II intron-based gene targeting reactions in eukaryotes", PLoS One, 3(9):e3121.
McCall and Bender, 1996, "Probes for chromatin accessibility in the *Drosophila* bithorax complex respond differently to Polycomb-mediated repression", The EMBO Journal, 15(3):569-580.
Miller et al., 2011, "A TALE nuclease architecture for efficient genome editing", Nat Biotechnol, 29(2):143-150.
Minton, 2015, "How can biochemical reactions within cells differ from those in test tubes", J Cell Sci, 119:2863-2869.
Mojica et al., 2009, "Short motif sequences determine the targets of the prokaryotic CRISPR defense system", Microbiology, 155:733-740.
Mussolino et al., 2011, "A novel TALE nuclease scaffold enables high genome editing activity in combination with low toxicity", Nucleic Acids Research, 39(21):9283-9293.
O'Neill et al., 1992, "Nucleosome arrays inhibit both initiation and elongation of transcripts by bacteriophage T7 RNA polymerase", J. Mol. Biol., 223:67-78.
Paddison et al., 2005, "Cloning of short hairpin RNAs for gene knockdown in mammalian cells", Nature Methods, 1(2):163-167.
Pandika, 2014, "Jennifer Doudna, CRISPR code killer", http://www.ozy.com/rising-stars.
Perez et al., 2008, "Establishment of HIV-1 resistance in CD4+ T cells by genome editing using zinc-finger nucleases", Nat Biotechnol, 26:808-816.
Pichlmair et al., 2006, "RIG-I-mediated antiviral responses to single-stranded RNA bearing 5'-phosphates", Science, 314(10):997-1001.
Pillich et al., 2012, "Activation of the unfolded protein response by Listeria monocytogenes", Cellular Microbiology, 14(6):949-964.
Porteus and Carroll et al., 2005, "Gene targeting using zinc finger nucleases", Nature Biotechnology, 23(8):967-973.
Raymond and Soriano, 2007, "High-efficiency FLP and φC31 site-specific recombination in mammalian cells", PLoS One, 2(1):e162.
Richter et al., 2008, "Macromolecular crowding and its potential impact on nuclear function", Biochimica et Biophysica Acta, 1783:2100-2107.
Ron and Walter, 2007, "Signal integration in the endoplasmic reticulum unfolded protein response", Molecular Cell Biology, 8:519-529.
Russell and Zomerdijk, 2005, "RNA-polymerase-I-directed rDNA transcription, life and works", Trends in Biochemical Sciences, 30(2):87-96.
Sanders, 2013, "Cheap and easy technique to snip DNA could revolutionize gene therapy", Berkeley News pp. 1-5.
Schmidt et al., 2000, "Illegitimate Cre-dependent chromosome rearrangements in transgenic mouse spermatids", PNAS, 97(25):13702-13707.
Schmidt et al., 2012, "Sensing of viral nucleic acids by RIG-I: from translocation to translation", Eur J Cell Biol., 91(1):78-85.
Thyagarajin et al., 2000, "Mammalian genomes contain active recombinase recognition sites", Gene, 244:47-54.
Turner et al., 1996, Carboxyl-terminal vesicular stomatitis virus G protein-tagged intestinal Na+ -dependent glucose cotransporter (SGLT1), J Biol Chem, 271(13):7738-7744.
Umbach et al., 2008, "MicroRNAs expressed by herpes simplex virus 1 during latent infection regulate viral mRNA's", Nature, 454:780-783.
Walker, G., 1994, "The roles of magnesium in biotechnology", Critical Reviews in Biotechnology, 14(4):311-354.
Wells et al., 1998, "Circularization of mRNA by eukaryotic translation initiation factors", Molecular Cell, 2:135-140.
Whisnant et al., 2013, "In depth analysis of the interaction of HIV-1 with cellular microRNA biogenesis and effector mechanisms", mBio 4:e00193-13.
Wirtz et al., 1998, "Regulated processive transcription of chromatin by T7 RNA polymerase in Trypanosoma brucei", Nucleic Acids Research, 26(20):4626-4634.
Zaret et al., 2011, "Pioneer transcription factors: establishing competence for gene expression", Genes & Development, 25:2227-2241.

(56) References Cited

OTHER PUBLICATIONS

Zimmerman, 1993, "Macromolecular crowding effects on macromolecular interactions some implications for genome structure and function", Biochimica et Biophysica Acta, 1216:175-185.
Office Action dated Jun. 14, 2017 of U.S. Appl. No. 14/685,510.
Office Action dated May 4, 2016 of U.S. Appl. No. 14/685,510.
Office Action dated Nov. 17, 2016 of U.S. Appl. No. 14/685,510.
First Declaration of Carol Greider, Ph.D, executed on May 23, 2016 in Support of University of California et al., Patent Interference No. 106,048 (DK).
Second Declaration of Carol Greider, Ph.D, executed on Aug. 15, 2016 in Support of University of California et al., Patent Interference No. 106,048 (DK).
First Declaration of Dana Carroll, Ph.D, executed on May 23, 2016 in Support of University of California et al., Patent Interference No. 106,048 (DK).
Second Declaration of Dana Carroll, Ph.D, executed on Aug. 15, 2016 in Support of University of California et al., Patent Interference No. 106,048 (DK).
Third Declaration of Technical Expert Ronald Breaker in Support of Broad et al., executed Aug. 15, 2016 in relation to Patent Interference No. 106,048 (DK).
Third Declaration of Technical Expert Paul Simon in Support of Broad et al., executed Aug. 15, 2016 in relation to Patent Interference No. 106,048 (DK).
Declaration of Paul Quinton Thomas, executed Jun. 15, 2017 in the matter of Opposition to the Australian Patent Application No. 2013335451.
Declaration of Dr. Marco Josef Herold, executed Jun. 15, 2017 in the matter of Opposition to the Australian Patent Application No. 2013335451.
Declaration of Grant William Fisher, executed Jun. 15, 2017 in the matter of Opposition to the Australian Patent Application No. 2013335451.
Declaration of Dr. Ron Firestein, executed Sep. 19, 2017 in the matter of Opposition to the Australian Patent Application No. 2013335451.
Declaration of Dr. Marco Josef Herold, executed Nov. 17, 2017 in the matter of Opposition to the Australian Patent Application No. 2013335451.
McShan et al., 2008, "Genome Sequence of a Nephritogenic and Highly Transformable M49 Strain of *Streptococcus pyogenes*", Journal of Bacteriology 190(23):7773-7785.
Minton, 2006, "How can biochemical reactions within cells differ from those in test tubes?", Journal of Cell Science 119:2863-2869.
Edge.org, Mar. 2016, at https://www.edge.org/conversation/george_church-the-augmented-human-being.
Decision on Motion Issued on Feb. 15, 2017 relating to Patent Interference No. 106,048 (DK).
Alberts et al., 1994, "Molecular Biology of the Cell, Third Edition," Garland Publishing, Inc., New York & London, pp. 228 and 335 (4 pages).
Baiker et al., 2004, "The immediate-early 63 protein of Varicella-Zoster virus: analysis of functional domains required for replication in vitro and for T-cell and skin tropism in the SCIDhu model in vivo," J Virol., 78(3):1181-1194.
Bitter et al., 1987, "Expression and secretion vectors for yeast," Methods Enzymol, 153:516-544.
Carroll, 2008, "Progress and prospects: zinc-finger nucleases as gene therapy agents," Gene Ther., 15(22):1463-1468.
Cerritelli et al., 2009, "Ribonuclease H: the enzymes in eukaryotes," FEBS J., 276(6):1494-1505.
Chalberg et al., 2005, "Integration specificity of phage phiC31 integrase in the human genome," J Mol Biol., 357(1):28-48.
Clark et al., 2011, "A TALE of two nucleases: gene targeting for the masses?" Zebrafish, 8(3):147-149.
Cyranoski, 2016, "Updated: NgAgo gene-editing controversy escalates in peer-reviewed papers," Nature, 540(7631):20-21.
Deng et al., 2012, "Structural basis for sequence-specific recognition of DNA by TAL effectors," Science, 335(6069):720-723.

Durai et al., 2005, "Zinc finger nucleases: custom-designed molecular scissors for genome engineering of plant and mammalian cells," Nucleic Acids Res., 33(18):5978-5990.
Feng et al., 2013, "Efficient genome editing in plants using a CRISPR/Cas system," Cell Res., 23(10):1229-1232.
Fujii et al., 2013, "Efficient generation of large-scale genome-modified mice using gRNA and CAS9 endonuclease," Nucleic Acids Res. Nov. 2013;41(20):e187.
Gao et al., 2016, "DNA-guided genome editing using the Natronobacterium gregoryi Argonaute," Nat Biotechnol., 34(7):768-773 and Online Methods, Epub version.
Jiang et al., 2013, "Demonstration of CRISPR/Cas9/sgRNA-mediated targeted gene modification in *Arabidopsis*, tobacco, sorghum and rice," Nucleic Acids Res., 41(20):e188.
Kim et al., 2015, "Discovery of a non-cationic cell penetrating peptide derived from membrane-interacting human proteins and its potential as a protein delivery carrier," Sci Rep., 5:11719 (15 pages).
Kuzuya et al., 2004, "Selective activation of two sites in RNA by acridine-bearing oligonucleotides for clipping of designated RNA fragments," J Am Chem Soc., 126(5):1430-1436.
Larson et al., 2011, "Real-time observation of transcription initiation and elongation on an endogenous yeast gene," Science, 332(6028):475-478.
Lee et al., 2003, "Inhibition of human immunodeficiency virus type 1 replication in primary macrophages by using Tat- or CCR5-specific small interfering RNAs expressed from a lentivirus vector," J Virol., 77(22):11964-11972.
Li et al., 2013, "Multiplex and homologous recombination-mediated genome editing in *Arabidopsis* and Nicotiana benthamiana using guide RNA and Cas9," Nat Biotechnol., 31(8):688-691 and Supplemental Material.
Maasho et al., 2004, "Efficient gene transfer into the human natural killer cell line, NKL, using the Amaxa nucleofection system," J Immunol Methods, 284(1-2):133-140.
Mahfouz et al., 2011, "De novo-engineered transcription activator-like effector (TALE) hybrid nuclease with novel DNA binding specificity creates double-strand breaks," Proc Natl Acad Sci USA, 108(6):2623-2628.
Mefferd et al., 2015, "Expression of CRISPR/Cas single guide RNAs using small tRNA promoters," RNA, 21(9):1683-1689.
Miao et al., 2013, "Targeted mutagenesis in rice using CRISPR-Cas system," Cell Res., 23(10):1233-1236.
Nakai et al., 1999, "PSORT: a program for detecting sorting signals in proteins and predicting their subcellular localization," Trends Biochem Sci., 24(1):34-35.
Nekrasov et al., 2013, "Targeted mutagenesis in the model plant *Nicotiana benthamiana* using Cas9 RNA-guided endonuclease," Nat Biotechnol., 31(8):691-693 and Supplemental Material.
Paddison et al., 2002, "Short hairpin RNAs (shRNAs) induce sequence-specific silencing in mammalian cells," Genes Dev., 16(8):948-958.
Ran et al., 2015, "In vivo genome editing using *Staphylococcus aureus* Cas9," Nature, 520(7546):186-191 and Supplemental Materials, Epub version.
Scherer, 2008, "A short guide to the human genome, Chapter 2—DNA and the Chromosomes," Cold Spring Harbor Laboratory Press (14 pages).
Shan et al., 2013, "Targeted genome modification of crop plants using a CRISPR-Cas system," Nat Biotechnol., 31(8):686-688 and Supplemental Material.
Strecker et al., 2019, "Engineering of CRISPR-Cas12b for human genome editing," Nat Commun., 10(1):212 (8 pages).
Wilusz et al., 2011, "tRNAs marked with CCACCA are targeted for degradation," Science, 334(6057):817-821.
Zetsche et al., 2015, "Cpf1 is a single RNA-guided endonuclease of a class 2 CRISPR-Cas system," Cell, 163(3):759-771.
Zolkiewaska, 2008, "ADAM proteases: ligand processing and modulation of the Notch pathway," Cell Mol Life Sci., 65(13):2056-2068.
Applicant-Initiated Interview Summary dated Dec. 30, 2015, in relation to U.S. Appl. No. 14/685,510 (4 pages).
Applicant-Initiated Interview Summary dated May 11, 2016, in relation to U.S. Appl. No. 14/685,510 (3 pages).

(56) References Cited

OTHER PUBLICATIONS

Applicant-Initiated Interview Summary dated Nov. 17, 2016, in relation to U.S. Appl. No. 14/685,510 (3 pages).
Applicant-Initiated Interview Summary dated Jul. 14, 2017, in relation to U.S. Appl. No. 14/685,510 (4 pages).
Advisory Action dated Aug. 21, 2017, in relation to U.S. Appl. No. 14/685,510 (3 pages).
Applicant-Initiated Interview Summary dated Sep. 22, 2017, in relation to U.S. Appl. No. 14/685,510 (4 pages).
Advisory Action dated Jun. 22, 2018, in relation to U.S. Appl. No. 14/685,510 (3 pages).
Examiner's Answer to Appeal Brief dated Nov. 9, 2018, in relation to U.S. Appl. No. 14/685,510 (29 pages).
Declaration of Technical Expert Paul Simons, executed Dec. 22, 2015, in relation to U.S. Appl. No. 14/704,551 (77 pages).
Declaration of Technical Expert Paul Simons in Support of Broad et al., executed May 23, 2016, in relation to Patent Interference No. 106,048 (DK) (91 pages).
Second Declaration of Technical Expert Paul Simons in Support of Broad et al., executed Jun. 22, 2016, in relation to Patent Interference No. 106,048 (DK) (20 pages).
Declaration of Technical Expert Ronald Breaker in Support of Broad et al., executed Aug. 15, 2016, in relation to Patent Interference No. 106,048 (DK) (34 pages).
Declaration of Dana Carroll in Support of Suggestion of Interference Pursuant to 37 C.F.R. § 41.202, executed Apr. 10, 2015, in relation to Patent Interference No. 106,048 (DK) (122 pages).
Supplemental Declaration of Dana Carroll in Support of Supplemental Suggestion of Interference Pursuant to 37 C.F.R. § 41.202, executed Nov. 4, 2015, in relation to Patent Interference No. 106,048 (DK) (32 pages).
Amended Statement of Grounds and Particulars in Support of Opposition dated Jul. 13, 2017 in marked-up and clean copies, in relation to Australian Patent Application No. 2013335451 (19 pages).
Australian Patent Office General Correspondence dated Aug. 10, 2017 related to Opponent's Amended Statement of Grounds and Particulars in Support of Opposition dated Jul. 13, 2017 and Applicant's letter dated Jul. 31, 2017, in relation to Australian Patent Application No. 2013335451 (3 pages).
Declaration of Marco Joseph Herold dated Nov. 17, 2017, in relation to Australian Patent Application No. 2013335451 (7 pages).
Opponent's Summary of Submission dated May 7, 2018, in relation to Australian Patent Application No. 2013335451 (58 pages).
Decision of Opposition dated Sep. 18, 2018 issued by Australian Patent Office, in relation to Australian Patent Application No. 2013335451 (36 pages).
Notice of Cross-Appeal filed by Respondents, Grant Fisher et al. on Nov. 6, 2018, in relation to Australian Patent Application No. 2013335451 (9 pages).
Third Party Observation filed Aug. 17, 2015, European Patent Application No. 13849670.8 (Publication No. EP 2912175 A1) (17 pages).
Third Party Observation filed May 11, 2018, European Patent Application No. 13849670.8 (Publication No. EP 2912175 A1) (3 pages).
Notice of Opposition filed by George W. Schlich on Aug. 22, 2018, in relation to European Patent Application No. 13849670.8 (Patent No. EP 2912175 B1) (8 pages).
Notice of Opposition filed by Martin Grund on Aug. 30, 2018, in relation to European Patent Application No. 13849670.8 (Patent No. EP 2912175 B1) (7 pages).
Notice of Opposition filed by CRISPR Therapeutics AG on Sep. 14, 2018, in relation to European Patent Application No. 13849670.8 (Patent No. EP 2912175 B1) (6 pages).
Third Party Observations dated Jan. 17, 2019, European Patent Application No. 18158147.1 (Publication No. EP 3372679 A1) (302 pages).
Notice of Allowance dated Feb. 20, 2014 in connection with U.S. Appl. No. 14/054,414 (12 pages).

Bhaya et al., 2011, "CRISPR-Cas systems in bacteria and archaea: versatile small RNAs for adaptive defense and regulation", Annu. Rev. Genet., vol. 45: 273-297.
Boch et al., 2009, "Breaking the code of DNA binding specificity of TAL-type III effectors", Science, 326: 1509-1512.
Brunet et al, 2009, "Chromosomal translocations induced at specified loci in human stem cells", PNAS, 106: 10620-10625.
Campeau et al., "A versatile viral system of expression and depletion of proteins in mammalian cells", PloS One, 2009, 4: e6529.
Carlson et al., 2012, "Targeting DNA with fingers and TALENs", Molecular Therapy-Nucleic Acids, 1, e3: 1-4.
Carney and Morgan, "Induction of DNA double-strand breaks by electroporation of restriction enzymes into mammalian cells", Methods in Mol. Biol., 1999, 113: 465-471.
Carroll, 2006, "Design, construction and in vitro testing of zinc finger nucleases", Nat Protoc, 1(3): 1329-1341.
Chapdelaine et al., 2010, "Meganucleases can restore the reading frame of a mutated dystrophin", Gene Therapy, 17:846-858.
Cho et al., 2013, "Heritable gene knockout in Caenorhabditis elegans by direct injection of Cas9-sgRNA ribonucleoproteins", Genetics, 195: 1177-1180.
Close et al., 2012, "The evolution of the bacterial luciferase gene cassette (lux) as a real-time bioreporter", Sensors, 12: 732-752.
ATCC record ATCC 700294, 2019, "*Streptococcus pyogenes* Rosenbach (ATTC 700294)", retrieved from the internet on Apr. 18, 2019 at <http://wwwlgcstandards-atcc.org/products/all/700294.aspx/geo_country=gb#history> (2 pages).
NCBI record for NC-002737.2, 2019, "*Streptococcus pyogenes* M1 GAS, complete sequence", retrieved from the internet at <https://www.ncbi.nlm.nih.gov/nuccore/NC_002737.2> (1 page).
Dai et al., 2002, "The transcription factors GATA4 and dHAND physically interact to synergistically activate cardiac gene expression through a p300-dependent mechanism", J. Biol. Chem., 277: 24390-24398.
Patent Trial and Appeal Board, USPTO, Ex parte Kim et al., Decision on Appeal No. 2019-001990 issued Jun. 22, 2020 in U.S. Appl. No. 14/685,510 (23 pages).
Declaration of Bryan Cullen, Ph.D. dated Feb. 8, 2018 as filed in U.S. Appl. No. 14/685,568 (250 pages).
Declaration of Dr. Boch dated Jan. 7, 2016 as filed in European Pat. No. 2784162 (17 pages).
Second Declaration of Dr. Boch dated Apr. 26, 2019 as filed in Opposition to European Pat. No. 2825654 (20 pages).
Declaration of Dr. Bao dated Nov. 14, 2017 as filed in Opposition to European Pat. No. 2771468 (32 pages).
Declaration of Dr. Marco Josef Herold, executed May 20, 2019 in the matter of Opposition to the European Pat. App. No. 2912175 (31 pages).
CV of Dr. Marco Josef Herold in the matter of Opposition to the European Pat. App. No. 2912175, 2019 (11 pages).
Declaration of Technical Expert Paul Simons, executed Aug. 15, 2016, in relation to U.S. Appl. No. 13/842,859 (116 pages).
Declaration of Prof. Cohn Stirling (plus CV) dated May 22, 2019 as filed in Opposition to European Pat. No. 2912175 (11 pages).
Declaration of Dr. Paula Cannon dated Apr. 24, 2019 as filed in relation to U.S. Appl. No. 15/188,924 (55 pages).
Declaration of Dr. Alan M. Lambowitz dated Oct. 5, 2017 as filed in relation to U.S. Appl. No. 15/188,924 (15 pages).
Declaration of Gregory Hannon, Ph.D. (plus CV) dated Nov. 15, 2017 as filed in relation to U.S. Appl. No. 90/013,694 (38 pages).
Declaration of Prof. Matthias W. Hentze dated Feb. 1, 2018 as filed in Opposition to European Pat. No. 2800811 (35 pages).
Derossi et al., 1996, "Cell internalization of the third helix of the Antennapedia homeodomain is receptor-independentD", The Journal of Biological Biochemistry, 271: 18188-18193.
Ding et al., 2013, "Enhanced efficiency of human pluripotent stem cell genome editing through replacing TALENs with CRISPRs", Cell Stem Cell, 12: 393-394.
Dingwall et al., 1988, "The nucleoplasmin nuclear location sequence is larger and more complex than that of SV-40 large T antigen", J. Cell. Biol., 107: 841-849.

(56) References Cited

OTHER PUBLICATIONS

Do et al., 2006, "Identification of multiple nuclear localization signals in murine Elf3, an ETS transcription factor", FEBS Letters, 580(7): 1865-1871; ePub:Feb. 28, 2006.
Ebina et al., 2013, "Harnessing the CRISPR/Cas9 system to disrupt latent HIV-1 provirus", Scientific Reports, 2013, vol. 3, Article No. 2510 (7 pages).
Efthyimiadis et al., 1998, "The HIV-1 Tat nuclear localization sequence confers novel nuclear import properties", JBC 273: 1623-1628.
Fischer-Fantuzzi et al., 1988, "Cell-dependent efficiency of reiterated nuclear signals in a mutant simian virus 40 oncoprotein targeted to the nucleus", Mol Cell Biol., 8(12): 5495-5503.
Freitas et al., 2009, "Mechanisms and signals for nuclear import of proteins", Current Genomics, vol. 10: 550-557.
Gratz et al., 2013, "Genome engineering of Drosophilia with the CRISPR RNA-guided Cas9 nuclease", Genetics, vol. 194: 1029-1035 and supplementary materials.
Ferretti et al., 2001, "Complete genome sequence of an MI strain of Streptococcus pyogenes", Proc. Natl. Acad. Sci. USA, vol. 98: 4658-4663.
Foecking and Hofstetter, 1986, "Powerful and versatile enhancer-promoter unit for mammalian expression vectors", Gene, 45(1): 101-105.
Fonfara et al., 2013, "Phylogeny of Cas9 determines functional exchangeability of dual-RNA and Cas9 among orthologous type II CRISPR-Cas systems", Nucl. Acid Research, vol. 42: 2577-2590.
Fu et al. 2014, "Improving CRISPR-Cas nuclease specificity using truncated guide RNAs", Nature Biotechnology, 32: 279-284, including online methods.
Golic, 2013, "RNA-Guided Nucleases: A New Era for Engineering the Genomes of Model and Nonmodel Organisms", Genetics, 195: 303-308.
Gopalan et al, 2002, "RNase P: variations and uses", The J of Biological Chemistry, 277(9): 6759-6762.
Groth et al., 2000, "A phage integrase directs efficient site-specific integration in human cells", PNAS, 97(11): 5995-6000.
Gunawardane et al., 2007, "A slicer-mediated mechanism for repeat-associated siRNA 5' end formation in Drosophila", Science, 315(5818): 1587-1590.
Handel et al., 2012, "Versatile and Efficient Genome Editing in Human Associated Viral Vectors", Human Gene Ther., 23: 321-329.
Horvath and Barrangou, 2010, "CRISPR/Cas, the immune system of bacteria and archaea", Science, vol. 327: 167-170.
Hu et al., 2018, "Comparison of various nuclear localization signal-fused Cas9 proteins and Cas9 mRNA for genome editing in zebrafish", G3, 8(3): 823-831.
Joung and Sander, 2013, "TALENs: a widely applicable technology for targeted genome editing", J Nat. Rev. Mol. Cell Biol., 14: 49-55.
Kalderon et al., 1984, "A short amino acid sequence able to specify nuclear location", Cell, 39: 499-509.
Kim and Rossi, 2008, "RNAi mechanisms and applications", Biotechniques, 44: 613-616.
Kim et al., 2014, "Highly efficient RNA-guided genome editing in human cells via delivery of purified Cas9 ribonucleoproteins", Genome Research, 24: 1012-1019.
Kouranova et al., 2016, "CRISPRs for optimal targeting: delivery of CRISPR components as DNA, RNA, and protein into cultured cells and single-cell embryos", Hum. Gene. Ther., 27(6): 464-475.
Kunin et al., 2007, "Evolutionary conversation of sequence and secondary structures in CRISPR repeats", Genome Biology, 8(4), Article R61.
Kuspa and Loomis, 1992, "Tagging developmental genes in Dictyostelium by restriction enzyme-mediated integration of plasmid DNA", PNAS, 89: 8803-8807.
Lacasse & Lefebvre, 1995, "Nuclear localization signals overlap DNA-or RNA binding domains in nucleic acid proteins", Nucl. Acid Res., vol. 23: 1647-1656.

Lange et al., 2007, "Classical Nuclear Localization Signals: Definition, Function, and Interaction with Importin alpha" J Biol Chem, 282:5101-5105.
Lee et al., 2014, "RNA-guided genome editing in Drosophila with the purified Cas9 protein", G3 (Bethesda), 4: 1291-1295.
Leenay et al., 2016, "Identifying and Visualizing Functional PAM Diversity across CRISPR-Cas Systems", Mol. Cell, 62: 137-147.
Li et al., 2010, "TAL nucleases (TALN5): hybrid proteins composed of TAL effectors and FokI DNA-cleavage domain", Nucleic Acid Res., 39: 359-372.
Lieber et al., 1989, "High level gene expression in mammalian cells by a nuclear T7-phage RNA polymerase", Nucleic Acids Research, 17(21): 8445-8493.
Liu, 2010, "Generation of a triple-gene knockout mammalian cell line using engineered zinc-finger nucleases", Biotechnol. Bioeng., 106: 97-105.
Lodish et al., 1995, Molecular Cell Biology, 3rd Ed., p. 842-844.
Ma et al., 2012, "Highly efficient and specific genome editing in silkworm using custom TALENs.", PLoS One 7, e45035.
Magnani et al., 2011, "Pioneer factors: directing transcriptional regulators within the chromatin environment", Trends in Genetics, 27(11): 465-474.
Marakova et al., 2011, "Evolution and classification of the CRISP-Cas systems", Nature Reviews Microbiology, vol. 9: 467-477.
Marfori et al., 2011, "Molecular basis for specificity of nuclear import and prediction of nuclear localization", Biochem. Biophys. Acta, 1813: 1562-1577.
Medina et al., 1999, "RNA-polymerase III-driven expression cassettes in human gene therapy", Current Opinion in Mol Therapeutics, 1(5): 580-594.
Mei et al, 2016, "Recent progress in CRISPR/Cas9 technology", J Genetics and Genomics, vol. 43: 63-75.
Miller et al., 1985, "Repetitive zinc-binding domains in the protein transcription factor IIIA from Xenopus oocytes", EMBO Journal, 4(6): 1609-1614.
Miyagishi, 2002, "U6 promoter-driven siRNAs with four uridine 3' overhangs efficiently suppress targeted gene expression in mammalian cells", Nature Biotechnology, 19: 497-500.
Mojica, 2016, "On the Origin of CRISPR-Cas Technology: From Prokaryotes to Mammals", Trends in Microbiol, 24(1): 811-820.
Morgan et al., 1988, "Inducible expression and cytogenetic effects of the EcoRI restriction endonuclease in Chinese hamster ovary cells", Molecular and Cellular Biology, 8: 4204-4211.
Moscou, 2009, "A simple cipher governs DNA recognition by TAL effectors", Science, 326: 1501.
Nannan Chang et al., 2013, "Genome editing with RNA-guided Cas9 nuclease in zebrafish embryos", Cell Research—Xibao Yanjui, 23(4): 465-472.
Nishimasu et al., 2014, "Crystal Structure of Cas9 in complex with guide RNA and target DNA", Cell, vol. 156: 935-949.
Noguchi et al., 2003, "PDX-1 protein containing its own antennapedia-like protein transduction domain can transduce pancreatic duct and islet cells", Diabetes, 52: 1732-37.
O'Gorman et al., 1991, "Recombinase-mediated gene activation and site-specific integration in mammalian cells", Science, 251: 1351-1355.
O'Hare et al., 1981, "Transformation of mouse fibroblasts to methotrexate resistance by a recombinant plasmid expressing a prokaryotic dihydrofolate reductase", PNAS, 78(3): 1527-1531.
Oakes et al., 2016, "Profiling of engineering hotspots identifies an allosteric CRISPR-Cas9 switch", Nature Biotech., doi:10.1038/nbt. 3528 (advanced online publication).
Pablo Perez-Pinera, 2012, "Advances in Targeted Genome Editing", Current Opinion in Chemical Biology, 16(3-4): 268-277.
Park et al., 2002, "Regulation of Ribosomal S6 Kinase 2 by Mammalian Target of Rapamycin", J. Biol Chem, 277: 31423-31429.
Planey et al., 2002, "Inhibition of glucocorticoid-induced apoptosis in 697 pre-B lymphocytes by the mineralocorticoid receptor N-terminal domain", J. Biol. Chem., 277: 42188-42196.
[PMC Author Manuscript of] Anders et al., 2014, "Structural basis of PAM-dependent target DNA recognition by the Cas9 endonuclease", Nature, Sep. 25, 513(7519): 569-573.

(56) References Cited

OTHER PUBLICATIONS

[PMC Author Manuscript of] Wang et al., 2013, "One-step generation of mice carrying mutations in multiple genes by CRISPR/Cas-mediated genome engineering", Cell, 153, May 9, 2013: 910-918.
Ramirez et al, 2012, "Engineered zinc finger nickases induce homology-directed repair with reduced mutagenic effects", Nucleic Acid Res., 40: 5560-5568.
Reiss et al., 1996, "RecA protein stimulates homologous recombination in plants", PNAS., 93: 3094-3098.
Roberts et al., 1987, "The effect of protein context on nuclear location signal function", Cell, 50: 465-475.
Ruben et al., 1989, "Structural and functional characterization of human immunodeficiency virus tat protein", J. Virol., 63(1): 1-8.
Sauer, 1987, "Functional expression of the cre-lox site-specific recombination system in the yeast *Saccharomyces cerevisiae*", Mol. Cell. Biol., 7(6): 2087-2096.
Schiestl, 1991, "Integration of DNA fragments by illegitimate recombination in *Saccharomyces cerevisiae*", PNAS, 88: 7585-7589.
Sheng et al., 2004, Nuclear and nucleolar localization of 18-kDa fibroblast growth factor-2 is controlled by c-terminal signals, J. Biol. Chem., 279(38): 40153-40160.
Shieh et al., 1993, "Nuclear targeting of the maize R protein requires two nuclear localization sequences", Plant Physiol.,101(2): 353-361.
Szczepankowska, 2012, "Role of CRISPR/cas system in the development of bacteriophage resistance", Advances in virus research, vol. 82: 289-338.
Tinland et al., 1992, "The T-DNA-linked VirD2 protein contains two distinct functional nuclear localization signals", PNAS, 89: 7442-7446.
Han-Na, Sep. 11, 2018, "ToolGen faces controversy over CRISP patent", The Investor, retrieved from the internet at <http://www.theinvestor.co.kr/view.php?ud=20180911000583> (2 pages).
Truant and Cullen, 1999, "The arginine-rich domains present in human immunodeficiency virus type 1 tat and rev function as direct importin beta-dependent nuclear localization signals", Mol. Cellular Biol.,19(2): 1210-1217.

Sanders, R., 2013, University of California press release "Cheap and easy technique to snip DNA could revolutionize gene therapy", retrieved from the internet on Jun. 21, 2017 at <http://news.berkeley.edu/2013/01/07/cheap-and-easy-technique-to-snip-dna-could-revolutionize-gene-therapy/> (3 pages).
Van Den Ackerveken, 1996, "Recognition of the bacterial avirulence protein AvrBs3 occurs inside the host plant cell", Cell,8: 1307-1316.
Villion & Moineau, 2013, "The double-edged sword of CRISPR-Cas9 systems", Cell Research, vol. 23: 15-17.
Waterhouse, 2003, "Exploring plant genomes by RNA-induced gene silencing", Nature Reviews, 4: 29-38.
Wieland et al., 2012, "Engineering of ribozyme-based riboswitches for mammalian cells", Methods, 56: 351-357.
Wolff, 2001, "Nuclear security breached", Nature Biotechnology, 19: 1118-1120.
Written Opinion accompanying the European Search Report dated Nov. 9, 2015 in EP Pat. App. No. 2912175 (5 pages).
Xu et al., 2013, "The next generation biotechnology for Apple improvement and beyond: The CRISPR/Cas9 Story", New York Fruit Quarterly, 21: 19-22.
Yang, 2012, "HIV-1 TAT-mediated protein transduction and subcellular localization using novel expression vectors", FEBS Letters, 532: 36-44.
Yarris, 2012, "Programmable DNA scissors found for bacterial immune system", downloaded from <http://newscenter.lbl.gov/2012/06/28/programmabledna.scissors/> (4 pages).
Zhang Declaration dated Jan. 30, 2014 as filed in U.S. Appl. No. 14/054,414 (20 pages).
Bassetf, A.R. and Liu, J.L., "CRISPR/Cas9 and Genome Editing in *Drosophila*," Journal of Genetics and Genomics, vol. 41, pp. 7-19 including supplementary materials, 2014.†
Baker, M., "Gene editing at CRISPR speed," Nature Biotechnology, vol. 32(4), pp. 309-312, 2014.†
Raymond, C.S. and Soriano, P., "High-Efficiency FLP and PhiC31 Site-Specific Recombination in Mammalian Cells," PLoS One, vol. 2(1), e162, 2007.†

\* cited by examiner
† cited by third party

FIG. 1B
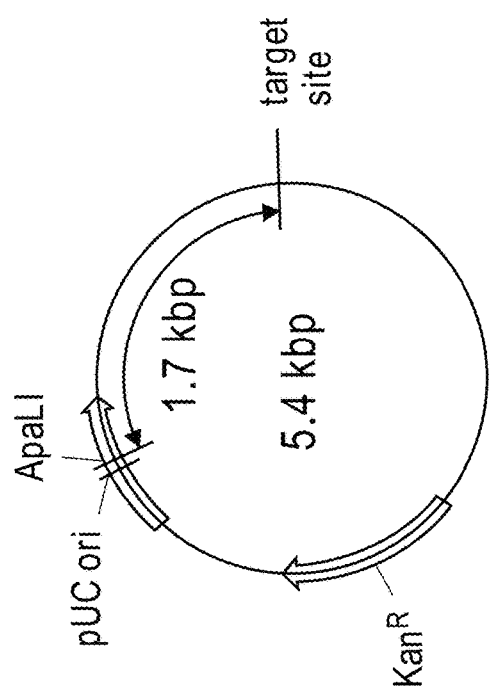
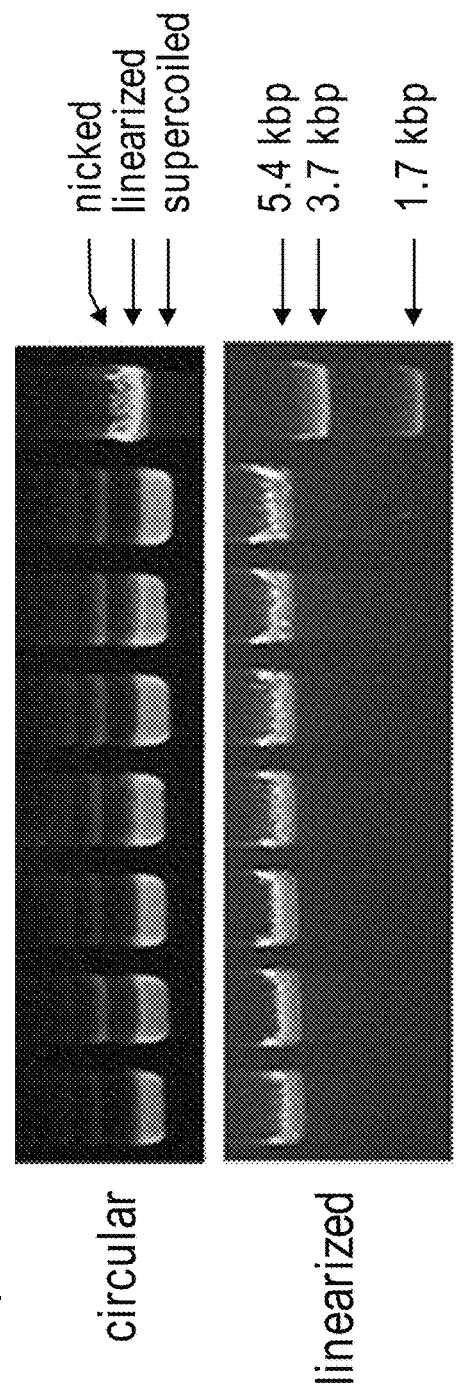

```
                        ▼
┌─────────────────────────┐
│TGACATCAATTATTATACAT│CGG   CCR5
└─────────────────────────┘
TGACATCAATTATTATAgATGa    ADCY5
TGACATCAcTTATTATgCATgGG   KCNJ6
TGACATaAATTATTcTACATgGG   CNTNAP2
TGAaATCAATTATcATAgATCGG   Chr. 5 N/A
```
FIG. 4A
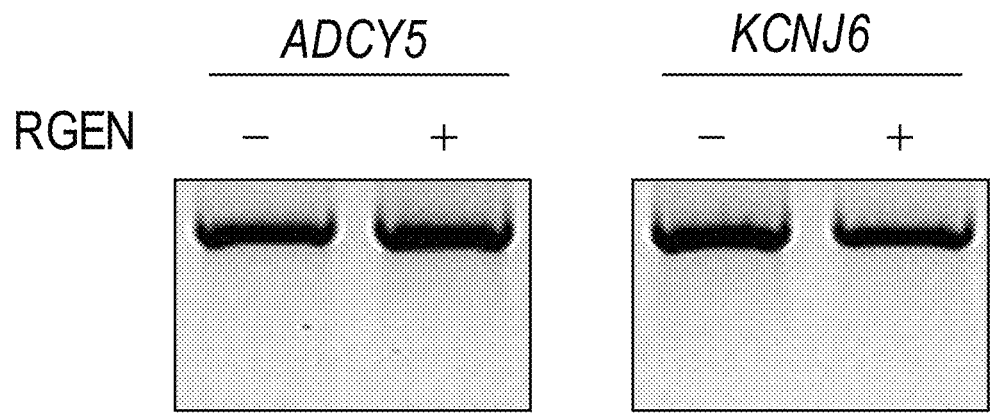
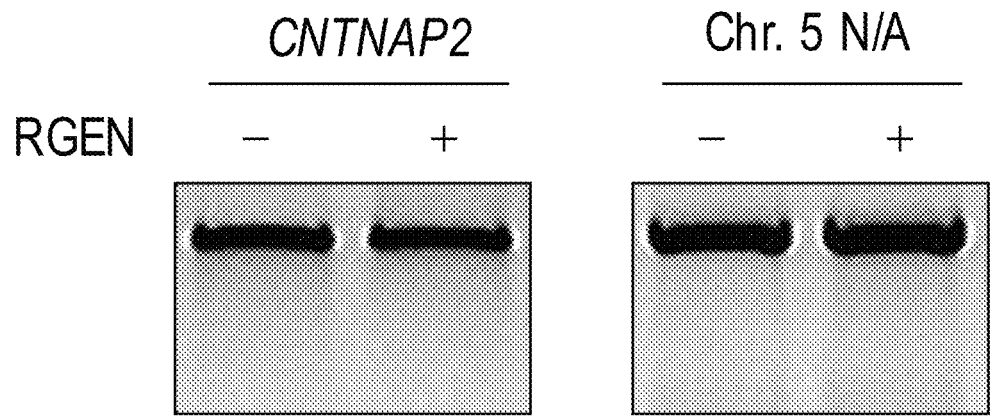
FIG. 4B

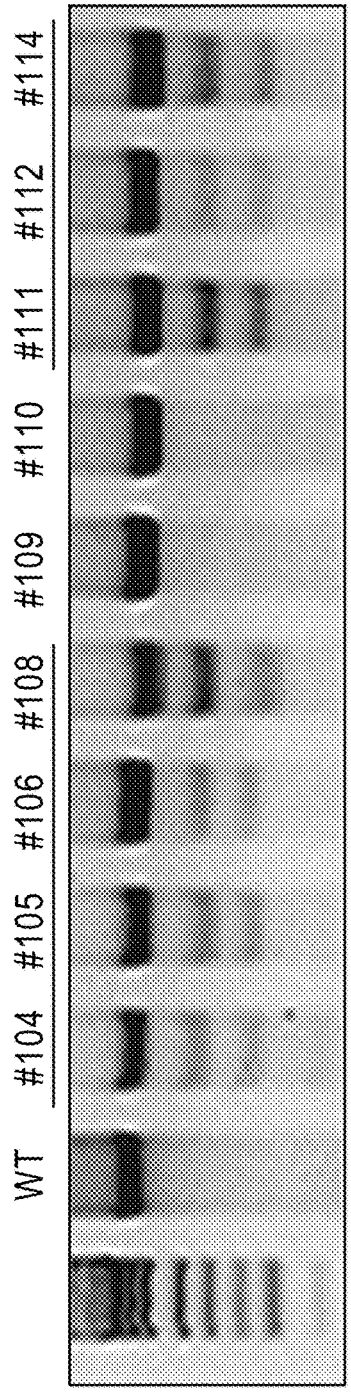

FIG. 5B

```
WT    ACTTCCAGGCTCCACCCGACT  ▸ GGAGGGGCGAACCCCAAGGGGGACCTCATGCAGG
#108
      ACTTCCAGGCTCC------------44bp-------------------------          -44  (X6)
      ACTTCCAGGCTCCACCCGAC------------------CTCATGCAGG                -23  (X2)
      ACTTCCAGGCTCCACCC------------CAAGGGGGACCTCATGCAGG               -17  (X1)
      ACTTCCAGGCTCCACCCGACT[T]▸GGAGGGGCGAACCCCAAGGGGGACCTCATGCAGG     [+1]  (X1)
#111
      ACTTCCAGGCTCCACCCGACT[T]▸GGAGGGGCGAACCCCAAGGGGGACCTCATGCAGG     [+1]  (X2)
      ACTTCCAGGCTCCACCCG----- ▸ --AACCCCAAGGGGGACCTCATGCAGG            -11  (X6)
#114
      ACTTCCAGGCTCCACCCGACT ▸ [CACTATCTTTCTGGGCTCCTCCATGTC]-----       [+25] (X3)
      ACTTCCAGGCTCCACCC-------------CAAGGGGACCTCATGCAGG                -17  (X6)
      ACTTCCAGGCTCCACCCGAC----------GAACCCCAAGGGGACCTCATGCAGG          -8   (X1)
```

FIG. 5C

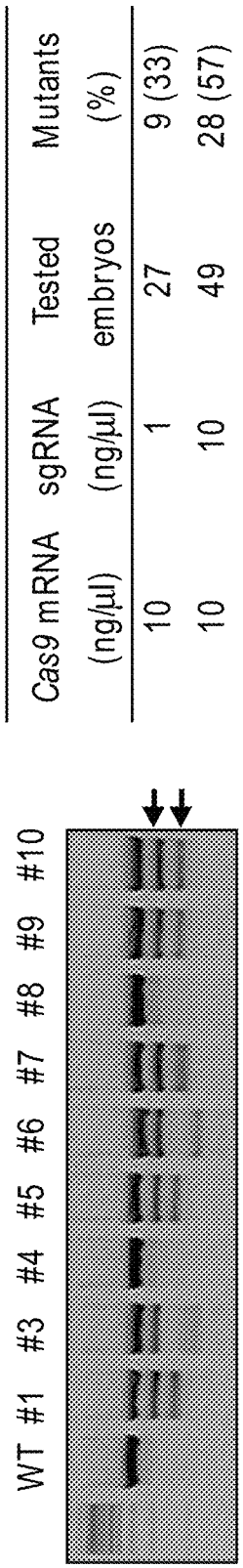
FIG. 6A
FIG. 6B
FIG. 6C

| Sequence | Indels | Embryo no. |
|---|---|---|
| ACTTCCAGGCTCCACCCGACTGGA\|GGGCGAACCCCAAGGGGACCCTCATGCAG | WT | 2 |
| ACTTCCAGGCTCCACCCGACTGGA------------------AAGGGGACCCTCATGCAG | Δ18 | 1 |
| ACTTCCAGGCTCCAC--------------------AAGGGGACCCTCATGCAG | Δ20 | 1 |
| ACTTCCAGGCTCCACCC-------------------AAGGGGACCCTCATGCCC | Δ19 | 1 |
| ACTTCCAGGCTCCACCC-----------------CAAGGGGACCCTCATGCAG | Δ17 | 3 |
| ACTTCCAGGCTCCACCCGA-----------ACCCCAAGGGGACCCTCATGCAG | Δ11 | 1 |
| ACTTCCAGGCTCCACCCGAA--GGAGGGCGAACCCCAAGGGGACCCTCATGCA | Δ3+1 | 1 |
| ACTTCCAGGCTCCACCCGACT--AGGGCGAACCCCAAGGGGACCCTCATGCAG | Δ2 | 1 |
| ACTTCCAGGCTCCACCCGACTGGGAGGGCGAACCCCAAGGGGACCCTCATGCA | +1 | 1 |
| ACTTCCAGGCTCCACCCGACTTGGAGGGCGAACCCCAAGGGGACCCTCATGCA | +1 | 10 |
| ACTTCCAGGCTCCACCCGA------GGCGAACCCCAAGGGGACCCTCATGCAG | Δ6 | 1 |
| ACTTCCAGGCTCCACCCGA-----GGGCGAACCCCAAGGGGACCCTCATGCAG | Δ5 | 2 |
| ACTTCCAGGCTCCACC----------------------------TCATGCAG | Δ28 | 1 |
| --------------------------------------AGGGCGAACCCCAAGGGGACCCTCATGCAG | Δ126 | 1 |
| Total | | 26 |

FIG. 7C

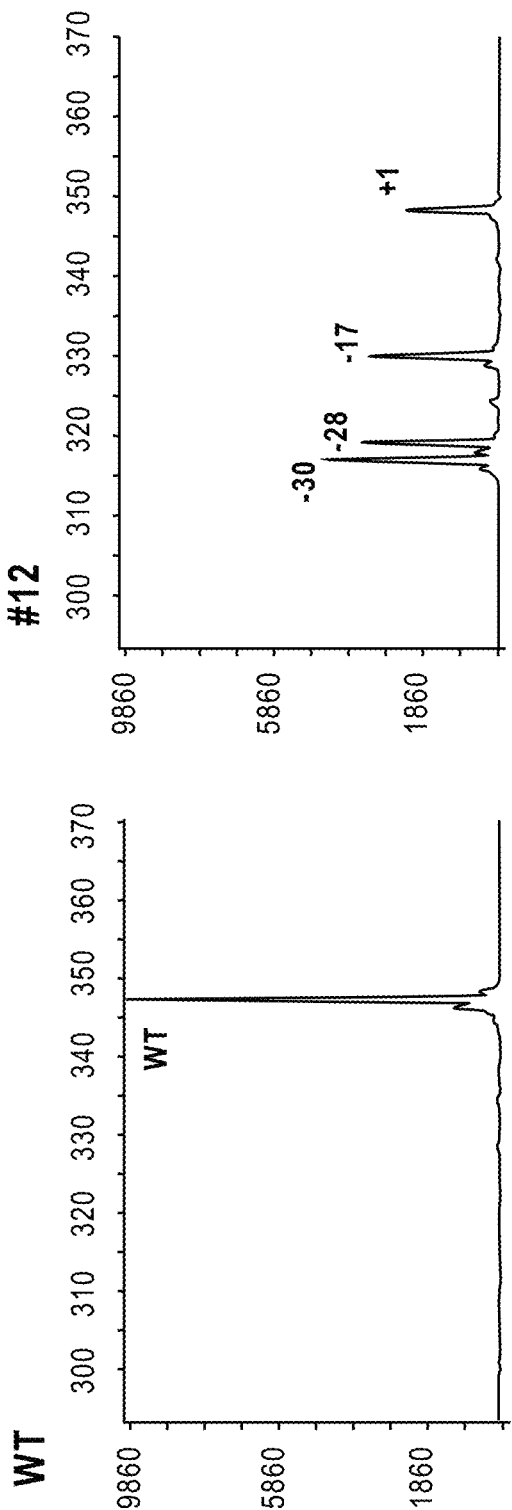
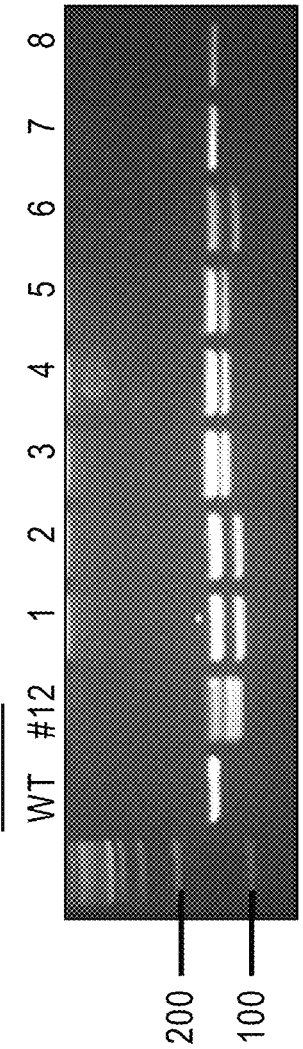
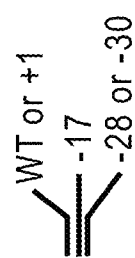
FIG. 8A
FIG. 8B
FIG. 8C

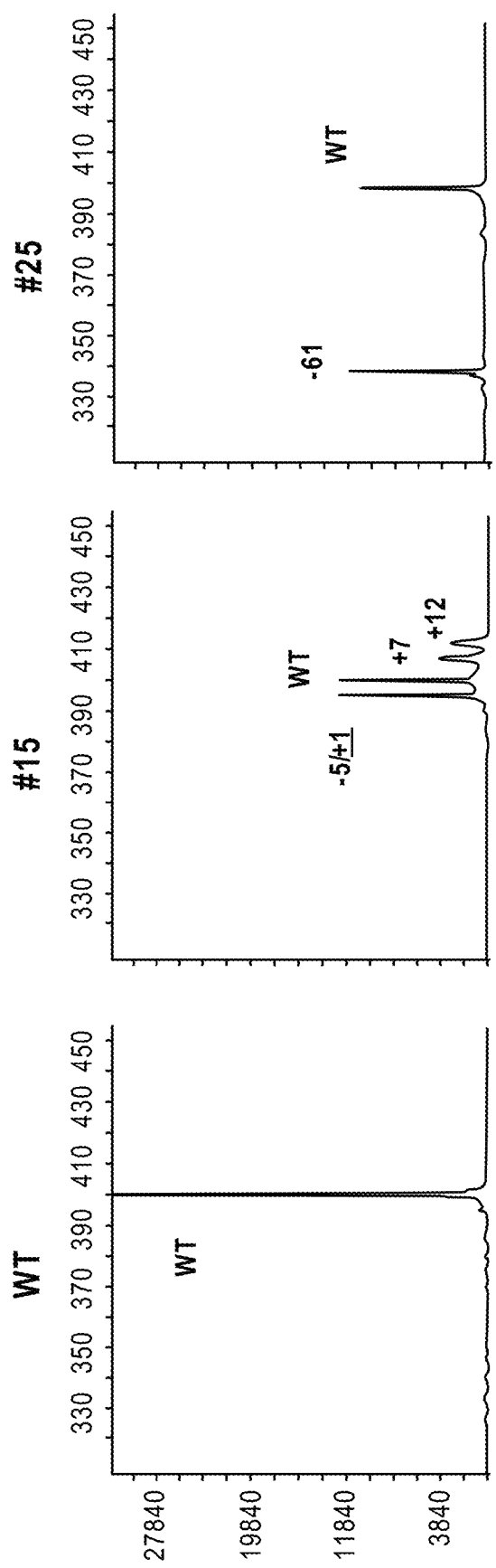
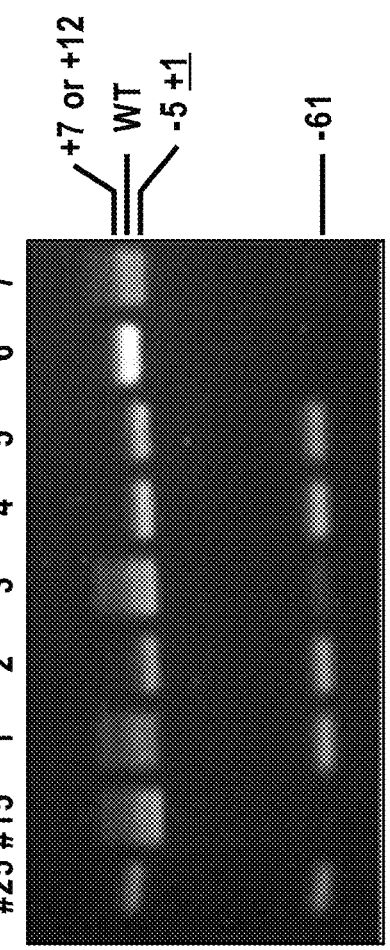
FIG. 9A
FIG. 9B

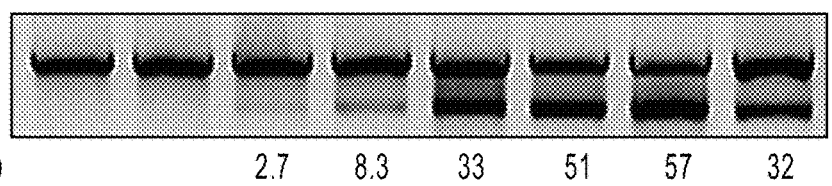
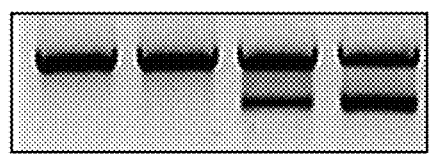
FIG. 10B

CCR5

```
CAATCTATGACATCAATTATTATA-CATCGGAGCCCTGCCAAAAATCAA    WT
CAATCTATGACATCAATTATTAT-----CGGAGCCCTGCCAAAAATCAA    -4
CAATCTATGACATCAATTAT-----CATCGGAGCCCTGCCAAAAATCAA    -4
CAATCTATGACATCAATTAT--------CGGAGCCCTGCCAAAAATCAA    -7
CAATCTATGACATCAATTATTAT--CATCGGAGCCCTGCCAAAAATCAA    -1
CAATCTATGACATCAATTATTATAACATCGGAGCCCTGCCAAAAATCAA    +1
CAATCTATGACAA------------------GAGCCCTGCCAAAAATCAA   -17,+1
```

FIG. 10C

ABCC11

| | | |
|---|---|---|
| Cas9 protein | - | 15(4.5) μg (μM) |
| sgRNA | - | 20(29) μg (μM) |

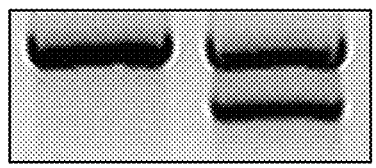

| Indel (%) | | 35 |

FIG. 10D

ABCC11

```
TTCTCAAGGCAGCATCATACTTCCCCCACGGTGGGACAGCTGCCCTCCCTGG    WT
TTCTCAAGGCAGCATCATACTTCC------CTGGGACAGCTGCCCTCCCTGG    -6
TTCTCAAGGCAGCATCATACTTC---CACGGTGGGACAGCTGCCCTCCCTGG    -3
TTCTCAAGGCAGC-------------------------TGCCCTCCCTGG    -29
TTCTCAAGGCAGCATCATACTT---------------------CCCTCCCTGG    -20
TTCTCAAGGCAGCATCATACTT---------------------CCCTCCCTGG    -20
TTCTC-----------------------------------------------  -256
```

FIG. 10E

Target sequence 1

```
ACAAAGCGATTTTGAAAGATGGAAGCGGG TGG TAT//..........190 bp..........//GGGGTGAAACTAAACTGGTCCACA GG GGGAAGATTG (wt)
ACAAAGCGATTTTGAAAGATGGAAGCGGG TGG TAT//..........190 bp..........//GGGGTGAAACTAAA------- ACA GG GGAAGATTG (-7)
ACAAAGCGATTTTGAAAGATGGAAGCG--------------------------------------ACA GG GGAAGATTG (-224)
ACAAAGCGATTTTGAAAGATGGAAGCG-------------------------------------CACA GG GGAAGATTG (-223)
ACAAAGCGATTTTGAAAGATGGAAGCGAAATAGCAAGTTAAAAATAAGGCTAGTCCGTTATCAACTTGAAAAGTGGCACCGAGTCGGTGCACA GG GGAAGATTG (-223+62)
```

Target sequence 2

FIG. 12

Human *BRCA2* locus
FIG. 18C
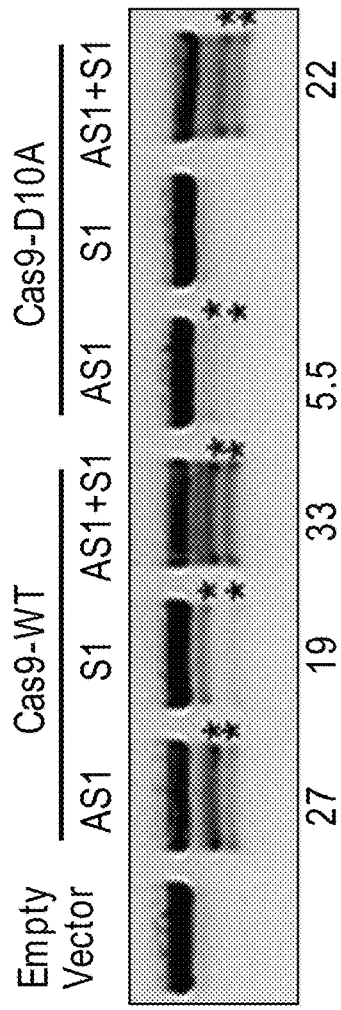
FIG. 18D

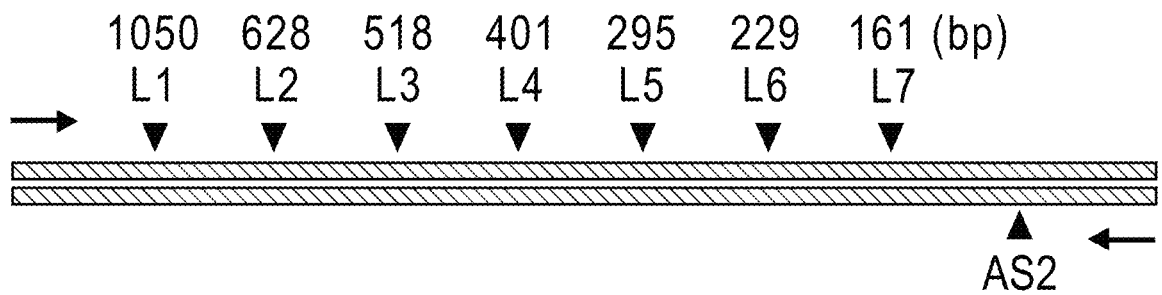
FIG. 20A
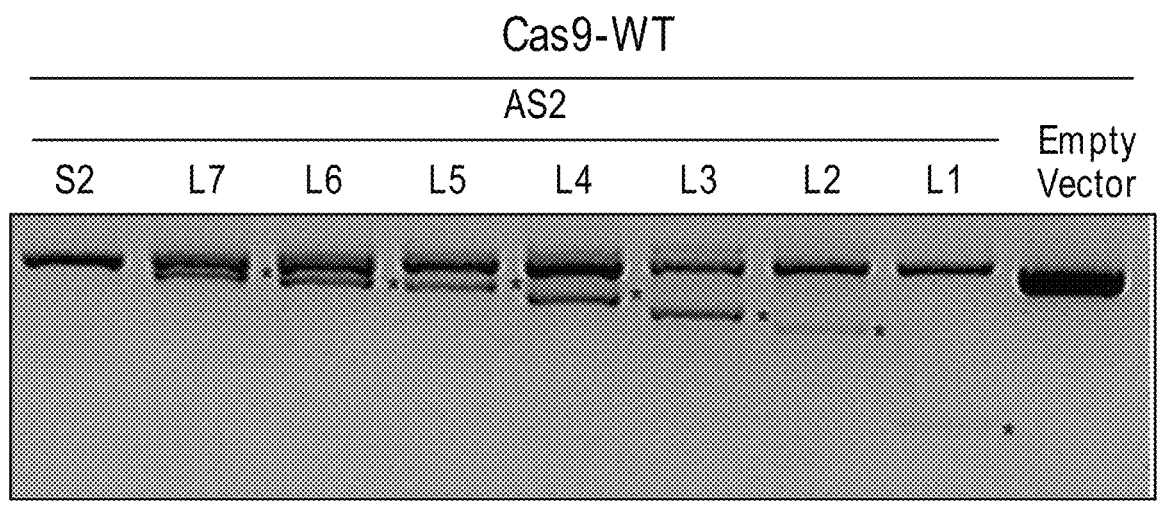
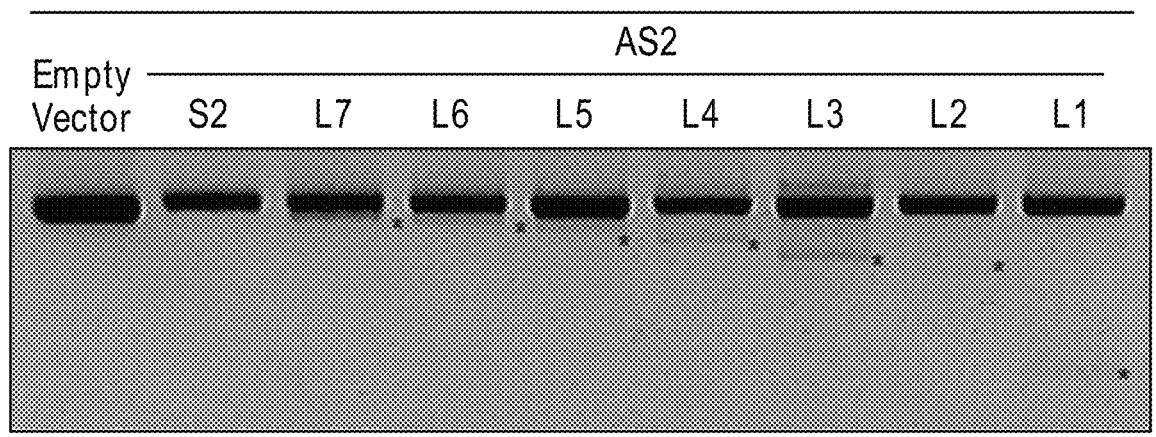
FIG. 20B

Cas9-WT AS2 + L1 (~1050bp deletion)

```
ggccgggaatcaagagtca[CCC]AGAGACAGTGACCAACCATCcctgttt...//...agtcCTCCCTCCCAGGATCCTCT[TGG]ctccatcgtaagcaaaccttagaggttctggcaaggagagagatg WT
ggccgggaatcaagagtca[CCC]AG----TGACCAACCATCcct--------------------------------------------gtaagcaaaccttagaggttctggcaaggagagagatg
ggccgggaatcaagagtca[CCC]AG--------------------------------------------------------------------------------------------------gaa
ggccgggaatcaagagtca[CCC]AGA------------------------------------------CCTCT[TGG]ctccatcgtaagcaaaccttagaggttctggcaaggagagagatg
ggccgggaatcaagagtca[CCC]-----------------------------------------------------------------------------------------------taacag
ggccgggaatcaaga----------------------------------------------------cg[TGG]tccatcgtaagcaaaccttagaggttctggcaaggagagagatg
ggc---------------------------------------------------------------------tcatcgtaagcaaaccttagaggttctggcaaggagagagatg
ggccgggaatcaagagtca[CCC]AGA---------------------------------------CTCT[TGG]ctccatcgtaagcaaaccttagaggttctggcaaggagagagatg
```

Cas9-D10A AS2 + L1 (~1050bp deletion)

```
ggccgggaatcaagagtca[CCC]AGAGACAGTGACCAACCATCcctgttt...//...agtcCTCCCTCCCAGGATCCTCT[TGG]ctccatcgtaagcaaaccttagaggttctggcaaggagagagatg WT
ggccgggaatcaagagtca[CCC]AGAGACAGTGACCAACCATC-------------------------------------------gtaagcaaaccttagaggttctggcaaggagagagatg
gg-------------------------------------------------------------------tctccatcgtaagcaaaccttagaggttctggcaaggagagagatg
ggccgggaatcaagagtca[CCC]A-------------------------------------CT[TGG]ctccatcgtaagcaaaccttagaggttctggcaaggagagagatg
ggccgggaatcaagagtca[CCC]AGA------------------------------------------tccatcgtaagcaaaccttagaggttctggcaaggagagagatg
gg---------------------------------------------------------------tccatcgtaagcaaaccttagaggttctggcaaggagagagatg
ggccgggaatcaagagtca[CCC]AGAGACAGTGACCAACCATCcc--------------------------------------------atatca
ggccgggaatcagagtca--------------------------------------------------tcgtaagcaaaccttagaggttctggcaaggagagagatg x2
```

FIG. 20C

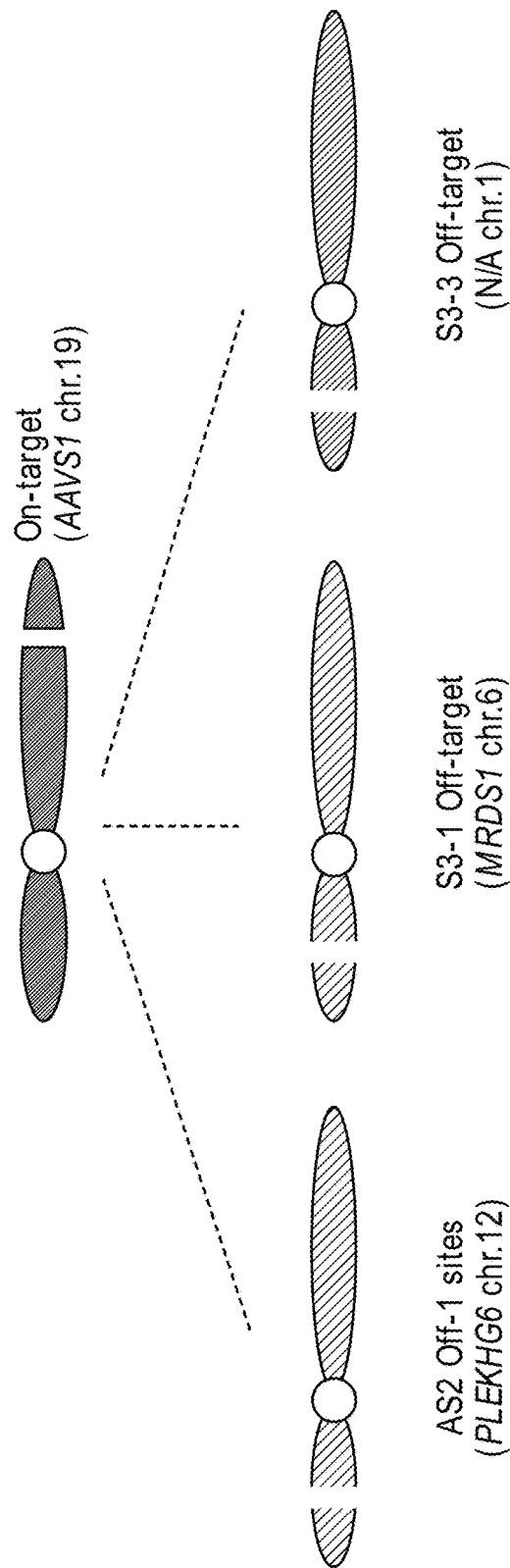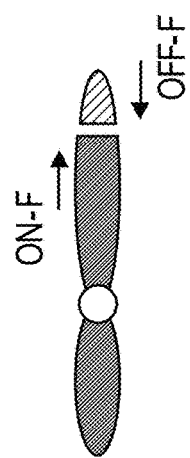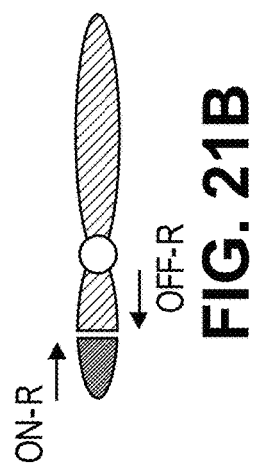
FIG. 21A
FIG. 21B

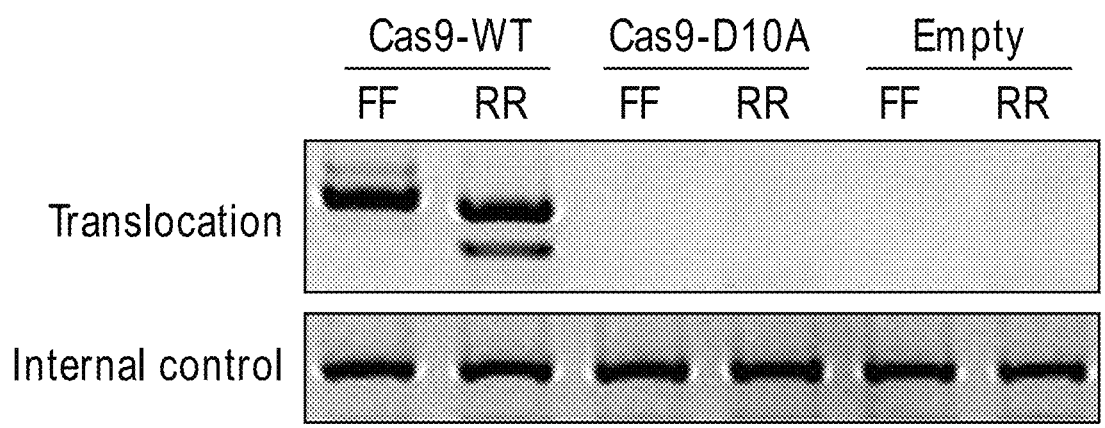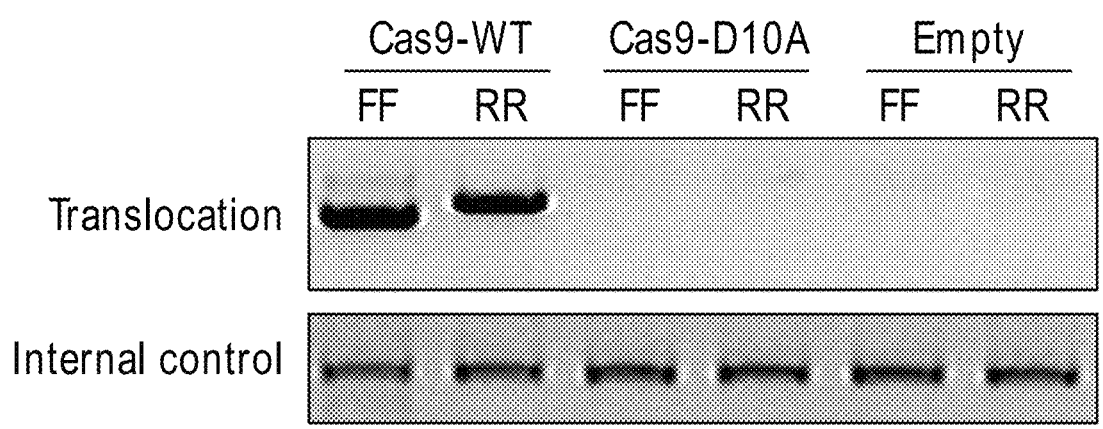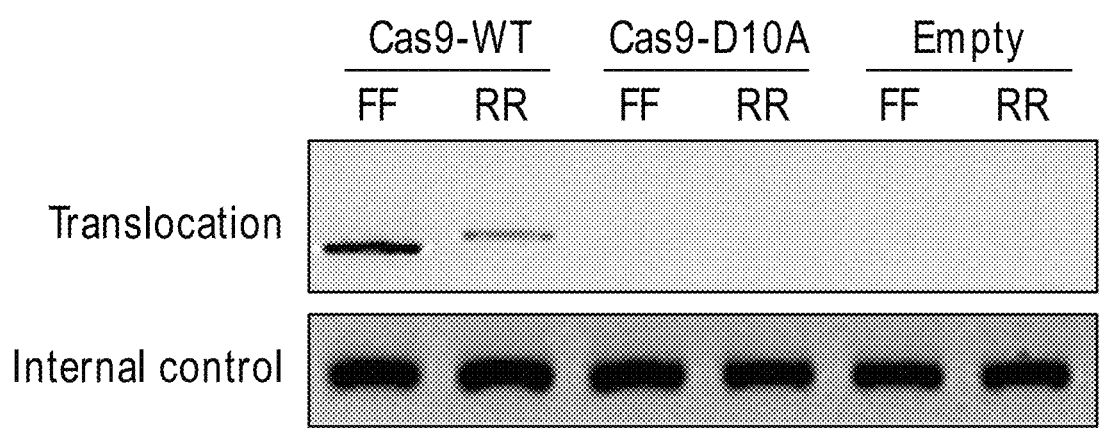
FIG. 21C

```
Plasmid target sequence
AATGACCACTACATCCT---CAAGGG   WT
AATGACCACTACATCCTT--CAAGGG   I1
AATGACCACTACATCCTTT-CAAGGG   I2
AATGACCACTACATCCTTTTCAAGGG   I3
AATGACCACTACATCCT----AAGGG   D1
AATGACCACTACATCCT-----AGGG   D2
AATGACCACTACATCCT------GGG   D3
```

1 (+/-)
```
TATGTGCAATGACCACTACATCCT---CAAGGGCAGCAATCGGAG    WT
TATGTGCAATGACCACTACATCCTCCTCAAGGGCAGCAATCGGAG    +3
```

2 (+/-)
```
TATGTGCAATGACCACTACATCCTCAAGGGCAGCAATCGGAG    WT
TATGTGCAATGACCACTACATC-----------AATCGGAG    -12
```

5 (+/-)
```
TATGTGCAATGACCACTACATCCTCAAGGGCAGCAATCGGAG    WT
TATGTGCAATGACCACTACAT---------CAGCAATCGGAG    -9
```

6 (+/-)
```
TATGTGCAATGACCACTACATCCTCAAGGGCAGCAATCGGAG    WT
TATGTGCAATGACCACTACATCC---------AGCAATCGGAG    -8
```

12 (-/-)
```
-------------------------------------CAGCAATCGG    -36
TATGTGCAATGACCACTACATCCT-----TCAAGGGCAGCAATCGG    +1
TATGTGCAATGACCACTACATCCT-----CCAAGGGCAGCAATCGG    +1
TATGTGCAATGACCACTACATCCT/67bp/CAAGGGCAGCAATCGG   +67
```

28 (-/-)
```
TATGTGCAATGACCACTACATCCTTCAAGGGCAGCAATCGG     +1
TATGTGCAATGACCACTACAT--T-----GGCAGCAATCGG     -7,+1
TATGTGCAATGACCACTACAT---------------------    -94
```

FIG. 24A

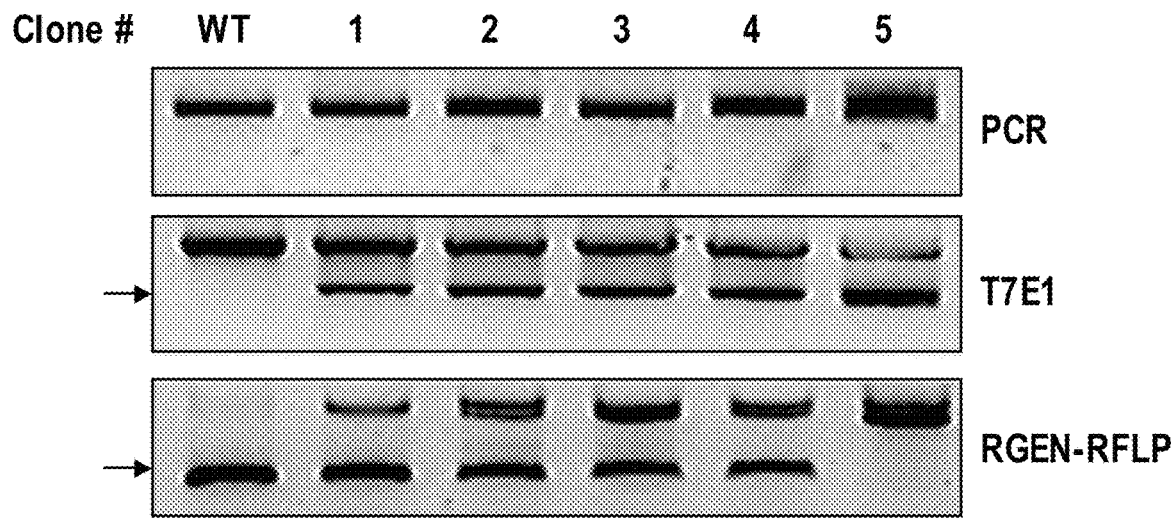
FIG. 25A
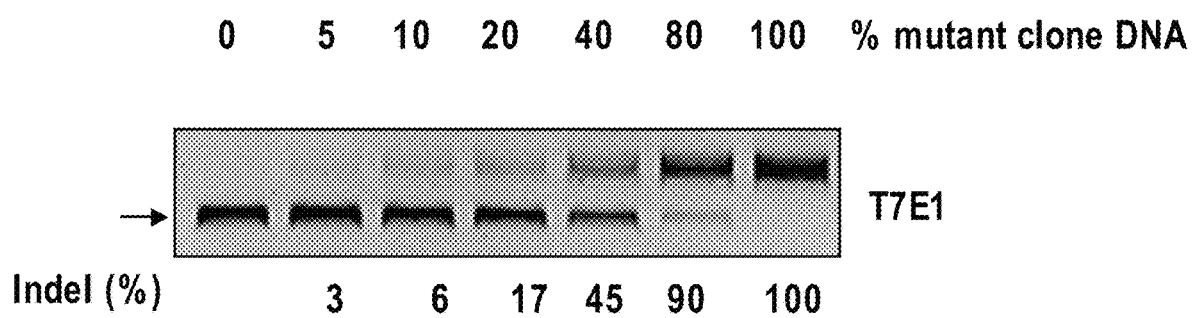
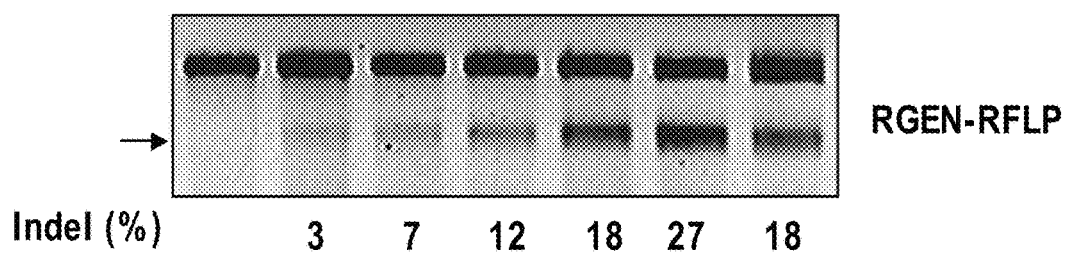
FIG. 25B

FIG. 26A

HeLa

ACTACCACAGCTCCTTCTCTGAGTGG  wild-type

HCT116

ACTACCACAGCTCCTTCTCTGAGTGG  wild-type
ACTACCACAGCTCCT---CTGAGTGG  c.133-135 del TCT

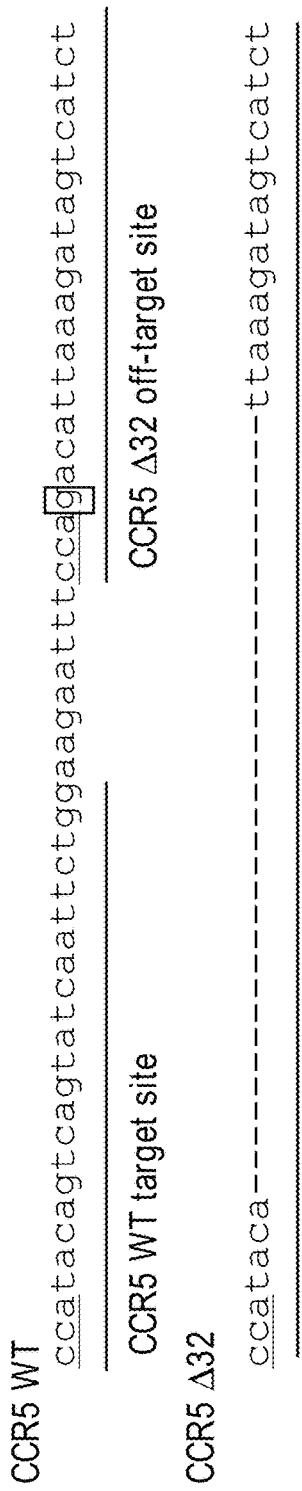
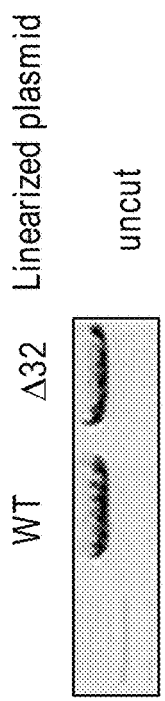
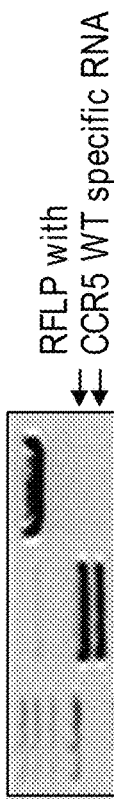
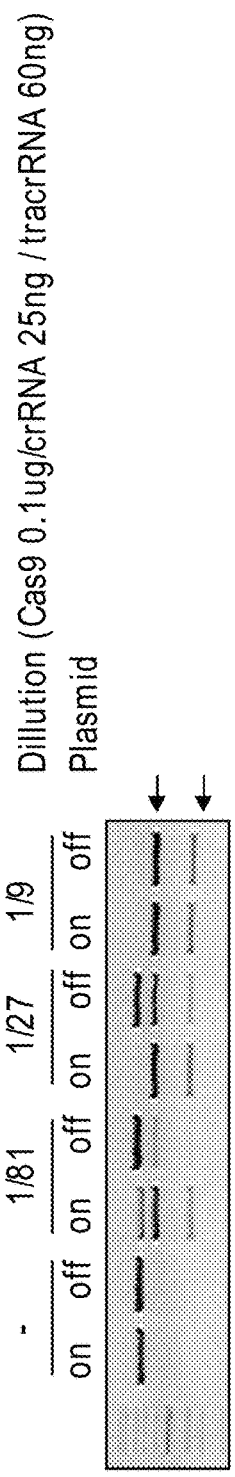

*KRAS*

HeLa

GTAGTTGGAGCTGGTGGCGTAGG Wild-type

A549

GTAGTTGGAGCT[a]GTGGCGTAGG c.34G>A

**RFLP with
WT-specific RNA**
GTAGTTGGAGCTGGTGGCGTAGG

**RFLP with
Mutant-specific RNA**
GTAGTTGGAGCT[a]GTGGCGTAGG

*PIK3CA*

HeLa

CAAATGAATGATGCACATCATGG Wild-type

HCT116

CAAATGAATGATGCACATCATGG Wild-type
CAAATGAATGATGCA⌐g⌐TCATGG C.3140A>G

**RFLP with
WT-specific RNA**
CAAATGAATGATGCACATCATGG

**RFLP with
Mutant-specific RNA**
CAAATGAATGATGCA⌐g⌐TCATGG

IDH1
HeLa
ATCATAGGTCGTCATGCTTATGG  Wild-type
HT1080
ATCATAGGTCGTCATGCTTATGG  Wild-typ
ATCATAGGT[t]GTCATGCTTATGG  c.394C>T
PCR
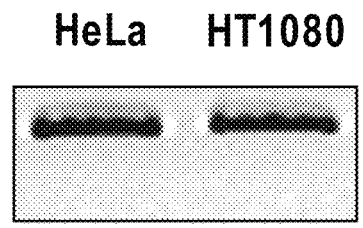
**RFLP with
WT-Specific RNA**
ATCATAGGTCGTC[c]TGCTTATGG
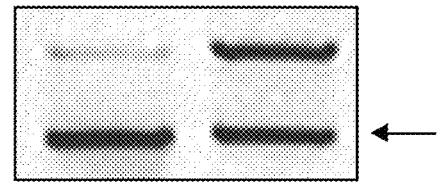
**RFLP with
Mutant-specific RNA**
ATCATAGGT[t]GTC[c]TGCTTATGG
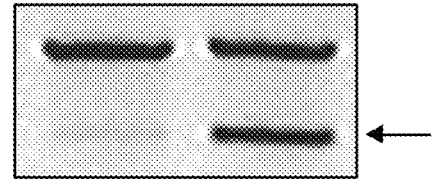
FIG. 33A

*NRAS*

HeLa
CTGGACAAGAAGAGTACAGTGCC    Wild-type

HT1080
CTGGACAAGAAGAGTACAGTGCC    Wild-type
CTGGA[a]AAGAAGAGTACAGTGCC    c.181C>A

PCR

RFLP with
WT-Specific RNA
CTGGACAAGAAGAGTACAGTGCC

RFLP with
Mutant-specific RNA
CTGGA[a]AAGAAGAGTACAGTGCC

*BRAF*

HeLa

ACTCCATCGAGATTTCACTGTAG Wild-type

HT29

ACTCCATCGAGATTTCACTGTAG Wild-type
ACTCCATCGAGATTT[t]CTGTAG (c.1799T>A)

PCR

**RFLP with
WT-Specific RNA**

ACTCCATCGAGATTTCACTGTAG

**RFLP with
Mutant-specific RNA**

ACTCCATCGAGATTT[t]CTGTAG

METHODS FOR CLEAVING A TARGET DNA USING A GUIDE RNA SPECIFIC FOR THE TARGET DNA AND CAS PROTEIN-ENCODING NUCLEIC ACID OR CAS PROTEIN

CROSS REFERENCE TO RELATED APPLICATIONS

The present application is a continuation application of PCT/KR2013/009488 filed Oct. 23, 2013, which claims priority to U.S. Provisional Application No. 61/837,481 filed on Jun. 20, 2013, U.S. Provisional Application No. 61/803,599 filed Mar. 20, 2013, and U.S. Provisional Application No. 61/717,324 filed Oct. 23, 2012, the entire contents of each aforementioned application are incorporated herein by reference.

SEQUENCE LISTING

The instant application contains a Sequence Listing which has been submitted electronically in ASCII format and is hereby incorporated by reference in its entirety. Said ASCII copy, created on Jun. 23, 2015, is named 0213.0001-CON2_SL-2015-06-23.txt and is 127,058 bytes in size.

TECHNICAL FIELD

The present invention relates to targeted genome editing in eukaryotic cells or organisms. More particularly, the present invention relates to a composition for cleaving a target DNA in eukaryotic cells or organisms comprising a guide RNA specific for the target DNA and Cas protein-encoding nucleic acid or Cas protein, and use thereof.

BACKGROUND ART

CRISPRs (Clustered Regularly Interspaced Short Palindromic Repeats) are loci containing multiple short direct repeats that are found in the genomes of approximately 40% of sequenced bacteria and 90% of sequenced archaea. CRISPR functions as a prokaryotic immune system, in that it confers resistance to exogenous genetic elements such as plasmids and phages. The CRISPR system provides a form of acquired immunity. Short segments of foreign DNA, called spacers, are incorporated into the genome between CRISPR repeats, and serve as a memory of past exposures. CRISPR spacers are then used to recognize and silence exogenous genetic elements in a manner analogous to RNAi in eukaryotic organisms.

Cas9, an essential protein component in the Type II CRISPR/Cas system, forms an active endonuclease when complexed with two RNAs termed CRISPR RNA (crRNA) and trans-activating crRNA (tracrRNA), thereby slicing foreign genetic elements in invading phages or plasmids to protect the host cells. crRNA is transcribed from the CRISPR element in the host genome, which was previously captured from such foreign invaders. Recently, Jinek et al. (1) demonstrated that a single-chain chimeric RNA produced by fusing an essential portion of crRNA and tracrRNA could replace the two RNAs in the Cas9/RNA complex to form a functional endonuclease.

CRISPR/Cas systems offer an advantage to zinc finger and transcription activator-like effector DNA-binding proteins, as the site specificity in nucleotide binding CRISPR-Cas proteins is governed by a RNA molecule instead of the DNA-binding protein, which can be more challenging to design and synthesize.

However, until now, a genome editing method using the RNA-guided endonuclease(RGEN) based on CRISPR/Cas system has not been developed.

Meanwhile, Restriction fragment length polymorphism (RFLP) is one of the oldest, most convenient, and least expensive methods of genotyping that is still used widely in molecular biology and genetics but is often limited by the lack of appropriate sites recognized by restriction endonucleases.

Engineered nuclease-induced mutations are detected by various methods, which include mismatch-sensitive T7 endonuclease I (T7E1) or Surveyor nuclease assays, RFLP, capillary electrophoresis of fluorescent PCR products, Dideoxy sequencing, and deep sequencing. The T7E1 and Surveyor assays are widely used but are cumbersome. Furthermore, theses enzymes tend to underestimate mutation frequencies because mutant sequences can form homoduplexes with each other and cannot distinguish homozygous bi-allelic mutant clones from wild type cells. RFLP is free of these limitations and therefore is a method of choice. Indeed, RFLP was one of the first methods to detect engineered nuclease-mediated mutations in cells and animals. Unfortunately, however, RFLP is limited by the availability of appropriate restriction sites. It is possible that no restriction sites are available at the target site of interest.

DISCLOSURE OF INVENTION

Technical Problem

Until now, a genome editing and genotyping method using the RNA-guided endonuclease(RGEN) based on CISPR/Cas system has not been developed.

Under these circumstances, the present inventors have made many efforts to develop a genome editing method based on CRISPR/Cas system and finally established a programmable RNA-guided endonuclease that cleave DNA in a targeted manner in eukaryotic cells and organisms.

In addition, the present inventors have made many efforts to develop a novel method of using RNA-guided endonucleases (RGENs) in RFLP analysis. They have used RGENs to genotype recurrent mutations found in cancer and those induced in cells and organisms by engineered nucleases including RGENs themselves, thereby completing the present invention.

Solution to Problem

It is an object of the present invention to provide a composition for cleaving target DNA in eukaryotic cells or organisms comprising a guide RNA specific for target DNA or DNA that encodes the guide RNA, and Cas protein-encoding nucleic acid or Cas protein.

It is another object of the present invention to provide a composition for inducing targeted mutagenesis in eukaryotic cells or organisms, comprising a guide RNA specific for target DNA or DNA that encodes the guide RNA, and Cas protein-encoding nucleic acid or Cas protein.

It is still another object of the present invention to provide a kit for cleaving a target DNA in eukaryotic cells or organisms comprising a guide RNA specific for target DNA or DNA that encodes the guide RNA, and Cas protein-encoding nucleic acid or Cas protein.

It is still another object of the present invention to provide a kit for inducing targeted mutagenesis in eukaryotic cells or organisms comprising a guide RNA specific for target DNA or DNA that encodes the guide RNA, and Cas protein-encoding nucleic acid or Cas protein.

It is still another object of the present invention to provide a method for preparing a eukaryotic cell or organism comprising Cas protein and a guide RNA comprising a step of co-transfecting or serial-transfecting the eukaryotic cell or organism with a Cas protein-encoding nucleic acid or Cas protein, and a guide RNA or DNA that encodes the guide RNA.

It is still another object of the present invention to provide a eukaryotic cell or organism comprising a guide RNA specific for target DNA or DNA that encodes the guide RNA, and Cas protein-encoding nucleic acid or Cas protein.

It is still another object of the present invention to provide a method for cleaving a target DNA in eukaryotic cells or organisms comprising a step of transfecting the eukaryotic cells or organisms comprising a target DNA with a composition comprising a guide RNA specific for target DNA or DNA that encodes the guide RNA, and Cas protein-encoding nucleic acid or Cas protein.

It is still another object of the present invention to provide a method for inducing targeted mutagenesis in a eukaryotic cell or organism comprising a step of treating a eukaryotic cell or organism with a composition comprising a guide RNA specific for target DNA or DNA that encodes the guide RNA, and Cas protein-encoding nucleic acid or Cas protein.

It is still another object of the present invention to provide an embryo, a genome-modified animal, or genome-modified plant comprising a genome edited by a composition comprising a guide RNA specific for target DNA or DNA that encodes the guide RNA, and Cas protein-encoding nucleic acid or Cas protein.

It is still another object of the present invention to provide a method of preparing a genome-modified animal comprising a step of introducing the composition comprising a guide RNA specific for target DNA or DNA that encodes the guide RNA, and Cas protein-encoding nucleic acid or Cas protein into an embryo of an animal; and a step of transferring the embryo into a oviduct of pseudopregnant foster mother to produce a genome-modified animal.

It is still another object of the present invention to provide a composition for genotyping mutations or variations in an isolated biological sample, comprising a guide RNA specific for the target DNA sequence Cas protein.

It is still another object of the present invention to provide a method of using a RNA-guided endonuclease (RGEN) to genotype mutations induced by engineered nucleases in cells or naturally-occurring mutations or variations, wherein the RGEN comprises a guide RNA specific for target DNA and Cas protein.

It is still another object of the present invention to provide a kit for genotyping mutations induced by engineered nucleases in cells or naturally-occurring mutations or variations, comprising a RNA-guided endonuclease (RGEN), wherein the RGEN comprises a guide RNA specific for target DNA and Cas protein.

It is an object of the present invention to provide a composition for cleaving target DNA in eukaryotic cells or organisms comprising a guide RNA specific for target DNA or DNA that encodes the guide RNA, and Cas protein-encoding nucleic acid or Cas protein.

It is another object of the present invention to provide a composition for inducing targeted mutagenesis in eukaryotic cells or organisms, comprising a guide RNA specific for target DNA or DNA that encodes the guide RNA, and Cas protein-encoding nucleic acid or Cas protein.

It is still another object of the present invention to provide a kit for cleaving a target DNA in eukaryotic cells or organisms comprising a guide RNA specific for target DNA or DNA that encodes the guide RNA, and Cas protein-encoding nucleic acid or Cas protein.

It is still another object of the present invention to provide a kit for inducing targeted mutagenesis in eukaryotic cells or organisms comprising a guide RNA specific for target DNA or DNA that encodes the guide RNA, and Cas protein-encoding nucleic acid or Cas protein.

It is still another object of the present invention to provide a method for preparing a eukaryotic cell or organism comprising Cas protein and a guide RNA comprising a step of co-transfecting or serial-transfecting the eukaryotic cell or organism with a Cas protein-encoding nucleic acid or Cas protein, and a guide RNA or DNA that encodes the guide RNA.

It is still another object of the present invention to provide a eukaryotic cell or organism comprising a guide RNA specific for target DNA or DNA that encodes the guide RNA, and Cas protein-encoding nucleic acid or Cas protein.

It is still another object of the present invention to provide a method for cleaving a target DNA in eukaryotic cells or organisms comprising a step of transfecting the eukaryotic cells or organisms comprising a target DNA with a composition comprising a guide RNA specific for target DNA or DNA that encodes the guide RNA, and Cas protein-encoding nucleic acid or Cas protein.

It is still another object of the present invention to provide a method for inducing targeted mutagenesis in a eukaryotic cell or organism comprising a step of treating a eukaryotic cell or organism with a composition comprising a guide RNA specific for target DNA or DNA that encodes the guide RNA, and Cas protein-encoding nucleic acid or Cas protein.

It is still another object of the present invention to provide an embryo, a genome-modified animal, or genome-modified plant comprising a genome edited by a composition comprising a guide RNA specific for target DNA or DNA that encodes the guide RNA, and Cas protein-encoding nucleic acid or Cas protein.

It is still another object of the present invention to provide a method of preparing a genome-modified animal comprising a step of introducing the composition comprising a guide RNA specific for target DNA or DNA that encodes the guide RNA, and Cas protein-encoding nucleic acid or Cas protein into an embryo of an animal; and a step of transferring the embryo into a oviduct of pseudopregnant foster mother to produce a genome-modified animal.

It is still another object of the present invention to provide a composition for genotyping mutations or variations in an isolated biological sample, comprising a guide RNA specific for the target DNA sequence Cas protein.

It is still another object of the present invention to provide a composition for genotyping nucleic acid sequences in pathogenic microorganisms in an isolated biological sample, comprising a guide RNA specific for the target DNA sequence and Cas protein.

It is still another object of the present invention to provide a kit for genotyping mutations or variations in an isolated biological sample, comprising the composition, specifically comprising a RNA-guided endonuclease (RGEN), wherein the RGEN comprises a guide RNA specific for target DNA and Cas protein.

It is still another object of the present invention to provide a method of genotyping mutations or variations in an isolated biological sample, using the composition, specifically comprising a PRA-guided endonuclease (RGEN), wherein the RGEN comprises a guide RNA specific for target DNA and Cas protein.

Advantageous Effects of Invention

The present composition for cleaving a target DNA or inducing a targeted mutagenesis in eukaryotic cells or organisms, comprising a guide RNA specific for the target DNA and Cas protein-encoding nucleic acid or Cas protein, the kit comprising the composition, and the method for inducing targeted mutagenesis provide a new convenient genome editing tools. In addition, because custom RGENs can be designed to target any DNA sequence, almost any single nucleotide polymorphism or small insertion/deletion (indel) can be analyzed via RGEN-mediated RFLP, therefore, the composition and method of the present invent ion may be used in detection and cleaving naturally-occurring variations and mutations.

BRIEF DESCRIPTION OF DRAWINGS

FIGS. 1A and 1B show Cas9-catalyzed cleavage of plasmid DNA in vitro. FIG. 1A: Schematic representation of target DNA (SEQ ID NO: 112) and chimeric RNA sequences (SEQ ID NO: 113). Red triangles indicate cleavage sites. The PAM sequence recognized by Cas9 is shown in bold. The sequences in the guide PNA (SEQ ID NO: 113) derived from crRNA and tracrRNA are shown in box and underlined, respectively. FIG. 1B: In vitro cleavage of plasmid DNA by Cas9. An intact circular plasmid or ApaLI-digested plasmid was incubated with Cas9 and guide RNA.

FIG. 2A: Schematic overview of cell-based assays using a RFP-GFP reporter. GFP is not expressed from this reporter because the GFP sequence is fused to the RFP sequence out-of-frame. The RFP-GFP fusion protein is expressed only when the target site between the two sequences is cleaved by a site-specific nuclease. FIG. 2B: Flow cytometry of cells transfected with Cas9. The percentage of cells that express the RFP-GFP fusion protein is indicated.

FIG. 3A: CCR5 locus. FIG. 3B: C4BPB locus. (Top) The T7E1 assay was used to detect RGEN-driven mutations. Arrows indicate the expected position of DNA bands cleaved by T7E. Mutation frequencies (Indels (%)) were calculated by measuring the band intensities. (Bottom) DNA sequences of the wild-type (WT) CCR5 (SEQ ID NO: 114) and C4BPB (SEQ ID NO: 122) and mutant clones. DNA sequences of RGEN-induced mutations at the CCR5 locus: +1 (SEQ ID NO: 115), −13 (SEQ ID NO: 116), −14 (SEQ ID NO: 117), −18 (SEQ ID NO: 118), −19 (SEQ ID NO: 119), −24 (SEQ ID NO: 120), and −30 (SEQ ID NO: 121). DNA sequences of RGEN-induced mutations at the C4BPB locus: +1 (SEQ ID NO: 122), +2 (SEQ ID NO: 123), −30 (SEQ ID NO: 125), and −180 (SEQ ID NO: 126). The region of the target sequence complementary to the guide RNA is shown in box. The PAM sequence is shown in bold. Triangles indicate the cleavage site. Bases corresponding to microhomologies are underlined. The column on the right indicates the number of inserted or deleted bases.

FIGS. 4A, 4B, and 4C show that RGEN-driven off-target mutations are undetectable. FIG. 4A: On-target and potential off-target sequences. The human genome was searched in silico for potential off-target sites. Four sites were identified. ADCY5 (SEQ ID NO: 128), KCNJ6 (SEQ ID NO: 129), CNTNAP2 (SEQ ID NO: 130), and Chr. 5 N/A (SEQ ID NO: 131), each of which carries 3-base mismatches with the CCR5 on-target (SEQ ID NO: 127). Mismatched bases are underlined. FIG. 4B: The T7E1 assay was used to investigate whether these sites were mutated in cells transfected with the Cas9/RNA complex. No mutations were detected at these sites. N/A (not applicable), an intergenic site. FIG. 4C: Cas9 did not induce off-target-associated chromosomal deletions. The CCR5-specific RGEN and ZFN were expressed in human cells. PCR was used to detect the induction of the 15-kb chromosomal deletions in these cells.

FIGS. 5A, 5B, 5C, and 5D show RGEN-induced Foxn1 gene targeting in mice. FIG. 5A: A schematic diagram depicting target DNA (SEQ ID NO: 132) and a sgRNA specific to exon 2 of the mouse Foxn1 gene (SEQ ID NO: 133). PAM in exon 2 is shown in red and the sequence in the sgRNA that is complementary to exon 2 is underlined. Triangles indicate cleavage sites. FIG. 5B: Representative T7E1 assays demonstrating gene-targeting efficiencies of Cas9 mRNA plus Foxn1-specific sgRNA that were delivered via intra-cytoplasmic injection into one-cell stage mouse embryos. Numbers indicate independent founder mice generated from the highest dose. Arrows indicate bands cleaved by T7E1. FIG. 5C: DNA sequences of wild-type (WT) Foxn1 (SEQ ID NO: 134) and mutant alleles (SEQ ID NOs. 135-141) observed in three Foxn1 mutant founders identified in FIG. 5B. DNA sequences of mutant alleles in founder #108: −44 (SEQ ID NO: 135), −23 (SEQ ID NO: 136), −17 (SEQ ID NO: 137), and +1 (SEQ ID NO: 138). DNA sequences of mutant alleles in founder #111: +1 (SEQ ID NO: 138) and −11 (SEQ ID NO: 139). DNA sequences of mutant alleles in founder #114: −6 (SEQ ID NO: 140), −17 (SEQ ID NO: 137), and −8 (SEQ ID NO: 141). The number of occurrences is shown in parentheses. FIG. 5D: PCR genotyping of F1 progenies derived from crossing Foxn1 founder #108 and wild-type FVB/NTac. Note the segregation of the mutant alleles found in Foxn1 founder #108 in the progenies.

FIGS. 6A, 6B, and 6C show Foxn1 gene targeting in mouse embryos by intra-cytoplasmic injection of Cas9 mRNA and Foxn1-sgRNA. FIG. 6A: A representative result of a T7E1 assay monitoring the mutation rate after injecting the highest dose. Arrows indicate bands cleaved by T7E1. FIG. 6B: A summary of T7E1 assay results. Mutant fractions among in vitro cultivated embryos obtained after intra-cytoplasmic injection of the indicated RGEN doses are indicated. FIG. 6C: DNA sequences of wild-type (WT) Foxn1 (SEQ ID NO: 143) and Foxn1 mutant alleles (SEQ ID Nos. 144-152) identified from a subset of T7E-1-positive mutant embryos. The DNA sequences of the mutant alleles are: Δ11 (SEQ ID NO: 144), Δ11+Δ17 (SEQ ID NO: 145) Δ57 (SEQ ID NO: 146), Δ17 (SEQ ID NO: 147), +1 (SEQ ID NO: 148), Δ12 (SEQ ID NO: 149, Δ72 (SEQ ID NO: 150), Δ25 (SEQ ID NO:151), Δ24 (SEQ ID NO: 152). The target sequence of the wild-type allele is denoted in box.

FIGS. 7A, 7B, and 7C show Foxn1 gene targeting in mouse embryos using the recombinant Cas9 protein: Foxn1-sgRNA complex. FIG. 7A and FIG. 7B are representative T7E1 assays results and their summaries. Embryos were cultivated in vitro after they underwent pronuclear (FIG. 7A) or intra-cytoplasmic injection (FIG. 7B). Numbers in red indicate T7E1-positive mutant founder mice. FIG. 7C: DNA sequences of wild-type (WT) Foxn1 (SEQ ID NO: 153) and Foxn1 mutant alleles (SEQ ID NOs. 154-166) identified from the in vitro cultivated embryos that were obtained by the pronucleus injection of recombinant Cas9 protein: Foxn1-sgRNA complex at the highest dose. The target sequence of the wild-type allele is denoted in box. The DNA sequences of the mutant alleles are: Δ18 (SEQ ID NO: 154), Δ20 (SEQ ID NO: 155), Δ19 (SEQ ID NO: 156), Δ17 (SEQ ID NO: 157), Δ11 (SEQ ID) NO: 158), Δ3+1 (SEQ ID NO: 159), Δ2 (SEQ ID NO: 160), +1, Embryo 1 (SEQ ID NO: 161), +1, Embryo 10 (SEQ ID NO: 162), Δ6 (SEQ ID NO: 163), Δ5 (SEQ ID NO: 164), Δ28 (SEQ ID NO: 165), and Δ126 (SEQ ID NO: 166).

FIGS. 8A, 8B, and 8C show Germ-line transmission of the mutant alleles found in Foxn1 mutant founder #12. FIG. 8A: wild type fPCR analysis. FIG. 8B: Foxn1 mutant founder #12 fPCR analysis. FIG. 8C: PCR genotyping of wild-type FVB/NTac, the founder mouse, and their F1 progenies.

FIGS. 9A and 9B show Genotypes of embryos generated by crossing Prkdc mutant founders. Prkdc mutant founders ♂25 and ♀15 were crossed and E13.5 embryos were isolated. FIG. 9A: fPCR analysis of wild-type, founder ♂25, and founder ♀15. Note that, due to the technical limitations of fPCR analysis, these results showed small differences from the precise sequences of the mutant alleles; e.g., from the sequence analysis, Δ269/Δ61/WT and Δ5+1/+7/+12/WT were identified in founders ♂25 and ♀15, respectively. FIG. 9B: Genotypes of the generated embryos.

FIGS. 10A, 10B, 10C, 10D, and 10E show Cas9 protein/sgRNA complex induced targeted mutation at CCR5 gene (FIGS. 10A-10C) and ABCC11 gene (FIGS. 10D-10E). FIG. 10A: Results of a T7E1 assay monitoring the mutation rate at CCR5 locus after introducing Cas9 protein and sgRNA or Cas9 protein and crRNA+tracrRNA into KS62 cells. FIG. 10B: Results of a T7E1 assay using 1/5 scaled down doses of Cas9 protein and sgRNA. FIG. 10C: Wild-type (WT) CCR5 sequence (SEQ ID NO: 1.14) and Cas protein induced mutant sequences (SEQ ID NOs. 167-171 and 115) identified in CCR5 locus. The DNA sequences of the mutant sequences are: −4 (SEQ ID NO: 167), −4 (SEQ ID NO: 168), −7 (SEQ ID NO: 169), −1 (SEQ ID NO: 170), +1 (SEQ ID NO: 115), and −17, +1 (SEQ ID NO: 171). FIG. 10D: Results of a T7E1 assay monitoring the mutation rate at ABCC11 locus after introducing Cas9 protein and sgRNA into K562 cells. FIG. 10E: Wild-type (WT) ABCC11 sequence (SEQ ID NO: 172) and Cas9 protein induced mutant sequences (SEQ ID NOs. 173-176) identified in ABCC11 locus. The DNA sequences of the mutant sequences are: −6 (SEQ ID NO: 173), −3 (SEQ ID NO: 174), −29 (SEQ ID NO: 175), −20 (SEQ ID NO: 176), and −256 (TTCTC).

FIG. 12 shows wild type BRI1 sequence (SEQ ID NO: 177) and recombinant Cas9 protein-induced mutant sequences (SEQ ID NOs. 178-181) in the *Arabidopsis* BRI1 gene. The DNA sequences of the mutant sequences are: −7 (SEQ ID NO: 178), −224 (SEQ ID NO: 179), −223 (SEQ ID NO: 180), and −223, +62 (SEQ ID NO: 181).

FIG. 14A: VEGFA site 1 on target sequence (SEQ ID NO: 182) and off target sequences, OT1-3 (SEQ ID NO: 183) and OT1-11 (SEQ ID NO: 184). VEGFA site 2 on target sequence (SEQ ID NO: 185) and off target sequences OT2-1 (SEQ ID NO: 186), OT2-9 (SEQ ID NO: 187) and OT2-24 (SEQ ID NO: 188). FIG. 14B: VEGFA site 3 on target sequence (SEQ ID NO: 189) and off target sequence OT3-18 (SEQ ID NO: 190) and EMX1 on target sequence (SEQ ID NO: 191) and off target sequence OT4-1 (SEQ ID NO: 192).

FIG. 15A: VEGFA site 1 on target sequence (SEQ ID NO: 182) and off target sequences OT1-3 (SEQ ID NO: 183 and OT1-11 (SEQ ID NO: 184). VEGFA site 2 on target sequence (SEQ ID NO: 185) and off target sequences OT2-1 (SEQ ID NO: 186), OT2-9 (SEQ ID NO: 187), and OT2-24 (SEQ ID NO: 188). FIG. 15B: VEGFA site 3 on target sequence (SEQ ID NO: 189) and off target sequence OT3-18 (SEQ ID NO: 190) and EMX1 on target sequence (SEQ ID NO: 191) and off target sequence OT4-1 (SEQ ID NO: 192).

FIG. 16A: Schematic overview of the Cas9 nuclease and the paired Cas9 nickase. The PAM sequences and cleavage sites are shown in box. FIG. 16B: Target sites in the human AAVS1 locus. The position of each target site is shown in triangle. FIG. 16C: Schematic overview of DNA cleavage reactions. FAM dyes (shown in box) were linked to both 5' ends of the DNA substrate. FIG. 16D: DSBs and SSBs analyzed using fluorescent capillary electrophoresis. Fluorescently-labeled DNA substrates were incubated with Cas9 nucleases or nickases before electrophoresis.

FIG. 17A: On-target mutation frequencies associated with Cas9 nucleases (WT), nickases (D10A), and paired nickases at the following target sequences of the AAVS1 locus: S1 (SEQ ID NO: 193), S2 (SEQ ID NO: 194), S3 (SEQ ID NO: 195), S4 (SEQ ID NO: 196), S5 (SEQ ID NO: 197), S6 (SEQ ID NO: 198), AS1 (SEQ ID NO: 199), AS2 (SEQ ID NO: 200), and AS3 (SEQ ID NO: 201). Paired nickases that would produce 5' overhangs or 3' overhangs are indicated. FIG. 17B: Analysis of off-target effects of Cas9 nucleases and paired nickases. A total of seven potential off-target sites (SEQ ID NOs. 202-208) for three sgRNAs were analyzed. The mutation frequency for the S2 on-target sequence (SEQ ID NO: 194) was compared to the off-target sequences, S2 Off-1 (SEQ ID NO: 202) and S2 Off-2 (SEQ ID NO: 203). The mutation frequency for the S3 on-target sequence (SEQ ID NO: 195) was compared to the off-target sequences, S3 Off-1 (SEQ ID NO: 204) and S3 Off-2 (SEQ ID NO: 205). The mutation frequency for the AS2 on-target sequence (SEQ ID NO: 198) was compared to the off-target sequences, AS2 Off-1 (SEQ ID NO: 206), AS2 Off-6 (SEQ ID NO 207), and AS2 Off-9 (SEQ ID NO: 208).

FIGS. 18A, 18B, 18C, and 18D show paired Cas9 nickases tested at other endogenous human loci. The sgRNA target sites at the human CCR5 locus (FIG. 18A; SEQ ID NO: 209) and the BRCA2 locus (FIG. 18C; SEQ ID NO: 210). PAM sequences are indicated in red. Genome editing activities at CCR5 (FIG. 18B) and BRCA2 (FIG. 18D) target sites were detected by the T7E1 assay. The repair of two nicks that would produce 5' overhangs led to the formation of indels much more frequently than did those producing 3' overhangs.

FIG. 19A: Strategy to detect homologous recombination. Donor DNA included an XbaI restriction enzyme site between two homology arms, whereas the endogenous target site lacked this site. A PCR assay was used to detect sequences that had undergone homologous recombination. To prevent amplification of contaminating donor DNA, primers specific to genomic DNA were used. FIG. 19B: Efficiency of homologous recombination. Only amplicons of a region in which homologous recombination had occurred could be digested with XbaI; the intensities of the cleavage bands were used to measure the efficiency of this method.

FIGS. 20A, 20B, 20C, and 20D show DNA splicing induced by paired Cas9 nickases. FIG. 20A: The target sites of paired nickases in the human AAVS1 locus. The distances between the AS2 site and each of the other sites are shown. Arrows indicate PCR primers. FIG. 20B: Genomic deletions detected using PCR. Asterisks indicate deletion-specific PCR products. FIG. 20C: DNA sequences of wild-type (WT) (SEQ ID NO: 211) and the following deletion-specific PCR products (SEQ ID Nos. 212-218) obtained using AS2 sgRNAs or deletion-specific PCR products (SEQ ID) NOs. 219-224) using L1 sgRNAs. Target site PAM sequences are shown in box and sgRNA-matching sequences are shown in capital letters. Intact sgRNA-matching sequences are underlined. FIG. 20D: A schematic model of paired Cas9 nickase-mediated chromosomal deletions. Newly-synthesized DNA strands are shown in box.

FIGS. 21A, 218, and 21C show that paired Cas9 nickases do not induce translocations. FIG. 21A: Schematic overview of chromosomal translocations between the on-target and off-target sites. FIG. 21B: PCR amplification to detect chromosomal translocations. FIG. 21C: Translocations induced by Cas9 nucleases but not by the nickase pair.

FIG. 22A: Comparison of assay cleavage reactions in four possible scenarios after engineered nuclease treatment in a diploid cell: (A) wild type, (B) amonoallelic mutation, (C) different biallelic mutations (hetero), and (D) identical biallelic mutations (homo). Black lines represent PCR products derived from each allele; dashed and dotted boxes indicate insertion/deletion mutations generated by NHEJ. FIG. 22B: Expected results of T7E1 and RGEN digestion resolved by electrophoresis.

FIGS. 24A and 24B show genotyping of mutations induced by engineered nucleases in cells via RGEN-mediated RFLP. FIG. 24A: Genotype of C4BPB wild type (SEQ ID NO: 231) and the following mutant K562 cell clones: +3 (SEQ ID NO: 232), −12 (SEQ ID NO: 233), −9 (SEQ ID NO: 234), −8 (SEQ ID NO: 235), −36 (SEQ ID NO: 236), +1 (SEQ ID NO: 237), +1 (SEQ ID NO: 238), +67 (SEQ ID NO: 239), −7, +1 (SEQ ID NO: 240), −94 (SEQ ID NO: 241). FIG. 24B: Comparison of the mismatch-sensitive T7E1 assay with RGEN-mediated RFLP analysis. Black arrows indicate the cleavage product by treatment of T7E1 enzyme or RGENs.

FIGS. 25A, 25B, and 25C show genotyping of RGEN-induced mutations via the RGEN-RFLP technique. FIG. 25A: Analysis of C4BPB-disrupted clones using RGEN-RFLP and T7E1 assays. Arrows indicate expected positions of DNA bands cleaved by RGEN or T7E1. FIG. 25B: Quantitative comparison of RGEN-RFLP analysis with T7E1 assays. Genomic DNA samples from wild-type and C4BPB-disrupted K562 cells were mixed in various ratios and subjected to PCR amplification. FIG. 25C: Genotyping of RGEN-induced mutations in the HLA-B gene in HeLa cells with RFLP and T7E1 analyses.

FIGS. 26A and 268 show genotyping of mutations induced by engineered nucleases in organisms via RGEN-mediated RFLP. FIG. 26A: Genotype of Pibf1 wild-type (WT) (SEQ ID NO: 242) and the following mutant founder mice: #1 (SEQ ID NO: 243 and SEQ ID NO: 244), #3 (SEQ ID NO: 245 and SEQ ID NO: 246), #4 (SEQ ID NO: 247 and SEQ ID NO: 242), #5 (SEQ ID NO: 246 and SEQ ID NO: 242), #6 (SEQ ID NO: 248 and SEQ ID NO: 249), #8 (SEQ ID NO: 250 and SEQ ID NO: 251), and #11 (SEQ ID NO: 252 and SEQ ID NO: 250).

FIG. 29A: A recurrent mutation (c.133-135 deletion of TCT; SEQ ID NO: 256) in the human CTNNB1 gene in HCT116 cells was detected by RGENs. The wild-type CTNNB1 sequence is represented by SEQ ID NO: 255. HeLa cells were used as a negative control. FIG. 29B: Genotyping of the KPAS substitution mutation (c.34 G>A) in the A549 cancer cell line with RGENs that contain mismatched guide RNA that are WT-specific (SEQ ID NO: 257) or mutant-specific (SEQ ID NO: 258). Mismatched nucleotides are shown in box. HeLa cells were used as a negative control. Arrows indicate DNA bands cleaved by RGENs. DNA sequences confirmed by Sanger sequencing are shown: wild-type (SEQ ID NO: 259) and c.34G>A (SEQ ID NO: 260).

FIGS. 30A, 30B, 30C, and 30D show genotyping of the CCR5 delta32 allele in HEK293T cells via RGEN-RFLP analysis. FIG. 30A: RGEN-RFLP assays of cell lines. DNA sequences of the wild-type CCR5 locus (SEQ ID NO: 262) and delta 32 mutation (SEQ ID NO: 261) are shown. K562, SKBR3, and HeLa cells were used as wild-type controls. Arrows indicate DNA bands cleaved by RGENs. FIG. 30B: DNA sequence of wild-type (SEQ ID NO: 263) and delta32 CCR5 alleles (SEQ ID NO: 264). Both on-target and off-target sites of RGENs used in RFLP analysis are underlined. A single-nucleotide mismatch between the two sites is shown in box. The PAM sequence is underlined. FIG. 30C: In vitro cleavage of plasmids harboring WT or del32 CCR5 alleles using the wild-type-specific RGEN. FIG. 30D Confirming the presence of an off-target site of the CCR5-delta32-specific RGEN at the CCR5 locus. In vitro cleavage assays of plasmids harboring either on-target (SEQ ID NO: 265) or off-target sequences (SEQ ID NO: 266) using various amounts of the del32-specific RGEN.

FIG. 31A: RGEN-RFLP analysis of the KRAS mutation (c.34 G>A) in cancer cell lines. PCR products from HeLa cells (used as a wild-type control) or A549 cells, which are homozygous for the point mutation, were digested with RGENs with perfectly matched crRNA specific to the wild-type sequence (SEQ ID NO: 259) or the mutant sequence (SEQ ID NO: 260). KRAS genotypes in these cells were confirmed by Sanger sequencing. FIG. 31B: Plasmids harboring either the wild-type (SEQ ID NO: 259) or mutant KRAS sequences (SEQ ID NO: 260) were digested using RGENs with perfectly matched crRNAs or attenuated, one-base mismatched crRNAs: m7 (SEQ ID NO: 267), m6 (SEQ ID NO: 257), m5 (SEQ ID NO: 268), m4 (SEQ ID NO: 269), m8 (SEQ ID NO: 260), m7,8 (SEQ ID NO: 270), m6,8 (SEQ ID NO: 258), m5,8 (SEQ ID NO: 271), and m4,8 (SEQ ID NO: 272). Attenuated crRNAs that were chosen for genotyping are labeled in box above the gels.

FIG. 32A: RGEN-RFLP analysis of the PIK3CA mutation (c.3140 A>G) in cancer cell lines. PCR products from HeLa cells (used as a wild-type control) or HCT116 cells that are heterozygous for the point mutation were digested with RGENs with perfectly matched crRNA specific to the wild-type sequence (SEQ ID NO: 273) or the mutant sequence (SEQ ID NO: 274). PIK3CA genotypes in these cells were confirmed by Sanger sequencing. FIG. 32B: Plasmids harboring either the wild-type PIK3CA sequence (SEQ ID NO: 273) or mutant PIK3CA sequence (SEQ ID NO: 274) were digested using RGENs with perfectly matched crRNAs or attenuated, one-base mismatched crP-NAs: m5 (SEQ ID NO: 275), m6 (SEQ ID NO: 276), m7 (SEQ ID NO: 277), m10 (SEQ ID NO: 278), m13 (SEQ ID NO: 279), m16 (SEQ ID NO: 280), m19 (SEQ ID NO: 281), m4 (SEQ ID NO:274), m4,5 (SEQ ID NO: 282), m4,6 (SEQ ID NO: 283), m4,7 (SEQ ID NO: 284), m4,10 (SEQ ID NO: 285), m4,13 (SEQ ID NO: 286), m4,16 (SEQ ID NO: 287), and m4,19 (SEQ ID NO: 288). Attenuated crRNAs that were chosen for genotyping are labeled in box above the gels.

FIGS. 33A, 33B, 33C, and 33D show genotyping of recurrent point mutations in cancer cell lines. FIG. 33A: RGEN-RFLP assays to distinguish between a wild-type IDH gene sequence (SEQ ID NO: 289) and a recurrent oncogenic point mutation sequence in the IDH gene (c.394c>T; SEQ ID NO: 290). RGENs with attenuated, one-base mismatched crRNAs, SEQ ID NO: 291 (WT-Specific RNA) and SEQ ID NO: 292 (Mutant-Specific RNA), distinguished the wild type and mutant IDH sequences. FIG. 33B: RGEN-RFLP assays to distinguish between a wild-type PIK3CA gene sequence (SEQ ID NO: 271) and a recurrent oncogenic point mutation sequence in the PIK3CA gene (c.3140A>G; SEQ ID NO: 273). RGENs with attenuated, one-base mismatched crRNAs, SEQ ID NO: 275 (WT-Specific RNA) and SEQ ID NO: 284 (Mutant-Specific RNA), distinguished the wild type and mutant PIK3CA sequences. FIG. 33C: RGEN-RFLP assays to distinguish between a wild-type NRAS gene sequence (SEQ ID NO: 293) and a recurrent oncogenic point mutation sequence in the NRAS gene (c.181C>A; SEQ ID NO: 294). RGENs with perfectly matched crRNAs, SEQ ID NO: 293 (WT-Specific RNA) and SEQ ID NO: 294 (Mutant-Specific RNA), distinguished the wild type and mutant NRAS sequences. FIG. 33D: RGEN-RFLP assays to distinguish between a wild-type BRAF gene sequence (SEQ ID NO: 295) and a recurrent oncogenic point mutation sequence in the BRAF gene (c.1799T>A; SEQ ID NO: 296). RGENs with perfectly matched crRNAs, SEQ ID NO: 295 (WT-Specific RNA) and SEQ ID NO: 296 (Mutant-Specific RNA), distinguished the wild type and mutant BRAF sequences. Genotypes of each cell line confirmed by Sanger sequencing are shown. Mismatched nucleotides are shown in box. Black arrows indicate DNA bands cleaved by RGENs.

BEST MODE FOR CARRYING OUT THE INVENTION

Figure 1A:
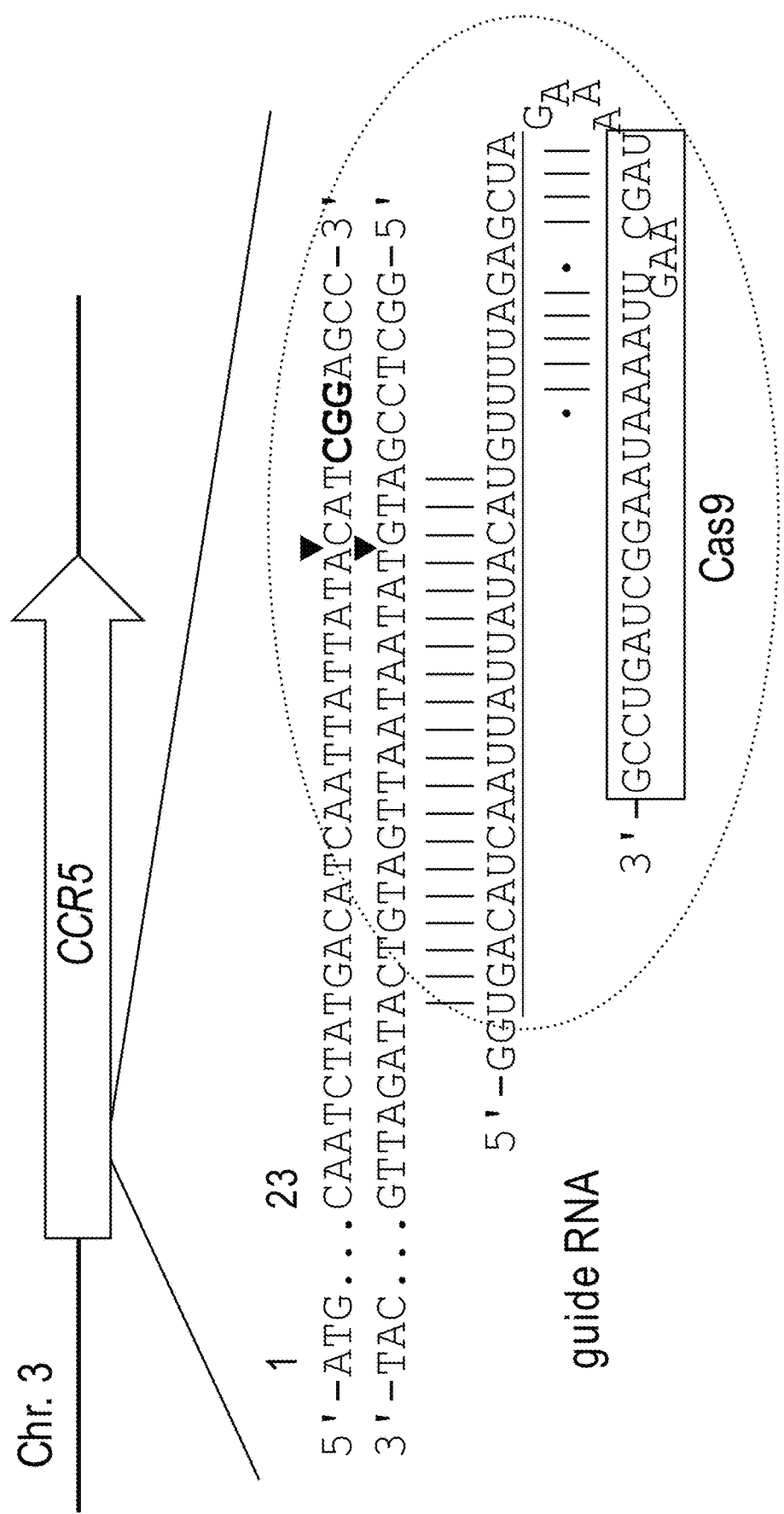

In accordance with one aspect of the invention, the present invention provides a composition for cleaving target DNA in eukaryotic cells or organisms comprising a guide RNA specific for target DNA or DNA that encodes the guide RNA, and Cas protein-encoding nucleic acid or Cas protein. In addition, the present invention provides a use of the composition for cleaving target DNA in eukaryotic cells or organisms comprising a guide RNA specific for target DNA or DNA that encodes the guide RNA, and Cas protein-encoding nucleic acid or Cas protein.

In the present invention, the composition is also referred to as a RNA-guided endonuclease (RGEN) composition.

ZFNs and TALENs enable targeted mutagenesis in mammalian cells, model organisms, plants, and livestock, but the mutation frequencies obtained with individual nucleases are widely different from each other. Furthermore, some ZFNs and TALENs fail to show any genome editing activities. DNA methylation may limit the binding of these engineered nucleases to target sites. In addition, it is technically challenging and time-consuming to make customized nucleases.

The present inventors have developed a new RNA-guided endonuclease composition based on Cas protein to overcome the disadvantages of ZFNs and TALENs.

Prior to the present invention, an endonuclease activity of Cas proteins has been known. However, it has not been known whether the endonuclease activity of Cas protein would function in an eukaryotic cell because of the complexity of the eukaryotic genome. Further, until now, a composition comprising Cas protein or Cas protein-encoding nucleic acid and a guide RNA specific for the target DNA to cleave a target DNA in eukaryotic cells or organisms has not been developed.

Compared to ZFNs and TALENs, the present RGEN composition based on Cas protein can be more readily customized because only the synthetic guide RNA component is replaced to make a new genome-editing nuclease. No sub-cloning steps are involved to make customized RNA guided endonucleases. Furthermore, the relatively small size of the Cas gene (for example, 4.2 kbp for Cas9) as compared to a pair of TALEN genes (~6 kbp) provides an advantage for this RNA-guided endonuclease composition in some applications such as virus-mediated gene delivery. Further, this RNA-guided endonuclease does not have off-target effects and thus does not induce unwanted mutations, deletion, inversions, and duplications. These features make the present RNA-guided endonuclease composition a scalable, versatile, and convenient tools for genome engineering in eukaryotic cells and organisms. In addition, RGEN can be designed to target any DNA sequence, almost any single nucleotide polymorphism or small insertion/deletion (indel) can be analyzed via RGEN-mediated RFLP. The specificity of RGENs is determined by the RNA component that hybridizes with a target DNA sequence of up to 20 base pairs (bp) in length and by the Cas9 protein that recognize the protospacer-adjacent motif (PAM). RGENs are readily reprogrammed by replacing the RNA component. Therefore, RGENs provide a platform to use simple and robust RFLP analysis for various sequence variations.

The target DNA may be an endogenous DNA, or artificial DNA, preferably, endogenous DNA.

As used herein, the term "Cas protein" refers to an essential protein component in the CRISPR/Cas system, forms an active endonuclease or nickase when complexed with two RNAs termed CRISPR RNA (crRNA) and transactivating crRNA (tracrRNA).

The information on the gene and protein of Cas are available from GenBank of National Center for Biotechnology Information (NCBI), without limitation.

The CRISPR-associated (cas) genes encoding Cas proteins are often associated with CRISPR repeat-spacer arrays. More than forty different Cas protein families have been described. Of these protein families, Cas1 appears to be ubiquitous among different CRISPR/Cas systems. There are three types of CRISPR-Cas system. Among them, Type II CRISPR/Cas system involving Cas9 protein and crRNA and tracrRNA is representative and is well known. Particular combinations of cas genes and repeat structures have been used to define 8 CRISPR subtypes (Ecoli, Ypest, Nmeni, Dvulg, Tneap, Hmari, Apern, and Mtube).

The Cas protein may be linked to a protein transduction domain. The protein transduction domain may be poly-arginine or a TAT protein derived from HIV, but it is not limited thereto.

The present composition may comprise Cas component in the form of a protein or in the form of a nucleic acid encoding Cas protein.

In the present invention, Cas protein may be any Cas protein provided that it has an endonuclease or nickase activity when complexed with a guide RNA.

Preferably, Cas protein is Cas9 protein or variants thereof.

The variant of the Cas9 protein may be a mutant form of Cas9 in which the cataylic asapartate residue is changed to any other amino acid. Preferably, the other amino acid may be an alanine, but it is not limited thereto.

Further, Cas protein may be the one isolated from an organism such as *Streptococcus* sp., preferably *Streptococcus pyogens* or a recombinant protein, but it is not limited thereto.

The Cas protein derived from *Streptococcus pyogens* may recognizes NGG trinucleotide. The Cas protein may comprise an amino acid sequence of SEQ ID NO: 109, but it is not limited thereto.

The term "recombinant" when used with reference, e.g., to a cell, nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, a recombinant Cas protein may be generated by reconstituting Cas protein-encoding sequence using the human codon table.

As for the present invention, Cas protein-encoding nucleic acid may be a form of vector, such as plasmid comprising Cas-encoding sequence under a promoter such as CMV or CAG. When Cas protein is Cas9, Cas9 encoding sequence may be derived from *Streptococcus* sp., and preferably derived from *Streptococcus pyogenes*. For example, Cas9 encoding nucleic acid may comprise the nucleotide sequence of SEQ ID. NO: 1. Moreover, Cas9 encoding nucleic acid may comprise the nucleotide sequence having homology of at least 50% to the sequence of SEQ ID NO: 1, preferably at least 60, 70, 80, 90, 95, 97, 98, or 99% to the SEQ ID NO:1, but it is not limited thereto. Cas9 encoding nucleic acid may comprise the nucleotide sequence of SEQ ID NOs. 108, 110, 106, or 107.

As used herein, the term "guide RNA" refers to a RNA which is specific for the target DNA and can form a complex with Cas protein and bring Cas protein to the target DNA.

In the present invention, the guide RNA may consist of two RNA, i.e., CRISPR RNA(crRNA) and transactivating crRNA(tracrRNA) or be a single-chain RNA(sgRNA) produced by fusion of an essential portion of crRNA and tracrRNA.

The guide RNA may be a dualRNA comprising a crRNA and a tracrRNA.

If the guide RNA comprises the essential portion of crRNA and tracrRNA and a portion complementary to a target, any guide RNA may be used in the present invention.

The crRNA may hybridize with a target DNA.

The RGEN may consist of Cas protein, and dualRNA (invariable tracrRNA and target-specific crRNA), or Cas protein and sgRNA (fusion of an essential portion of invariable tracrRNA and target-specific crRNA), and may be readily reprogrammed by replacing crRNA.

The guide RNA further comprises one or more additional nucleotides at the 5' end of the single-chain guide RNA or the crRNA of the dualRNA.

Preferably, the guide RNA further comprises 2-additional guanine nucleotides at the 5' end of the single-chain guide RNA or the crRNA of the dualRNA.

The guide RNA may be transferred into a cell or an organism in the form of RNA or DNA that encodes the guide RNA. The guide RNA may be in the form of an isolated RNA, RNA incorporated into a viral vector, or is encoded in a vector. Preferably, the vector may be a viral vector, plasmid vector, or *agrobacterium* vector, but it is not limited thereto.

A DNA that encodes the guide RNA may be a vector comprising a sequence coding for the guide RNA. For example, the guide RNA may be transferred into a cell or organism by transfecting the cell or organism with the isolated guide RNA or plasmid DNA comprising a sequence coding for the guide RNA and a promoter.

Alternatively, the guide RNA may be transferred into a cell or organism using virus-mediated gene delivery.

When the guide RNA is transfected in the form of an isolated RNA into a cell or organism, the guide RNA may be prepared by in vitro transcription using any in vitro transcription system known in the art. The guide RNA is preferably transferred to a cell in the form of isolated RNA rather than in the form of plasmid comprising encoding sequence for a guide RNA. As used herein, the term "isolated RNA" may be interchangeable to "naked RNA". This is cost- and time-saving because it does not require a step of cloning. However, the use of plasmid DNA or virus-mediated gene delivery for transfection of the guide RNA is not excluded.

The present RGEN composition comprising Cas protein or Cas protein-encoding nucleic acid and a guide RNA can specifically cleave a target DNA due to a specificity of the guide RNA for a target and an endonuclease or nickase activity of Cas protein.

As used herein, the term "cleavage" refers to the breakage of the covalent backbone of a nucleotide molecule.

In the present invention, a guide RNA may be prepared to be specific for any target which is to be cleaved. Therefore, the present RGEN composition can cleave any target DNA by manipulating or genotyping the target-specific portion of the guide RNA.

The guide RNA and the Cas protein may function as a pair. As used herein, the term "paired Cas nickase" may refer to the guide RNA and the Cas protein functioning as a pair. The pair comprises two guide RNAs. The guide RNA and Cas protein may function as a pair, and induce two nicks on different DNA strand. The two nicks may be separated by at least 100 bps, but are not limited thereto.

In the Example, the present inventors confirmed that paired Cas nickase allow targeted mutagenesis and large deletions of up to 1-kbp chromosomal segments in human cells. Importantly, paired nickases did not induce indels at off-target sites at which their corresponding nucleases induce mutations. Furthermore, unlike nucleases, paired nickases did not promote unwanted translocations associated with off-target DNA cleavages. In principle, paired nickases double the specificity of Cas9-mediated mutagenesis and will broaden the utility of RNA-guided enzymes in applications that require precise genome editing such as gene and cell therapy.

In the present invention, the composition may be used in the genotyping of a genome in the eukaryotic cells or organisms in vitro.

In one specific embodiment, the guide RNA may comprise the nucleotide sequence of Seq ID. No. 1, wherein the portion of nucleotide position 3-22 is a target-specific portion and thus, the sequence of this portion may be changed depending on a target.

As used herein, a eukaryotic cell or organism may be yeast, fungus, protozoa, plant, higher plant, and insect, or amphibian cells, or mammalian cells such as CHO, HeLa, HEK293, and COS-1, for example, cultured cells (in vitro), graft cells and primary cell culture (in vitro and ex vivo), and in vivo cells, and also mammalian cells including human, which are commonly used in the art, without limitation.

In one specific embodiment, it was found that Cas9 protein/single-chain guide RNA could generate site-specific DNA double-strand breaks in vitro and in mammalian cells, whose spontaneous repair induced targeted genome mutations at high frequencies.

Moreover, it was found that gene-knockout mice could be induced by the injection of Cas9 protein/guide RNA complexes or Cas9 mRNA/guide RNA into one-cell stage embryo and germ-line transmittable mutations could be generated by Cas9/guide RNA system.

Using Cas protein rather than a nucleic acid encoding Cas protein to induce a targeted mutagenesis is advantageous because exogenous DNA is not introduced into an organism. Thus, the composition comprising Cas protein and a guide RNA may be used to develop therapeutics or value-added crops, livestock, poultry, fish, pets, etc.

In accordance with another aspect of the invention, the present invent ion provides a composition for inducing targeted mutagenesis in eukaryotic cells or organisms, comprising a guide RNA specific for target DNA or DNA that encodes the guide RNA, and Cas protein-encoding nucleic acid or Cas protein. In addition, the present invention provides a use of the composition for inducing targeted mutagenesis in eukaryotic cells or organisms, comprising a guide RNA specific for target DNA or DNA that encodes the guide RNA, and Cas protein-encoding nucleic acid or Cas protein.

A guide RNA, Cas protein-encoding nucleic acid or Cas protein are as described in the above.

In accordance with another aspect of the invention, the present invention provides a kit for cleaving a target DNA or inducing targeted mutagenesis in eukaryotic cells or organisms comprising a guide RNA specific for target DNA or DNA that encodes the guide RNA, and Cas protein-encoding nucleic acid or Cas protein.

A guide RNA, Cas protein-encoding nucleic acid or Cas protein are as described in the above.

The kit may comprise a guide RNA and Cas protein-encoding nucleic acid or Cas protein as separate components or as one composition.

The present kit may comprise some additional components necessary for transferring the guide RNA and Cas component to a cell or an organism. For example, the kit may comprise an injection buffer such as DEPC-treated injection buffer, and materials necessary for analysis of mutation of a target DNA, but are not limited thereto.

In accordance with another aspect, the present invention provides a method for preparing a eukaryotic cell or organism comprising Cas protein and a guide RNA comprising a step of co-transfecting or serial-transfecting the eukaryotic cell or organism with a Cas protein-encoding nucleic acid or Cas protein, and a guide RNA or DNA that encodes the guide RNA.

A guide RNA, Cas protein-encoding nucleic acid or Cas protein are as described in the above.

In the present invention, a Cas protein-encoding nucleic acid or Cas protein and a guide RNA or DNA that encodes the guide RNA may be transferred into a cell by various methods known in the art, such as microinjection, electroporation, DEAE-dextran treatment, lipofection, nanoparticle-mediated transfection, protein transduction domain mediated transduction, virus-mediated gene delivery, and PEG-mediated transfection in protoplast, and so on, but are not limited thereto. Also, a Cas protein encoding nucleic acid or Cas protein and a guide RNA may be transferred into an organism by various method known in the art to administer a gene or a protein such as injection. A Cas protein-encoding nucleic acid or Cas protein may be transferred into a cell in the form of complex with a guide RNA, or separately. Cas protein fused to a protein transduction domain such as Tat can also be delivered efficiently into cells.

Preferably, the eukarotic cell or organisms is co-transfected or serial-transfected with a Cas9 protein and a guide RNA.

The serial-transfection may be performed by transfection with Cas protein-encoding nucleic acid first, followed by second transfection with naked guide RNA. Preferably, the second transfection is after 3, 6, 12, 18, 24 hours, but it is not limited thereto.

In accordance with another aspect, the present invention provides a eukaryotic cell or organism comprising a guide RNA specific for target DNA or DNA that encodes the guide RNA, and Cas protein-encoding nucleic acid or Cas protein.

The eukaryotic cells or organisms may be prepared by transferring the composition comprising a guide RNA specific for target DNA or DNA that encodes the guide RNA, and Cas protein-encoding nucleic acid or Cas protein into the cell or organism.

The eukaryotic cell may be yeast, fungus, protozoa, higher plant, and insect, or amphibian cells, or mammalian cells such as CHO, HeLa, HEK293, and COS-1, for example, cultured cells (in vitro), graft cells and primary cell culture (in vitro and ex vivo), and in vivo cells, and also mammalian cells including human, which are commonly used in the art, without limitation. Further the organism may be yeast, fungus, protozoa, plant, higher plant, insect, amphibian, or mammal.

In accordance with another aspect of the invent ion, the present invention provides a method for cleaving a target DNA or inducing targeted mutagenesis in eukaryotic cells or organisms, comprising a step of treating a cell or organism comprising a target DNA with a composition comprising a guide RNA specific for target DNA or DNA that encodes the guide RNA, and Cas protein-encoding nucleic acid or Cas protein.

The step of treating a cell or organism with the composition may be performed by transferring the present composition comprising a guide RNA specific for target DNA or DNA that encodes the guide RNA, and Cas protein-encoding nucleic acid or Cas protein into the cell or organism.

As described in the above, such transfer may be performed by microinjection, transfection, electroporation, and so on.

In accordance with another aspect of the invention, the present invention provides an embryo comprising a genome edited by the present RGEN composition comprising a guide RNA specific for target DNA or DNA that encodes the guide RNA, and Cas protein-encoding nucleic acid or Cas protein.

Any embryo can be used in the present invention, and for the present invent ion, the embryo may be an embryo of a mouse. The embryo may be produced by injecting PMSG (Pregnant Mare Serum Gonadotropin) and hCG (human Choirinic Gonadotropin) into a female mouse of 4 to 7 weeks and the super-ovulated female mouse may be mated to males, and the fertilized embryos may be collected from oviduts.

The present RGEN composition introduced into an embryo can cleave a target DNA complementary to the guide RNA by the action of Cas protein and cause a mutation in the target DNA. Thus, the embryo into which the present RGEN composition has been introduced has an edited genome.

In one specific embodiment, it was found that the present RGEN composition could cause a mutation in a mouse embryo and the mutation could be transmitted to offsprings.

A method for introducing the RGEN composition into the embryo may be any method known in the art, such as microinjection, stem cell insertion, retrovirus insertion, and so on. Preferably, a microinjection technique can be used.

In accordance with another aspect, the present invention provides a genome-modified animal obtained by transferring the embryo comprising a genome edited by the present RGEN composition into the oviducts of an animal.

In the present invention, the term "genome-modified animal" refers to an animal of which genome has been modified in the stage of embryo by the present RGEN composition and the type of the animal is not limited.

The genome-modified animal has mutations caused by a targeted mutagenesis based on the present RGEN composition. The mutations may be any one of deletion, insertion, translocation, inversion. The site of mutation depends on the sequence of guide RNA of the RGEN composition.

The genome-modified animal having a mutation of a gene may be used to determine the function of the gene.

In accordance with another aspect of the invention, the present invention provides a method of preparing a genome-modified animal comprising a step of introducing the present RGEN composition comprising a guide RNA specific for the target DNA or DNA that encodes the guide RNA and Cas protein-encoding nucleic acid or Cas protein into an embryo of an animal; and a step of transferring the embryo into a oviduct of pseudopregnant foster mother to produce a genome-modified animal.

The step of introducing the present RGEN composition may be accomplished by any method known in the art such as microinjection, stem cell insertion, retroviral insertion, and so on.

In accordance with another aspect of the invention, the present invention provides a plant regenerated form the genome-modified protoplasts prepared by the method for eukaryotic cells comprising the RGEN composition.

In accordance with another aspect of the invention, the present invention provides a composition for genotyping mutations or variations in an isolated biological sample, comprising a guide RNA specific for the target DNA sequence Cas protein. In addrion, the present invention provides a composition for genotyping nucleic acid sequences in pathogenic microorganisms in an isolated biological sample, comprising a guide RNA specific for the target DNA sequence and Cas protein.

A guide RNA, Cas protein-encoding nucleic acid or Cas protein are as described in the above.

As used herein the term "genotyping" refers to the "Restriction fragment length polymorphism (RFLP) assay".

RFLP may be used in 1) the detection of indel in cells or organisms induced by the engineered nucleases, 2) the genotyping naturally-occuring mutations or variations in cells or organisms, or 3) the genotyping the DNA of infected pathogenic microorganisms including virus or bacteria, etc.

The mutations or variation may be induced by engineered nucleases in cells.

The engineered nuclease may be a Zinc Finger Nuclease (ZFNs), Transcription Activator-Like Effector Nucleases (TALENs), or RGENs, but it is not limited thereto.

As used herein the term "biological sample" includes samples for analysis, such as tissues, cells, whole blood, semm, plasma, saliva, sputum, cerebrospinal fluid or urine, but is not limited thereto The mutations or variation may be a naturally-occurring mutations or variations.

The mutations or variations are induced by the pathogenic microorganisms. Namely, the mutations or variation occurs due to the infection of pathogenic microorganisms, when the pathogenic microorganisms are detected, the biological sample is identified as infected.

The pathogenic microorganisms may be virus or bacteria, but are not limited thereto.

Figure 22A:
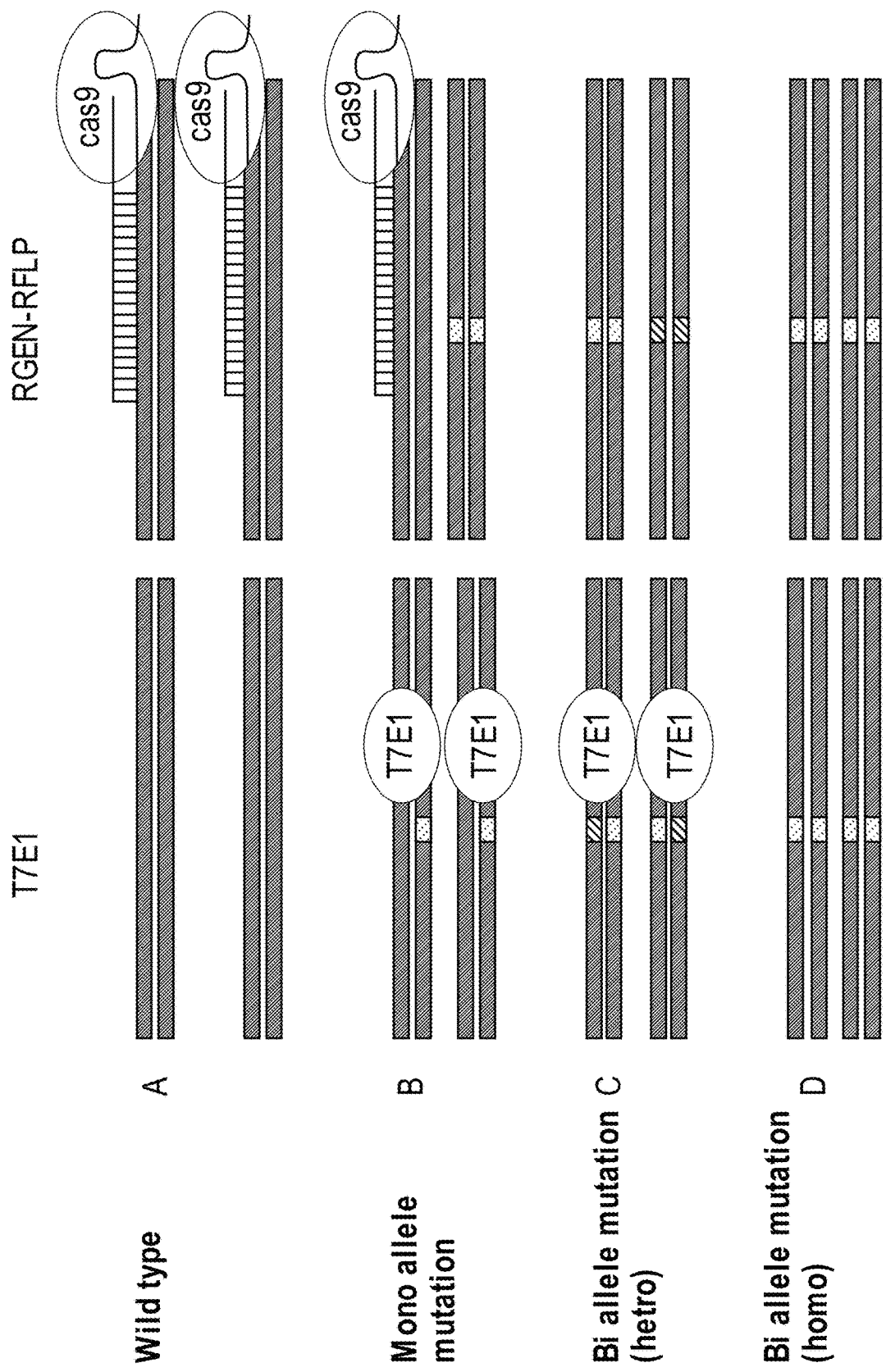
FIGS. 22A and 22B show a conceptual diagram of the T7E1 and RFLP assays.
Figure 22B:
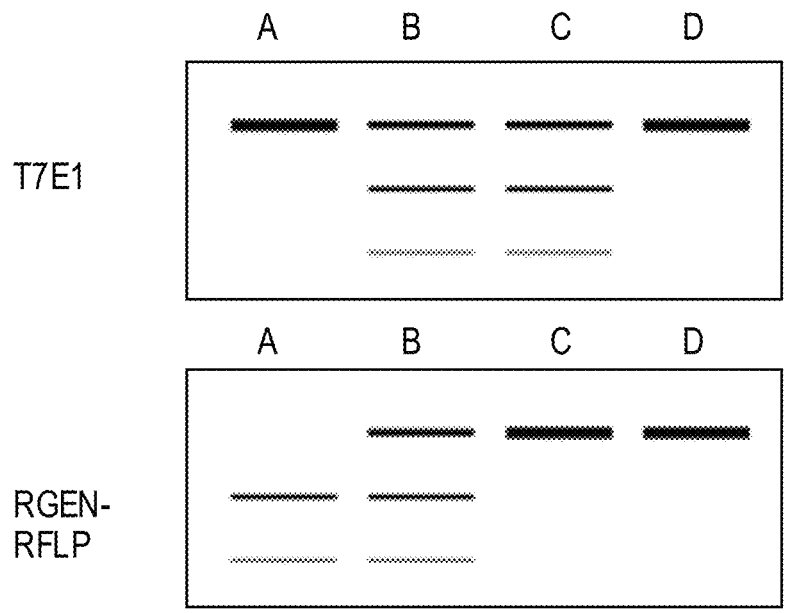

Engineered nuclease-induced mutations are detected by various methods, which include mismatch-sensitive Surveyor or T7 endonuclease I (T7E1) assays, RFLP analysis, fluorescent PCR, DNA melting analysis, and Sanger and deep sequencing. The T7E1 and Surveyor assays are widely used but often underestimate mutation frequencies because the assays detect heteroduplexes (formed by the hybridization of mutant and wild-type sequences or two different mutant sequences); they fail to detect homoduplexes formed by the hybridization of two identical mutant sequences. Thus, these assays cannot distinguish homozygous bialleic mutant clones from wild-type cells nor heterozygous biallelic mutants from heterozygous monoalleic mutants (FIG. 22). In addition, sequence polymorphisms near the nuclease target site can produce confounding results because the enzymes can cleave heteroduplexes formed by hybridization of these different wild-type alleles. RFLP analysis is free of these limitations and therefore is a method of choice. Indeed, RFLP analysis was one of the first methods used to detect engineered nuclease-mediated mutations. Unfortunately, however, it is limited by the availability of appropriate restriction sites.

In accordance with another aspect of the invention, the present invention provides a kit for genotyping mutations or variations in an isolated biological sample, comprising the composition for genotyping mutations or variations in an isolated biological sample. In addition, the present invention provides a kit for genotyping nucleic acid sequences in pathogenic microorganisms in an isolated biological sample, comprising a guide RNA specific for the target DNA sequence and Cas protein.

A guide RNA, Cas protein-encoding nucleic acid or Cas protein are as described in the above.

In accordance with another aspect of the invention, the present invention provides a method of genotyping mutations or variations in an isolated biological sample, using the composition for genotyping mutations or variations in an isolated biological sample. In addition, the present invention provides a method of genotyping nucleic acid sequences in pathogenic microorganisms in an isolated biological sample, comprising a guide RNA specific for the target DNA sequence and Cas protein.

A guide RNA, Cas protein-encoding nucleic acid or Cas protein are as described in the above.

MODE FOR THE INVENTION

Hereinafter, the present invention will be described in more detail with reference to Examples. However, these Examples are for illustrative purposes only, and the invention is not intended to be limited by these Examples.

Example 1

Genome Editing Assay 1-1. DNA Cleavage Activity of Cas9 Protein

Firstly, the DNA cleavage activity of Cas9 derived from *Streptococcus pyogenes* in the presence or absence of a chimeric guide RNA in vitro was tested.

To this end, recombinant Cas9 protein that was expressed in and purified from *E. coli* was used to cleave a predigested or circular plasmid DNA that contained the 23-base pair (bp) human CCR5 target sequence. A Cas9 target sequence consists of a 20-bp DNA sequence complementary to crRNA or a chimeric guide RNA and the trinucleotide (5'-NGG-3') protospacer adjacent motif (PAM) recognized by Cas9 itself (FIG. 1A).

Specifically, the Cas9-coding sequence (4,104 bp), derived from *Streptococcus pyogenes* strain M1 GAS (NC_002737.1), was reconstituted using the human codon usage table and synthesized using oligonucleotides. First, 1-kb DNA segments were assembled using overlapping ~35-mer oligonucleotides and Phusion polymerase (New England Biolabs) and cloned into T-vector (SolGent). A full-length Cas9 sequence was assembled using four 1-kbp DNA segments by overlap PCR. The Cas9-encoding DNA segment was subcloned into p3s, which was derived from pcDNA3.1 (Invitrogen). In this vector, a peptide tag (NH2-GGSGPPKKRKVYPYDVPDYA-COOH, SEQ ID NO: 2) containing the HA epitope and a nuclear localization signal (NLS) was added to the C-terminus of Cas9. Expression and nuclear localization of the Cas9 protein in HEK 293T cells were confirmed by western blotting using anti-HA antibody (Santa Cruz).

Then, the Cas9 cassette was subcloned into pET28-b(+) and transformed into BL21 (DE3). The expression of Cas9 was induced using 0.5 mM IPTG for 4 b at 25° C. The Cas9 protein containing the His6-tag at the C terminus was purified using Ni-NTA agarose resin (Qiagen) and dialyzed against 20 mM HEPES (pH 7.5), 150 mM KCl, 1 mM DTT, and 10% glycerol (1). Purified Cas9 (50 nM) was incubated with super-coiled or pre-digested plasmid DNA (300 ng) and chimeric RNA (50 nM) in a reaction volume of 20 μl in NEB buffer 3 for 1 h at 37° C. Digested DNA was analyzed by electrophoresis using 0.8% agarose gels.

Cas9 cleaved the plasmid DNA efficiently at the expected position only in the presence of the synthetic RNA and did not cleave a control plasmid that lacked the target sequence (FIG. 1B).

1-2. DNA Cleavage by Cas9/Guide RNA Complex in Human Cells

A RFP-GFP reporter was used to investigate whether the Cas9/guide RNA complex can cleave the target sequence incorporated between the RFP and GFP sequences in mammalian cells.

Figure 2A:
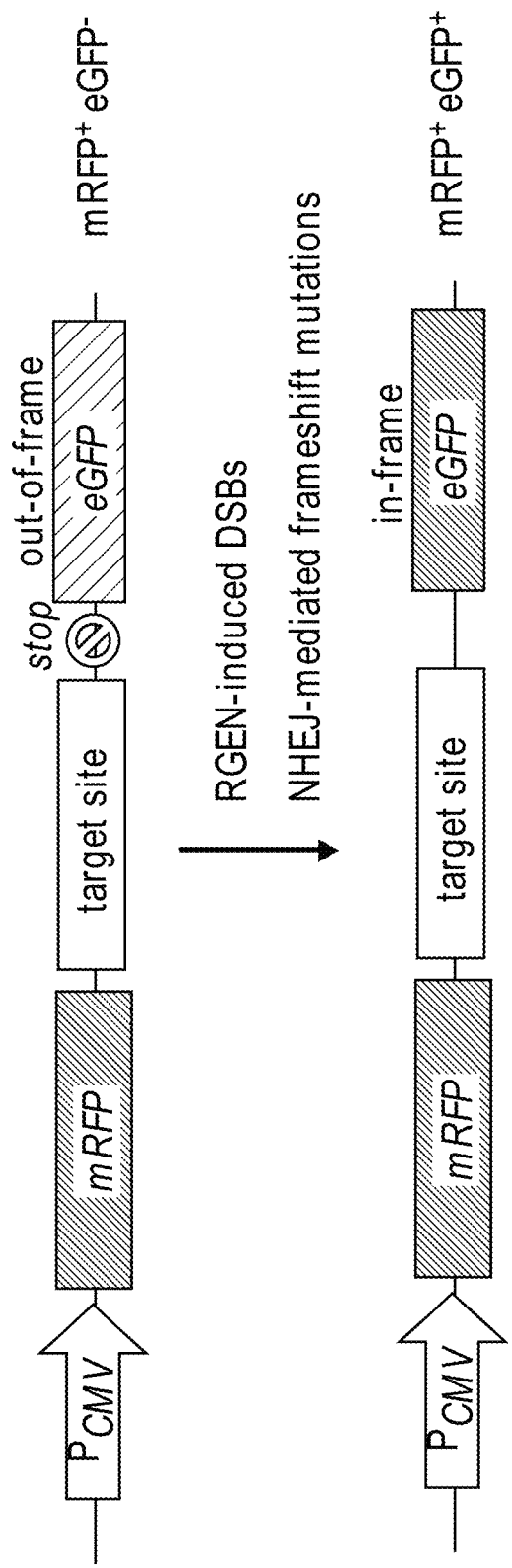
FIGS. 2A and 2B show Cas9-induced mutagenesis at an episomal target site.
Figure 2B:
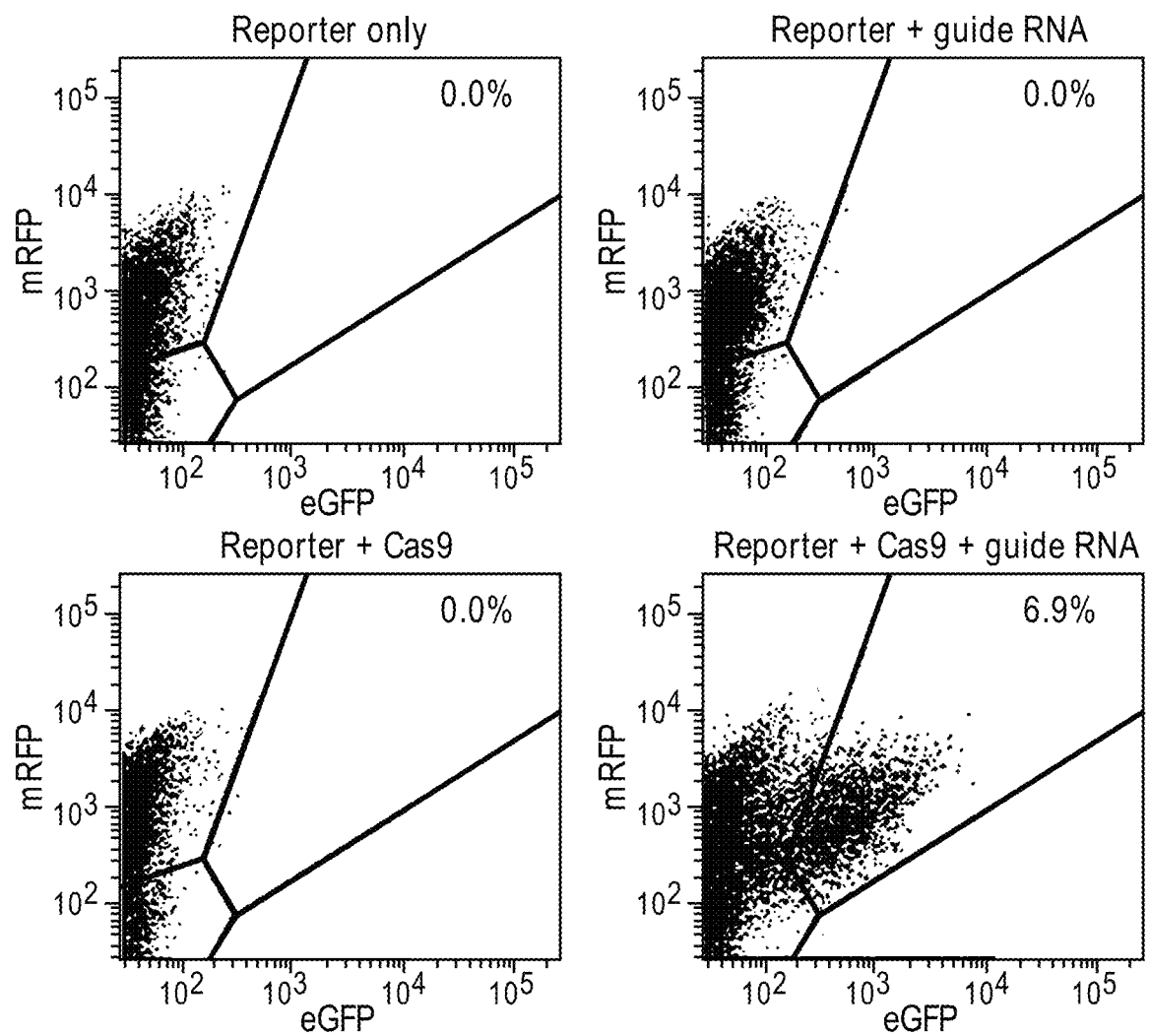

In this reporter, the GFP sequence is fused to the RFP sequence out-of-frame (2). The active GFP is expressed only when the target sequence is cleaved by site-specific nucleases, which causes frameshifting small insertions or deletions (indels) around the target sequence via error-prone non-homologous end-joining (NHEJ) repair of the double-strand break (DSB) (FIG. 2).

The RFP-GFP reporter plasmids used in this study were constructed as described previously (2). Oligonucleotides corresponding to target sites (Table 1) were synthesized (Macrogen) and annealed. The annealed oligonucleotides were ligated into a reporter vector digested with EcoRI and BamHI.

HEK 293T cells were co-transfected with Cas9-encoding plasmid (0.8 μg) and the RFP-GFP reporter plasmid (0.2 μg) in a 24-well plate using Lipofectamine 2000 (Invitrogen).

Meanwhile, the in vitro transcribed chimeric RNA had been prepared as follows. RNA was in vitro transcribed through run-off reactions using the MEGAshortscript T7 kit (Ambion) according to the manufacturer's manual. Templates for RNA in vitro transcription were generated by annealing two complementary single strand DNAs or by PCR amplification (Table 1). Transcribed RNA was resolved on a 8% denaturing urea-PAGE gel. The gel slice containing RNA was cut out and transferred to probe elution buffer. RNA was recovered in nuclease-free water followed by phenol:chloroform extraction, chloroform extraction, and ethanol precipitation. Purified RNAs were quantified by spectrometry.

At 12 h post transfection, chimeric RNA (1 μg) prepared by in vitro transcription was transfected using Lipofectamine 2000.

At 3d post-transfection, transfected cells were subjected to flow cytometry and cells expressing both RFP and GFP were counted.

It was found that GFP-expressing cells were obtained only when the cells were transfected first with the Cas9 plasmid and then with the guide RNA 12 h later (FIG. 2), demonstrating that RGENs could recognize and cleave the target DNA sequence in cultured human cells. Thus GFP-expressing cells were obtained by serial-transfection of the Cas9 plasmid and the guide RNA rather than co-transfection.

TABLE 1

| Gene | | sequence (5' to 3') | SEQ ID NO. |
|---|---|---|---|
| Oligonucleotides used for the construction of the reporter plasmid ||||
| CCR5 | F | AATTCATGACATCAATTATTATACATCGGAGGAG | 3 |
|  | R | GATCCTCCTCCGATGTATAATAATTGATGTCATG | 4 |
| Primers used in the T7E1 assay ||||
| CCR5 | F1 | CTCCATGGTGCTATAGAGCA | 5 |
|  | F2 | GAGCCAAGCTCTCCATCTAGT | 6 |
|  | R | GCCCTGTCAAGAGTTGACAC | 7 |
| C4BPB | F1 | TATTTGGCTGGTTGAAAGGG | 8 |
|  | R1 | AAAGTCATGAAATAAACACACCCA | 9 |
|  | F2 | CTGCATTGATATGGTAGTACCATG | 10 |
|  | R2 | GCTGTTCATTGCAATGGAATG | 11 |
| Primers used for the amplification of off-target sites ||||
| ADCY5 | F1 | GCTCCCACCTTAGTGCTCTG | 12 |
|  | R1 | GGTGGCAGGAACCTGTATGT | 13 |
|  | F2 | GTCATTGGCCAGAGATGTGGA | 14 |
|  | R2 | GTCCCATGACAGGCGTGTAT | 15 |
| KCNJ6 | F | GCCTGGCCAAGTTTCAGTTA | 16 |
|  | R1 | TGGAGCCATTGGTTTGCATC | 17 |
|  | R2 | CCAGAACTAAGCCGTTTCTGAC | 18 |
| CNTNAP2 | F1 | ATCACCGACAACCAGTTTCC | 19 |
|  | F2 | TGCAGTGCAGACTCTTTCCA | 20 |
|  | R | AAGGACACAGGGCAACTGAA | 21 |
| N/A Chr. 5 | F1 | TGTGGAACGAGTGGTGACAG | 22 |
|  | R1 | GCTGGATTAGGAGGCAGGATTC | 23 |
|  | F2 | GTGCTGAGAACGCTTCATAGAG | 24 |
|  | R2 | GGACCAAAGGACATTCTTCTCAC | 25 |
| Primers used for the detection of chromosomal deletions ||||
| Deletion | F | CCACATCTCGTTCTCGGTTT | 26 |
|  | R | TCACAAGCCCACAGATATTT | 27 |

1-3. Targeted Disruption of Endogeneous Genes in Mammalian Cells by RGEN

To test whether RGENs could be used for targeted disruption of endogenous genes in mammalian cells, genomic DNA isolated from transfected cells using T7 endonuclease I (T7E1), a mismatch-sensitive endonuclease that specifically recognizes and cleaves heteroduplexes formed by the hybridization of wild-type and mutant DNA sequences was analyzed (3).

To introduce DSBs in mammalian cells using RGENs, $2\times10^6$ K562 cells were transfected with 20 μg of Cas9-encoding plasmid using the 4D-Nucleofector, SF Cell Line 4D-Nucleofector X Kit, Program FF-120 (Lonza) according to the manufacturer's protocol. For this experiment, K562 (ATCC, CCL-243) cells were grown in RPMI-1640 with 10% FBS and the penicillin/streptomycin mix (100 U/ml and 100 μg/ml, respectively).

After 24 h, 10-40 μg of in vitro transcribed chimeric RNA was nucleofected into $1\times10^6$ K562 cells. The in vitro transcribed chimeric RNA had been prepared as described in the Example 1-2.

Cells were collected two days after RNA transfection and genomic DNA was isolated. The region including the target site was PCR-amplified using the primers described in Table 1. The amplicons were subjected to the T7E1 assay as described previously (3). For sequencing analysis, PCR products corresponding to genomic modifications were purified and cloned into the T-Blunt vector using the T-Blunt PCR Cloning Kit (SolGent). Cloned products were sequenced using the M13 primer.

Figure 3A:
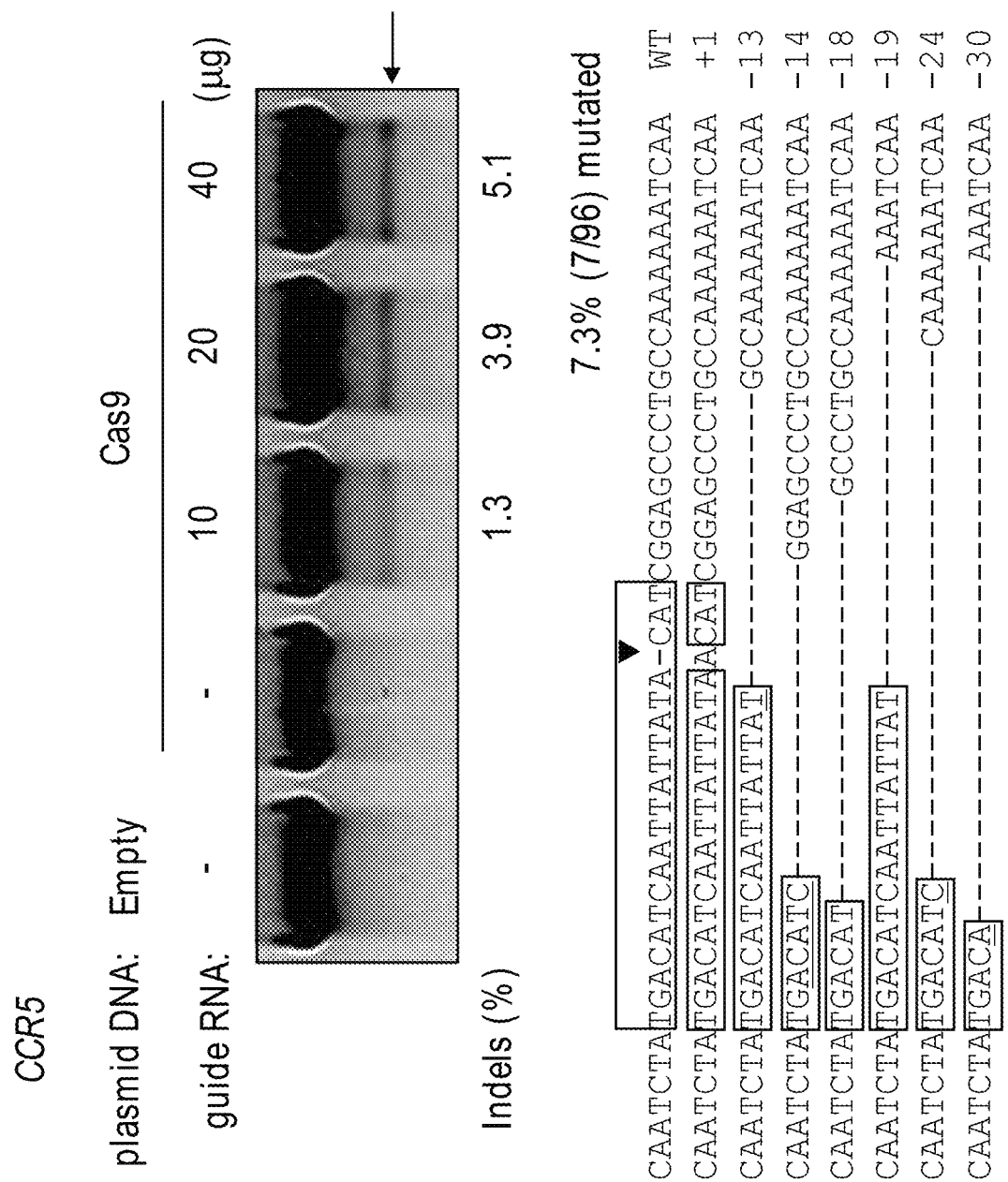
FIGS. 3A and 3B show RGEN-driven mutations at endogenous chromosomal sites.

It was found that mutations were induced only when the cells were transfected serially with Cas9-encoding plasmid and then with guide RNA (FIG. 3). Mutation frequencies (Indels (%) in FIG. 3A) estimated from the relative DNA band intensities were RNA-dosage dependent, ranging from 1.3% to 5.1%. DNA sequencing analysis of the PCR amplicons corroborated the induction of RGEN-mediated mutations at the endogenous sites. Indels and microhomologies, characteristic of error-prone NHEJ, were observed at the target site. The mutation frequency measured by direct sequencing was 7.3% (=7 mutant clones/96 clones), on par with those obtained with zinc finger nucleases (ZFNs) or transcription-activator-like effector nucleases (TALENs).

Serial-transfection of Cas9 plasmid and guide RNA was required to induce mutations in cells. But when plasmids that encode guide RNA, serial transfection was unnecessary and cells were co-transfected with Cas9 plasmid and guide RNA-encoding plasmid.

In the meantime, both ZFNs and TALENs have been successfully developed to disrupt the human CCR5 gene (3-6), which encodes a G-protein-coupled chemokine receptor, an essential co-receptor of HIV infection. A CCR5-specific ZFN is now under clinical investigation in the US for the treatment of AIDS (7). These ZFNs and TALENs, however, have off-target effects, inducing both local mutations at sites whose sequences are homologous to the on-target sequence (6, 8-10) and genome rearrangements that arise from the repair of two concurrent DSBs induced at on-target and off-target sites (11-12). The most striking off-target sites associated with these CCR5-specific engineered nucleases reside in the CCR2 locus, a close homolog of CCR5, located 15-kbp upstream of CCR5. To avoid off-target mutations in the CCR2 gene and unwanted deletions, inversions, and duplications of the 15-kbp chromosomal segment between the CCR5 on-target and CCR2 off-target sites, the present inventors intentionally chose the target site of our CCR5-specific RGEN to recognize a region within the CCR5 sequence that has no apparent homology with the CCR2 sequence.

Figure 4C:
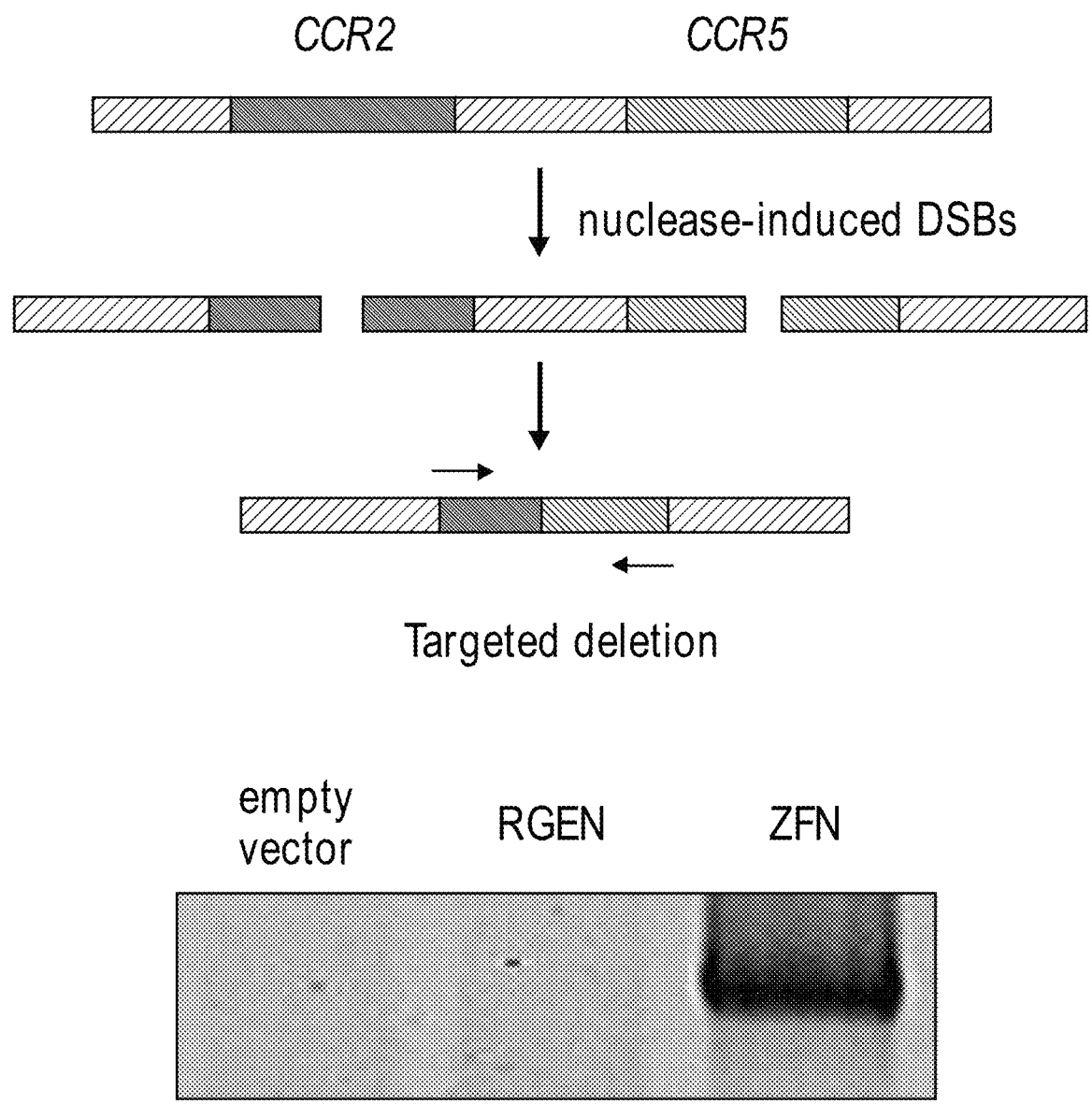

The present inventors investigated whether the CCR5-specific RGEN had off-target effects. To this end, we searched for potential off-target sites in the human genome by identifying sites that are most homologous to the intended 23-bp target sequence. As expected, no such sites were found in the CCR2 gene. Instead, four sites, each of which carries 3-base mismatches with the on-target site, were found (FIG. 4A). The T7E1 assays showed that mutations were not detected at these sites (assay sensitivity, ~0.5%), demonstrating exquisite specificities of RGENs (FIG. 4B). Furthermore, PCR was used to detect the induction of chromosomal deletions in cells separately transfected with plasmids encoding the ZFN and RGEN specific to CCR5. Whereas the ZFN induced deletions, the RGEN did not (FIG. 4C).

Figure 3B:
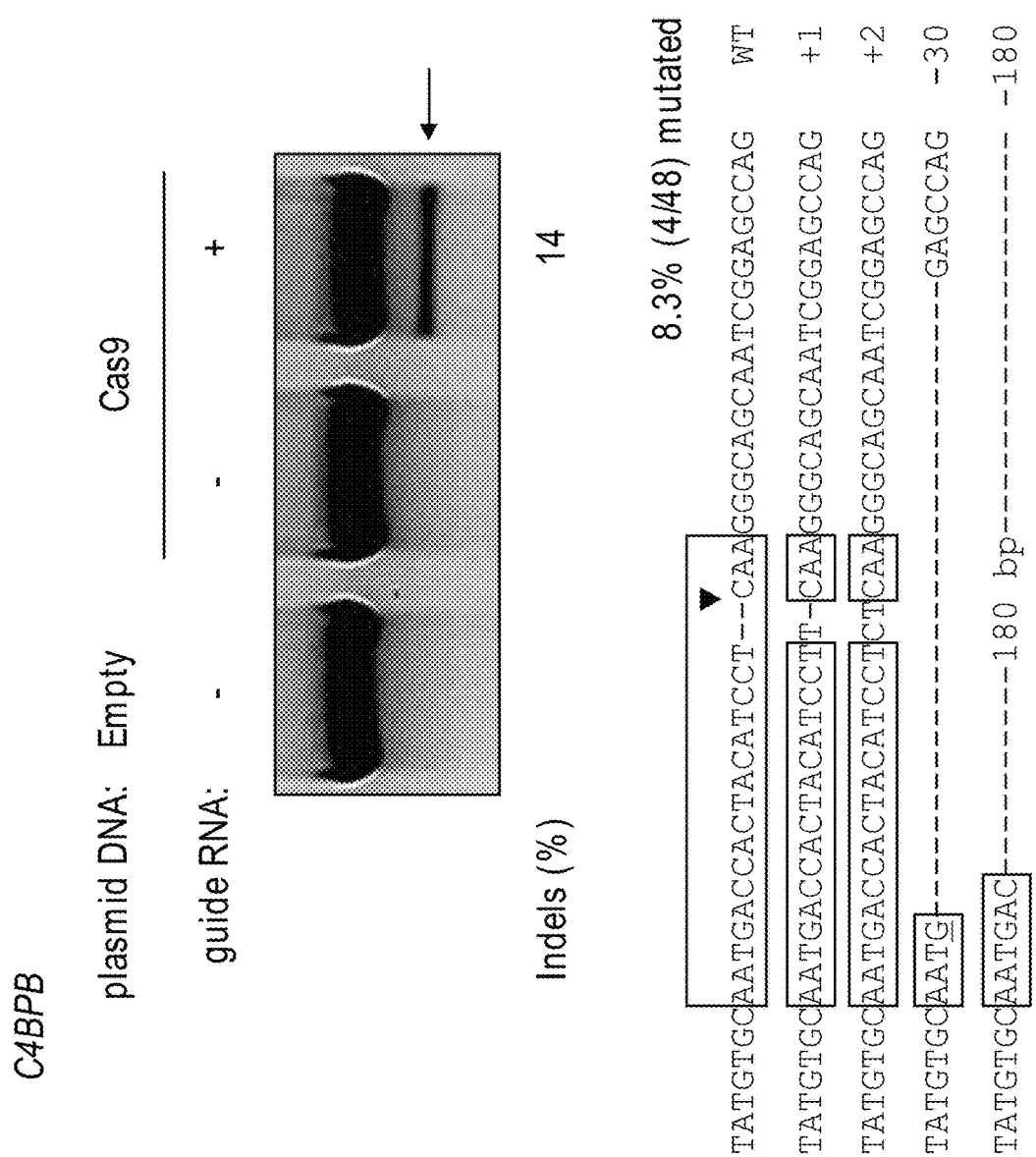

Next, RGENs was reprogrammed by replacing the CCR5-specific guide RNA with a newly-synthesized RNA designed to target the human C4BPB gene, which encodes the beta chain of C4b-binding protein, a transcription factor. This RGEN induced mutations at the chromosomal target site in K562 cells at high frequencies (FIG. 3B). Mutation frequencies measured by the T7E1 assay and by direct sequencing were 14% and 8.3% (=4 mutant clones/48 clones), respectively. Out of four mutant sequences, two clones contained a single-base or two-base insertion precisely at the cleavage site, a pattern that was also observed at the CCR5 target site. These results indicate that RGENs cleave chromosomal target DNA at expected positions in cells.

Example 2

Proteinaceous RGEN-Mediated Genome Editing

RGENs can be delivered into cells in many different forms. RGENs consist of Cas9 protein, crRNA, and tracrRNA. The two RNAs can be fused to form a single-chain guide RNA (sgRNA). A plasmid that encodes Cas9 under a promoter such as CMV or CAG can be transfected into cells. crRNA, tracrRNA, or sgRNA can also be expressed in cells using plasmids that encode these RNAs. Use of plasmids, however, often results in integration of the whole or part of the plasmids in the host genome. The bacterial sequences incorporated in plasmid DNA can cause unwanted immune response in vivo. Cells transfected with plasmid for cell therapy or animals and plants derived from DNA-transfected cells must go through a costly and lengthy regulation procedure before market approval in most developed countries. Furthermore, plasmid DNA can persist in cells for several days post-transfection, aggravating off-target effects of RGENs.

Here, we used recombinant Cas9 protein complexed with in vitro transcribed guide RNA to induce targeted disruption of endogenous genes in human cells. Recombinant Cas9 protein fused with the hexa-histidine tag was expressed in and purified from *E. coli* using standard Ni ion affinity chromatography and gel filtration. Purified recombinant Cas9 protein was concentrated in storage buffer (20 mM HEPES pH 7.5, 150 mM KCl, 1 mM DTT, and 10% glycerol). Cas9 protein/sgRNA complex was introduced directly into K562 cells by nucleofection: $1 \times 10^6$ K562 cells were transfected with 22.5-225 (1.4-14 µM) of Cas9 protein mixed with 100 ug (29 µM) of in vitro transcribed sgRNA (or crRNA 40 ug and tracrRNA 80 ug) in 100 µl solution using the 4D-Nucleofector, SF Cell Line 4D-Nucleofector X Kit, Program FF-120 (Lonza according to the manufacturer's protocol. After nucleofection, cells were placed in growth media in 6-well plates and incubated for 48 hr. When $2 \times 10^5$ K562 cells were transfected with 1/5 scale-downed protocol, 4.5-45 µg of Cas9 protein mixed with 6-60 ug of in vitro transcribed sgRNA (or crRNA 8 µg and tracrRNA 16 µg; were used and nucleofected in 20 µl solution. Nucleofected cell were then placed in growth media in 48-well plates. After 48 hr, cells were collected and genomic DNA was isolated. The genomic DNA region spanning the target site was PCR-amplified and subjected to the T7E1 assay.

Figure 10A:
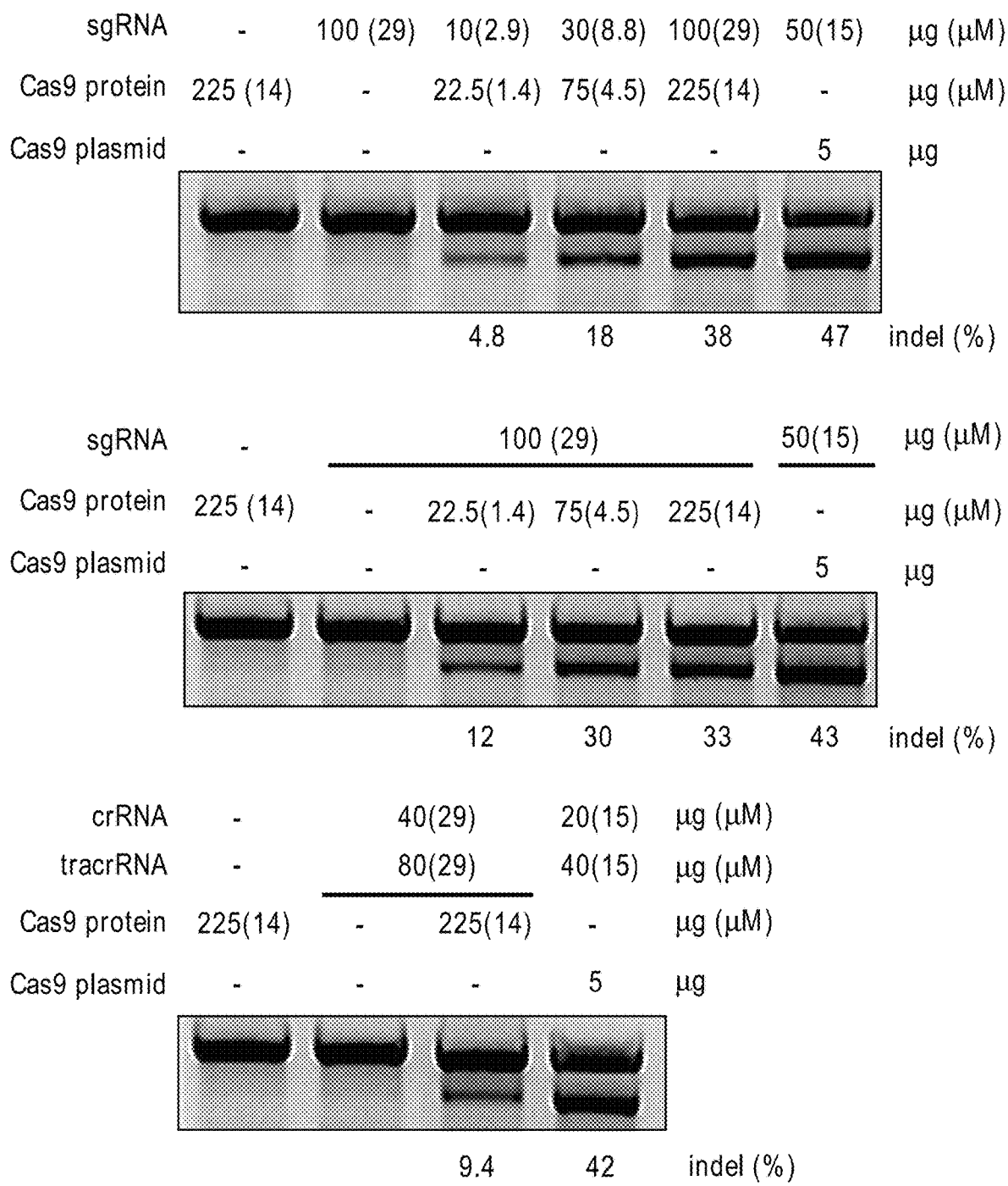

As shown in FIG. 10, Cas9 protein/sgRNA complex induced targeted mutation at the CCR5 locus at frequencies that ranged from 4.8 to 38% in a sgRNA or Cas9 protein dose-dependent manner, on par with the frequency obtained with Cas9 plasmid transfection (45%). Cas9 protein/crRNA/tracrRNA complex was able to induce mutations at a frequency of 9.4%. Cas9 protein alone failed to induce mutations. When $2 \times 10^5$ cells were transfected with 1/5 scale-downed doses of Cas9 protein and sgRNA, mutation frequencies at the CCR5 locus ranged from 2.7 to 57% in a dose-dependent manner, greater than that obtained with co-transfection of Cas9 plasmid and sgRNA plasmid (32%).

We also tested Cas9 protein/sgRNA complex that targets the ABCC11 gene and found that this complex induced indels at a frequency of 35%, demonstrating general utility of this method.

TABLE 2

Sequences of guide RNA

| Target | RNA type | RNA sequence (5' to 3') | Length | SEQ ID NO |
|---|---|---|---|---|
| CCR5 | sgRNA | GGUGACAUCAAUUAUUAUACAUGUUUUAGAGCUAG<br>AAAUAGCAAGUUAAAAUAAGGCUAGUCCGUUAUCA<br>ACUUGAAAAAGUGGCACCGAGUCGGUGCUUUUUUU | 104 bp | 28 |
| | crRNA | GGUGACAUCAAUUAUUAUACAUGUUUUAGAGCUAU<br>GCUGUUUUG | 44 bp | 29 |
| | tracrRNA | GGAACCAUUCAAAACAGCAUAGCAAGUUAAAAUAA<br>GGCUAGUCCGUUAUCAACUUGAAAAAGUGGCACCG<br>AGUCGGUGCUUUUUUU | 86 bp | 30 |

Example 3

RNA-Guided Genome Editing in Mice

To examine the gene-targeting potential of RGENs in pronuclear (PN)-stage mouse embryos, the forkhead box N1 (Foxn1) gene, which is important for *thymus* development and keratinocyte differentiation (Nehls et al., 1996), and the protein kinase, DNA activated, catalytic polypeptide (Prkdc) gene, which encodes an enzyme critical for DNA DSB repair and recombination (Taccioli et al., 1998) were used.

Figure 5A:
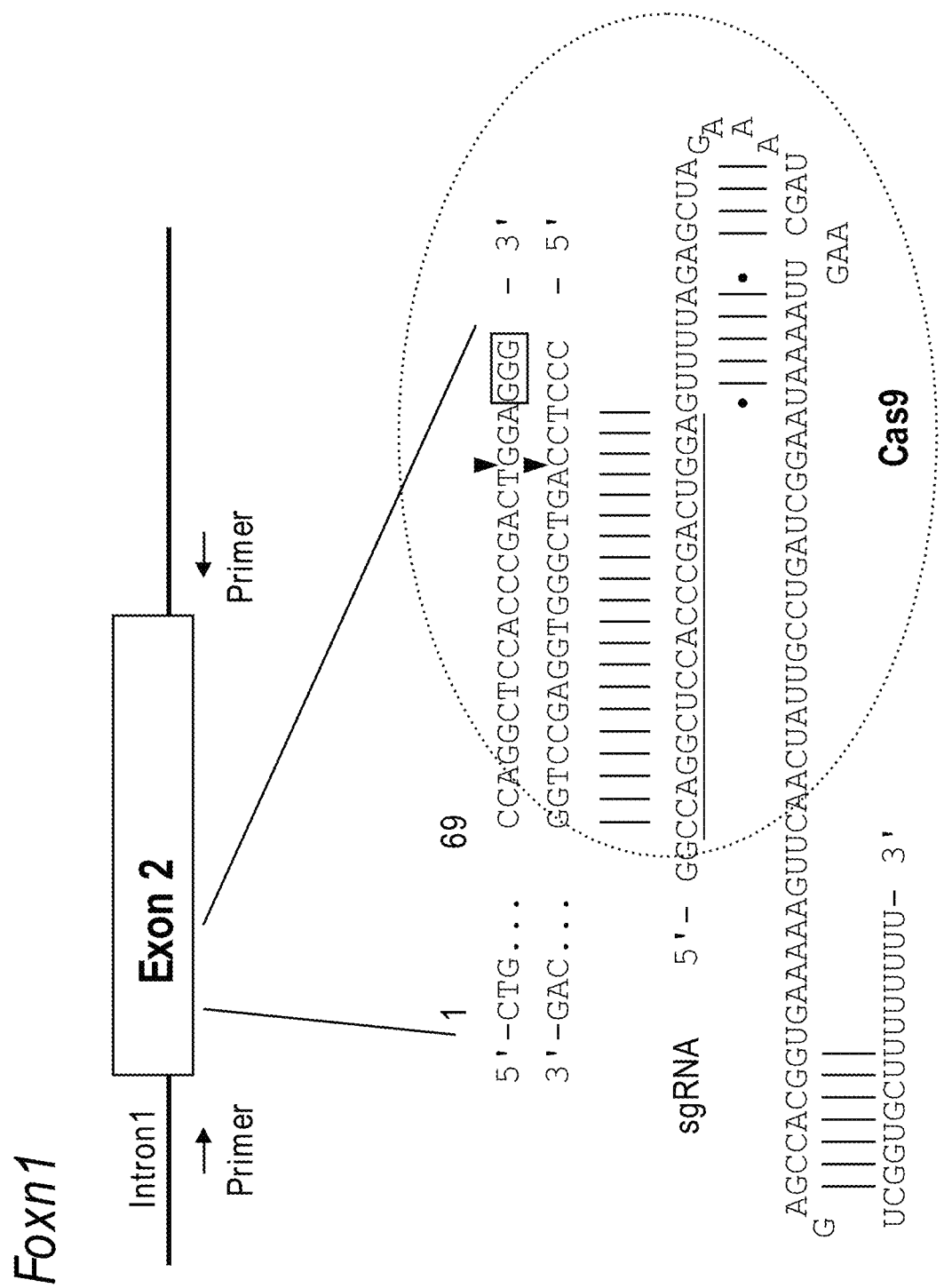

To evaluate the genome-editing activity of the Foxn1-RGEN, we injected Cas9 mRNA (10-ng/µl solution) with various doses of the sgRNA (FIG. 5a) into the cytoplasm of PN-stage mouse embryos, and conducted T7 endonuclease I (T7E1) assays (Kim et al. 2009) using genomic DNAs obtained from in vitro cultivated embryos (FIG. 6a).

Alternatively, we directly injected the RGEN in the form of recombinant Cas9 protein (0.3 to 30 ng/µl) complexed with the two-fold molar excess of Foxn1-specific sgRNA (0.14 to 14 ng/µl) into the cytoplasm or pronucleus of one-cell mouse embryos, and analyzed mutations in the Foxn1 gene using in vitro cultivated embryos (FIG. 7).

Specifically, Cas9 mRNA and sgRNAs were synthesized in vitro from linear DNA templates using the mMESSAGE mMACHINE T7 Ultra kit (Ambion) and MEGAshortscript T7 kit (Ambion), respectively, according to the manufacturers' instructions, and were diluted with appropriate amounts of diethyl pyrocarbonate (DEPC, Sigma)-treated injection buffer (0.25 mM EDTA, 10 mM Tris, pH 7.4). Templates for sgRNA synthesis were generated using oligonucleotides listed in Table 3. Recombinant Cas9 protein was obtained from ToolGen, Inc.

TABLE 3

| RNA Name | Direction | Sequence (5' to 3') | SEQ ID NO |
|---|---|---|---|
| Foxn1 #1 sgRNA | F | GAAATTAATACGACTCACTATAGGCAGTCTGACG TCACACTTCCGTTTTAGAGCTAGAAATAGCAAGT TAAAATAAGGCTAGTCCG | 31 |
| Foxn1 #2 sgRNA | F | GAAATTAATACGACTCACTATAGGACTTCCAGGC TCCACCCGACGTTTTAGAGCTAGAAATAGCAAGT TAAAATAAGGCTAGTCCG | 32 |
| Foxn1 #3 sgRNA | F | GAAATTAATACGACTCACTATAGGCCAGGCTCCA CCCGACTGGAGTTTTAGAGCTAGAAATAGCAAGT TAAAATAAGGCTAGTCCG | 33 |
| Foxn1 #4 sgRNA | F | GAAATTAATACGACTCACTATAGGACTGGAGGGC GAACCCCAAGGTTTTAGAGCTAGAAATAGCAAGT TAAAATAAGGCTAGTCCG | 34 |
| Foxn1 #5 sgRNA | F | GAAATTAATACGACTCACTATAGGACCCCAAGGG GACCTCATGCGTTTTAGAGCTAGAAATAGCAAGT TAAAATAAGGCTAGTCCG | 35 |
| Prkdc #1 sgRNA | F | GAAATTAATACGACTCACTATAGGTTAGTTTTTT CCAGAGACTTGTTTTAGAGCTAGAAATAGCAAGT TAAAATAAGGCTAGTCCG | 36 |
| Prkdc #2 sgRNA | F | GAAATTAATACGACTCACTATAGGTTGGTTTGCT TGTGTTTATCGTTTTAGAGCTAGAAATAGCAAGT TAAAATAAGGCTAGTCCG | 37 |
| Prkdc #3 sgRNA | F | GAAATTAATACGACTCACTATAGGCACAAGCAAA CCAAAGTCTCGTTTTAGAGCTAGAAATAGCAAGT TAAAATAAGGCTAGTCCG | 38 |
| Prkdc #4 sgRNA | F | GAAATTAATACGACTCACTATAGGCCTCAATGCT AAGCGACTTCGTTTTAGAGCTAGAAATAGCAAGT TAAAATAAGGCTAGTCCG | 39 |

All animal experiments were performed in accordance with the Korean Food and Drug Administration (KFDA) guidelines. Protocols were reviewed and approved by the Institutional Animal Care and Use Committees (IACUC) of the Laboratory Animal Research Center at Yonsei University (Permit Number: 2013-0099). All mice were maintained in the specific pathogen-free facility of the Yonsei Laboratory Animal Research Center. FVB/NTac (Taconic) and ICR mouse strains were used as embryo donors and foster mothers, respectively. Female FVB/NTac mice (7-8 weeks old) were super-ovulated by intra-peritoneal injections of 5 IU pregnant mare serum gonadotropin (PMSG, Sigma) and 5 IU human chorionic gonadotropin (hCG, Sigma) at 48-hour intervals. The super-ovulated female mice were mated to PVB/NTac stud males, and fertilized embryos were collected from oviducts.

Cas9 mRNA and sgRNAs in M2 medium (Sigma) were injected into the cytoplasm of fertilized eggs with well-recognized pronuclei using a Piezo-driven micromanipulator (Prime Tech).

In the case of injection of recombinant Cas9 protein, the recombinant Cas9 protein: Foxn1-sgRNA complex was diluted with DEPC-treated injection buffer (0.25 mM EDTA, 10 mM Tris, pH 7.4) and injected into male pronuclei using a TransferMan NK2 micromanipulator and a FemtoJet microinjector (Eppendorf).

The manipulated embryos were transferred into the oviducts of pseudopregnant foster mothers to produce live animals, or were cultivated in vitro for further analyses.

To screen F0 mice and in vitro cultivated mouse embryos with RGEN-induced mutations, T7E1 assays were performed as previously described using genomic DNA samples from tail biopsies and lysates of whole embryos (Cho et al., 2013).

Briefly, the genomic region encompassing the RGEN target site was PCR-amplified, melted, and re-annealed to form heteroduplex DNA, which was treated with T7 endonuclease 1 (New England Biolabs), and then analyzed by agarose gel electrophoresis. Potential off-target sites were identified by searching with bowtie 0.12.9 and were also similarly monitored by T7E1 assays. The primer pairs used in these assays were listed in Tables 4 and 5.

TABLE 4

Primers used in the T7E1 assay

| Gene | Direction | Sequence (5' to 3') | SEQ ID NO |
|---|---|---|---|
| Foxn1 | F1 | GTCTGTCTATCATCTCTTCCCTTCTCTCC | 40 |
|  | F2 | TCCCTAATCCGATGGCTAGCTCCAG | 41 |
|  | R1 | ACGAGCAGCTGAAGTTAGCATGC | 42 |
|  | R2 | CTACTCAATGCTCTTAGAGCTACCAGGCTTGC | 43 |
| Prkdc | F | GACTGTTGTGGGGAGGGCCG | 44 |
|  | F2 | GGGAGGGCCGAAAGTCTTATTTTG | 45 |
|  | R1 | CCTGAAGACTGAAGTTGGCAGAAGTGAG | 46 |
|  | R2 | CTTTAGGGCTTCTTCTCTACAATCACG | 47 |

TABLE 5

Primers used for amplification of off-target sites

| Gene | Notation | Direction | Sequence (5' to 3') | SEQ ID NO |
|---|---|---|---|---|
| Foxn1 | off 1 | F | CTCGGTGTGTAGCCCTGAC | 48 |
|  |  | R | AGACTGGCCTGGAACTCACAG | 49 |
|  | off 2 | F | CACTAAAGCCTGTCAGGAAGCCG | 50 |
|  |  | R | CTGTGGAGAGCACACAGCAGC | 51 |
|  | off 3 | F | GCTGCGACCTGAGACCATG | 52 |
|  |  | R | CTTCAATGGCTTCCTGCTTAGGCTAC | 53 |
|  | off 4 | F | GGTTCAGATGAGGCCATCCTTTC | 54 |
|  |  | R | CCTGATCTGCAGGCTTAACCCTTG | 55 |
| Prkdc | off 1 | F | CTCACCTGCACATCACATGTGG | 56 |
|  |  | R | GGCATCCACCCTATGGGGTC | 57 |
|  | off 2 | F | GCCTTGACCTAGAGCTTAAAGAGCC | 58 |
|  |  | R | GGTCTTGTTAGCAGGAAGGACACTG | 59 |
|  | off 3 | F | AAAACTCTGCTTGATGGGATATGTGG | 60 |
|  |  | R | CTCTCACTGGTTATCTGTGCTCCTTC | 61 |
|  | off 4 | F | GGATCAATAGGTGGTGGGGATG | 62 |
|  |  | R | GTGAATGACACAATGTGACAGCTTCAG | 63 |
|  | off 5 | F | CACAAGACAGACCTCTCAACATTCAGTC | 64 |
|  |  | R | GTGCATGCATATAATCCATTCTGATTGCTCTC | 65 |
|  | off 6 | F1 | GGGAGGCAGAGGCAGGT | 66 |
|  |  | F2 | GGATCTCTGTGAGTTTGAGGCCA | 67 |
|  |  | R1 | GCTCCAGAACTCACTCTTAGGCTC | 68 |

Mutant founders identified by the T7E1 assay were further analyzed by fPCR. Appropriate regions of genomic DNA were sequenced as described previously (Sung et al., 2013). For routine PCR genotyping of F1 progenies, the following primer pairs were used for both wild-type and mutant alleles: 5'-CTACTCCCTCCGCAGTCTGA-3' (SEQ ID NO: 69) and 5'-CCAGGCCTAGGTTCCAGGTA-3' (SEQ ID NO: 70) for the Foxn1 gene, 5'-CCCCAGCATT-GCAGATTTCC-3' (SEQ ID NO: 71) and 5'-AGGGCTTCT-TCTCTACAATCACG-3' (SEQ ID NO: 72) for Prkdc gene.

In the case of injection of Cas9 mPRNA, mutant fractions (the number of mutant embryos/the number of total embryos) were dose-dependent, ranging from 33% (1 ng/μl sgRNA) to 91% (100 ng/μl) (FIG. 6b). Sequence analysis confirmed mutations in the Foxn1 gene; most mutations were small deletions (FIG. 6c), reminiscent of those induced by ZFNs and TALENs (Kim et al., 2013).

Figure 7A:
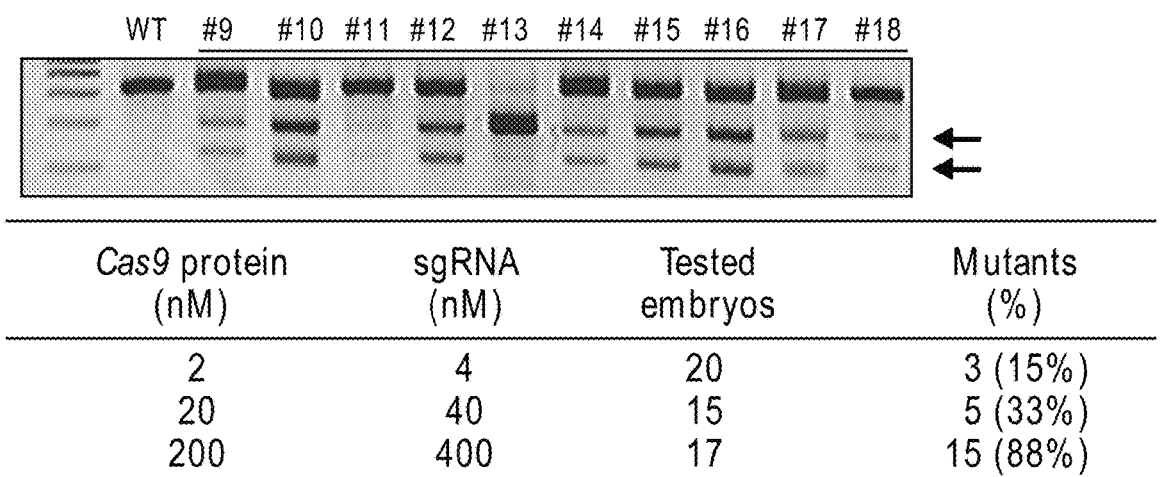
Figure 7B:
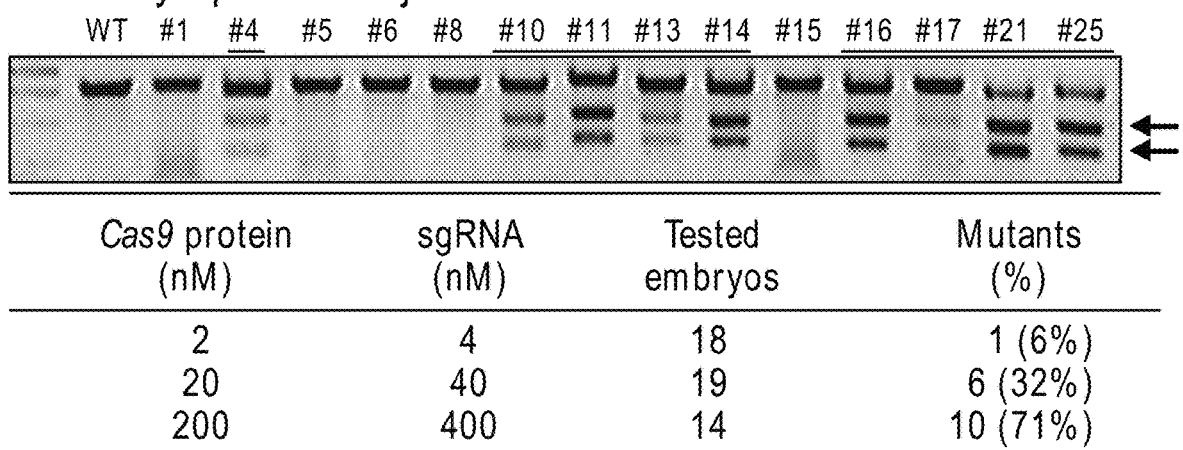

In the case of injection of Cas9 protein, these injection doses and methods minimally affected the survival and development of mouse embryos in vitro: over 70% of RGEN-injected embryos hatched out normally in both experiments. Again, mutant fractions obtained with Cas9 protein injection were dose-dependent, and reached up to 88% at the highest dose via pronucleus injection and to 71% vii: intra-cytoplasmic injection (FIGS. 7a and 7b). Similar to the mutation patterns induced by Cas9 mRNA plus sgRNA (FIG. 6c), those induced by the Cas9 protein-sgRNA complex were mostly small deletions (FIG. 7c). These results clearly demonstrate that RGENs have high gene-targeting activity in mouse embryos.

Encouraged by the high mutant frequencies and low cytotoxicity induced by RGENs, we produced live animals by transferring the mouse embryos into the oviducts of pseudo-pregnant foster mothers.

Notably, the birth rates were very high, ranging from 58% to 73%, and were not affected by the increasing doses of Foxn1-sgRNA (Table 6).

TABLE 6

RGEN-mediated gene-targeting in FVB/NTaC mice

| Target Gene | Cas9 mRNA + sgRNA (ng/μl) | Injected embryos | Transfer red embryos (%) | Total newborns (%) | Live newborns * (%) | Founders † (%) |
|---|---|---|---|---|---|---|
| Foxn1 | 10 + 1 | 76 | 62 (82) | 45 (73) | 31 (50) | 12 (39) |
|  | 10 + 10 | 104 | 90 (87) | 52 (58) | 58 (64) | 33 (57) |
|  | 10 + 100 | 100 | 90 (90) | 62 (69) | 58 (64) | 54 (93) |
|  | Total | 280 | 242 (86) | 159 (66) | 147 (61) | 99 (67) |
| Prkdc | 50 + 50 | 73 | 58 (79) | 35 (60) | 33 (57) | 11 (33) |
|  | 50 + 100 | 79 | 59 (75) | 22 (37) | 21 (36) | 7 (33) |
|  | 50 + 250 | 94 | 73 (78) | 37 (51) | 37 (51) | 21 (57) |
|  | Total | 246 | 190 (77) | 94 (49) | 91 (48) | 39 (43) |

Out of 147 newborns, we obtained 99 mutant founder mice. Consistent with the results observed in cultivated embryos (FIG. 6b), mutant fractions were proportional to the doses of Foxn1-sgRNA, and reached up to 93% (100 ng/μl Foxn1-sgRNA) (Tables 6 and 7, FIG. 5b).

TABLE 7

DNA sequences of Foxn1 mutant alleles identified from a subset of T7E1-positive mutant founders

| Sequence | del + ins | # | Founder mice |
|---|---|---|---|
| ACTTCCAGGCTCCACCCGACTGGAGGGCGAACCCCAAGGGGA CCTCATGCAGG |  |  |  |
| ACTTCCAGGC------------------AACCCCAAGGGGA CCTCATGCAGG | Δ19 | 1 | 20 |
| ACTTCCAGGC-----------------GAACCCCAAGGGGA CCTCATGCAGG | Δ18 | 1 | 115 |
| ACTTCCAGGCTCC--------------------------- ----------- | Δ60 | 1 | 19 |
| ACTTCCAGGCTCC--------------------------- ----------- | Δ44 | 1 | 108 |
| ACTTCCAGGCTCC-------------------CAAGGGGA CCTCATGCAGG | Δ21 | 1 | 64 |
| ACTTCCAGGCTCC-----------TTAGGAGGCGAACCCCA AGGGGACCTCA | Δ12 + 6 | 1 | 126 |
| ACTTCCAGGCTCCACC------------------------ --TCATGCAGG | Δ28 | 1 | 5 |
| ACTTCCAGGCTCCACCC-------------------CCAA GGGACCTCATG | Δ21 + 4 | 1 | 61 |

TABLE 7-continued

DNA sequences of Foxn1 mutant alleles identified from a subset of T7E1-positive mutant founders

| Sequence | del + ins | # | Founder mice |
|---|---|---|---|
| ACTTCCAGGCTCCACCCGACTGGAGGGCGAACCCCAAGGGGA CCTCATGCAGG | | | |
| ACTTCCAGGCTCCACCC-----------------AAGGGGA CCTCATGCAGG | Δ18 | 2 | 95, 29 |
| ACTTCCAGGCTCCACCC----------------CAAGGGGA CCTCATGCAGG | Δ17 | 7 | 12, 14, 27, 66, 108, 114, 126 |
| ACTTCCAGGCTCCACCC---------------ACCCAAGGGG ACCTCATGCAG | Δ15 + 1 | 1 | 32 |
| ACTTCCAGGCTCCACCC---------------CACCCAAGGG GACCTCATGCA | Δ15 + 2 | 1 | 124 |
| ACTTCCAGGCTCCACCC-------------ACCCCAAGGGGA CCTCATGCAGG | Δ13 | 1 | 32 |
| ACTTCCAGGCTCCACCC--------GGCGAACCCCAAGGGGA CCTCATGCAGG | Δ8 | 1 | 110 |
| ACTTCCAGGCTCCACCCT-------------------GGGGA CCTCATGCAGG | Δ20 + 1 | 1 | 29 |
| ACTTCCAGGCTCCACCCG-----------AACCCCAAGGGGA CCTCATGCAGG | Δ11 | 1 | 111 |
| ACTTCCAGGCTCCACCCGA---------------------A CCTCATGCAGG | Δ22 | 1 | 79 |
| ACTTCCAGGCTCCACCCGA------------------GGGGA CCTCATGCAGG | Δ18 | 2 | 13, 127 |
| ACTTCCAGGCTCCACCCCA-----------------AGGGGA CCTCATGCAGG | Δ17 | 1 | 24 |
| ACTTCCAGGCTCCACCCGA-----------ACCCCAAGGGGA CCTCATGCAGG | Δ11 | 5 | 14, 53, 58, 69, 124 |
| ACTTCCAGGCTCCACCCGA----------GACCCCAAGGGGA CCTCATGCAGG | Δ10 | 1 | 14 |
| ACTTCCAGGCTCCACCCGA-----GGGCGAACCCCAAGGGGA CCTCATGCAGG | Δ5 | 3 | 53, 79, 115 |
| ACTTCCAGGCTCCACCCGAC--------------------- -CTCATGCAGG | Δ23 | 1 | 108 |
| ACTTCCAGGCTCCACCCGAC-----------CCCCAAGGGGA CCTCATGCAGG | Δ11 | 1 | 3 |
| ACTTCCAGGCTCCACCCGAC-----------GAAGGGCCCCA AGGGGACCTCA | Δ11 + 6 | 1 | 66 |
| ACTTCCAGGCTCCACCCGAC--------GAACCCCAAGGGGA CCTCATGCAGG | Δ8 | 2 | 3, 66 |
| ACTTCCAGGCTCCACCCGAC-----GGCGAACCCCAAGGGGA CCTCATGCAGG | Δ5 | 1 | 27 |
| ACTTCCAGGCTCCACCCGAC--GTGCTTGAGGGCGAACCCCA AGGGGACCTCA | Δ2 + 6 | 2 | 5 |
| ACTTCCAGGCTCCACCCGACT------CACTATCTTCTGGGC TCCTCCATGTC | Δ6 + 25 | 2 | 21, 114 |
| ACTTCCAGGCTCCACCCGACT----TGGCGAACCCCAAGGGG ACCTCATGCAG | Δ4 + 1 | 1 | 53 |
| ACTTCCAGGCTCCACCCGACT--TGCAGGGCGAACCCCAAGG GGACCTCATGC | Δ2 + 3 | 1 | 126 |

TABLE 7-continued

DNA sequences of Foxn1 mutant alleles identified from a subset of T7E1-positive mutant founders

| Sequence | del + ins | # | Founder mice |
|---|---|---|---|
| ACTTCCAGGCTCCACCCGACTGGAGGGCGAACCCCAAGGGGA CCTCATGCAGG | | | |
| ACTTCCAGGCTCCACCCGACTTGGAGGGCGAACCCCAAGGGG ACCTCATGCAG | +1 | 15 | 3, 5, 12, 19, 29, 55, 56, 61, 66, 68, 81, 108, 111, 124, 127 |
| ACTTCCAGGCTCCACCCGACTTTGGAGGGCGAACCCCAAGGG GACCTCATGCA | +2 | 2 | 79, 120 |
| ACTTCCAGGCTCCACCCGACTGTTGGAGGGCGAACCCCAAGG GGACCTCATGC | +3 | 1 | 55 |
| ACTTCCAGGCTCCACCCGACTGGAG(+455)GGCGAACCCCA AGGGGACCTCC | +455 | 1 | 13 |

To generate Prkdc-targeted mice, we applied a 5-fold higher concentration of Cas9 mRNA (50 ng/μl) with increasing doses of Prkdc-sgRNA (50, 100, and 250 ng/μl). Again, the birth rates were very high, ranging from 51% to 60%, enough to produce a sufficient number of newborns for the analysis (Table 6). The mutant fraction was 57% (21 mutant founders among 37 newborns) at the maximum dose of Prkdc-sgRNA. These birth rates obtained with RGENs were approximately 2- to 10-fold higher than those with TALENs reported in our previous study (Sung et al., 2013). These results demonstrate that RGENs are potent gene-targeting reagents with minimal toxicity.

To test the germ-line transmission of the mutant alleles, we crossed the Foxn1 mutant founder #108, a mosaic with four different alleles (FIG. 5c, and Table 8) with wild-type mice, and monitored the genotypes of F1 offspring.

TABLE 8

Genotypes of Foxn1 mutant mice

| Founder NO. | sgRNA (ng/ml) | Genotyping Summary | Detected alleles |
|---|---|---|---|
| 58* | 1 | not determined | Δ11 |
| 19 | 100 | bi-allelic | Δ60/+1 |
| 20 | 100 | bi-allelic | Δ67/Δ19 |
| 13 | 100 | bi-allelic | Δ18/+455 |
| 32 | 10 | bi-allelic (heterozygote) | Δ13/Δ15 + 1 |
| 115 | 10 | bi-allelic (heterozygote) | Δ18/Δ5 |
| 111 | 10 | bi-allelic (heterozygote) | Δ11/+1 |
| 110 | 10 | bi-allelic (homozygote) | Δ8/Δ8 |
| 120 | 10 | bi-allelic (homozygote) | +2/+2 |
| 81 | 100 | heterozygote | +1/WT |
| 69 | 100 | homozygote | Δ11/Δ11 |
| 55 | 1 | mosaic | Δ18/Δ1/+1/+3 |
| 56 | 1 | mosaic | Δ127/Δ41/Δ2/+1 |
| 127 | 1 | mosaic | Δ18/+1/WT |
| 53 | 1 | mosaic | Δ11/Δ5/Δ4 + 1/WT |
| 27 | 10 | mosaic | Δ17/Δ5/WT |
| 29 | 10 | mosaic | Δ18/Δ20 + 1/+1 |
| 95 | 10 | mosaic | Δ18/Δ14/Δ8/Δ4 |
| 108 | 10 | mosaic | +1/Δ17/Δ23/Δ44 |
| 114 | 10 | mosaic | Δ17/Δ8/Δ6 + 25 |

TABLE 8-continued

Genotypes of Foxn1 mutant mice

| Founder NO. | sgRNA (ng/ml) | Genotyping Summary | Detected alleles |
|---|---|---|---|
| 124 | 10 | mosaic | Δ11/Δ15 + 2/+1 |
| 126 | 10 | mosaic | Δ17/Δ2 + 3/Δ12 + 6 |
| 12 | 100 | mosaic | Δ30/Δ28/Δ17/+1 |
| 5 | 100 | mosaic | Δ28/Δ11/Δ2 + 6/+1 |
| 14 | 100 | mosaic | Δ17/Δ11/Δ10 |
| 21 | 100 | mosaic | Δ127/Δ41/Δ2/Δ6 + 25 |
| 24 | 100 | mosaic | Δ17/+1/WT |
| 64 | 100 | mosaic | Δ31/Δ21/+1/WT |
| 68 | 100 | mosaic | Δ17/Δ11/+1/WT |
| 79 | 100 | mosaic | Δ22/Δ5/+2/WT |
| 61 | 100 | mosaic | Δ21 + 4/Δ6/+1/+9 |
| 66** | 100 | mosaic | Δ17/Δ8/Δ11 + 6/+1/WT |
| 3 | 100 | mosaic | Δ11/Δ8/+1 |

Underlined alleles were sequenced. Alleles in red, detected by sequencing, but not by fPCR.
*only one clone sequenced.
**Not determined by fPCR.

Figure 5D:
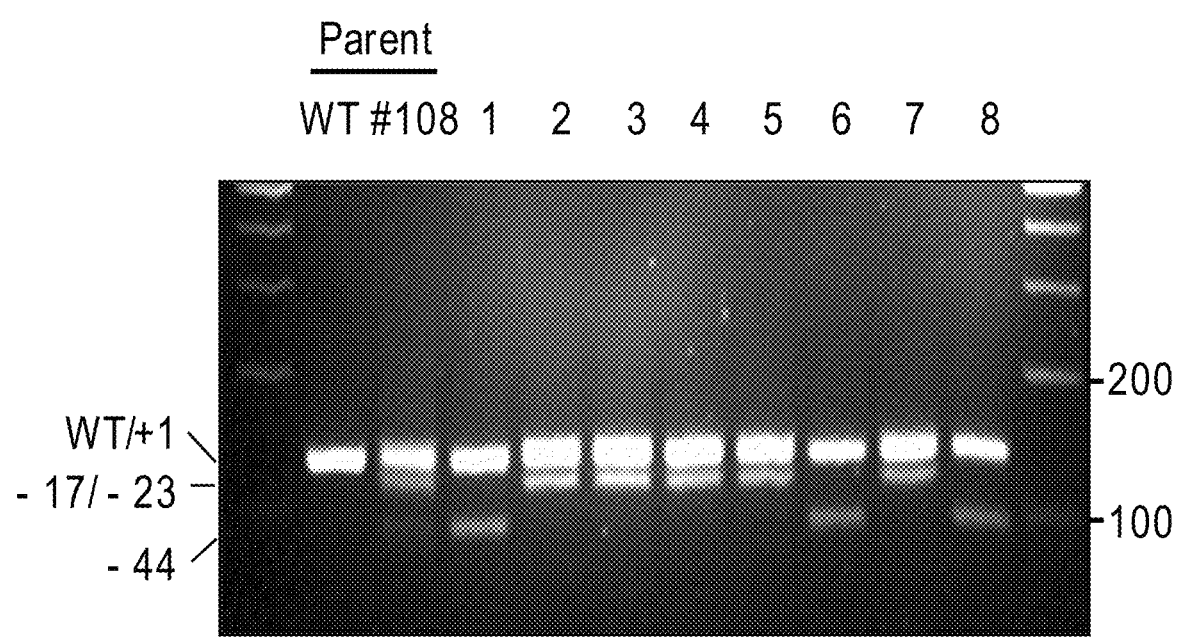

As expected, all the progenies were heterozygous mutants possessing the wild-type allele and one of the mutant alleles (FIG. 5d). We also confirmed the germ-line transmission in independent founder mice of Foxn1 (FIG. 8) and Prkdc (FIG. 9). To the best of our knowledge, these results provide the first evidence that RGEN-induced mutant alleles are stably transmitted to F1 progenies in animals.

Example 4

RNA-Guided Genome Editing in Plants 4-1. Production of Cas9 Protein

The Cas9 coding sequence (4104 bps), derived from *Streptococcus pyogenes* strain M1 GAS (NC_002737.1), was cloned to pET28-b(+) plasmid. A nuclear targeting sequence (NLS) was included at the protein N terminus to ensure the localization of the protein to the nucleus. pET28-b (+) plasmid containing Cas9 ORF was transformed into BL21(DE3). Cas9 was then induced using 0.2 mM IPTG for 16 hrs at 18° C. and purified using Ni-NTA agarose beads (Qiagen) following the manufacturer's instructions. Purified Cas9 protein was concentrated using Ultracel-100K (Millipore).

4-2. Production of Guide RNA

The genomic sequence of the *Arabidopsis* gene encoding the BRI1 was screened for the presence of a NGG motif, the so called protospacer adjacent motif (PAM), in an exon which is required for Cas9 targeting To disrupt the BRI1 gene in *Arabidopsis*, we identified two RGEN target sites in an exon that contain the NGG motif. sgRNAs were produced in vitor using template DNA. Each template DNA was generated by extension with two partially overlapped oligonucleotides (Macrogen, Table X1) and Phusion polymerase (Thermo Scientific using the following conditions—98° C. 30 sec {98° C. 10 sec, 54° C. 20 sec, 72° C. 2 min}×20, 72° C. 5 min.

TABLE 9

Oligonucleotides for the production of the template DNA for in vitro transcription

| Oligonucleotides | Sequence (5'-3') | SEQ ID NO |
|---|---|---|
| BRI1 target 1 (Forward) | GAAATTAATACGACTCACTATAGGTTTGAAAGAT GGAAGCGCGGGTTTTAGAGCTAGAAATAGCAAGT TAAAATAAGGCTAGTCCG | 73 |
| BRI1 target 2 (Forward) | GAAATTAATACGACTCACTATAGGTGAAACTAAA CTGGTCCACAGTTTTAGAGCTAGAAATAGCAAGT TAAAATAAGGCTAGTCCG | 74 |
| Universal (Reverse) | AAAAAAGCACCGACTCGGTGCCACTTTTTCAAGT TGATAACGGACTAGCCTTATTTTAACTTGC | 75 |

The extended DNA was purified and used as a template for the in vitro production of the guide RNA's using the MEGAshortscript T7 kit (Life Technologies). Guide RNA were then purified by Phenol/Chloroform extraction and ethanol precipitation. To prepare Cas9/sgRNA complexes, 10 ul of purified Cas9 protein (12 μg/μl) and 4 ul each of two sgRNAs (11 μg/μl) were mixed in 20 μl NEB3 buffer (New England Biolabs) and incubated for 10 min at 37° C.

4-3. Transfection of Cas9/sgRNA Complex to Protoplast

The leaves of 4-week-old *Arabidopsis* seedlings grown aseptically in petri dishes were digested in enzyme solution (1% cellulose R10, 0.5% macerozyme R10, 450 mM mannitol, 20 mM MES pH 5.7 and CPW salt) for 8~16 hrs at 25° C. with 40 rpm shaking in the dark. Enzyme/protoplast solutions were filtered and centrifuged at 100×g for 3~5 min. Protoplasts were re-suspended in CPW solution after counting cells under the microscope (×100) using a hemacytometer. Finally, protoplasts were re-suspended at $1 \times 10^6$/ml in MMG solution (4 mM HEPES pH 5.7, 400 mM mannitol and 15 mM MgCl2). To transfect the protoplasts with Cas9/sgRNA complex, 200 μL (200,000 protoplasts) of the protoplast suspension were gently mixed with 3.3 or 10 uL of Cas9/sgRNA complex [Cas9 protein (6 μg/μL) and two sgRNAs (2.2 μg/μL each)] and 200 ul of 40% polyethylene glycol transfection buffer (40% PEG4000, 200 mM mannitol and 100 mM CaCl2) in 2 ml tubes. After 5-20 min incubation at room temperature, transfection was stopped by adding wash buffer with W5 solution (2 mM MES pH 5.7, 154 mM NaCl, 125 mM CaCl2 and 5 mM KC). Protoplasts were then collected by centrifugation for 5 min at 100×g, washed with 1 ml of W5 solution, centrifuged for another 5 min at 100×g. The density of protoplasts was adjusted to $1 \times 10^5$/ml and they were cultured in modified KM 8p liquid medium with 400 mM glucose.

4-4. Detection of Mutations in *Arabidopsis* Protoplasts and Plants

Figure 11:
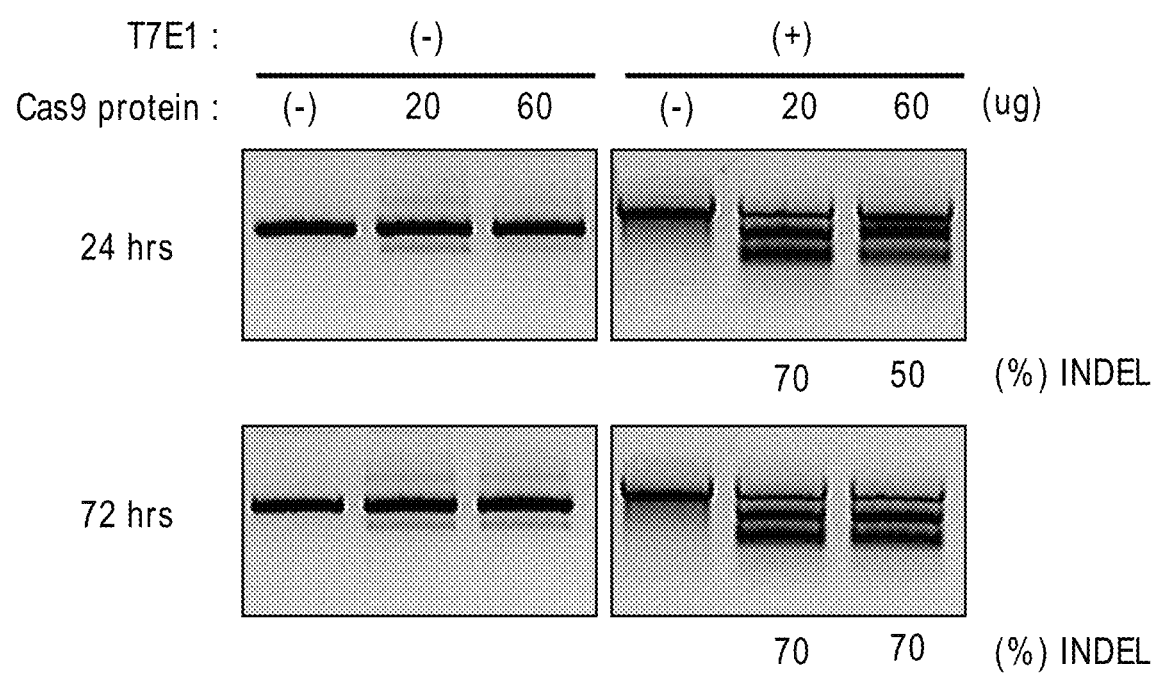
FIG. 11 shows recombinant Cas9 protein-induced mutations in *Arabidopsis protoplasts*.

After 24 hr or 72 hr post-transfection, protoplasts were collected and genomic DNA was isolated. The genomic DNA region spanning the two target sites was PCR-amplified and subjected to the T7E1 assay. As shown in FIG. 11, indels were induced by RGENs at high frequencies that ranged from 50% to 70%. Surprisingly, mutations were induced at 24 hr post-transfection. Apparently, Cas9 protein functions immediately after transfection. PCR products were purified and cloned into T-Blunt PCR Cloning Kit (Solgent). Plasmids were purified and subjected to Sanger sequencing with M13F primer. One mutant sequence had a 7-bp deletion at one site (FIG. 12). The other three mutant sequences had deletions of ~220-bp DNA segments between the two RGEN site.

Example 5

Cas9 Protein Transduction Using a Cell-Penetrating Peptide or Protein Transduction Domain 5-1. Construction of His-Cas9-Encoding Plasmid Cas9 with a cysteine at the C-terminal was prepared by PCR amplification using the previously described Cas9 plasmid (Cho, 2013 #166) as the template and cloned into pET28-(a) vector (Novagen, Merk Millipore, Germany) containing His-tag at the N-terminus.

5-2. Cell Culture 293T (Human embryonic kidney cell line), and HeLa (human ovarian cancer cell line) were grown in DMEM (GIBCO-BRL Rockville) supplemented with 10% FBS and it penicillin and streptomycin.

5-3. Expression and Purification of Cas9 Protein

To express the Cas9 protein, *E. coli* BL21 cells were transformed with the pET28-(a) vector encoding Cas9 and plated onto Luria-Bertani (LB) agar medium containing 50 μg/mL kanamycin (Amresco, Solon, Ohio). Next day, a single colony was picked and cultured in LB broth containing 50 μg/mL kanamycin at 37° C. overnight. Following day, this starter culture at 0.1 OD600 was inoculated into Luria broth containing 50 μg/mL kanamycin and incubated for 2 hrs at 37° C. until OD600 reached to 0.6-0.8. To induce Cas9 protein expression, the cells were cultured at 30° C. overnight after addition of isopropyl-β-D-thiogalactopyranoside (IPTG) (Promega, Madison, Wis.) to the final concentration of 0.5 mM.

The cells were collected by centrifugation at 4000 rpm for 15-20 mins, resuspended in a lysis buffer (20 mM Tris-Cl pH8.0, 300 mM NaCl, 20 mM imidazole, 1× protease inhibitor cocktail, 1 mg/ml lysozyme), and lysed by sonication (40% duty, 10 sec pulse, 30 sec rest, for 10 mins on ice). The soluble fraction was separated as the supernatant after centrifugation at 15,000 rpm for 20 mins at 4° C. Cas9 protein was purified at 4° C. using a column containing Ni-NTA agarose resin (QIAGEN) and AKTA prime instrument (AKTA prime, GE Healthcare, UK). During this chromatography step, soluble protein fractions were loaded onto Ni-NTA agarose resin column (GE Healthcare, UK) at the flow rate of 1 mL/min. The column was washed with a washing buffer (20 mM Tris-Cl pH8.0, 300 mM NaCl, 20 mM imidazole, 1× protease inhibitor cocktail) and the bound protein was eluted at the flow rate of 0.5 ml/min with an elution buffer (20 mM Tris-Cl pH8.0, 300 mM NaCl, 250 mM imidazole, IX protease inhibitor cocktail). The pooled eluted fraction was concentrated and dialyzed against storage buffer (50 mM Tris-HCl, pH8.0, 200 mM KCl, 0.1 mM EDTA, 1 mM DTT, 0.5 mM PMSF, 20% Glycerol). Protein concentration was quantitated by Bradford assay (Biorad, Hercules, Calif.) and purity was analyzed by SDS-PAGE using bovine serum albumin as the control.

5-4. Conjugation of Cas9 to 9R4L 1 mg Cas9 protein diluted in PBS at the concentration of 1 mg/mL and 50 µg of maleimide-9R4L peptide in 25 µL DW (Peptron, Korea) were gently mixed using a rotor at room temperature for 2 hrs and at 4° C. overnight. To remove unconjugated maleimide-9R4L, the samples were dialyzed using 50 kDa molecular weight cutoff membrane against of DPBS (pH 7.4) at 4° C. for 24 hrs. Cas9-9R4L protein was collected from the dialysis membrane and the protein amount was determined using Bradford assay.

5-5. Preparation of sgRNA-9R4L sgRNA (1 µg) was gently added to various amounts of C9R4LC peptide (ranging from 1 to 40 weight ratio) in 100 µl of DPBS (pH 7.4). This mixture was incubated at room temperature for 30 mins and diluted to 10 folds using RNAse-free deionized water. The hydrodynamic diameter and z-potential of the formed nanoparticles were measured using dynamic light scattering (Zetasizer-nano analyzer ZS; Malvern instruments, Worcestershire, UK).

5-6. Cas9 Protein and sgRNA Treatments

Cas9-9R4L and sgRNA-C9R4LC were treated to the cells as follows: 1 µg of sgRNA and 15 µg of C9R4LC peptide were added to 250 mL of OPTIMEM medium and incubated at room temperature for 30 mins. At 24 hrs after seeding, cells were washed with OPTIMEM medium and treated with sgRNA-C9R4LC complex for 4 hrs at 37° C. Cells were washed again with OPTIMEM medium and treated with Cas9-9R4L for 2 hrs at 37° C. After treatment, culture media was replaced with serum-containing complete medium and incubated at 37° C. for 24 hrs before the next treatment. Same procedure was followed for multiple treatments of Cas9 and sgRNA for three consecutive days.

Figure 13:
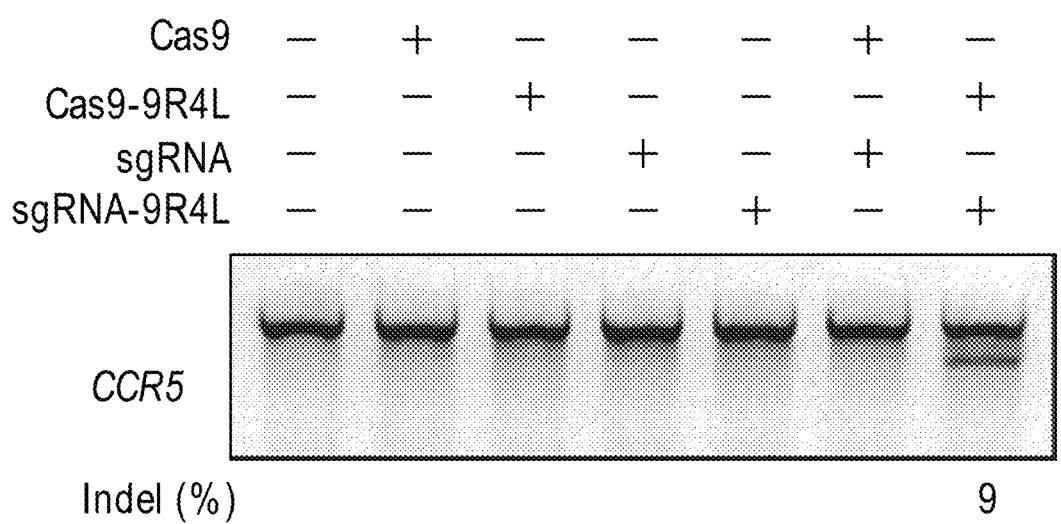
FIG. 13 shows T7E1 assay showing endogenous CCR5 gene disruption in 293 cells by treatment of Cas9-mal-9R4L and sgRNA/C9R4LC complex.

5-7. Cas9-9R4L and sgRNA-9R4L can Edit Endogenous Genes in Cultured Mammalian Cells without the Use of Additional Delivery Tools To determine whether Cas9-9R4L and sgRNA-9R4L can edit endogenous genes in cultured mammalian cells without the use of additional delivery tools, we treated 293 cells with Cas9-9R4L and sgRNA-9R4L targeting the CCR5 gene and analyzed the genomic DNA. T7E1 assay showed that 9% of CCR5 gene was disrupted in cells treated with both Cas9-9R4L and sgRNA-9R4L and that the CCR5 gene disruption was not observed in control cells including those untreated, treated with either Cas9-9R or sgRNA-9R4L, or treated with both unmodified Cas-9 and sgRNA (FIG. 13), suggesting that the treatment with Cas9-9R4L protein and sgRNA conjugated with 9R4L, but not unmodified Cas9 and sgRNA, can lead to efficient genome editing in mammalian cells.

Example 6

Control of Off-Target Mutation According to Guide RNA Structure

Figure 14A:
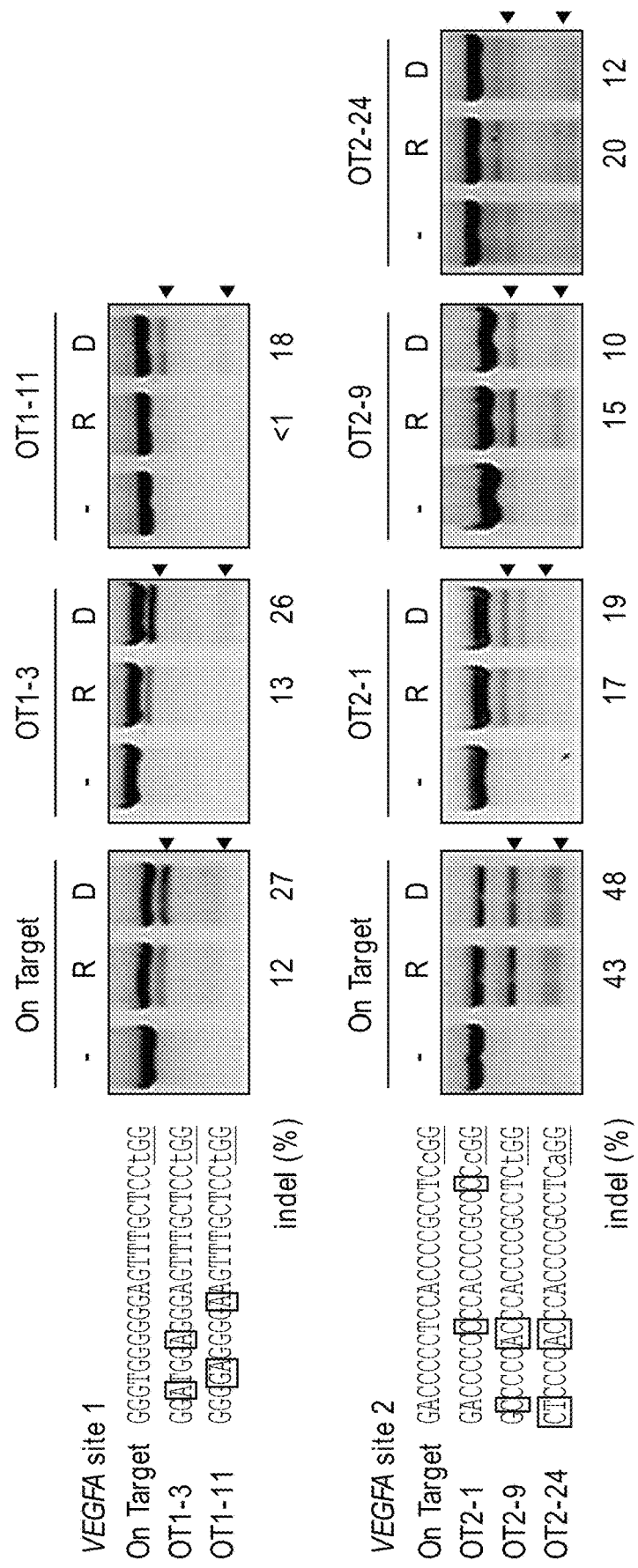
FIGS. 14A and 14B show mutation frequencies at on-target and off-target sites of RGENs reported in Fu et al. (2013). T7E1 assays analyzing genomic DNA from K562 cells (R) transfected serially with 20 µg of Cas9-encoding plasmid and with 60 µg and 120 µg of in vitro transcribed GX19 crRNA and tracrRNA, respectively (1×10$^6$ cells), or (D) co-transfected with 1 µg of Cas9-encoding plasmid and 1 µg of GX$_{19}$ sgRNA expression plasmid (2×10$^5$ cells).
Figure 14B:
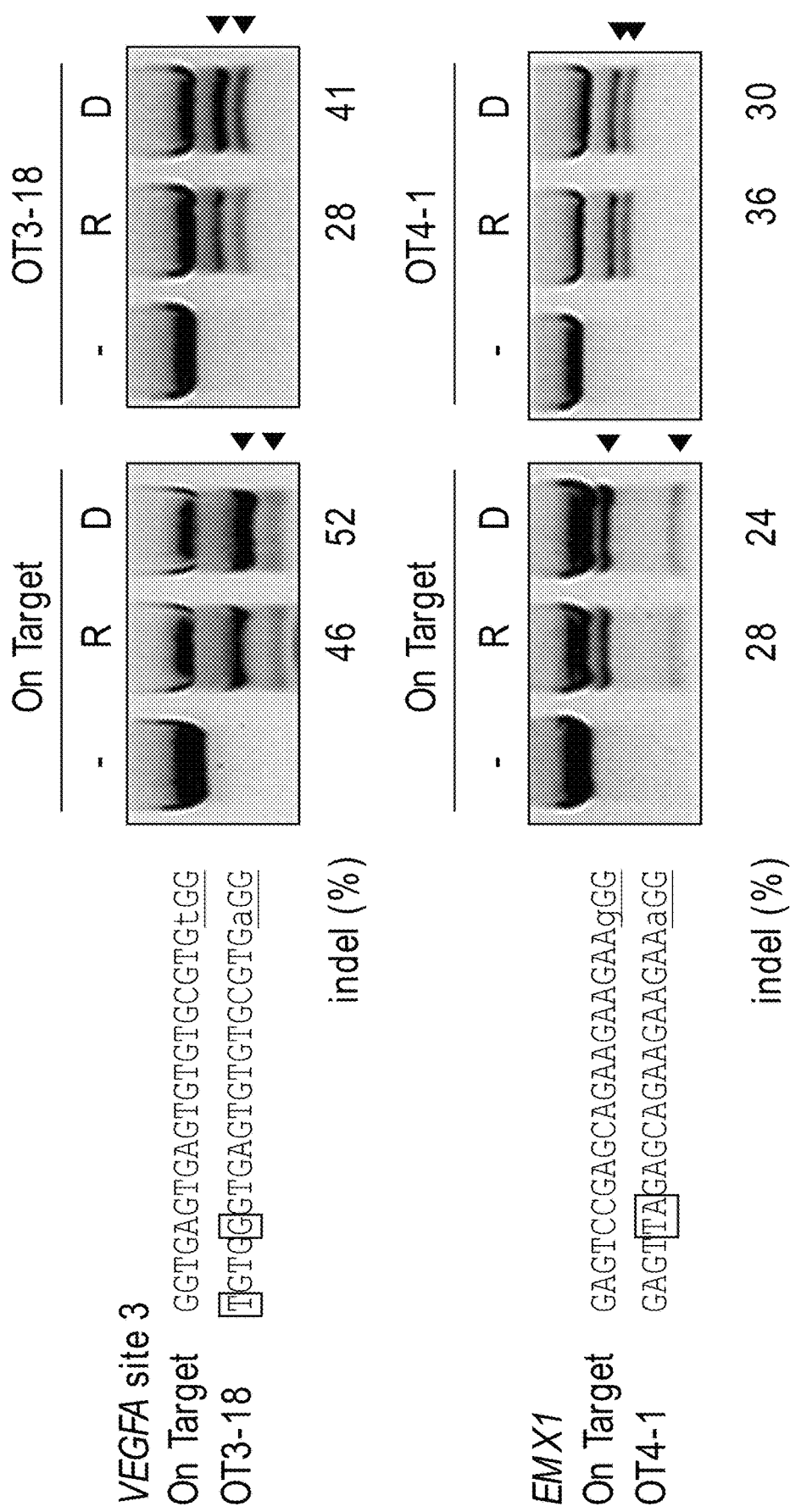

Recently, three groups reported that RGENs had off-target effects in human cells. To our surprise, RGENs induced mutations efficiently at off-target sites that differ by 3 to 5 nucleotides from on-target sites. We noticed, however, that there were several differences between our RGENs and those used by others. First, we used dualRNA, which is crRNA plus tracrRPNA, rather than single-guide RNA (sgRNA) that is composed of essential portions of crRNA and tracrRNA. Second, we transfected K562 cells (but not HeLa cells) with synthetic crRNA rather than plasmids encoding crRNA. HeLa cells were transfected with crRNA-encoding plasmids. Other groups used sgRNA-encoding plasmids. Third, our guide RNA had two additional guanine nucleotides at the 5' end, which are required for efficient transcription by T7 polymerase in vitro. No such additional nucleotides were included in the sgRNA used by others. Thus, the RNA sequence of our guide RNA can be shown as 5'-GGX$_{20}$, whereas 5'-GX$_{19}$, in which X$_{20}$ or GX$_{19}$ corresponds to the 20-bp target sequence, represents the sequence used by others. The first guanine nucleotide is required for transcription by RNA polymerase in cells. To test whether off-target RGEN effects can be attributed to these differences, we chose four RGENs that induced off-target mutations in human cells at high frequencies (13). First, we compared our method of using in vitro transcribed dualRNA with the method of transfecting sgRNA-encoding plasmids in K562 cells and measured mutation frequencies at the on-target and off-target sites via the T7E1 assay. Three RGENs showed comparable mutation frequencies at on-target and off-target sites regardless of the composition of guide RNA. Interestingly, one RGEN (VEFGA site 1) did not induce indels at one validated off-target site, which differs by three nucleotides from the on-target site (termed OT1-11, FIG. 14), when synthetic dualRNA was used. But the synthetic dualRNA did not discriminate the other validated off-target site (OT1-3), which differs by two nucleotides from the on-target site.

Figure 15A:
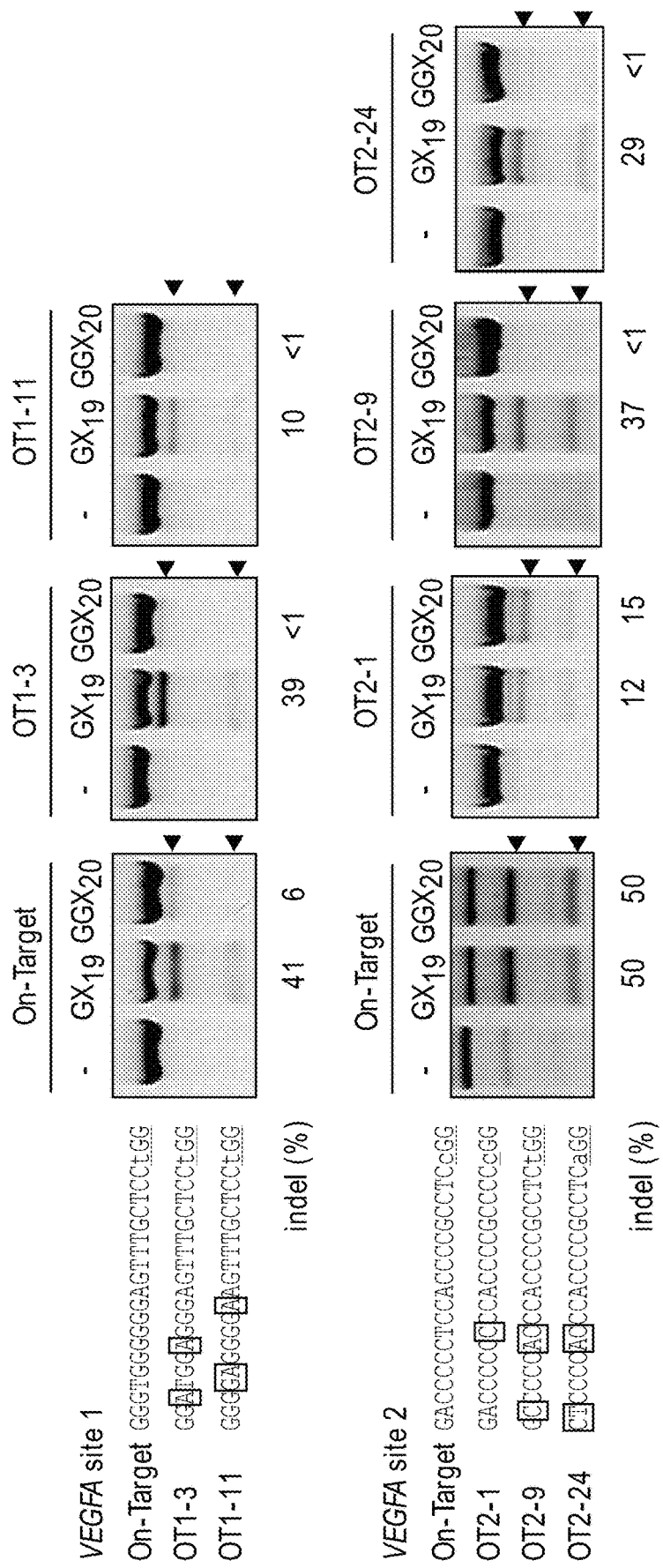
FIGS. 15A and 15B show comparison of guide RNA structure. Mutation frequencies of the RGENs reported in Fu et al. (2013) were measured at on-target and off-target sites using the T7E1 assay. K562 cells were co-transfected with the Cas9-encoding plasmid and the plasmid encoding GX19 sgRNA or GGX20 sgRNA. Off-target sites (OT1-3 etc.) are labeled as in Fu et al. (2013).
Figure 15B:
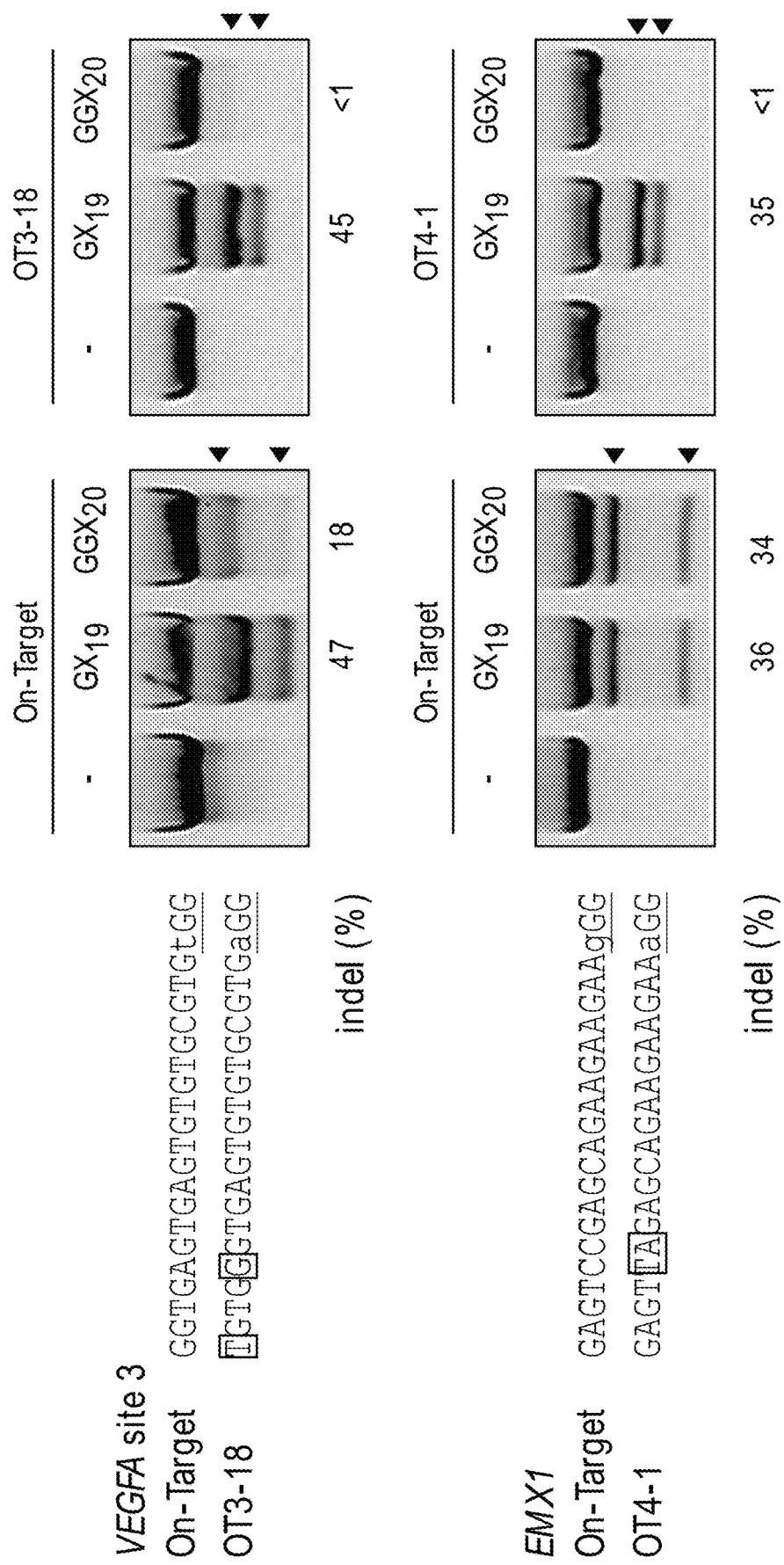

Next, we tested whether the addition of two guanine nucleotides at the 5' end of sgRNA could make RGENs more specific by comparing 5'-GGX$_{20}$; (or 5'-GGGX$_{19}$) s RNA with 5'-GX$_{19}$ sgRNA. Four GX$_{19}$ sgRNAs complexed with Cas9 induced indels equally efficiently at on-target and off-target sites, tolerating up to four nucleotide mismatches. In sharp contrast, GGX$_{20}$ sgRNAs discriminated off-target sites effectively. In fact, the T7E1E assay barely detected RGEN-induced indels at six out of the seven validated off-target sites when we used the four GGX$_{20}$ sgRNAs (FIG. 15). We noticed, however, that two GGX$_{20}$ sgRNAs (VEGFA sites 1 and 3) were less active at on-target sites than were the corresponding GX$_{19}$ sgRNAs. These results show that the extra nucleotides at the 5' end can affect mutation frequencies at on-target and off-target sites, perhaps by altering guide RNA stability, concentration, or secondary structure.

These results suggest that three factors—the use of synthetic guide RNA rather than guide RNA-encoding plasmids, dualRNA rather than sgRNA, and GGX$_{20}$ sgRNA rather than GX$_{19}$ sgRNA-have cumulative effects on the discrimination of off-target sites.

Example 7

Paired Cas9 Nickases

Figure 16A:
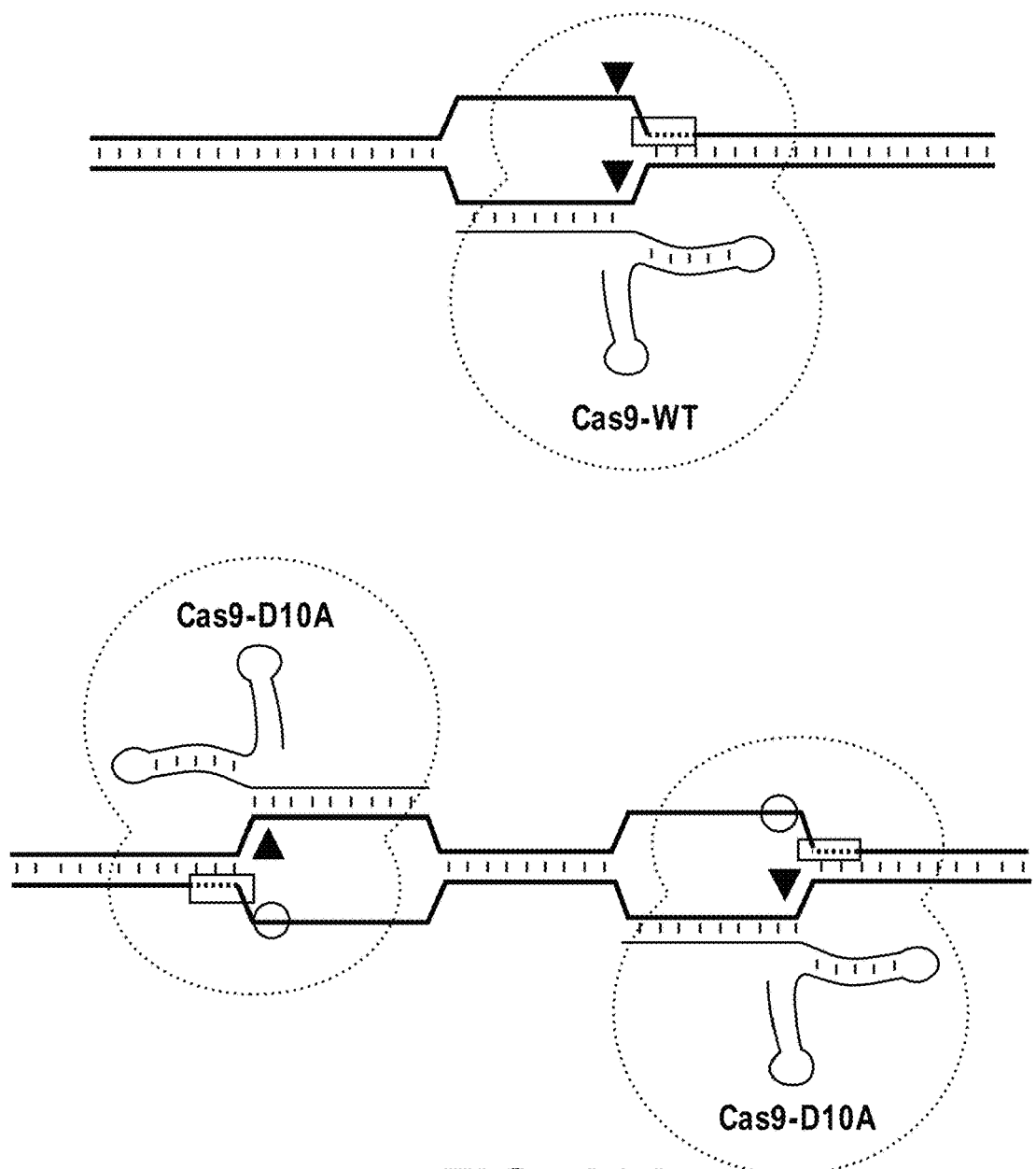
FIGS. 16A, 16B, 16C, and 16D show that in vitro DNA cleavage by Cas9 nickases.
Figure 16B:
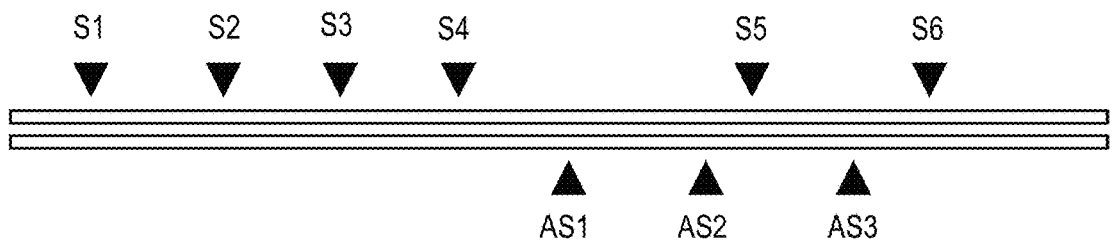

In principle, single-strand breaks (SSBs) cannot be repaired by error-prone NHEJ but still trigger high fidelity homology-directed repair (HDR) or base excision repair. But nickase-induced targeted mutagenesis via HDR is much less efficient than is nuclease-induced mutagenesis. We reasoned that paired Cas9 nickases would produce composite DSBs, which trigger DNA repair via NHEJ or HDR, leading to efficient mutagenesis (FIG. 16A). Furthermore, paired nickases would double the specificity of Cas9-based genome editing.

Figure 16C:
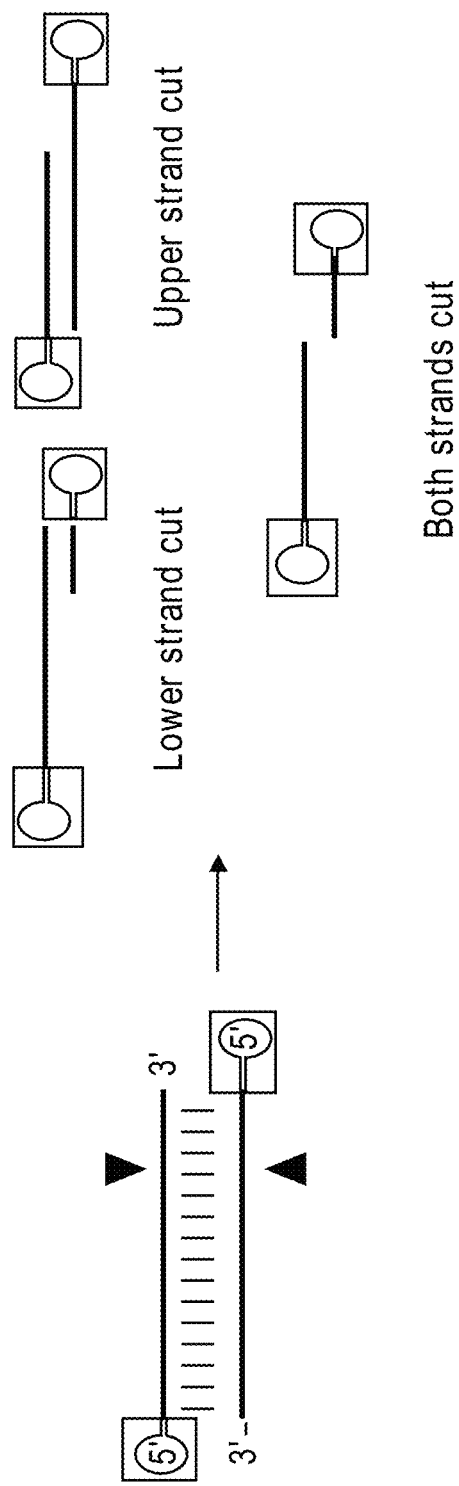
Figure 16D:
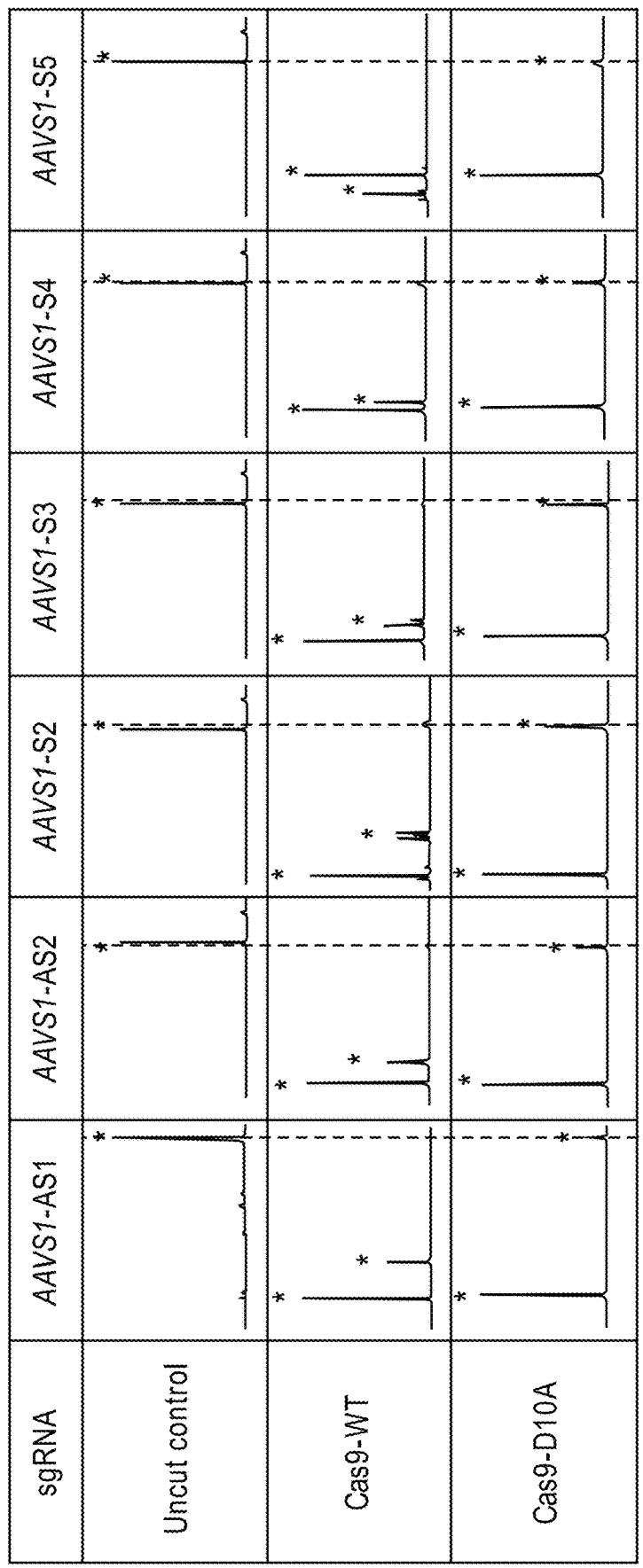
Figure 17A:
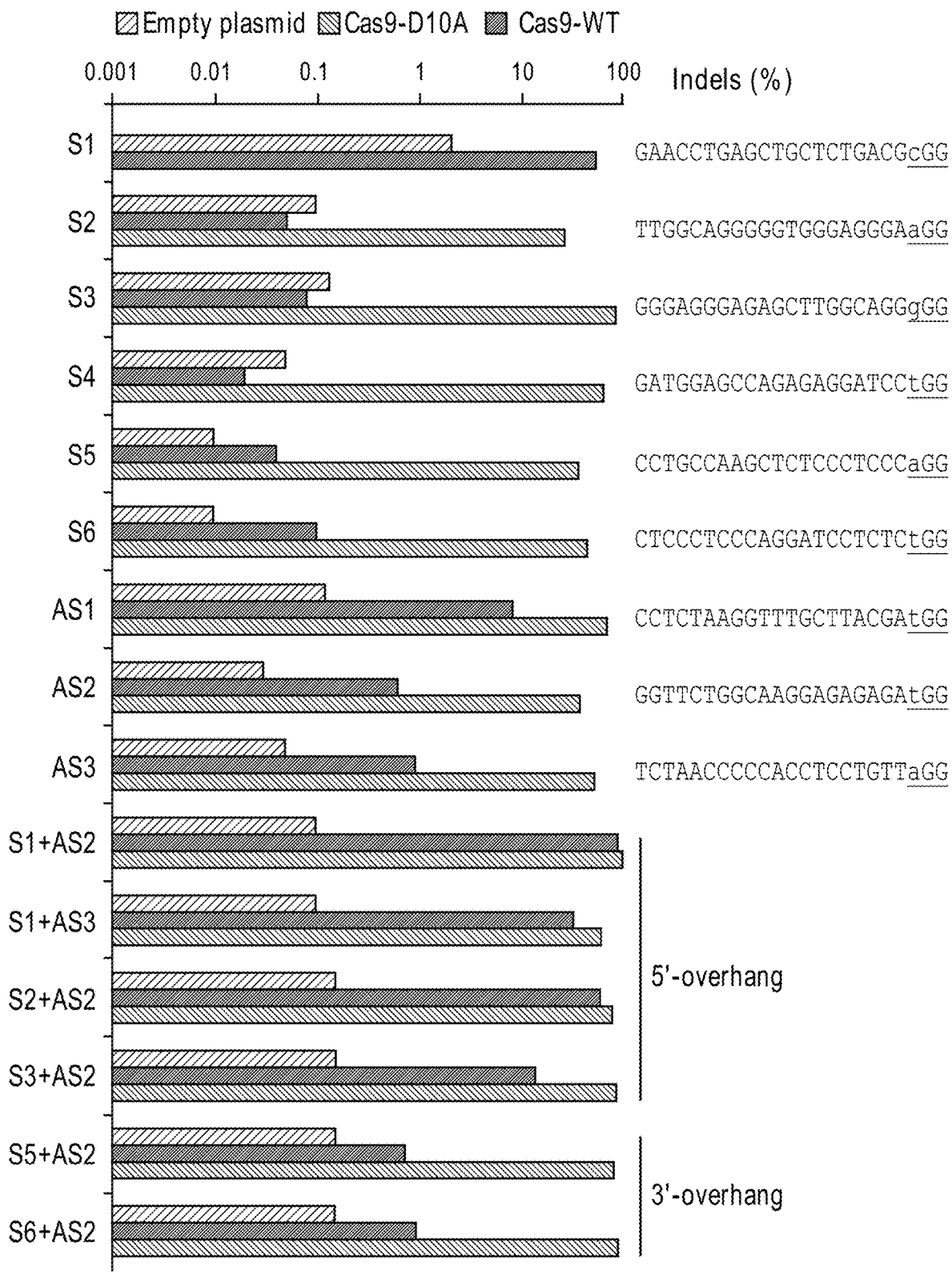
FIGS. 17A and 17B show comparison of Cas9 nuclease and nickase behavior.
Figure 18A:
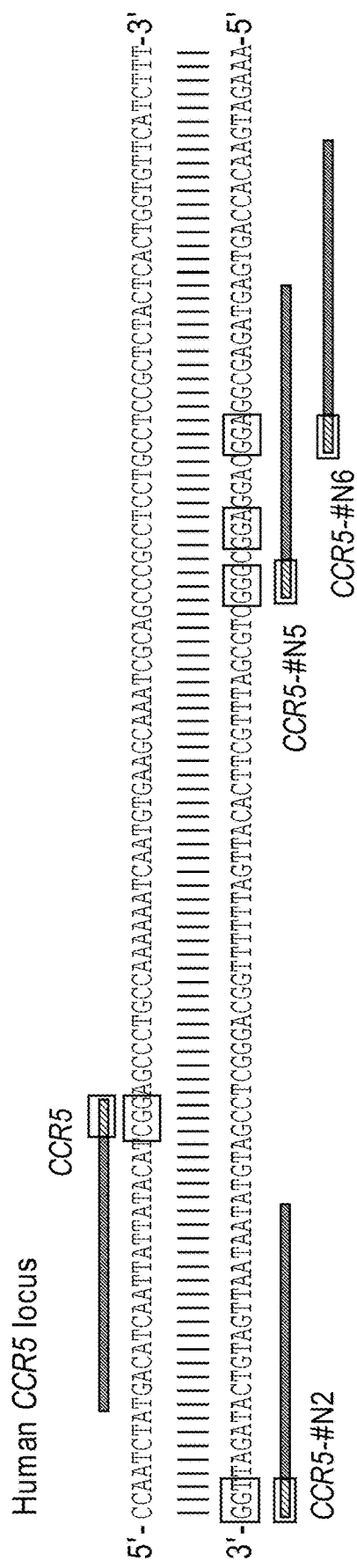
Figure 18B:
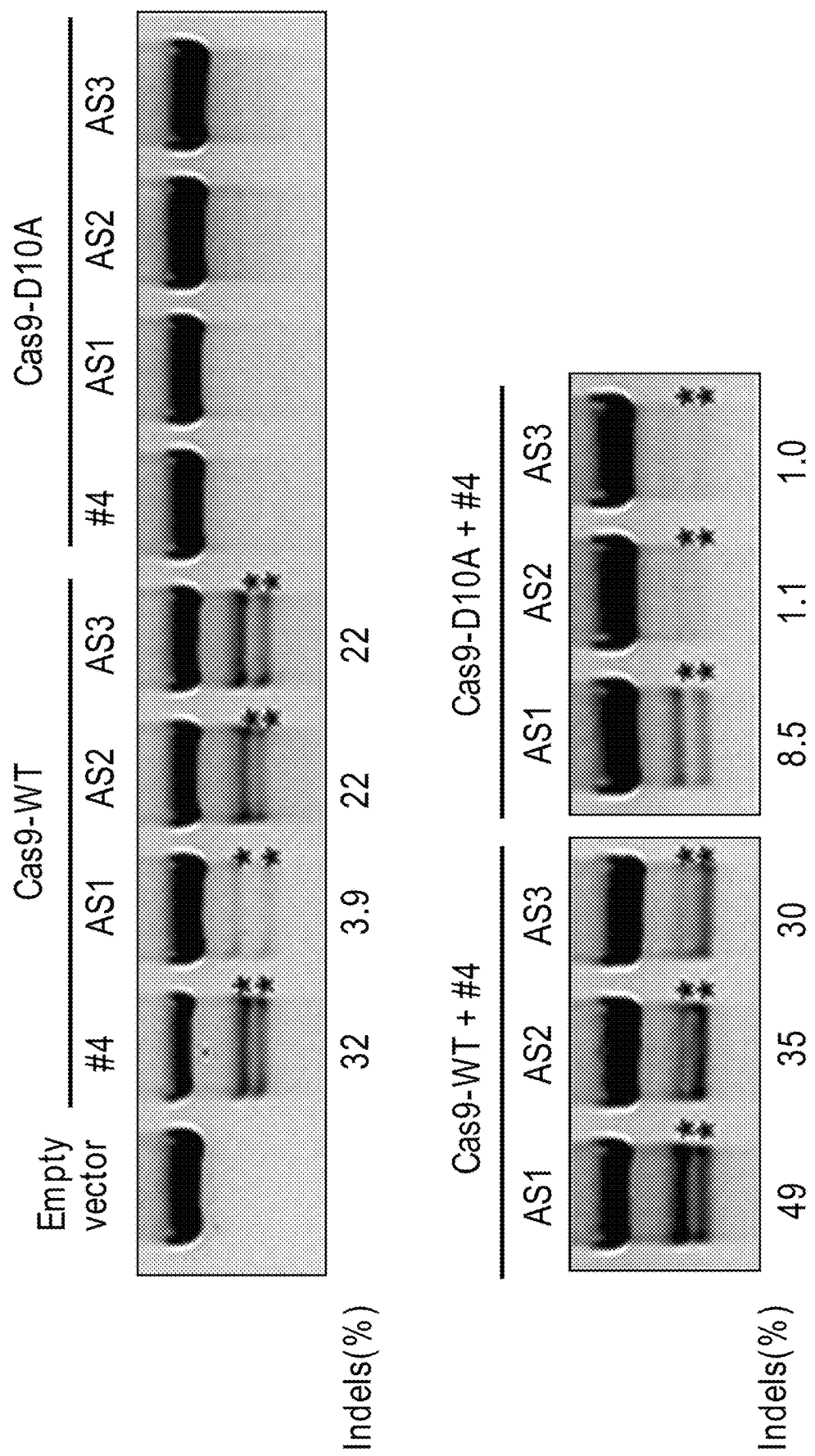
Figure 19A:
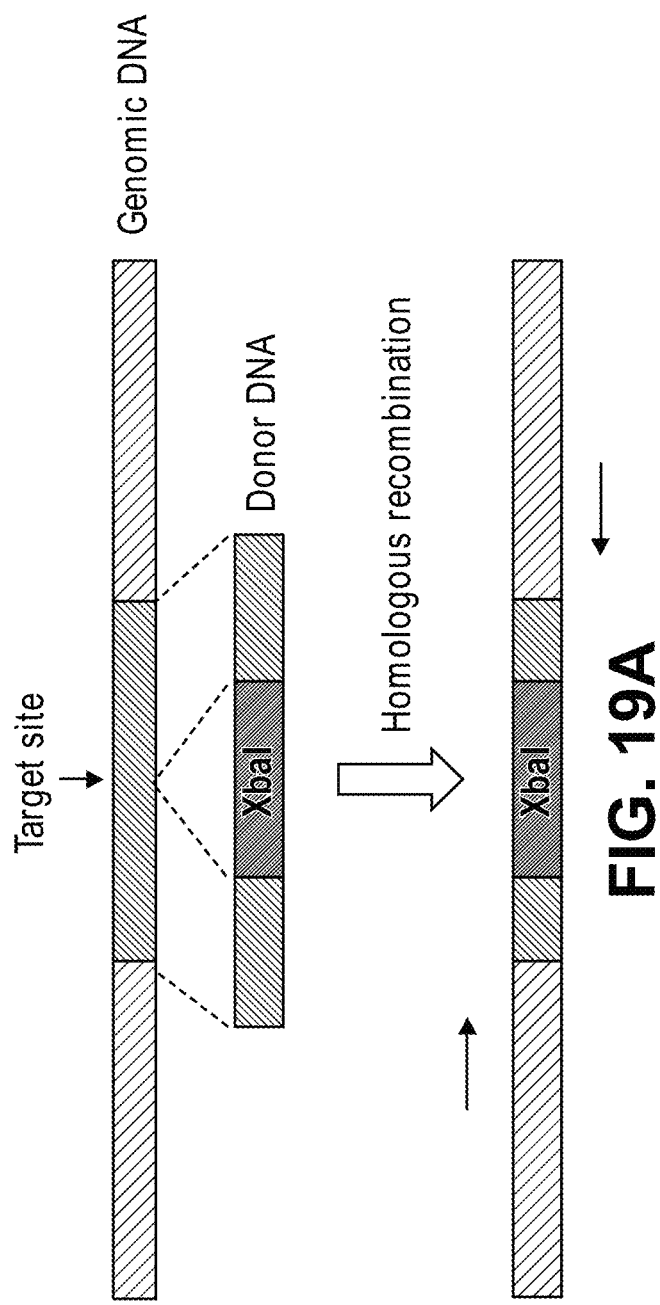
FIGS. 19A and 19B show that paired Cas9 nickases mediate homologous recombination.
Figure 19B:
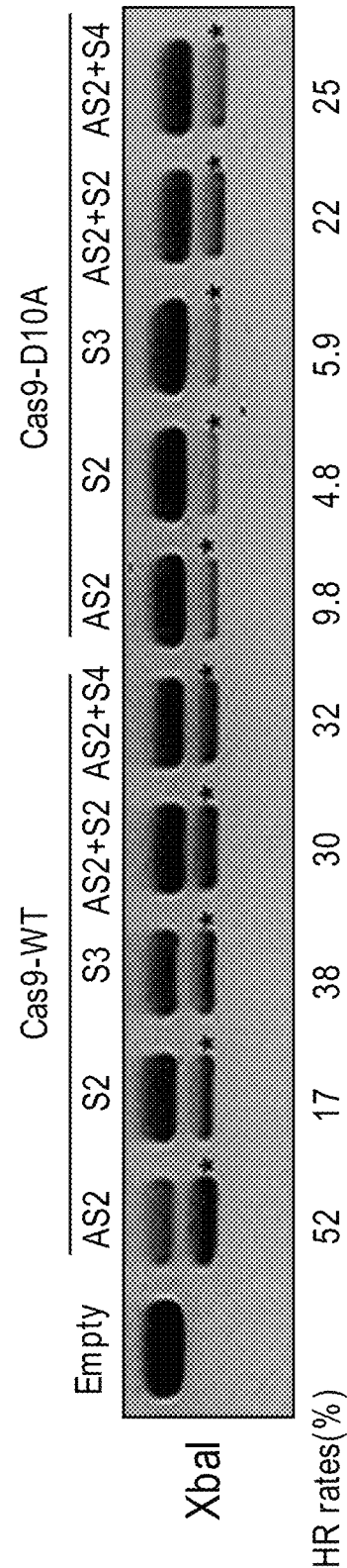

We first tested several Cas9 nucleases and nickases designed to target sites in the AAVS1 locus (FIG. 6) in vitro, via fluorescent capillary electrophoresis. Unlike Cas9 nucleases that cleaved both strands of DNA substrates, Cas9 nickases composed of guide RNA and a mutant form of Cas9 in which a catalytic aspartate residue is changed to an alanine (D10A Cas9) cleaved only one strand, producing site-specific nicks (FIG. 16C,D). Interestingly, however, some nickases (AS1, AS2, AS3, and S6 in FIG. 17A) induced indels at target sites in human cells, suggesting that nicks can be converted to DSBs, albeit inefficiently, in vivo. Paired Cas9 nickases producing two adjacent nicks on opposite DNA strands yielded indels at frequencies that ranged from 14% to 91%, comparable to the effects of paired nucleases (FIG. 17A). The repair of two nicks that would produce 5' overhangs led to the formation of indels much more frequently than those producing 3' overhangs at three genomic loci (FIG. 17A and FIG. 18). In addition, paired nickases enabled targeted genome editing via homology-directed repair more efficiently than did single nickases (FIG. 19).

Figure 17B:
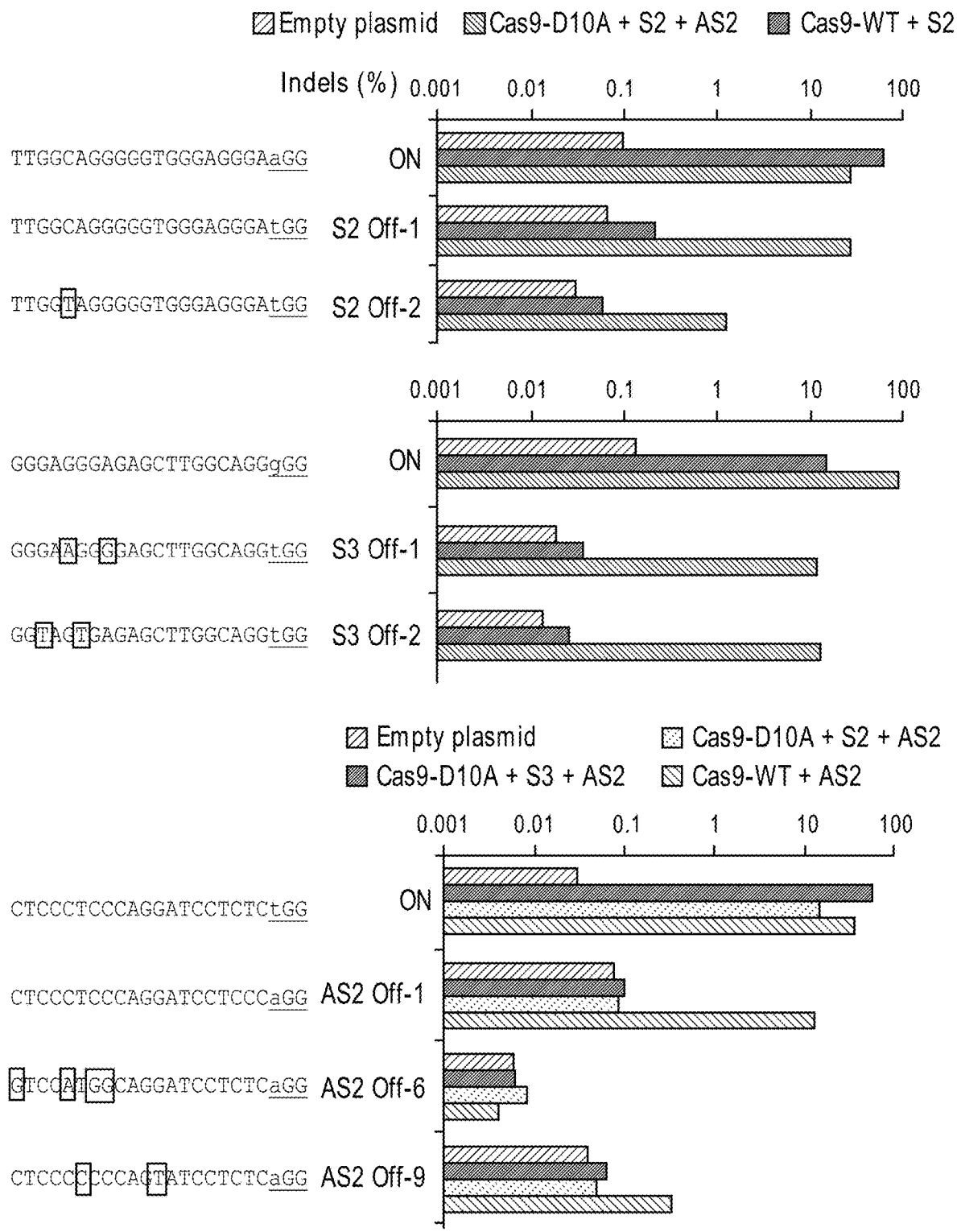

We next measured mutation frequencies of paired nickases and nucleases at off-target sites using deep sequencing. Cas9 nucleases complexed with three sgRNAs induced off-target mutations at six sites that differ by one or two nucleotides from their corresponding on-target sites with frequencies that ranged from 0.5% to 10% (FIG. 17B). In contrast, paired Cas9 nickases did not produce indels above the detection limit of 0.1% at any of the six off-target sites. The S2 Off-1 site that differs by a single nucleotide at the first position in the PAM (i.e., N in NGG) from its on-target site can be considered as another on-target site. As expected, the Cas9 nuclease complexed with the S2 sgRNA was equally efficient at this site and the on-target site. In sharp contrast, D10A Cas9 complexed with the S2 and AS2 sgRNAs discriminated this site from the on-target site by a factor of 270 fold. This paired nickase also discriminated the AS2 off-target sites (Off-1 and Off-9 in FIG. 17B) from the on-target site by factors of 160 fold and 990 fold, respectively.

Example 8

Chromosomal DNA Splicing Induced by Paired Cas9 Nickases

Two concurrent DSBs produced by engineered nucleases such as ZFNs and TALENs can promote large deletions of the intervening chromosomal segments has reproted. We tested whether two SSBs induced by paired Cas9 nickases can also produce deletions in human cells. We used PCR to detect deletion events and found that seven paired nickases induced deletions of up to 1.1-kbp chromosomal segments as efficiently as paired Cas9 nucleases did (FIG. 20A,B). DNA sequences of the PCR products confirmed the deletion events (FIG. 20C). Interestingly, the sgRNA-matching sequence remained intact in two out of seven deletion-specific PCR amplicons (underlined in FIG. 20C). In contrast, Cas9 nuclease pairs did not produce sequences that contained intact target sites. This finding suggests that two distant nicks were not converted to two separate DSBs to promote deletions of the intervening chromosomal segment. In addition, it is unlikely that two nicks separated by more than a 100 bp can produce a composite DSB with large overhangs under physiological conditions because the melting temperature is very high.

Figure 20D:
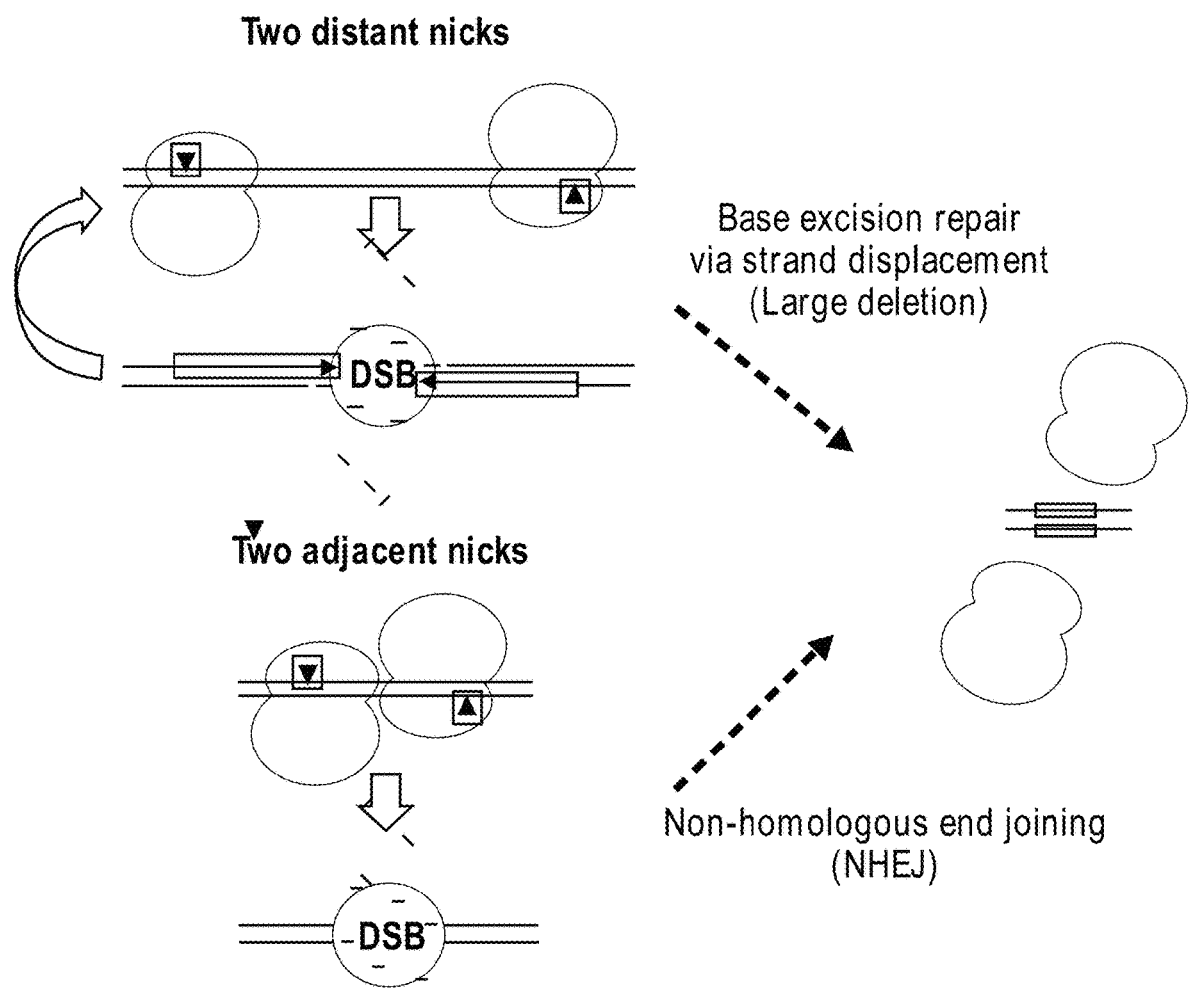

We propose that two distant nicks are repaired by strand displacement in a head-to-head direction, resulting in the formation of a DSB in the middle, whose repair via NHEJ causes small deletions (FIG. 20D). Because the two target sites remain intact during this process, nickases can induce SSBs again, triggering the cycle repeatedly until the target sites are deleted. This mechanism explains why two offset nicks producing 5' overhangs but not those producing 3' overhangs induced indels efficiently at three loci.

We then investigated whether Cas9 nucleases and nickases can induce unwanted chromosomal translocations that result from NHEJ repair of on-target and off-target DNA cleavages (FIG. 21A). We were able to detect translocations induced by Cas9 nucleases using PCR (FIG. 21B, C). No such PCR products were amplified using genomic DNA isolated from cells transfected with the plasmids encoding the AS2+S3 Cas9 nickase pair. This result is in line with the fact that both AS2 and S3 nickases, unlike their corresponding nucleases, did not produce indels at off-target sites (FIG. 17B).

These results suggest that paired Cas9 nickases allow targeted mutagenesis and large deletions of up to 1-kbp chromosomal segments in human cells. Importantly, paired nickases did not induce indels at off-target sites at which their corresponding nucleases induce mutations. Furthermore, unlike nucleases, paired nickases did not promote unwanted translocations associated with off-target DNA cleavages. In principle, paired nickases double the specificity of Cas9-mediated mutagenesis and will broaden the utility of RNA-guided enzymes in applications that require precise genome editing such as gene and cell therapy. One caveat to this approach is that two highly active sgRNAs are needed to make an efficient nickase pair, limiting targetable sites. As shown in this and other studies, not all sgRNAs are equally active. When single clones rather than populations of cells are used for further studies or applications, the choice of guide RNAs that represent unique sequences in the genome and the use of optimized guide RNAs would suffice to avoid off-target mutations associated with Cas9 nucleases. We propose that both Cas9 nucleases and paired nickases are powerful options that will facilitate precision genome editing in cells and organisms.

Example 9

Genotyping with CRISPR/Cas-Derived RNA-Guided Endonucleases

Next, We reasoned that RGENs can be used in Restriction fragment length polymorphism (RFLP) analysis, replacing conventional restriction enzymes. Engineered nucleases including RGENs induce indels at target sites, when the DSBs caused by the nucleases are repaired by the error-prone non-homologous end-joining (NHEJ) system. RGENs that are designed to recognize the target sequences cannot cleave mutant sequences with indels but will cleave wild-type target sequences efficiently.

9-1. RGEN Components crRNA and tracrRNA were prepared by in vitro transcription using MEGAshortcript T7 kit (Ambion) according to the manufacturer's instruction. Transcribed RNAs were resolved on a 8% denaturing urea-PAGE gel. The gel slice containing RNA was cut out and transferred to elution buffer. RNA was recovered in nuclease-free water followed by phenol:chloroform extraction, chloroform extraction, and ethanol precipitation. Purified RNA was quantified by spectrometry. Templates for crRNA were prepared by annealing an oligonucleotide whose sequence is shown as 5'-GAAATTAATACGACTCACTATAGGX$_{20}$GTTTTAGA-GCTATGCTGTTTTG-3' (SEQ ID NO: 76), in which X$_{20}$ is the target sequence, and its complementary oligonucleotide.

The template for tracrRNA was synthesized by extension of forward and reverse oligonucleotides (5'-GAAATTAATAC-GACTCACTATAGGAACCATTCAAAACAGCATAG-CAAGTTAAAATAAG GCTAGTCCG-3' (SEQ ID NO: 77) and 5'-AAAAAAAGCACCGACTCGGTGC-CACTTTTTCAAGTTGATAACGGACTAGCCTT-ATTTTA ACTTGCTATG-3' (SEQ ID NO: 78)) using Phusion polymerase (New England Biolabs).

9-2. Recombinant Cas9 Protein Purification

The Cas9 DNA construct used in our previous Example, which encodes Cas9 fused to the His6-tag at the C terminus, was inserted in the pET-28a expression vector. The recombinant Cas9 protein was expressed in E. coli strain BL21 (DE3) cultured in LB medium at 25° C. for 4 hour after induction with 1 mM IPTG. Cells were harvested and resuspended in buffer containing 20 mM Tris PH 8.0, 500 mM NaCl, 5 mM immidazole, and 1 mM PMSF. Cells were frozen in liquid nitrogen, thawed at 4° C., and sonicated. After centrifugation, the Cas9 protein in the lysate was bound to Ni-NTA agarose resin (Qiagen), washed with buffer containing 20 mM Tris pH 8.0, 500 mM NaCl, and 20 mM immidazole, and eluted with buffer containing 20 mM Tris pH 8.0, 500 mM NaCl, and 250 mM immidazole. Purified Cas9 protein was dialyzed against 20 mM HEPES (pH 7.5), 150 mM KCl, 1 mM DTT, and 10% glycerol and analyzed by SDS-PAGE.

9-3. T7 Endonuclease I Assay

The T7E1 assay was performed as following. In brief, PCR products amplified using genomic DNA were denatured at 95° C., reannealed at 16° C., and incubated with 5 units of T7 Endonuclease I (New England BioLabs) for 20 min at 37° C. The reaction products were resolved using 2 to 2.5% agarose gel electrophoresis.

9-4. RGEN-RFLP Assay

PCR products (100-150 ng) were incubated for 60 min at 37° C. with optimized concentrations (Table 10) of Cas9 protein, tracrRNA, crRNA in 10 μl NEB buffer 3 (1×). After the cleavage reaction, RNase A (4 μg) was added, and the reaction mixture was incubated for 30 min at 37° C. to remove RNA. Reactions were stopped with 6× stop solution buffer containing 30% glycerol, 1.2% SDS, and 100 mM EDTA. Products were resolved with 1-2.5% agarose gel electrophoresis and visualized with BtBr staining.

TABLE 10

Concentration of RGEN components in RFLP assays

| Target Name | Cas9 (ng/μl) | crRNA (ng/μl) | tracrRNA (ng/μl) |
|---|---|---|---|
| C4BPB | 100 | 25 | 60 |
| PIBF-NGG-RGEN | 100 | 25 | 60 |
| HLA-B | 1.2 | 0.3 | 0.7 |
| CCR5-ZFN | 100 | 25 | 60 |
| CTNNB1 Wild type specific | 30 | 10 | 20 |
| CTNNB1 mutant specific | 30 | 10 | 20 |
| CCR5 WT-specific | 100 | 25 | 60 |
| CCR5 Δ32-specific | 10 | 2.5 | 6 |
| KRAS WT specific (wt) | 30 | 10 | 20 |
| KRAS mutant specific (m8) | 30 | 10 | 20 |
| KRAS WT specific (m6) | 30 | 10 | 20 |
| KRAS mutant specific (m6,8) | 30 | 10 | 20 |
| PIK3CA WT specific (wt) | 100 | 25 | 60 |
| PIK3CA mutant specific (m4) | 30 | 10 | 20 |
| PIK3CA WT specific (m7) | 100 | 25 | 60 |
| PIK3CA mutant specific (m4,7) | 30 | 10 | 20 |
| BRAF WT-specific | 30 | 10 | 20 |
| BRAF mutant-specific | 100 | 25 | 60 |
| NRAS WT-specific | 100 | 25 | 60 |
| NRAS mutant-specific | 30 | 10 | 20 |
| IDH WT-specific | 30 | 10 | 20 |
| IDH mutant-specific | 30 | 10 | 20 |
| PIBF-NAG-RGEN | 30 | 10 | 60 |

TABLE 11

Primers

| Gene (site) | Direction | Sequence (5' to 3') | SEQ ID NO |
|---|---|---|---|
| CCR5 (RGEN) | F1 | CTCCATGGTGCTATAGAGCA | 79 |
| | F2 | GAGCCAAGCTCTCCATCTAGT | 80 |
| | R | GCCCTGTCAAGAGTTGACAC | 81 |
| CCR5 (ZFN) | F | GCACAGGGTGGAACAAGATGGA | 82 |
| | R | GCCAGGTACCTATCGATTGTCAGG | 83 |
| CCR5 (del32) | F | GAGCCAAGCTCTCCATCTAGT | 84 |
| | R | ACTCTGACTG GGTCACCAGC | 85 |
| C4BPB | F1 | TATTTGGCTGGTTGAAAGGG | 86 |
| | R1 | AAAGTCATGAAATAAACACACCCA | 87 |
| | F2 | CTGCATTGATATGGTAGTACCATG | 88 |
| | R2 | GCTGTTCATTGCAATGGAATG | 89 |
| CTNNB1 | F | ATGGAGTTGGACATGGCCATGG | 90 |
| | R | ACTCACTATCCACAGTTCAGCATTTACC | 91 |
| KRAS | F | TGGAGATAGCTGTCAGCAACTTT | 92 |
| | R | CAACAA AGCAAAGGTAAAGTTGGTAATAG | 93 |
| PIK3CA | F | GGTTTCAGGAGATGTGTTACAAGGC | 94 |
| | R | GATTGTGCAATTCCTATGCAATCGGTC | 95 |
| NRAS | F | CACTGGGTACTTAATCTGTAGCCTC | 96 |
| | R | GGTTCCAAGTCATTCCCAGTAGC | 97 |
| IDH1 | F | CATCACTGCAGTTGTAGGTTATAACTATCC | 98 |
| | R | TTGAAAACCACAGATCTGGTTGAACC | 99 |
| BRAF | F | GGAGTGCCAAGAGAATATCTGG | 100 |
| | R | CTGAAACTGGTTTCAAAATATTCGTTTTAAGG | 101 |
| PIBF | F | GCTCTGTATGCCCTGTAGTAGG | 102 |
| | R | TTTGCATCTGACCTTACCTTTG | 103 |

9-5. Plasmid Cleavage Assay

Restriction enzyme-treated linearized plasmid (100 ng) was incubated for 60 min at 37° C. with Cas9 protein (0.1 μg), tracrRNA (60 ng), and crRNA (25 ng) in 10 μl NEB 3 buffer (1×). Reactions were stopped with 6× stop solution containing 30% glycerol, 1.2% SDS, and 100 mM EDTA. Products were resolved with 1% agarose gel electrophoresis and visualized with EtBr staining.

9-6. Strategy of RFLP

New RGENs with desired DNA specificities can be readily created by replacing crRNA; no de novo purification of custom proteins is required once recombinant Cas9 protein is available. Engineered nucleases, including RGENs, induce small insertions or deletions (indels) at target sites when the DSBs caused by the nucleases are repaired by error-prone non-homologous end-joining (NHEJ). RGENs that are designed to recognize the target sequences cleave wild-type sequences efficiently but cannot cleave mutant sequences with indels (FIG. 22).

Figure 23:
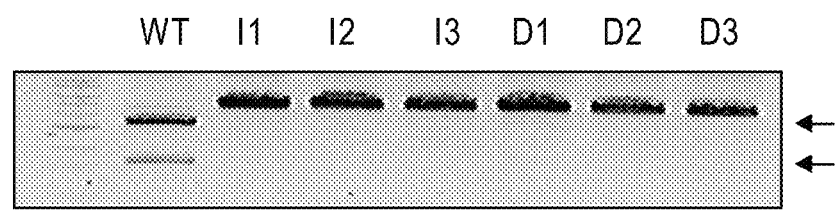
FIG. 23 shows in vitro cleavage assay of a linearized plasmid containing the C4BPB target site bearing indels. DNA sequences of individual plasmid substrates (upper panel): WT (SEQ ID NO: 104), I1 (SEQ ID NO: 225), I2 (SEQ ID NO: 226), I3 (SEQ ID NO: 227), D1 (SEQ ID NO: 228), D2 (SEQ ID NO: 229), and D3 (SEQ ID NO: 230). The PAM sequence is underlined. Inserted bases are shown in box. Arrows (bottom panel) indicate expected positions of DNA bands cleaved by the wild-type-specific RGEN after electrophoresis.

We first tested whether RGENs can differentially cleave plasmids that contain wild-type or modified C4BPB target sequences that harbor 1- to 3-base indels at the cleavage site. None of the six plasmids with these indels were cleaved by a C4BPB-specific RGEN5 composed of target-specific crRNA, tracrRNA, and recombinant Cas9 protein (FIG. 23). In contrast, the plasmid with the intact target sequence was cleaved efficiently by this RGEN.

9-7. Detection of Mutations Induced by the Same RGENs Using RGEN-Mediated RFLP

Next, to test the feasibility of RGEN-mediated RFLP for detection of mutations induced by the same RGENs, we utilized gene-modified K562 human cancer cell clones established using an RGEN targeting C4BPB gene (Table 12).

TABLE 12

Target sequence of RGENs used in this study

| Gene | Target sequence | SEQ ID NO |
|---|---|---|
| human C4BPB | AATGACCACTACATCCTCAAGGG | 104 |
| mouse Pibf1 | AGATGATGTCTCATCATCAGAGG | 105 |

C4BPB mutant clones used in this study have various mutations ranging from 94 bp deletion to 67 bp insertion (FIG. 24A). Importantly, all mutations occurred in mutant clones resulted in the loss of RGEN target site. Among 6 C4BPB clones analyzed, 4 clones have both wildtype and mutant alleles (+/−) and 2 clones have only mutant alleles (−/−).

Figure 24B:
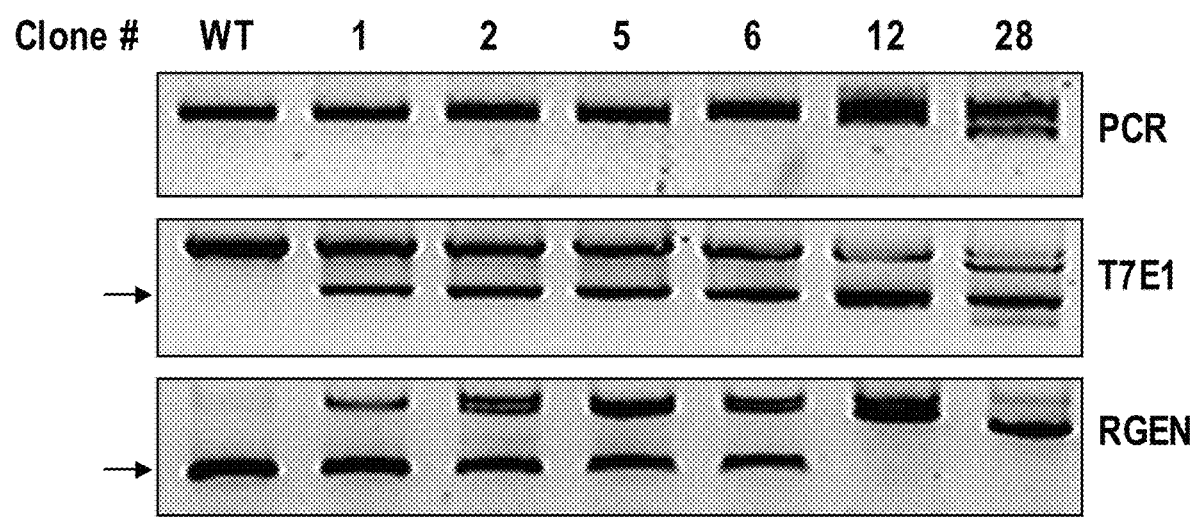

The PCR products spanning the RGEN target site amplified from wildtype K562 genomic DNA were digested completely by the RGEN composed of target-specific crRNA, tracrRNA, and recombinant Cas9 protein expressed in and purified from E. coli (FIG. 24B/Lane 1). When the C4BPB mutant clones were subjected to RFLP analysis using the RGEN, PCR amplicons of +/− clones that contained both wildtype and mutant alleles were partially digested, and those of −/− cloned that did not contain the wildtype allele were not digested at all, yielding no cleavage products corresponding to the wildtype sequence (FIG. 24B). Even a single-base insertion at the target site blocked the digestion (#12 and #28 clones) of amplified mutant alleles by the C4BPB RGEN, showing the high specificity of RGEN-mediated RFLP. We subjected the PCR amplicons to the mismatch-sensitive T7E1 assay in parallel (FIG. 24B). Notably, the T7E1 assay was not able to distinguish −/− clones from +/− clones. To make it matters worse, the T7E1 assay cannot distinguish homozygous mutant clones that contain the same mutant sequence from wildtype clones, because annealing of the same mutant sequence will form a homoduplex. Thus, RGEN-mediated RFLP has a critical advantage over the conventional mismatch-sensitive nuclease assay in the analysis of mutant clones induced by engineered nucleases including ZFNs, TALENs and RGENs.

9-8. Quantitative Assay for RGEN-RFLP Analysis

We also investigated whether RGEN-RFLP analysis is a quantitative method. Genomic DNA samples isolated from the C4BPB null clone and the wild-type cells were mixed at various ratios and used for PCR amplifications. The PCR products were subjected to RGEN genotyping and the T7E1 assay in parallel (FIG. 25b). As expected, DNA cleavage by the RGEN was proportional to the wild type to mutant ratio. In contrast, results of the T7E1 assay correlated poorly with mutation frequencies inferred from the ratios and were inaccurate, especially at high mutant %, a situation in which complementary mutant sequences can hybridize with each other to form homoduplexes.

9-9. Analysis of Mutant Mouse Founders Using a RGEN-Mediated RFLP Genotyping

Figure 26A:
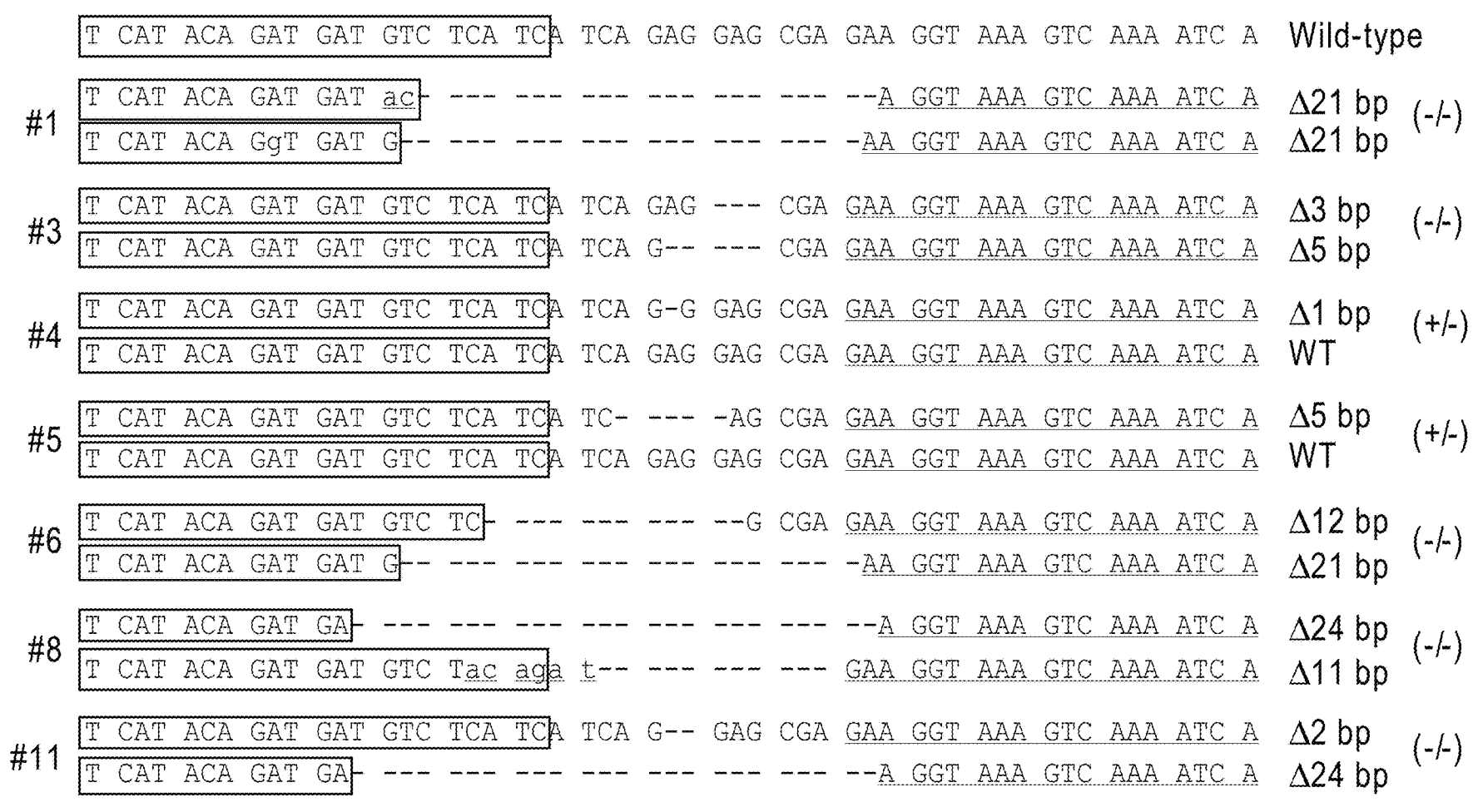
Figure 26B:
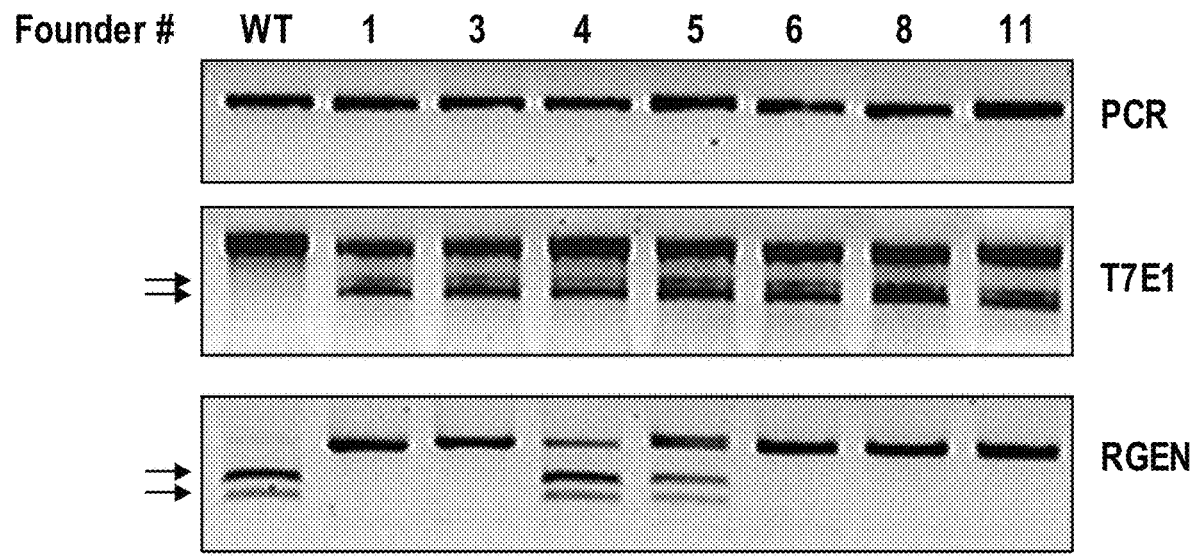
FIG. 26B: Comparison of the mismatch-sensitive T7E1 assay with RGEN-mediated RFLP analysis. Black arrows indicate the cleavage product by treatment of T7E1 enzyme or RGENs.

We also applied RGEN-mediated RFLP genotyping (RGEN genotyping in short) to the analysis of mutant mouse founders that had been established by injection of TALENs into mouse one-cell embryos (FIG. 26A). We designed and used an RGEN that recognized the TALEN target site in the Pibf1 gene (Table 10). Genomic DNA was isolated from a wildtype mouse and mutant mice and subjected to RGEN genotyping after PCR amplification. RGEN genotyping successfully detected various mutations, which ranged from one to 27-bp deletions (FIG. 26B). Unlike the T7E1 assay, RGEN genotyping enabled differential detection of +/− and −/− founder.

Figure 27:
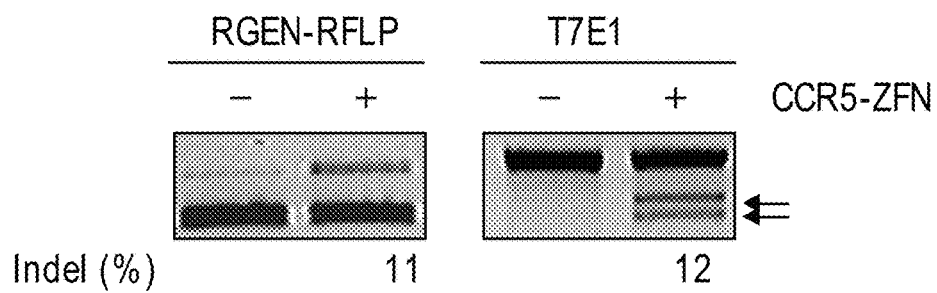
FIG. 27 shows RGEN-mediated genotyping of ZFN-induced mutations at a wild-type CCR5 sequence (SEQ ID NO: 253). The ZFN target site is shown in box. Black arrows indicate DNA bands cleaved by T7E1.

9-10. Detection of Mutations Induced in Human Cells by a CCR5-Specific ZFN Using RGENs In addition, we used RGENs to detect mutations induced in human cells by a CCR5-specific ZFN, representing yet another class of engineered nucleases (FIG. 27). These results show that RGENs can detect mutations induced by nucleases other than RGENs themselves. In fact, we expect that RGENs can be designed to detect mutations induced by most, if not all, engineered nucleases. The only limitation in the design of an RGEN genotyping assay is the requirement for the GG or AG (CC or CT on the complementary strand) dinucleotide in the PAM sequence recognized by the Cas9 protein, which occurs once per 4 bp on average. Indels induced anywhere within the seed region of several bases in crRNA and the PAM nucleotides are expected to disrupt RGEN-catalyzed DNA cleavage. Indeed, we identified at least one RGEN site in most (98%) of the ZFN and TALEN sites.

9-11. Detection of Polymorphisms or Variations Using RGEN

Figure 25C:
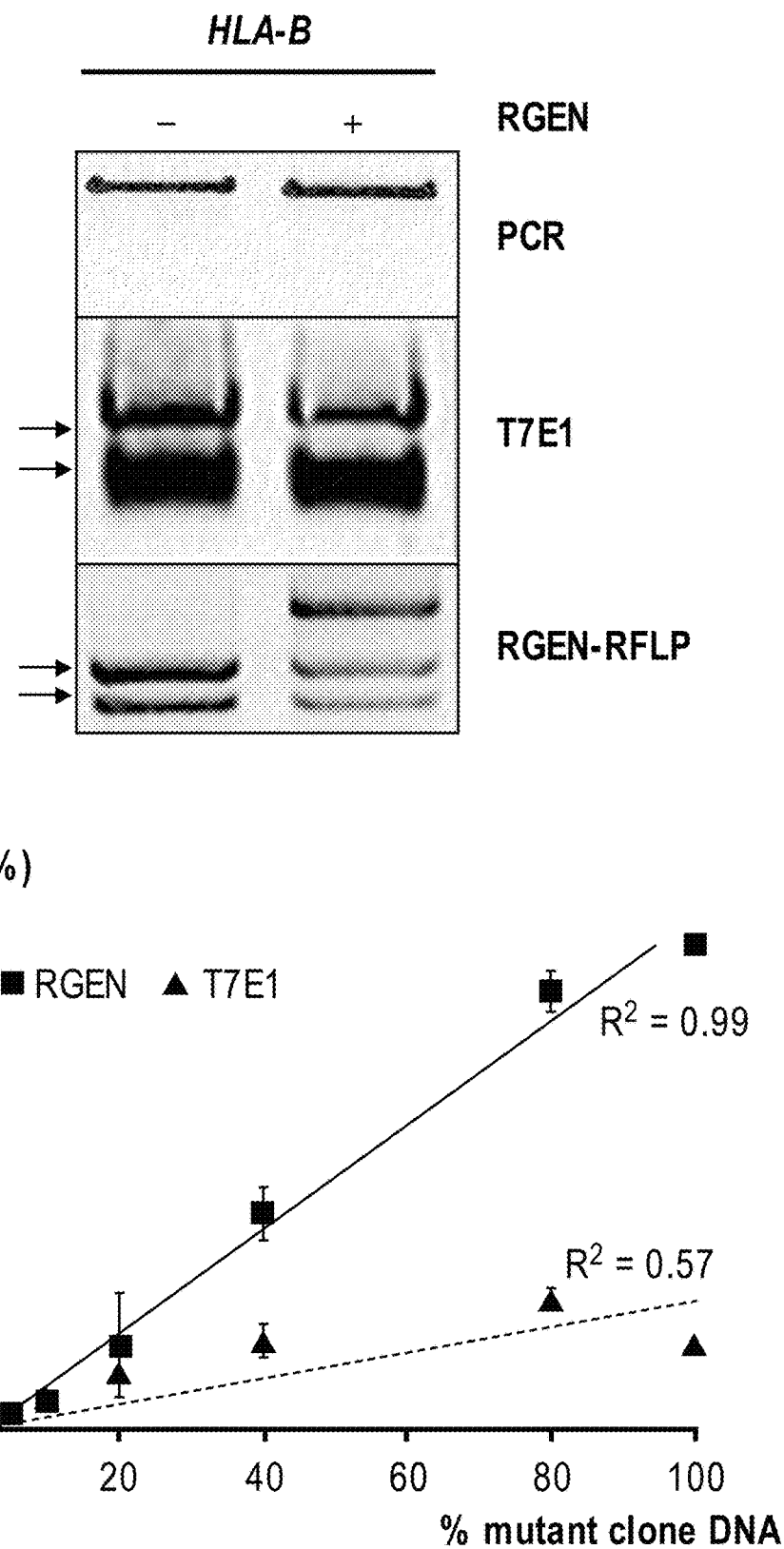
Figure 28:
FIG. 28 shows polymorphic sites in a region of the human HLA-B gene (SEQ ID NO: 254). The sequence, which surrounds the RGEN target site, is that of a PCR amplicon from HeLa cells. Polymorphic positions are shown in box. The RGEN target site and the PAM sequence are shown in dashed and bolded box, respectively. Primer sequences are underlined.

Next, we designed and tested a new RGEN that targets a highly polymorphic locus, HLA-B, that encodes Human Leukocyte Antigen B (a.k.a. MHC class I protein) (FIG. 28). HeLa cells were transfected with RGEN plasmids, and the genomic DNA was subjected to T7E1 and RGEN-RFLP analyses in parallel. T7E1 produced false positive bands that resulted from sequence polymorphisms near the target site (FIG. 25c). As expected, however, the same RGEN used for gene disruption cleaved PCR products from wild-type cells completely but those from RGEN-transfected cells partially, indicating the presence of RGEN-induced indels at the target site. This result shows that RGEN-RFLP analysis has a clear advantage over the T7E1 assay, especially when it is not known whether target genes have polymorphisms or variations in cells of interest.

Figure 29A:
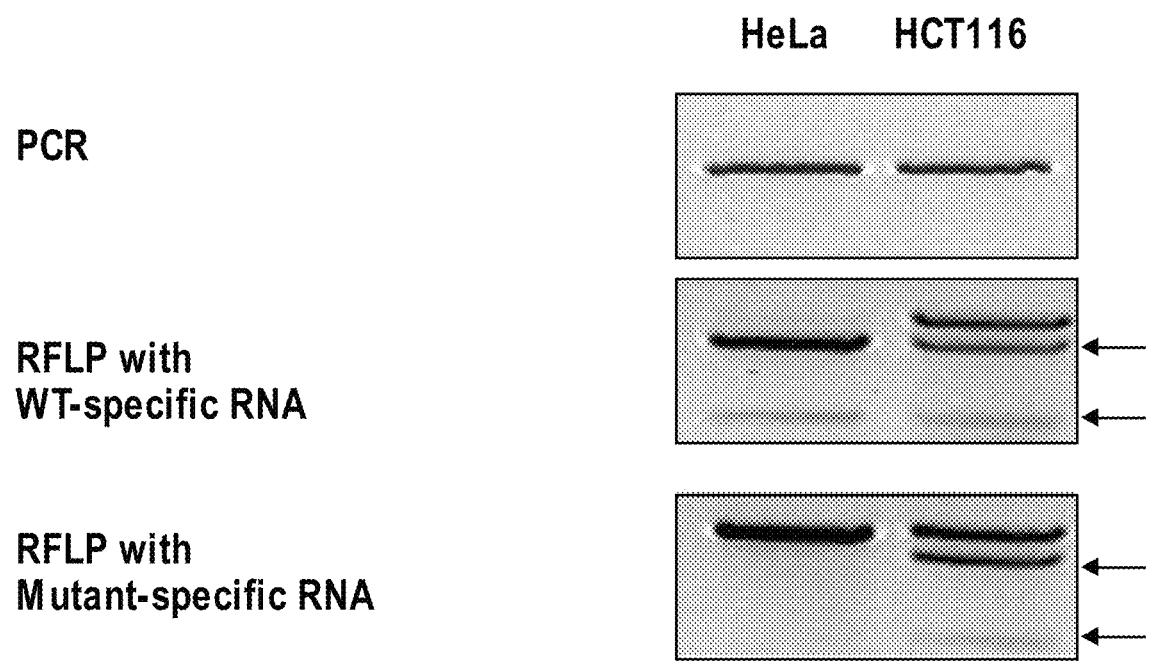
FIGS. 29A and 29B show genotyping of oncogenic mutations via RGEN-RFLP analysis.

9-12. Detection of Recurrent Mutations Found in Cancer and Naturally-Occurring Polymorphisms through RGEN-RFLP Analysis RGEN-RFLP analysis has applications beyond genotyping of engineered nuclease-induced mutations. We sought to use RGEN genotyping to detect recurrent mutations found in cancer and naturally-occurring polymorphisms. We chose the human colorectal cancer cell line, HCT116, which carries a gain-of-function 3-bp deletion in the oncogenic CTNNB1 gene encoding beta-catenin. PCR products amplified from HCT116 genomic DNA were cleaved partially by both wild-type-specific and mutant-specific RGENs, in line with the heterozygous genotype in HCT116 cells (FIG. 29a). In sharp contrast, PCR products amplified from DNA from HeLa cells harboring only wild-type alleles were digested completely by the wild-type-specific RGEN and were not cleaved at all by the mutation-specific RGEN.

Figure 30A:
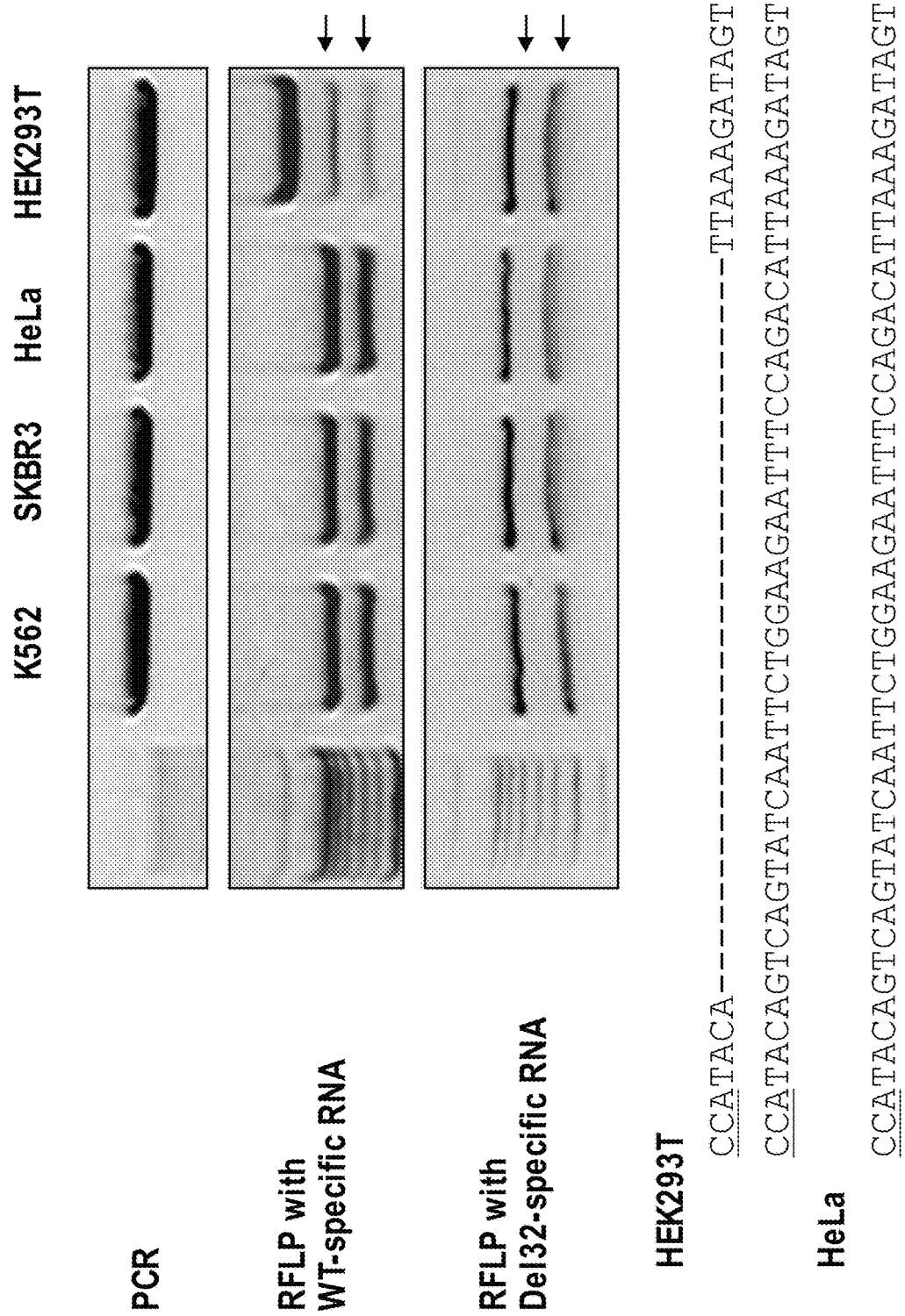

We also noted that HEK293 cells harbor the 32-bp deletion (del32) in the CCR5 gene, which encodes an essential co-receptor of HIV infection: Homozygous del32 CCR5 carriers are immune to HIV infection. We designed one RGEN specific to the del32 allele and the other to the wild-type allele. As expected, the wild-type-specific RGEN cleaved the PCR products obtained from K562, SKBR3, or HeLa cells (used as wild-type controls) completely but those from HEK293 cells partially (FIG. 30a), confirming the presence of the uncleavable del32 allele in HEK293 cells. Unexpectedly, however, the del32-specific RGEN cleaved the PCR products from wild-type cells as efficiently as those from HEK293 cells. Interestingly, this RGEN had an off-target site with a single-base mismatch immediately downstream of the on-target site (FIG. 30). These results suggest that RGENs can be used to detect naturally-occurring indels but cannot distinguish sequences with single nucleotide polymorphisms or point mutations due to their off-target effects.

Figure 29B:
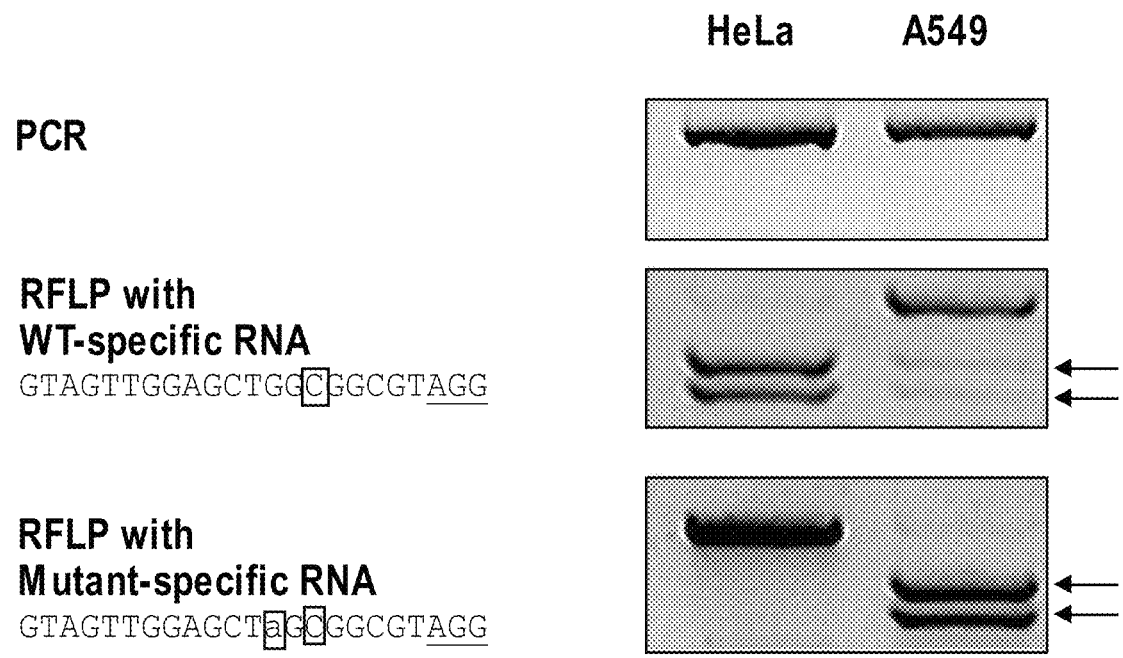
Figure 31A:
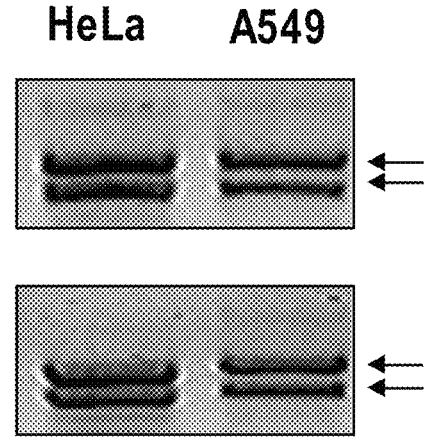
FIGS. 31A and 31B show genotyping of a KRAS point mutation (c. 34 G>A).
Figure 31B:
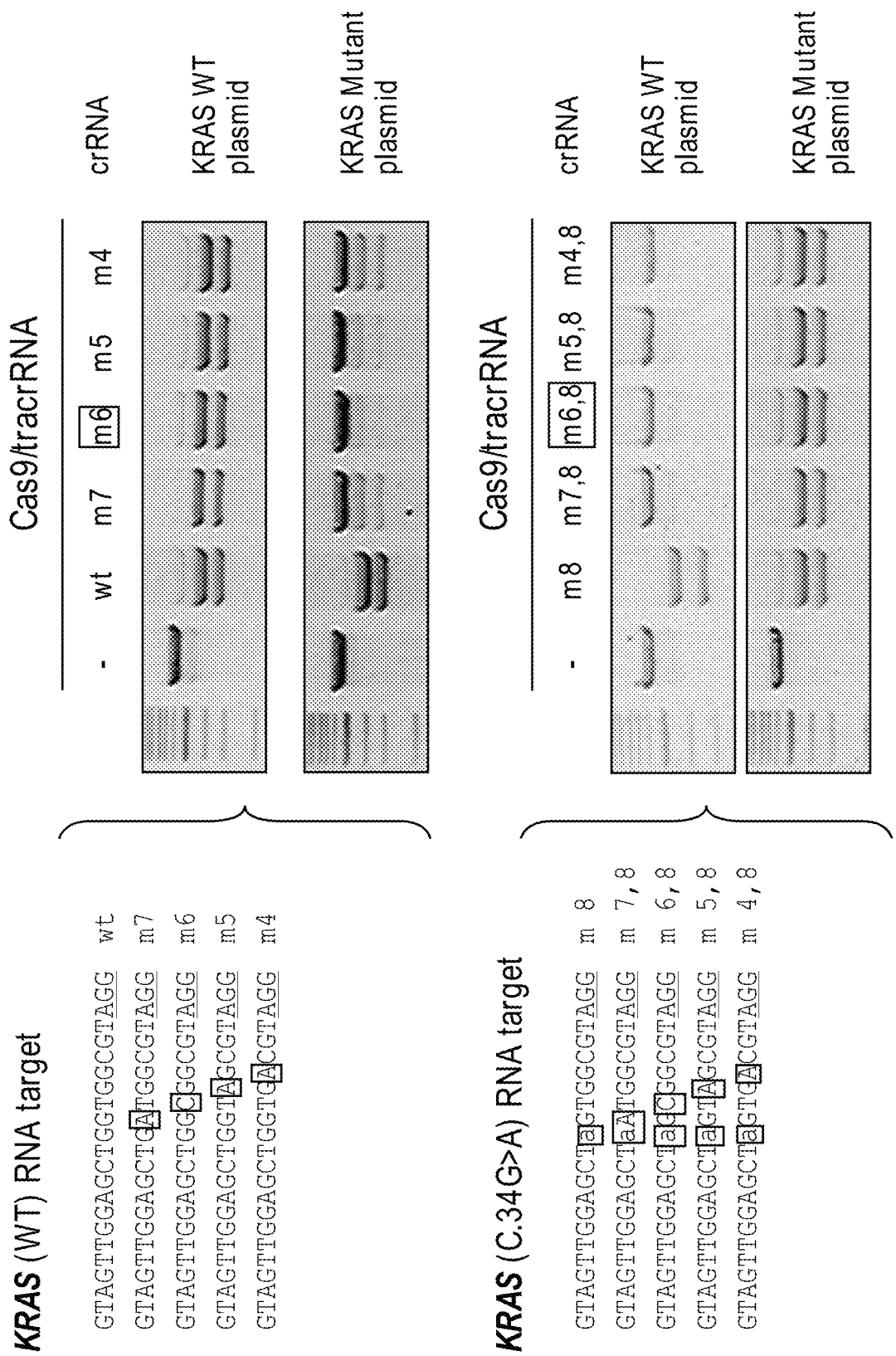
Figure 32A:
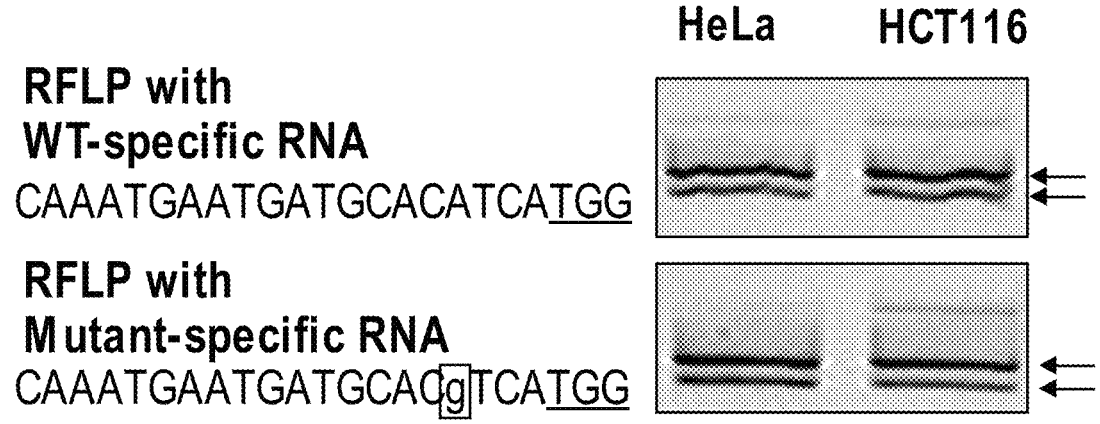
FIGS. 32A and 32B show genotyping of a PIK3CA point mutation (c.3140 A>G).
Figure 32B:
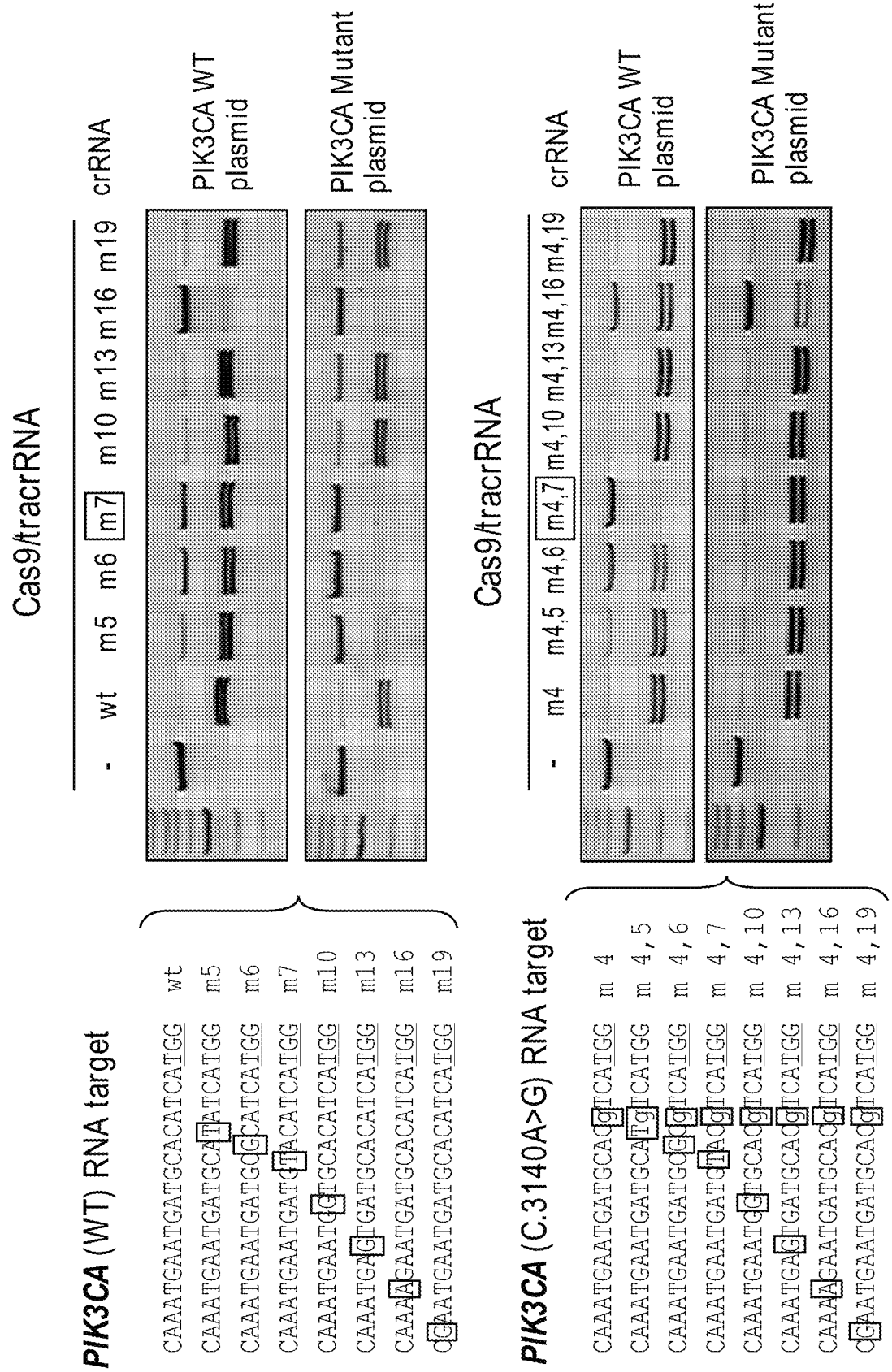
Figure 33B:
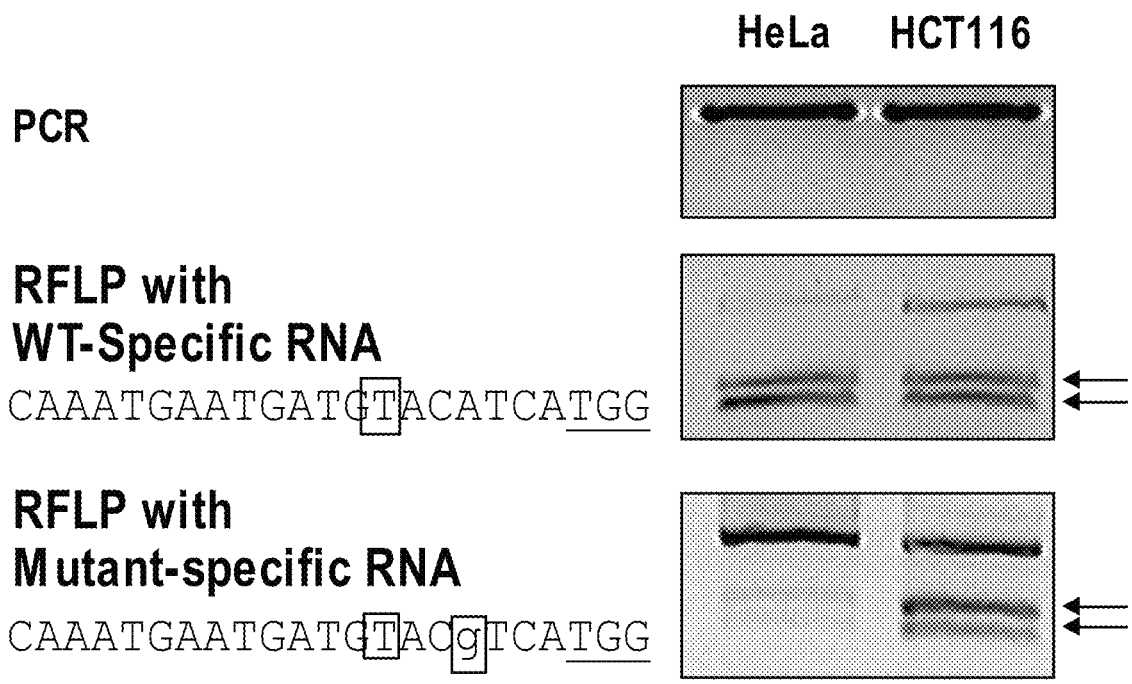
Figure 33C:
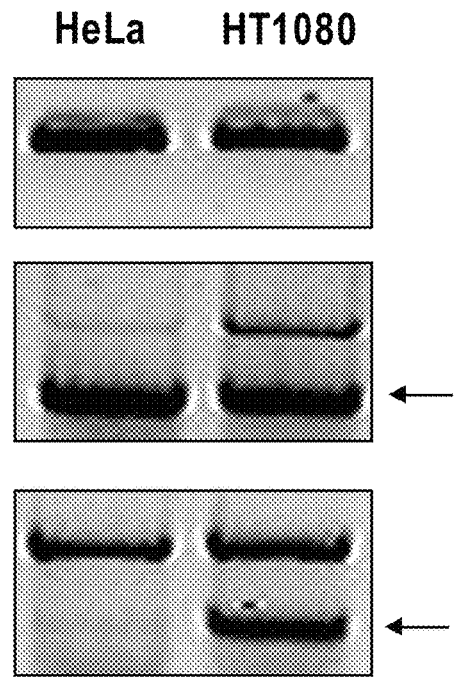
Figure 33D:
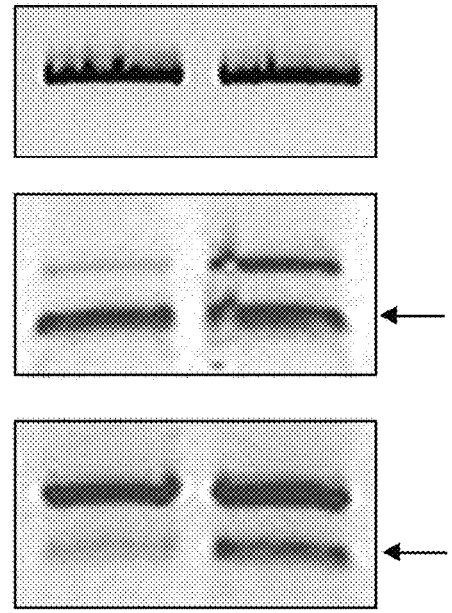

To genotype oncogenic single-nucleotide variations using RGENs, we attenuated RGEN activity by employing a single-base mismatched guide RNA instead of a perfectly-matched RNA. RGENs that contained the perfectly-matched guide RNA specific to the wild-type sequence or mutant sequence cleaved both sequences (FIGS. 31a and 32a). In contrast, RGENs that contained a single-base mismatched guide RNA distinguished the two sequences, enabling genotyping of three recurrent oncogenic point mutations in the KRAS, PIK3CA, and IDH1 genes in human cancer cell lines (FIG. 29b and FIGS. 33a, b). In addition, we were able to detect point mutations in the BRAF and NRAS genes using RGENs that recognize the NAG PAM sequence (FIGS. 33c, d). We believe that we can use RGEN-RFLP to genotype almost any, if not all, mutations or polymorphisms in the human and other genomes.

The above data proposes RGENs as providing a platform to use simple and robust RFLP analysis for various sequence variations. With high flexibility in reprogramming target sequence, RGENs can be used to detect various genetic variations (single nucleotide variations, small insertion/deletions, structural variations) such as disease-related recurring mutations, genotypes related to drug-response by a patient and also mutations induced by engineered nucleases in cells. Here, we used RGEN genotyping to detect mutations induced by engineered nucleases in cells and animals. In principle, one could also use RGENs that will specifically detect and cleave naturally-occurring variations and mutations.

Based on the above description, it should be understood by those ski lied in the art that various alternatives to the embodiments of the invention described herein may be employed in practicing the invention without departing from the technical idea or essential features of the invention as defined in the following claims. In this regard, the above-described examples are for illustrative purposes only, and the invention is not intended to be limited by these examples. The scope of the present invention should be understood to include all of the modifications or modified form derived from the meaning and scope of the following claims or its equivalent concepts.

REFERENCES

1. M. Jinek et al., Science 337, 816 (Aug. 17, 2012).
2. H. Kim, E. Um, S. R. Cho, C. Jung, J. S. Kim, Nat Methods 8, 941 (November, 2011).
3. H. J. Kim, H. J. Lee, H. Kim, S. W. Cho, J. S. Kim, Genome Res 19, 1279 (July, 2009).
4. E. E. Perez et al., Nat Biotechnol 26, 808 (July, 2008).
5. J. C. Miller et al., Nat Biotechnol 29, 143 (February, 2011).
6. C. Mussolino et al., Nucleic Acids Res 39, 9283 (November, 2011).
7. J. Cohen, Science 332, 784 (May 13, 2011).
8. V. Pattanayak, C. L. Ramirez, J. K. Joung, D. R. Liu, Nat Methods 8, 765 (September, 2011).
9. R. Gabriel et al., Nat Biotechnol 29, 816 (September, 2011).
10. E. Kim et al., Genome Res, (Apr. 20, 2012).
11. H. J. Lee, J. Kweon, E. Kim, S. Kim, J. S. Kim, Genome Res 22, 539 (March, 2012).
12. H. J. Lee, E. Kim, J. S. Kim, Genome Res 20, 81 (January, 2010).
13. Pu Y, Foden J A, Khayter C, Maeder M L, Reyon D, Joung J K, Sander J D. High-frequency off-target mutagenesis induced by CRISPR-Cas nucleases in human cells. Nat Biotech advance online publication (2013)

The invention claimed is:

1. A method of introducing a site-specific, double-stranded break at a target nucleic acid sequence in a eukaryotic cell, the method comprising introducing into the eukaryotic cell a Type II Clustered Regularly Interspaced Short Palindromic Repeats (CRISPR)/Cas system, wherein the CRISPR/Cas system comprises:
   a) a nucleic acid encoding a Cas9 polypeptide comprising a nuclear localization signal, wherein the nucleic acid is codon-optimized for expression in eukaryotic cells, and
   b) a guide RNA that hybridizes to the target nucleic acid, wherein the guide RNA is a chimeric guide RNA comprising a CRISPR RNA (crRNA) portion fused to a trans activating crRNA (tracrRNA) portion, wherein the guide RNA comprises two guanines at its 5' end, and there are no additional nucleic acid residues between the two guanines at the 5' end and the crRNA portion of the guide RNA;
   whereby a site-specific, double stranded break at the target nucleic acid sequence is introduced.

2. The method of claim 1, wherein the nuclear localization signal is located at the C terminus of the Cas9 polypeptide.

3. The method of claim 1, wherein the eukaryotic cell is a mammalian cell.

4. The method of claim 3, wherein the mammalian cell is a human cell.

5. The method of claim 1, wherein the nucleic acid encoding the Cas 9 polypeptide is codon-optimized for expression in mammalian cells.

6. The method of claim 1, wherein the target nucleic acid sequence is a genomic sequence located at its endogenous site in the genome of the eukaryotic cell.

7. The method of claim 1, wherein the nucleic acid encoding the Cas9 polypeptide is a vector.

8. The method of claim 1, wherein the Cas9 polypeptide is a *Streptococcus pyogenes* Cas9 polypeptide.

9. The method of claim 1, wherein the nucleic acid encoding the Cas9 polypeptide is introduced into the eukaryotic cell before introducing the guide RNA into the eukaryotic cell.

10. The method of claim 1, wherein the Cas9 polypeptide is a *Streptococcus* Cas9 polypeptide.

* * * * *

SEQUENCE LISTING

<160> NUMBER OF SEQ ID NOS: 296

<210> SEQ ID NO 1
<211> LENGTH: 4107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cas9-coding sequence

<400> SEQUENCE: 1
atggacaaga agtacagcat cggcctggac atcggtacca acagcgtggg ctgggccgtg      60
atcaccgacg agtacaaggt gcccagcaag aagttcaagg tgctgggcaa caccgaccgc     120

```
cacagcatca agaagaacct gatcggcgcc ctgctgttcg acagcggcga gaccgccgag    180
gccacccgcc tgaagcgcac cgcccgccgc cgctacaccc gccgcaagaa ccgcatctgc    240
tacctgcagg agatcttcag caacgagatg gccaaggtgg acgacagctt cttccaccgc    300
ctggaggaga gcttcctggt ggaggaggac aagaagcacg agcgccaccc catcttcggc    360
aacatcgtgg acgaggtggc ctaccacgag aagtacccca ccatctacca cctgcgcaag    420
aagctggtgg acagcaccga caaggccgac ctgcgcctga tctacctggc cctggcccac    480
atgatcaagt ccgcggcca cttcctgatc gagggcgacc tgaaccccga caacagcgac    540
gtggacaagc tgttcatcca gctggtgcag acctacaacc agctgttcga ggagaacccc    600
atcaacgcca gcggcgtgga cgccaaggcc atcctgagcg cccgcctgag caagagccgc    660
cgcctggaga acctgatcgc ccagctgccc ggcgagaaga gaacggcct gttcggcaac    720 ctgatcgccc tgagcctggg cctgaccccc aacttcaaga gcaacttcga cctggccgag    780
gacgccaagc tgcagctgag caaggacacc tacgacgacg acctggacaa cctgctggcc    840
cagatcggcg accagtacgc cgacctgttc ctggccgcca agaacctgag cgacgccatc    900
ctgctgagcg acatcctgcg cgtgaacacc gagatcacca aggccccct gagcgccagc    960 atgatcaagc gctacgacga gcaccaccag gacctgaccc tgctgaaggc cctggtgcgc   1020
cagcagctgc ccgagaagta caaggagatc ttcttcgacc agagcaagaa cggctacgcc   1080
ggctacatcg acggcggcgc cagccaggag gagttctaca gttcatcaa gcccatcctg   1140 gagaagatgg acggcaccga ggagctgctg gtgaagctga accgcgagga cctgctgcgc   1200
aagcagcgca ccttcgacaa cggcagcatc ccccaccaga tccacctggg cgagctgcac   1260
gccatcctgc gccgccagga ggacttctac cccttcctga aggacaaccg cgagaagatc   1320
gagaagatcc tgaccttccg catcccctac tacgtgggcc ccctggcccg cggcaacagc   1380
cgcttcgcct ggatgacccg caagagcgag gagaccatca ccccctgaa cttcgaggag   1440 gtggtggaca agggcgccag cgcccagagc ttcatcgagc gcatgaccaa cttcgacaag   1500
aacctgccca acgagaaggt gctgcccaag cacagcctgc tgtacgagta cttcaccgtg   1560
tacaacgagc tgaccaaggt gaagtacgtg accgagggca tgcgcaagcc cgccttcctg   1620
agcggcgagc agaagaaggc catcgtggac ctgctgttca agaccaaccg caaggtgacc   1680
gtgaagcagc tgaaggagga ctacttcaag aagatcgagt gcttcgacag cgtggagatc   1740
agcggcgtgg aggaccgctt caacgccagc ctgggcacct accacgacct gctgaagatc   1800
atcaaggaca aggacttcct ggacaacgag gagaacgagg acatcctgga ggacatcgtg   1860
ctgaccctga cctgttcga ggaccgcgag atgatcgagg agcgcctgaa gacctacgcc   1920
cacctgttcg acgacaaggt gatgaagcag ctgaagcgcc gccgctacac cggctggggc   1980
cgcctgagcc gcaagcttat caacggcatc cgcgacaagc agagcggcaa gaccatcctg   2040
gacttcctga gagcgacgg cttcgccaac cgcaacttca tgcagctgat ccacgacgac   2100
agcctgacct tcaaggagga catccagaag gcccaggtga gcggccaggg cgacagcctg   2160
cacgagcaca tcgccaacct ggccggcagc cccgccatca agagggcat cctgcagacc   2220 gtgaaggtgg tggacgagct ggtgaaggtg atggccgcc acaagcccga gaacatcgtg   2280
atcgagatgg cccgcgagaa ccagaccacc cagaagggcc agaagaacag ccgcgagcgc   2340
atgaagcgca tcgaggaggg catcaaggag ctgggcagcc agatcctgaa ggagcacccc   2400
gtggagaaca cccagctgca gaacgagaag ctgtacctgt actacctgca gaacggccgc   2460
```

```
gacatgtacg tggaccagga gctggacatc aaccgcctga gcgactacga cgtggaccac  2520
atcgtgcccc agagcttcct gaaggacgac agcatcgaca acaaggtgct gacccgcagc  2580
gacaagaacc gcggcaagag cgacaacgtg cccagcgagg aggtggtgaa gaagatgaag  2640
aactactggc gccagctgct gaacgccaag ctgatcaccc agcgcaagtt cgacaacctg  2700
accaaggccg agcgcggcgg cctgagcgag ctggacaagg ccggcttcat caagcgccag  2760
ctggtggaga cccgccagat caccaagcac gtggcccaga tcctggacag ccgcatgaac  2820
accaagtacg acgagaacga caagctgatc cgcgaggtga aggtgatcac cctgaagagc  2880
aagctggtga gcgacttccg caaggacttc cagttctaca aggtgcgcga gatcaacaac  2940
taccaccacg cccacgacgc ctacctgaac gccgtggtgg gcaccgccct gatcaagaag  3000
taccccaagc tggagagcga gttcgtgtac ggcgactaca aggtgtacga cgtgcgcaag  3060
atgatcgcca agagcgagca ggagatcggc aaggccaccg ccaagtactt cttctacagc  3120
aacatcatga acttcttcaa gaccgagatc accctggcca acggcgagat ccgcaagcgc  3180
cccctgatcg agaccaacgg cgagaccggc gagatcgtgt gggacaaggg ccgcgacttc  3240
gccaccgtgc gcaaggtgct gagcatgccc caggtgaaca tcgtgaagaa gaccgaggtg  3300
cagaccggcg gcttcagcaa ggagagcatc ctgcccaagc gcaacagcga caagctgatc  3360
gcccgcaaga aggactggga ccccaagaag tacggcggct cgacagccc caccgtggcc  3420 tacagcgtgc tggtggtggc caaggtggag aagggcaaga gcaagaagct gaagagcgtg  3480
aaggagctgc tgggcatcac catcatggag cgcagcagct tcgagaagaa ccccatcgac  3540
ttcctggagg ccaagggcta caaggaggtg aagaaggacc tgatcatcaa gctgcccaag  3600
tacagcctgt tcgagctgga gaacggccgc aagcgcatgc tggccagcgc cggcgagctg  3660
cagaagggca acgagctggc cctgcccagc aagtacgtga acttcctgta cctggccagc  3720
cactacgaga agctgaaggg cagccccgag gacaacgagc agaagcagct gttcgtggag  3780
cagcacaagc actacctgga cgagatcatc gagcagatca gcgagttcag caagcgcgtg  3840
atcctggccg acgccaacct ggacaaggtg ctgagcgcct acaacaagca ccgcgacaag  3900
cccatccgcg agcaggccga gaacatcatc cacctgttca ccctgaccaa cctgggcgcc  3960
cccgccgcct tcaagtactt cgacaccacc atcgaccgca gcgcctacac cagcaccaag  4020
gaggtgctgg acgccaccct gatccaccag agcatcaccg tgctgtacga cccgcatc    4080 gacctgagcc agctgggcgg cgactaa                                        4107

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Peptide tag

<400> SEQUENCE: 2

Gly Gly Ser Gly Pro Pro Lys Lys Lys Arg Lys Val Tyr Pro Tyr Asp
1               5                   10                  15

Val Pro Asp Tyr Ala
            20

<210> SEQ ID NO 3
<211> LENGTH: 34
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F primer for CCR5

<400> SEQUENCE: 3
aattcatgac atcaattatt atacatcgga ggag                                 34

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for CCR5

<400> SEQUENCE: 4
gatcctcctc cgatgtataa taattgatgt catg                                 34

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F1 primer for CCR5

<400> SEQUENCE: 5
ctccatggtg ctatagagca                                                 20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F2 primer for CCR5

<400> SEQUENCE: 6
gagccaagct ctccatctag t                                               21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for CCR5

<400> SEQUENCE: 7
gccctgtcaa gagttgacac                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: F1 primer for C4BPB

<400> SEQUENCE: 8
tatttggctg gttgaaaggg                                              20

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R1 primer for C4BPB

<400> SEQUENCE: 9
aaagtcatga ataaacaca ccca                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F2 primer for C4BPB

<400> SEQUENCE: 10
ctgcattgat atggtagtac catg                                         24

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R2 primer for C4BPB

<400> SEQUENCE: 11
gctgttcatt gcaatggaat g                                            21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F1 primer for ADCY5

<400> SEQUENCE: 12
gctcccacct tagtgctctg                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R1 primer for ADCY5

<400> SEQUENCE: 13
```

-continued

```
ggtggcagga acctgtatgt                                              20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F2 primer for ADCY5

<400> SEQUENCE: 14
gtcattggcc agagatgtgg a                                            21

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R2 primer for ADCY5

<400> SEQUENCE: 15
gtcccatgac aggcgtgtat                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F primer for KCNJ6

<400> SEQUENCE: 16
gcctggccaa gtttcagtta                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R1 primer for KCNJ6

<400> SEQUENCE: 17
tggagccatt ggtttgcatc                                              20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R2 primer for KCNJ6

<400> SEQUENCE: 18
ccagaactaa gccgtttctg ac                                           22
```

```
<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F1 primer for CNTNAP2

<400> SEQUENCE: 19
atcaccgaca accagtttcc                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F2 primer for CNTNAP2

<400> SEQUENCE: 20
tgcagtgcag actctttcca                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for CNTNAP2

<400> SEQUENCE: 21
aaggacacag ggcaactgaa                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F1 primer for N/A Chr. 5

<400> SEQUENCE: 22
tgtggaacga gtggtgacag                                              20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R1 primer for N/A Chr. 5

<400> SEQUENCE: 23
gctggattag gaggcaggat tc                                           22

<210> SEQ ID NO 24
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: F2 primer for N/A Chr. 5

<400> SEQUENCE: 24
gtgctgagaa cgcttcatag ag                                              22

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R2 primer for N/A Chr. 5

<400> SEQUENCE: 25
ggaccaaacc acattcttct cac                                             23

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F primer for deletion

<400> SEQUENCE: 26
ccacatctcg ttctcggttt                                                 20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for deletion

<400> SEQUENCE: 27
tcacaagccc acagatattt                                                 20

<210> SEQ ID NO 28
<211> LENGTH: 105
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: sgRNA for CCR5

<400> SEQUENCE: 28
ggugacauca auuauuauac auguuuuaga gcuagaaaua gcaaguuaaa auaaggcuag      60
uccguuauca acuugaaaaa guggcaccga gucggugcuu uuuuu                    105

<210> SEQ ID NO 29
<211> LENGTH: 44
<212> TYPE: RNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: crRNA for CCR5

<400> SEQUENCE: 29
ggugacauca auuauuauac auguuuuaga gcuaugcugu uuug            44

<210> SEQ ID NO 30
<211> LENGTH: 86
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: tracrRNA for CCR5

<400> SEQUENCE: 30
ggaaccauuc aaaacagcau agcaaguuaa aauaaggcua guccguuauc aacuugaaaa    60
aguggcaccg agucggugcu uuuuuu                                        86

<210> SEQ ID NO 31
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Foxn1 #1 sgRNA

<400> SEQUENCE: 31
gaaattaata cgactcacta taggcagtct gacgtcacac ttccgtttta gagctagaaa    60
tagcaagtta aaataaggct agtccg                                        86

<210> SEQ ID NO 32
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Foxn1 #2 sgRNA

<400> SEQUENCE: 32
gaaattaata cgactcacta taggacttcc aggctccacc cgacgtttta gagctagaaa    60
tagcaagtta aaataaggct agtccg                                        86

<210> SEQ ID NO 33
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Foxn1 #3 sgRNA

<400> SEQUENCE: 33
gaaattaata cgactcacta taggccaggc tccacccgac tggagtttta gagctagaaa    60
tagcaagtta aaataaggct agtccg                                        86

<210> SEQ ID NO 34
<211> LENGTH: 86

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Foxn1 #4 sgRNA

<400> SEQUENCE: 34
gaaattaata cgactcacta taggactgga gggcgaaccc caaggtttta gagctagaaa    60
tagcaagtta aaataaggct agtccg                                         86

<210> SEQ ID NO 35
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Foxn1 #5 sgRNA

<400> SEQUENCE: 35
gaaattaata cgactcacta taggacccca aggggacctc atgcgtttta gagctagaaa    60
tagcaagtta aaataaggct agtccg                                         86

<210> SEQ ID NO 36
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Prkdc #1 sgRNA

<400> SEQUENCE: 36
gaaattaata cgactcacta taggttagtt ttttccagag acttgtttta gagctagaaa    60
tagcaagtta aaataaggct agtccg                                         86

<210> SEQ ID NO 37
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Prkdc #2 sgRNA

<400> SEQUENCE: 37
gaaattaata cgactcacta taggttggtt tgcttgtgtt tatcgtttta gagctagaaa    60
tagcaagtta aaataaggct agtccg                                         86

<210> SEQ ID NO 38
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Prkdc #3 sgRNA

<400> SEQUENCE: 38
gaaattaata cgactcacta taggcacaag caaaccaaag tctcgtttta gagctagaaa    60
```
tagcaagtta aaataaggct agtccg                                                86

<210> SEQ ID NO 39
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Prkdc #4 sgRNA

<400> SEQUENCE: 39
gaaattaata cgactcacta taggcctcaa tgctaagcga cttcgtttta gagctagaaa   60
tagcaagtta aaataaggct agtccg                                                86

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F1 primer for Foxn1

<400> SEQUENCE: 40
gtctgtctat catctcttcc cttctctcc                                             29

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F2 primer for Foxn1

<400> SEQUENCE: 41
tccctaatcc gatggctagc tccag                                                 25

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R1 primer for Foxn1

<400> SEQUENCE: 42
acgagcagct gaagttagca tgc                                                   23

<210> SEQ ID NO 43
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R2 primer for Foxn1

<400> SEQUENCE: 43
ctactcaatg ctcttagagc taccaggctt gc                                         32

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: F primer for Prkdc

<400> SEQUENCE: 44
gactgttgtg gggagggccg                                                 20

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: F2 primer for Prkdc

<400> SEQUENCE: 45
gggagggccg aaagtcttat tttg                                            24

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: R1 primer for Prkdc

<400> SEQUENCE: 46
cctgaagact gaagttggca gaagtgag                                        28

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: R2 primer for Prkdc

<400> SEQUENCE: 47
ctttagggct tcttctctac aatcacg                                         27

<210> SEQ ID NO 48
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: F primer for Foxn1

<400> SEQUENCE: 48
ctcggtgtgt agccctgacc tcggtgtgta gccctgac                             38

<210> SEQ ID NO 49
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for Foxn1

<400> SEQUENCE: 49
agactggcct ggaactcaca g                                             21

<210> SEQ ID NO 50
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F primer for Foxn1

<400> SEQUENCE: 50
cactaaagcc tgtcaggaag ccg                                           23

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for Foxn1

<400> SEQUENCE: 51
ctgtggagag cacacagcag c                                             21

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F primer for Foxn1

<400> SEQUENCE: 52
gctgcgacct gagaccatg                                                19

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for Foxn1

<400> SEQUENCE: 53
cttcaatggc ttcctgctta ggctac                                        26

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                                    oligonucleotide
<220> FEATURE:
<223> OTHER INFORMATION: F primer for Foxn1

<400> SEQUENCE: 54
ggttcagatg aggccatcct ttc                                            23

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for Foxn1

<400> SEQUENCE: 55
cctgatctgc aggcttaacc cttg                                           24

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F primer for Prkdc

<400> SEQUENCE: 56
ctcacctgca catcacatgt gg                                             22

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for Prkdc

<400> SEQUENCE: 57
ggcatccacc ctatggggtc                                                20

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F primer for Prkdc

<400> SEQUENCE: 58
gccttgacct agagcttaaa gagcc                                          25

<210> SEQ ID NO 59
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for Prkdc
```

<400> SEQUENCE: 59
ggtcttgtta gcaggaagga cactg                                              25

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F primer for Prkdc

<400> SEQUENCE: 60
aaaactctgc ttgatgggat atgtggg                                            27

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for Prkdc

<400> SEQUENCE: 61
ctctcactgg ttatctgtgc tccttc                                             26

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F primer for Prkdc

<400> SEQUENCE: 62
ggatcaatag gtggtggggg atg                                                23

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for Prkdc

<400> SEQUENCE: 63
gtgaatgaca caatgtgaca gcttcag                                            27

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F primer for Prkdc

<400> SEQUENCE: 64
cacaagacag acctctcaac attcagtc                                           28

<210> SEQ ID NO 65
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R primer for Prkdc

<400> SEQUENCE: 65
gtgcatgcat ataatccatt ctgattgctc tc                                    32

<210> SEQ ID NO 66
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F1 primer for Prkdc

<400> SEQUENCE: 66
gggaggcaga ggcaggt                                                     17

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: F2 primer for Prkdc

<400> SEQUENCE: 67
ggatctctgt gagtttgagg cca                                              23

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: R1 primer for Prkdc

<400> SEQUENCE: 68
gctccagaac tcactcttag gctc                                             24

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer for Foxn1

<400> SEQUENCE: 69
ctactccctc cgcagtctga                                                  20

<210> SEQ ID NO 70
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer for Foxn1

<400> SEQUENCE: 70
ccaggcctag gttccaggta                                                      20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer for Prkdc

<400> SEQUENCE: 71
ccccagcatt gcagatttcc                                                      20

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer for Prkdc

<400> SEQUENCE: 72
agggcttctt ctctacaatc acg                                                  23

<210> SEQ ID NO 73
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: BRI1 target 1

<400> SEQUENCE: 73
gaaattaata cgactcacta taggtttgaa agatggaagc gcgggtttta gagctagaaa          60
tagcaagtta aaataaggct agtccg                                               86

<210> SEQ ID NO 74
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: BRI1 target 2

<400> SEQUENCE: 74
gaaattaata cgactcacta taggtgaaac taaactggtc cacagtttta gagctagaaa          60
tagcaagtta aaataaggct agtccg                                               86

<210> SEQ ID NO 75
<211> LENGTH: 64
<212> TYPE: DNA
```

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Universal

<400> SEQUENCE: 75

```
aaaaaagcac cgactcggtg ccacttttc aagttgataa cggactagcc ttattttaac    60
ttgc                                                                 64
```

<210> SEQ ID NO 76
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Templates for crRNA
<220> FEATURE:
<221> NAME/KEY: modified_base
<222> LOCATION: (25)..(44)
<223> OTHER INFORMATION: a, c, t, g, unknown or other

<400> SEQUENCE: 76

```
gaaattaata cgactcacta taggnnnnnn nnnnnnnnnn nnngttttta gagctatgct    60
gtttt                                                                65
```

<210> SEQ ID NO 77
<211> LENGTH: 67
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: tracrRNA

<400> SEQUENCE: 77

```
gaaattaata cgactcacta taggaaccat tcaaaacagc atagcaagtt aaaataaggc    60
tagtccg                                                              67
```

<210> SEQ ID NO 78
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: tracrRNA

<400> SEQUENCE: 78

```
aaaaaagca ccgactcggt gccactttt caagttgata acggactagc cttatttta      60 cttgctatg                                                            69
```

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Primer

```
<400> SEQUENCE: 79
ctccatggtg ctatagagca                                              20

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 80
gagccaagct ctccatctag t                                            21

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 81
gccctgtcaa gagttgacac                                              20

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 82
gcacagggtg gaacaagatg ga                                           22

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 83
gccaggtacc tatcgattgt cagg                                         24

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 84
gagccaagct ctccatctag t                                            21
```

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Primer

<400> SEQUENCE: 85
actctgactg ggtcaccagc                                           20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Primer

<400> SEQUENCE: 86
tatttggctg gttgaaaggg                                           20

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Primer

<400> SEQUENCE: 87
aaagtcatga aataaacaca ccca                                      24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Primer

<400> SEQUENCE: 88
ctgcattgat atggtagtac catg                                      24

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Primer

<400> SEQUENCE: 89
gctgttcatt gcaatggaat g                                         21

<210> SEQ ID NO 90
<211> LENGTH: 22
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 90
atggagttgg acatggccat gg                                            22

<210> SEQ ID NO 91
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 91
actcactatc cacagttcag catttacc                                      28

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 92
tggagatagc tgtcagcaac ttt                                           23

<210> SEQ ID NO 93
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 93
caacaaagca aggtaaagt tggtaatag                                      29

<210> SEQ ID NO 94
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 94
ggtttcagga gatgtgttac aaggc                                         25

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Primer

<400> SEQUENCE: 95
gattgtgcaa ttcctatgca atcggtc                                              27

<210> SEQ ID NO 96
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 96
cactgggtac ttaatctgta gcctc                                                25

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 97
ggttccaagt cattcccagt agc                                                  23

<210> SEQ ID NO 98
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 98
catcactgca gttgtaggtt ataactatcc                                           30

<210> SEQ ID NO 99
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 99
ttgaaaacca cagatctggt tgaacc                                               26

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 100
```

```
ggagtgccaa gagaatatct gg                                            22

<210> SEQ ID NO 101
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 101
ctgaaactgg tttcaaaata ttcgttttaa gg                                 32

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 102
gctctgtatg ccctgtagta gg                                            22

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Primer

<400> SEQUENCE: 103
tttgcatctg accttacctt tg                                            22

<210> SEQ ID NO 104
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence of RGEN

<400> SEQUENCE: 104
aatgaccact acatcctcaa ggg                                           23

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Target sequence of RGEN

<400> SEQUENCE: 105
agatgatgtc tcatcatcag agg                                           23
```

<210> SEQ ID NO 106
<211> LENGTH: 4170
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cas9-coding sequence in p3s-Cas9HC (humanized, C-term tagging, human cell experiments)

<400> SEQUENCE: 106

```
atggacaaga agtacagcat cggcctggac atcggtacca acagcgtggg ctgggccgtg     60
atcaccgacg agtacaaggt gcccagcaag aagttcaagg tgctgggcaa caccgaccgc    120
cacagcatca agaagaacct gatcggcgcc ctgctgttcg acagcggcga gaccgccgag    180
gccacccgcc tgaagcgcac cgcccgccgc cgctacaccc gccgcaagaa ccgcatctgc    240
tacctgcagg agatcttcag caacgagatg gccaaggtgg acgacagctt cttccaccgc    300
ctggaggaga gcttcctggt ggaggaggac aagaagcacg agcgccaccc catcttcggc    360
aacatcgtgg acgaggtggc ctaccacgag aagtacccca ccatctacca cctgcgcaag    420
aagctggtgg acagcaccga caaggccgac ctgcgcctga tctacctggc cctgcccac    480 atgatcaagt tccgcggcca cttcctgatc gagggcgacc tgaaccccga caacagcgac    540
gtggacaagc tgttcatcca gctggtgcag acctacaacc agctgttcga ggagaacccc    600
atcaacgcca gcggcgtgga cgccaaggcc atcctgagcg cccgcctgag caagagccgc    660
cgcctggaga acctgatcgc ccagctgccc ggcgagaaga gaacggcct gttcggcaac    720 ctgatcgccc tgagcctggg cctgacccc aacttcaaga gcaacttcga cctggccgag    780
gacgccaagc tgcagctgag caaggacacc tacgacgacg acctggacaa cctgctggcc    840
cagatcggcg accagtacgc cgacctgttc ctggccgcca gaacctgag cgacgccatc    900 ctgctgagcg acatcctgcg cgtgaacacc gagatcacca aggcccccct gagcgccagc    960
atgatcaagc gctacgacga gcaccaccag gacctgaccc tgctgaaggc cctggtgcgc   1020
cagcagctgc ccgagaagta caaggagatc ttcttcgacc agagcaagaa cggctacgcc   1080
ggctacatcg acggcggcgc cagccaggag gagttctaca agttcatcaa gcccatcctg   1140
gagaagatgg acggcaccga ggagctgctg gtgaagctga accgcgagga cctgctgcgc   1200
aagcagcgca ccttcgacaa cggcagcatc ccccaccaga tccacctggg cgagctgcac   1260
gccatcctgc gccgccagga ggacttctac cccttcctga aggacaaccg cgagaagatc   1320
gagaagatcc tgaccttccg catcccctac tacgtgggcc ccctggcccg cggcaacagc   1380
cgcttcgcct ggatgacccg caagagcgag gagaccatca cccctggaa cttcgaggag   1440 gtggtggaca agggcgccag cgcccagagc ttcatcgagc gcatgaccaa cttcgacaag   1500
aacctgccca acgagaaggt gctgcccaag cacagcctgc tgtacgagta cttcaccgtg   1560
tacaacgagc tgaccaaggt gaagtacgtg accgagggca tgcgcaagcc cgccttcctg   1620
agcggcgagc agaagaaggc catcgtggac ctgctgttca gaccaaccg caaggtgacc   1680 gtgaagcagc tgaaggagga ctacttcaag aagatcgagt gcttcgacag cgtggagatc   1740
agcggcgtgg aggaccgctt caacgccagc ctgggcacct accacgacct gctgaagatc   1800
atcaaggaca aggacttcct ggacaacgag gagaacgagg acatcctgga ggacatcgtg   1860
ctgacccctg acctgttcga ggaccgcgag atgatcgagg agcgcctgaa gacctacgcc   1920
cacctgttcg acgacaaggt gatgaagcag ctgaagcgcc gccgctacac cggctggggc   1980
```

```
cgcctgagcc gcaagcttat caacggcatc cgcgacaagc agagcggcaa gaccatcctg    2040
gacttcctga agagcgacgg cttcgccaac cgcaacttca tgcagctgat ccacgacgac    2100
agcctgacct tcaaggagga catccagaag gcccaggtga gcggccaggg cgacagcctg    2160
cacgagcaca tcgccaacct ggccggcagc ccgccatca agaagggcat cctgcagacc     2220
gtgaaggtgg tggacgagct ggtgaaggtg atgggccgcc acaagcccga gaacatcgtg    2280
atcgagatgg cccgcgagaa ccagaccacc cagaagggcc agaagaacag ccgcgagcgc    2340
atgaagcgca tcgaggaggg catcaaggag ctgggcagcc agatcctgaa ggagcacccc    2400
gtggagaaca cccagctgca gaacgagaag ctgtacctgt actacctgca gaacggccgc    2460
gacatgtacg tggaccagga gctggacatc aaccgcctga gcgactacga cgtggaccac    2520
atcgtgcccc agagcttcct gaaggacgac agcatcgaca caaggtgct gacccgcagc     2580 gacaagaacc gcggcaagag cgacaacgtg cccagcgagg aggtggtgaa gaagatgaag    2640
aactactggc gccagctgct gaacgccaag ctgatcaccc agcgcaagtt cgacaacctg    2700
accaaggccg agcgcggcgg cctgagcgag ctggacaagg ccggcttcat caagcgccag    2760
ctggtggaga cccgccagat caccaagcac gtggcccaga tcctggacag ccgcatgaac    2820
accaagtaca cgagaacga caagctgatc cgcgaggtga aggtgatcac cctgaagagc    2880
aagctggtga cgacttccg caaggacttc cagttctaca aggtgcgcga gatcaacaac    2940
taccaccacg cccacgacgc ctacctgaac gccgtggtgg caccgccct gatcaagaag     3000 taccccaagc tggagagcga gttcgtgtac ggcgactaca aggtgtacga cgtgcgcaag    3060
atgatcgcca gagcgagca ggagatcggc aaggccaccg ccaagtactt cttctacagc     3120
aacatcatga acttcttcaa gaccgagatc accctggcca cggcgagat ccgcaagcgc     3180 cccctgatcg agaccaacgg cgagaccggc gagatcgtgt gggacaaggg ccgcgacttc    3240
gccaccgtgc gcaaggtgct gagcatgccc caggtgaaca tcgtgaagaa gaccgaggtg    3300
cagaccggcg gcttcagcaa ggagagcatc ctgcccaagc gcaacagcga caagctgatc    3360
gcccgcaaga aggactggga ccccaagaag tacgcggct cgacagcccc caccgtggcc     3420
tacagcgtgc tggtggtggc caaggtggag aagggcaaga gcaagaagct gaagagcgtg    3480
aaggagctgc tgggcatcac catcatggag cgcagcagct tcgagaagaa ccccatcgac    3540
ttcctggagg ccaagggcta caaggaggtg aagaaggacc tgatcatcaa gctgcccaag    3600
tacagcctgt tcgagctgga aacggccgc aagcgcatgc tggccagcgc cggcgagctg     3660
cagaagggca cgagctggc cctgcccagc aagtacgtga acttcctgta cctggccagc     3720
cactacgaga agctgaaggg cagccccgag acaacgagc agaagcagct gttcgtggag     3780
cagcacaagc actacctgga cgagatcatc gagcagatca gcgagttcag caagcgcgtg    3840
atcctggccg acgccaacct ggacaaggtg ctgagcgcct acaacaagca ccgcgacaag    3900
cccatccgcg agcaggccga gaacatcatc cacctgttca ccctgaccaa cctgggcgcc    3960
cccgccgcct tcaagtactt cgacaccacc atcgaccgca gcgctacac cagcaccaag    4020 gaggtgctgg acgccaccct gatccaccag agcatcaccg tctgtacga cccgcatc      4080 gacctgagcc agctgggcgg cgacggcggc tccggacctc aaagaaaaa gagaaagta     4140 taccccctacg acgtgcccga ctacgcctaa                                    4170
```

<210> SEQ ID NO 107
<211> LENGTH: 4194
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Cas9 coding sequence in p3s-Cas9HN (humanized codon, N-term tagging (underlined), human cell experiments)

<400> SEQUENCE: 107

```
atggtgtacc cctacgacgt gcccgactac gccgaattgc ctccaaaaaa gaagagaaag      60
gtagggatcc gaattcccgg ggaaaaaccg gacaagaagt acagcatcgg cctggacatc     120
ggtaccaaca cgtgggctg gccgtgatc accgacgagt acaaggtgcc cagcaagaag       180
ttcaaggtgc tgggcaacac cgaccgccac agcatcaaga gaacctgat cggcgccctg      240
ctgttcgaca cggcgagac cgccgaggcc acccgcctga gcgcaccgc ccgccgccgc       300
tacacccgcc gcaagaaccg catctgctac ctgcaggaga tcttcagcaa cgagatggcc     360
aaggtggacg acagcttctt ccaccgcctg gaggagagct tcctggtgga ggaggacaag     420
aagcacgagc gccacccat cttcggcaac atcgtggacg aggtggccta ccacgagaag      480
taccccacca tctaccacct gcgcaagaag ctggtggaca gcaccgacaa ggccgacctg     540
cgcctgatct acctggccct ggcccacatg atcaagttcc gcggccactt cctgatcgag     600
ggcgacctga accccgacaa cagcgacgtg gacaagctgt tcatccagct ggtgcagacc     660
tacaaccagc tgttcgagga gaaccccatc aacgccagcg gcgtggacgc caaggccatc     720
ctgagcgccc gcctgagcaa gagccgccgc ctggagaacc tgatcgccca gctgcccggc     780
gagaagaaga acggcctgtt cggcaacctg atcgccctga gcctgggcct gaccccccaac    840
ttcaagagca acttcgacct ggccgaggac gccaagctgc agctgagcaa ggacacctac     900
gacgacgacc tggacaacct gctggcccag atcggcgacc agtacgccga cctgttcctg     960
gccgccaaga acctgagcga cgccatcctg ctgagcgaca tcctgcgcgt gaacaccgag    1020
atcaccaagg ccccctgag cgccagcatg atcaagcgct acgacgagca ccaccaggac    1080
ctgaccctgc tgaaggccct ggtgcgccag cagctgcccg agaagtacaa ggagatcttc    1140
ttcgaccaga gcaagaacgg ctacgccggc tacatcgacg gcggcgccag ccaggaggag    1200
ttctacaagt tcatcaagcc catcctggag aagatggacg gcaccgagga gctgctggtg    1260
aagctgaacc gcgaggacct gctgcgcaag cagcgcacct tcgacaacgg cagcatcccc    1320
caccagatcc acctgggcga gctgcacgcc atcctgcgcc gccaggagga cttctacccc    1380
ttcctgaagg acaaccgcga gaagatcgag aagatcctga ccttccgcat ccctactac    1440
gtgggccccc tggcccgcgg caacagccgc ttcgcctgga tgacccgcaa gagcgaggag    1500
accatcaccc cctggaactt cgaggaggtg gtggacaagg gcgccagcgc ccagagcttc    1560
atcgagcgca tgaccaactt cgacaagaac ctgcccaacg agaaggtgct gcccaagcac    1620
agcctgctgt acgagtactt caccgtgtac aacgagctga ccaaggtgaa gtacgtgacc    1680
gagggcatgc gcaagcccgc cttcctgagc ggcgagcaga agaaggccat cgtggacctg    1740
ctgttcaaga ccaaccgcaa ggtgaccgtg aagcagctga aggaggacta cttcaagaag    1800
atcgagtgct cgacagcgt ggagatcagc ggcgtggagg accgcttcaa cgccagcctg    1860
ggcacctacc acgacctgct gaagatcatc aaggacaagg acttcctgga caacgaggag    1920
aacgaggaca tcctggagga catcgtgctg accctgaccc tgttcgagga ccgcgagatg    1980
atcgaggagc gcctgaagac ctacgcccac ctgttcgacg acaaggtgat gaagcagctg    2040
aagcgccgcc gctacaccgg ctgggccgc ctgagccgca agcttatcaa cggcatccgc    2100
```

```
gacaagcaga gcggcaagac catcctggac ttcctgaaga gcgacggctt cgccaaccgc    2160
aacttcatgc agctgatcca cgacgacagc ctgaccttca aggaggacat ccagaaggcc    2220
caggtgagcg ccagggcga cagcctgcac gagcacatcg ccaacctggc cggcagcccc    2280
gccatcaaga agggcatcct gcagaccgtg aaggtggtgg acgagctggt gaaggtgatg    2340
ggccgccaca agcccgagaa catcgtgatc gagatggccc gcgagaacca gaccacccag    2400
aagggccaga agaacagccg cgagcgcatg aagcgcatcg aggagggcat caaggagctg    2460
ggcagccaga tcctgaagga gcaccccgtg gagaacaccc agctgcagaa cgagaagctg    2520
tacctgtact acctgcagaa cggccgcgac atgtacgtgg accaggagct ggacatcaac    2580
cgcctgagcg actacgacgt ggaccacatc gtgccccaga gcttcctgaa ggacgacagc    2640
atcgacaaca aggtgctgac ccgcagcgac aagaaccgcg gcaagagcga caacgtgccc    2700
agcgaggagg tggtgaagaa gatgaagaac tactggcgcc agctgctgaa cgccaagctg    2760
atcacccagc gcaagttcga caacctgacc aaggccgagc gcggcggcct gagcgagctg    2820
gacaaggccg gcttcatcaa gcgccagctg gtggagaccc gccagatcac caagcacgtg    2880
gcccagatcc tggacagccg catgaacacc aagtacgacg agaacgacaa gctgatccgc    2940
gaggtgaagg tgatcaccct gaagagcaag ctggtgagcg acttccgcaa ggacttccag    3000
ttctacaagg tgcgcgagat caacaactac caccacgccc acgacgccta cctgaacgcc    3060
gtggtgggca ccgccctgat caagaagtac cccaagctgg agagcgagtt cgtgtacggc    3120
gactacaagg tgtacgacgt gcgcaagatg atcgccaaga gcgagcagga gatcggcaag    3180
gccaccgcca agtacttctt ctacagcaac atcatgaact tcttcaagac cgagatcacc    3240
ctggccaacg gcgagatccg caagcgcccc ctgatcgaga ccaacggcga gaccggcgag    3300
atcgtgtggg acaagggccg cgacttcgcc accgtgcgca aggtgctgag catgccccag    3360
gtgaacatcg tgaagaagac cgaggtgcag accggcggct tcagcaagga gagcatcctg    3420
cccaagcgca cagcgacaa gctgatcgcc cgcaagaagg actgggaccc caagaagtac    3480
ggcggcttcg acagccccac cgtggcctac agcgtgctgg tggtggccaa ggtggagaag    3540
ggcaagagca gaagctgaa gagcgtgaag gagctgctgg gcatcaccat catggagcgc    3600
agcagcttcg agaagaaccc catcgacttc ctggaggcca agggctacaa ggaggtgaag    3660
aaggacctga tcatcaagct gcccaagtac agcctgttcg agctggagaa cggccgcaag    3720
cgcatgctgg ccagcgccgg cgagctgcag aagggcaacg agctggccct gcccagcaag    3780
tacgtgaact tcctgtacct ggccagccac tacgagaagc tgaagggcag ccccgaggac    3840
aacgagcaga gcagctgtt cgtggagcag cacaagcact acctggacga gatcatcgag    3900
cagatcagcg agttcagcaa gcgcgtgatc ctggccgacg ccaacctgga caaggtgctg    3960
agcgcctaca acaagcaccg cgacaagccc atccgcgagc aggccgagaa catcatccac    4020
ctgttcaccc tgaccaacct gggcgccccc gccgccttca agtacttcga caccaccatc    4080
gaccgcaagc gctacaccag caccaaggag gtgctggacc ccaccctgat ccaccagagc    4140
atcaccggtc tgtacgagac ccgcatcgac ctgagccagc tgggcggcga ctaa          4194
```

<210> SEQ ID NO 108
<211> LENGTH: 4107
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: Cas9-coding sequence in Streptococcus pyogenes

<400> SEQUENCE: 108

```
atggataaga atactcaat aggcttagat atcggcacaa atagcgtcgg atgggcggtg      60
atcactgatg aatataaggt tccgtctaaa aagttcaagg ttctgggaaa tacagaccgc    120
cacagtatca aaaaaatct tatagggct cttttatttg acagtggaga gacagcggaa     180
gcgactcgtc tcaaacggac agctcgtaga aggtatacac gtcggaagaa tcgtatttgt   240
tatctacagg agatttttc aaatgagatg gcgaaagtag atgatagttt ctttcatcga    300
cttgaagagt ctttttggt ggaagaagac aagaagcatg aacgtcatcc tattttgga    360
aatatagtag atgaagttgc ttatcatgag aaatatccaa ctatctatca tctgcgaaaa    420
aaattggtag attctactga taaagcggat ttgcgcttaa tctatttggc cttagcgcat    480
atgattaagt ttcgtggtca tttttgatt gagggagatt taaatcctga taatagtgat    540
gtggacaaac tatttatcca gttggtacaa acctacaatc aattatttga agaaaaccct    600
attaacgcaa gtgagtaga tgctaaagcg attctttctg cacgattgag taaatcaaga    660
cgattagaaa atctcattgc tcagctcccc ggtgagaaga aaaatggctt atttgggaat    720
ctcattgctt tgtcattggg tttgaccct aattttaaat caattttga tttggcagaa     780
gatgctaaat tacagctttc aaaagatact tacgatgatg atttagataa tttattggcg    840
caaattggag atcaatatgc tgatttgttt ttggcagcta agaattatc agatgctatt     900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taaagaaatc ttttttgatc aatcaaaaaa cggatatgca   1080
ggttatattg atgggggagc tagccaagaa gaattttata aatttatcaa accaatttta   1140
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctatttga aagacaaga agactttat ccatttttaa aagacaatcg tgagaagatt    1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat aaaagaaga ttatttcaaa aaaatagaat gttttgatag tgttgaaatt   1740
tcaggagttg aagatagatt taatgcttca ttaggtacct accatgattt gctaaaaatt   1800
attaaagata aagattttt ggataatgaa gaaatgaag atatcttaga ggatattgtt    1860
ttaacattga ccttatttga agataggag atgattgagg aaagacttaa acatatgct    1920
cacctctttg atgataaggt gatgaaacag cttaacgtc gccgttatac tggttgggga   1980
cgtttgtctc gaaattgat taatggtatt agggataagc aatctggcaa acaatatta    2040
gattttttga atcagatgg ttttgccaat cgcaattta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
```

```
attgaaatgg cacgtgaaaa tcagacaact caaaagggcc agaaaaattc gcgagagcgt    2340
atgaaacgaa tcgaagaagg tatcaaagaa ttaggaagtc agattcttaa agagcatcct    2400
gttgaaaata ctcaattgca aaatgaaaag ctctatctct attatctcca aaatggaaga    2460
gacatgtatg tggaccaaga attagatatt aatcgtttaa gtgattatga tgtcgatcac    2520
attgttccac aaagttttcct taaagacgat tcaatagaca ataaggtctt aacgcgttct    2580
gataaaaatc gtggtaaatc ggataacgtt ccaagtgaag aagtagtcaa aaagatgaaa    2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta aagtgattac cttaaaatct    2880
aaattagttt ctgacttccg aaaagatttc caattctata agtacgtgta gattaacaat    2940
taccatcatg cccatgatgc gtatctaaat gccgtcgttg gaactgcttt gattaagaaa    3000
tatccaaaac ttgaatcgga gtttgtctat ggtgattata agtttatga tgttcgtaaa    3060 atgattgcta agtctgagca agaaataggc aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatggaa agaagttcct ttgaaaaaaa tccgattgac    3540
tttttagaag ctaaaggata taaggaagtt aaaaaagact taatcattaa actacctaaa    3600
tatagtcttt ttgagttaga aaacggtcgt aaacggatgc tggctagtgc cggagaatta    3660
caaaaaggaa atgagctggc tctgccaagc aaatatgtga attttttata tttagctagt    3720
cattatgaaa agttgaaggg tagtccagaa gataacgaac aaaaacaatt gtttgtggag    3780
cagcataagc attattaga tgagattatt gagcaaatca gtgaatttc taagcgtgtt    3840 attttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgactaa                                        4107
```

<210> SEQ ID NO 109
<211> LENGTH: 1368
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequence of Cas9 from S.pyogenes

<400> SEQUENCE: 109

Met Asp Lys Lys Tyr Ser Ile Gly Leu Asp Ile Gly Thr Asn Ser Val
1               5                   10                  15

-continued

```
Gly Trp Ala Val Ile Thr Asp Glu Tyr Lys Val Pro Ser Lys Lys Phe
             20                  25                  30
Lys Val Leu Gly Asn Thr Asp Arg His Ser Ile Lys Lys Asn Leu Ile
         35                  40                  45
Gly Ala Leu Leu Phe Asp Ser Gly Glu Thr Ala Glu Ala Thr Arg Leu
     50                  55                  60
Lys Arg Thr Ala Arg Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                 85                  90                  95
Phe Phe His Arg Leu Glu Glu Ser Phe Leu Val Glu Glu Asp Lys Lys
            100                 105                 110
His Glu Arg His Pro Ile Phe Gly Asn Ile Val Asp Glu Val Ala Tyr
        115                 120                 125
His Glu Lys Tyr Pro Thr Ile Tyr His Leu Arg Lys Lys Leu Val Asp
    130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
```

-continued

```
                435                 440                 445
Pro Tyr Tyr Val Gly Pro Leu Ala Arg Gly Asn Ser Arg Phe Ala Trp
450                 455                 460
Met Thr Arg Lys Ser Glu Glu Thr Ile Thr Pro Trp Asn Phe Glu Glu
465                 470                  475                480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
                515                 520                 525
Tyr Val Thr Glu Gly Met Arg Lys Pro Ala Phe Leu Ser Gly Glu Gln
530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
                595                 600                 605
Asn Glu Glu Asn Glu Asp Ile Leu Glu Asp Ile Val Leu Thr Leu Thr
610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
                755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
            820                 825                 830
Leu Ser Asp Tyr Asp Val Asp His Ile Val Pro Gln Ser Phe Leu Lys
                835                 840                 845
Asp Asp Ser Ile Asp Asn Lys Val Leu Thr Arg Ser Asp Lys Asn Arg
850                 855                 860
```

-continued

```
Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260
```

| His | Tyr | Leu | Asp | Glu | Ile | Ile | Glu | Gln | Ile | Ser | Glu | Phe | Ser | Lys |
| | 1265 | | | | 1270 | | | | | 1275 | | | | |

| Arg | Val | Ile | Leu | Ala | Asp | Ala | Asn | Leu | Asp | Lys | Val | Leu | Ser | Ala |
| 1280 | | | | | 1285 | | | | | 1290 | | | | |

| Tyr | Asn | Lys | His | Arg | Asp | Lys | Pro | Ile | Arg | Glu | Gln | Ala | Glu | Asn |
| 1295 | | | | | 1300 | | | | | 1305 | | | | |

| Ile | Ile | His | Leu | Phe | Thr | Leu | Thr | Asn | Leu | Gly | Ala | Pro | Ala | Ala |
| 1310 | | | | | 1315 | | | | | 1320 | | | | |

| Phe | Lys | Tyr | Phe | Asp | Thr | Thr | Ile | Asp | Arg | Lys | Arg | Tyr | Thr | Ser |
| 1325 | | | | | 1330 | | | | | 1335 | | | | |

| Thr | Lys | Glu | Val | Leu | Asp | Ala | Thr | Leu | Ile | His | Gln | Ser | Ile | Thr |
| 1340 | | | | | 1345 | | | | | 1350 | | | | |

| Gly | Leu | Tyr | Glu | Thr | Arg | Ile | Asp | Leu | Ser | Gln | Leu | Gly | Gly | Asp |
| 1355 | | | | | 1360 | | | | | 1365 | | | | |

<210> SEQ ID NO 110
<211> LENGTH: 4221
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Cas9-coding sequence in pET-Cas9N3T for the
      production of recombinant Cas9 protein in E. coli (humanized
      codon; hexa-His-tag and a nuclear localization signal at the
      N terminus)

<400> SEQUENCE: 110

| atgggcagca | gccatcatca | tcatcatcat | gtgtacccct | acgacgtgcc | cgactacgcc | 60 |
| gaattgcctc | caaaaaagaa | gagaaaggta | gggatcgaga | acctgtactt | ccagggcgac | 120 |
| aagaagtaca | gcatcggcct | ggacatcggt | accaacagcg | tgggctgggc | cgtgatcacc | 180 |
| gacgagtaca | aggtgcccag | caagaagttc | aaggtgctgg | gcaacaccga | ccgccacagc | 240 |
| atcaagaaga | acctgatcgg | cgccctgctg | ttcgacagcg | gcgagaccgc | cgaggccacc | 300 |
| cgcctgaagc | gcaccgcccg | ccgccgctac | acccgccgca | agaaccgcat | ctgctacctg | 360 |
| caggagatct | tcagcaacga | gatggccaag | gtggacgaca | gcttcttcca | ccgcctggag | 420 |
| gagagcttcc | tggtggagga | ggacaagaag | cacgagcgcc | accccatctt | cggcaacatc | 480 |
| gtggacgagg | tggcctacca | cgagaagtac | cccaccatct | accacctgcg | caagaagctg | 540 |
| gtggacagca | ccgacaaggc | cgacctgcgc | ctgatctacc | tggccctggc | ccacatgatc | 600 |
| aagttccgcg | ccacttcct | gatcgagggc | gacctgaacc | ccgacaacag | cgacgtggac | 660 |
| aagctgttca | tccagctggt | gcagacctac | aaccagctgt | tcgaggagaa | ccccatcaac | 720 |
| gccagcggcg | tggacgccaa | ggccatcctg | agcgcccgcc | tgagcaagag | ccgccgcctg | 780 |
| gagaacctga | tcgcccagct | gcccggcgag | aagaagaacg | gcctgttcgg | caacctgatc | 840 |
| gccctgagcc | tgggcctgac | ccccaacttc | aagagcaact | tcgacctggc | cgaggacgcc | 900 |
| aagctgcagc | tgagcaagga | cacctacgac | gacgacctgg | acaacctgct | ggcccagatc | 960 |
| ggcgaccagt | acgccgacct | gttcctggcc | gccaagaacc | tgagcgacgc | catcctgctg | 1020 |
| agcgacatcc | tgcgcgtgaa | caccgagatc | accaaggccc | ccctgagcgc | cagcatgatc | 1080 |
| aagcgctacg | acgagcacca | ccaggacctg | accctgctga | aggccctggt | gcgccagcag | 1140 |
| ctgcccgaga | gtacaagga | gatcttcttc | gaccagagca | agaacggcta | cgccggctac | 1200 |
| atcgacggcg | cgccagcca | ggaggagttc | tacaagttca | tcaagcccat | cctggagaag | 1260 |

```
atggacggca ccgaggagct gctggtgaag ctgaaccgcg aggacctgct gcgcaagcag    1320
cgcaccttcg acaacggcag catcccccac cagatccacc tgggcgagct gcacgccatc    1380
ctgcgccgcc aggaggactt ctaccccttc ctgaaggaca ccgcgagaa gatcgagaag     1440 atcctgacct tccgcatccc ctactacgtg ggccccctgg cccgcggcaa cagccgcttc    1500
gcctggatga cccgcaagag cgaggagacc atcaccccct ggaacttcga ggaggtggtg    1560
gacaagggcg ccagcgccca gagcttcatc gagcgcatga ccaacttcga caagaacctg    1620
cccaacgaga aggtgctgcc caagcacagc ctgctgtacg agtacttcac cgtgtacaac    1680
gagctgacca aggtgaagta cgtgaccgag ggcatgcgca agcccgcctt cctgagcggc    1740
gagcagaaga aggccatcgt ggacctgctg ttcaagacca accgcaaggt gaccgtgaag    1800
cagctgaagg aggactactt caagaagatc gagtgcttcg acagcgtgga gatcagcggc    1860
gtggaggacc gcttcaacgc cagcctgggc acctaccacg acctgctgaa gatcatcaag    1920
gacaaggact ccctggacaa cgaggagaac gaggacatcc tggaggacat cgtgctgacc    1980 ctgacctgt tcgaggaccg cgagatgatc gaggagcgcc tgaagaccta cgcccacctg    2040
ttcgacgaca aggtgatgaa gcagctgaag cgccgccgct acaccggctg gggccgcctg    2100
agccgcaagc ttatcaacgg catccgcgac aagcagagcg gcaagaccat cctggacttc    2160
ctgaagagcg acggcttcgc caaccgcaac ttcatgcagc tgatccacga cgacagcctg    2220
accttcaagg aggacatcca gaaggcccag gtgagcggcc agggcgacag cctgcacgag    2280
cacatcgcca acctggccgg cagccccgcc atcaagaagg gcatcctgca gaccgtgaag    2340 gtggtggacga gctggtgaa ggtgatgggc cgccacaagc ccgagaacat cgtgatcgag    2400
atggcccgcg agaaccagac cacccagaag ggccagaaga cagccgcga gcgcatgaag    2460 cgcatcgagg agggcatcaa ggagctgggc agccagatcc tgaaggagca ccccgtggag    2520
aacacccagc tgcagaacga gaagctgtac ctgtactacc tgcagaacgg ccgcgacatg    2580
tacgtggacc aggagctgga catcaaccgc ctgagcgact acgacgtgga ccacatcgtg    2640
ccccagagct tcctgaagga cgacagcatc gacaacaagg tgctgacccg cagcgacaag    2700
aaccgcggca gagcgacaa cgtgcccagc gaggaggtgg tgaagaagat gaagaactac    2760
tggcgccagc tgctgaacgc caagctgatc acccagcgca gttcgacaa cctgaccaag    2820 gccgagcgcg gcggcctgag cgagctggac aaggccggct tcatcaagcg ccagctggtg    2880
gagacccgcc agatcaccaa gcacgtggcc cagatcctgg acagccgcat gaacaccaag    2940
tacgacgaga cgacaagct gatccgcgag gtgaaggtga tcaccctgaa gagcaagctg    3000
gtgagcgact ccgcaagga cttccagttc tacaaggtgc gcgagatcaa caactaccac    3060
cacgcccacg acgcctacct gaacgccgtg gtgggcaccg ccctgatcaa gaagtacccc    3120
aagctggaga gcgagttcgt gtacggcgac tacaaggtgt acgacgtgcg caagatgatc    3180
gccaagagcg agcaggagat cggcaaggcc accgccaagt acttcttcta cagcaacatc    3240
atgaacttct tcaagaccga gatcaccctg gccaacggcg agatccgcaa gcgcccctg    3300 atcgagacca acggcgagac cggcgagatc gtgtgggaca agggccgcga cttcgccacc    3360
gtgcgcaagg tgctgagcat gccccaggtg aacatcgtga agaagaccga ggtgcagacc    3420
ggcggcttca gcaaggagag catcctgccc aagcgcaaca gcgacaagct gatcgcccgc    3480
aagaaggact gggaccccaa gaagtacggc ggcttcgaca gccccaccgt ggcctacagc    3540
gtgctggtgg tggccaaggt ggagaagggc aagagcaaga agctgaagag cgtgaaggag    3600
ctgctgggca tcaccatcat ggagcgcagc agcttcgaga agaaccccat cgacttcctg    3660
```

-continued

```
gaggccaagg gctacaagga ggtgaagaag gacctgatca tcaagctgcc caagtacagc    3720
ctgttcgagc tggagaacgg ccgcaagcgc atgctggcca cgccggcga gctgcagaag    3780 ggcaacgagc tggccctgcc cagcaagtac gtgaacttcc tgtacctggc cagccactac    3840
gagaagctga agggcagccc cgaggacaac gagcagaagc agctgttcgt ggagcagcac    3900
aagcactacc tggacgagat catcgagcag atcagcgagt tcagcaagcg cgtgatcctg    3960
gccgacgcca acctggacaa ggtgctgagc gcctacaaca gcaccgcga caagcccatc    4020 cgcgagcagg ccgagaacat catccacctg ttcaccctga ccaacctggg cgcccccgcc    4080
gccttcaagt acttcgacac caccatcgac cgcaagcgct acaccagcac caaggaggtg    4140
ctggacgcca ccctgatcca ccagagcatc accggtctgt acgagacccg catcgacctg    4200
agccagctgg gcggcgacta a                                              4221
```

<210> SEQ ID NO 111
<211> LENGTH: 1406
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Amino acid sequence of Cas9 (pET-Cas9N3T)

<400> SEQUENCE: 111

```
Met Gly Ser Ser His His His His His His Val Tyr Pro Tyr Asp Val
1               5                   10                  15

Pro Asp Tyr Ala Glu Leu Pro Pro Lys Lys Lys Arg Lys Val Gly Ile
                20                  25                  30

Glu Asn Leu Tyr Phe Gln Gly Asp Lys Lys Tyr Ser Ile Gly Leu Asp
            35                  40                  45

Ile Gly Thr Asn Ser Val Gly Trp Ala Val Ile Thr Asp Glu Tyr Lys
        50                  55                  60

Val Pro Ser Lys Lys Phe Lys Val Leu Gly Asn Thr Asp Arg His Ser
65                  70                  75                  80

Ile Lys Lys Asn Leu Ile Gly Ala Leu Leu Phe Asp Ser Gly Glu Thr
                85                  90                  95

Ala Glu Ala Thr Arg Leu Lys Arg Thr Ala Arg Arg Tyr Thr Arg
                100                 105                 110

Arg Lys Asn Arg Ile Cys Tyr Leu Gln Glu Ile Phe Ser Asn Glu Met
            115                 120                 125

Ala Lys Val Asp Asp Ser Phe Phe His Arg Leu Glu Glu Ser Phe Leu
        130                 135                 140

Val Glu Asp Lys Lys His Glu Arg His Pro Ile Phe Gly Asn Ile
145                 150                 155                 160

Val Asp Glu Val Ala Tyr His Glu Lys Tyr Pro Thr Ile Tyr His Leu
                165                 170                 175

Arg Lys Lys Leu Val Asp Ser Thr Asp Lys Ala Asp Leu Arg Leu Ile
            180                 185                 190

Tyr Leu Ala Leu Ala His Met Ile Lys Phe Arg Gly His Phe Leu Ile
        195                 200                 205

Glu Gly Asp Leu Asn Pro Asp Asn Ser Asp Val Asp Lys Leu Phe Ile
    210                 215                 220

Gln Leu Val Gln Thr Tyr Asn Gln Leu Phe Glu Glu Asn Pro Ile Asn
225                 230                 235                 240
```

-continued

```
Ala Ser Gly Val Asp Ala Lys Ala Ile Leu Ser Ala Arg Leu Ser Lys
                245                 250                 255
Ser Arg Arg Leu Glu Asn Leu Ile Ala Gln Leu Pro Gly Glu Lys Lys
            260                 265                 270
Asn Gly Leu Phe Gly Asn Leu Ile Ala Leu Ser Leu Gly Leu Thr Pro
        275                 280                 285
Asn Phe Lys Ser Asn Phe Asp Leu Ala Glu Asp Ala Lys Leu Gln Leu
    290                 295                 300
Ser Lys Asp Thr Tyr Asp Asp Leu Asp Asn Leu Leu Ala Gln Ile
305                 310                 315                 320
Gly Asp Gln Tyr Ala Asp Leu Phe Leu Ala Ala Lys Asn Leu Ser Asp
                325                 330                 335
Ala Ile Leu Leu Ser Asp Ile Leu Arg Val Asn Thr Glu Ile Thr Lys
            340                 345                 350
Ala Pro Leu Ser Ala Ser Met Ile Lys Arg Tyr Asp Glu His His Gln
        355                 360                 365
Asp Leu Thr Leu Leu Lys Ala Leu Val Arg Gln Gln Leu Pro Glu Lys
    370                 375                 380
Tyr Lys Glu Ile Phe Phe Asp Gln Ser Lys Asn Gly Tyr Ala Gly Tyr
385                 390                 395                 400
Ile Asp Gly Gly Ala Ser Gln Glu Glu Phe Tyr Lys Phe Ile Lys Pro
                405                 410                 415
Ile Leu Glu Lys Met Asp Gly Thr Glu Glu Leu Leu Val Lys Leu Asn
            420                 425                 430
Arg Glu Asp Leu Leu Arg Lys Gln Arg Thr Phe Asp Asn Gly Ser Ile
        435                 440                 445
Pro His Gln Ile His Leu Gly Glu Leu His Ala Ile Leu Arg Arg Gln
    450                 455                 460
Glu Asp Phe Tyr Pro Phe Leu Lys Asp Asn Arg Glu Lys Ile Glu Lys
465                 470                 475                 480
Ile Leu Thr Phe Arg Ile Pro Tyr Tyr Val Gly Pro Leu Ala Arg Gly
                485                 490                 495
Asn Ser Arg Phe Ala Trp Met Thr Arg Lys Ser Glu Glu Thr Ile Thr
            500                 505                 510
Pro Trp Asn Phe Glu Glu Val Val Asp Lys Gly Ala Ser Ala Gln Ser
        515                 520                 525
Phe Ile Glu Arg Met Thr Asn Phe Asp Lys Asn Leu Pro Asn Glu Lys
    530                 535                 540
Val Leu Pro Lys His Ser Leu Leu Tyr Glu Tyr Phe Thr Val Tyr Asn
545                 550                 555                 560
Glu Leu Thr Lys Val Lys Tyr Val Thr Glu Gly Met Arg Lys Pro Ala
                565                 570                 575
Phe Leu Ser Gly Glu Gln Lys Lys Ala Ile Val Asp Leu Leu Phe Lys
            580                 585                 590
Thr Asn Arg Lys Val Thr Val Lys Gln Leu Lys Glu Asp Tyr Phe Lys
        595                 600                 605
Lys Ile Glu Cys Phe Asp Ser Val Glu Ile Ser Gly Val Glu Asp Arg
    610                 615                 620
Phe Asn Ala Ser Leu Gly Thr Tyr His Asp Leu Leu Lys Ile Ile Lys
625                 630                 635                 640
Asp Lys Asp Phe Leu Asp Asn Glu Glu Asn Glu Asp Ile Leu Glu Asp
                645                 650                 655
Ile Val Leu Thr Leu Thr Leu Phe Glu Asp Arg Glu Met Ile Glu Glu
```

-continued

```
                660                 665                 670
Arg Leu Lys Thr Tyr Ala His Leu Phe Asp Asp Lys Val Met Lys Gln
            675                 680                 685

Leu Lys Arg Arg Arg Tyr Thr Gly Trp Gly Arg Leu Ser Arg Lys Leu
        690                 695                 700

Ile Asn Gly Ile Arg Asp Lys Gln Ser Gly Lys Thr Ile Leu Asp Phe
705                 710                 715                 720

Leu Lys Ser Asp Gly Phe Ala Asn Arg Asn Phe Met Gln Leu Ile His
                725                 730                 735

Asp Asp Ser Leu Thr Phe Lys Glu Asp Ile Gln Lys Ala Gln Val Ser
            740                 745                 750

Gly Gln Gly Asp Ser Leu His Glu His Ile Ala Asn Leu Ala Gly Ser
        755                 760                 765

Pro Ala Ile Lys Lys Gly Ile Leu Gln Thr Val Lys Val Val Asp Glu
    770                 775                 780

Leu Val Lys Val Met Gly Arg His Lys Pro Glu Asn Ile Val Ile Glu
785                 790                 795                 800

Met Ala Arg Glu Asn Gln Thr Thr Gln Lys Gly Gln Lys Asn Ser Arg
                805                 810                 815

Glu Arg Met Lys Arg Ile Glu Glu Gly Ile Lys Glu Leu Gly Ser Gln
            820                 825                 830

Ile Leu Lys Glu His Pro Val Glu Asn Thr Gln Leu Gln Asn Glu Lys
        835                 840                 845

Leu Tyr Leu Tyr Tyr Leu Gln Asn Gly Arg Asp Met Tyr Val Asp Gln
    850                 855                 860

Glu Leu Asp Ile Asn Arg Leu Ser Asp Tyr Asp Val Asp His Ile Val
865                 870                 875                 880

Pro Gln Ser Phe Leu Lys Asp Asp Ser Ile Asp Asn Lys Val Leu Thr
                885                 890                 895

Arg Ser Asp Lys Asn Arg Gly Lys Ser Asp Asn Val Pro Ser Glu Glu
            900                 905                 910

Val Val Lys Lys Met Lys Asn Tyr Trp Arg Gln Leu Leu Asn Ala Lys
        915                 920                 925

Leu Ile Thr Gln Arg Lys Phe Asp Asn Leu Thr Lys Ala Glu Arg Gly
    930                 935                 940

Gly Leu Ser Glu Leu Asp Lys Ala Gly Phe Ile Lys Arg Gln Leu Val
945                 950                 955                 960

Glu Thr Arg Gln Ile Thr Lys His Val Ala Gln Ile Leu Asp Ser Arg
                965                 970                 975

Met Asn Thr Lys Tyr Asp Glu Asn Asp Lys Leu Ile Arg Glu Val Lys
            980                 985                 990

Val Ile Thr Leu Lys Ser Lys Leu Val Ser Asp Phe Arg Lys Asp Phe
        995                 1000                1005

Gln Phe Tyr Lys Val Arg Glu Ile Asn Asn Tyr His His Ala His
    1010                1015                1020

Asp Ala Tyr Leu Asn Ala Val Val Gly Thr Ala Leu Ile Lys Lys
    1025                1030                1035

Tyr Pro Lys Leu Glu Ser Glu Phe Val Tyr Gly Asp Tyr Lys Val
    1040                1045                1050

Tyr Asp Val Arg Lys Met Ile Ala Lys Ser Glu Gln Glu Ile Gly
    1055                1060                1065

Lys Ala Thr Ala Lys Tyr Phe Phe Tyr Ser Asn Ile Met Asn Phe
    1070                1075                1080
```

```
Phe Lys Thr Glu Ile Thr Leu Ala Asn Gly Glu Ile Arg Lys Arg
    1085            1090                1095

Pro Leu Ile Glu Thr Asn Gly Glu Thr Gly Glu Ile Val Trp Asp
    1100            1105                1110

Lys Gly Arg Asp Phe Ala Thr Val Arg Lys Val Leu Ser Met Pro
    1115            1120                1125

Gln Val Asn Ile Val Lys Lys Thr Glu Val Gln Thr Gly Gly Phe
    1130            1135                1140

Ser Lys Glu Ser Ile Leu Pro Lys Arg Asn Ser Asp Lys Leu Ile
    1145            1150                1155

Ala Arg Lys Lys Asp Trp Asp Pro Lys Lys Tyr Gly Gly Phe Asp
    1160            1165                1170

Ser Pro Thr Val Ala Tyr Ser Val Leu Val Val Ala Lys Val Glu
    1175            1180                1185

Lys Gly Lys Ser Lys Lys Leu Lys Ser Val Lys Glu Leu Leu Gly
    1190            1195                1200

Ile Thr Ile Met Glu Arg Ser Ser Phe Glu Lys Asn Pro Ile Asp
    1205            1210                1215

Phe Leu Glu Ala Lys Gly Tyr Lys Glu Val Lys Lys Asp Leu Ile
    1220            1225                1230

Ile Lys Leu Pro Lys Tyr Ser Leu Phe Glu Leu Glu Asn Gly Arg
    1235            1240                1245

Lys Arg Met Leu Ala Ser Ala Gly Glu Leu Gln Lys Gly Asn Glu
    1250            1255                1260

Leu Ala Leu Pro Ser Lys Tyr Val Asn Phe Leu Tyr Leu Ala Ser
    1265            1270                1275

His Tyr Glu Lys Leu Lys Gly Ser Pro Glu Asp Asn Glu Gln Lys
    1280            1285                1290

Gln Leu Phe Val Glu Gln His Lys His Tyr Leu Asp Glu Ile Ile
    1295            1300                1305

Glu Gln Ile Ser Glu Phe Ser Lys Arg Val Ile Leu Ala Asp Ala
    1310            1315                1320

Asn Leu Asp Lys Val Leu Ser Ala Tyr Asn Lys His Arg Asp Lys
    1325            1330                1335

Pro Ile Arg Glu Gln Ala Glu Asn Ile Ile His Leu Phe Thr Leu
    1340            1345                1350

Thr Asn Leu Gly Ala Pro Ala Ala Phe Lys Tyr Phe Asp Thr Thr
    1355            1360                1365

Ile Asp Arg Lys Arg Tyr Thr Ser Thr Lys Glu Val Leu Asp Ala
    1370            1375                1380

Thr Leu Ile His Gln Ser Ile Thr Gly Leu Tyr Glu Thr Arg Ile
    1385            1390                1395

Asp Leu Ser Gln Leu Gly Gly Asp
    1400            1405

<210> SEQ ID NO 112
<211> LENGTH: 34
<212> TYPE: DNA
<213> ORGANISM: Homo sapiens

<400> SEQUENCE: 112
caatctatga catcaattat tatacatcgg agcc                            34

<210> SEQ ID NO 113
```

<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 113
ggugacauca auuauuauac auguuuuaga gcuagaaaua gcaaguuaaa auaaggcuag    60
uccg                                                                64

<210> SEQ ID NO 114
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
caatctatga catcaattat tatacatcgg agccctgcca aaaaatcaa                49

<210> SEQ ID NO 115
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
caatctatga catcaattat tataacatcg gagccctgcc aaaaaatcaa               50

<210> SEQ ID NO 116
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
caatctatga catcaattat tatgccaaaa aatcaa                              36

<210> SEQ ID NO 117
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
caatctatga catcggagcc ctgccaaaaa atcaa                               35

<210> SEQ ID NO 118
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
caatctatga catgccctgc caaaaaatca a                                   31

```
<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
caatctatga catcaattat tataaatcaa                                          30

<210> SEQ ID NO 120
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
caatctatga catccaaaaa atcaa                                               25

<210> SEQ ID NO 121
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
caatctatga caaaatcaa                                                      19

<210> SEQ ID NO 122
<211> LENGTH: 46
<212> TYPE: DNA
<213> ORGANISM: Homo sapiens

<400> SEQUENCE: 122
tatgtgcaat gaccactaca tcctcaaggg cagcaatcgg agccag                        46

<210> SEQ ID NO 123
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
tatgtgcaat gaccactaca tccttcaagg gcagcaatcg gagccag                       47

<210> SEQ ID NO 124
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
tatgtgcaat gaccactaca tcctctcaag ggcagcaatc ggagccag                      48

<210> SEQ ID NO 125
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 125
tatgtgcaat ggagccag                                                    18

<210> SEQ ID NO 126
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
tatgtgcaat gac                                                         13

<210> SEQ ID NO 127
<211> LENGTH: 23
<212> TYPE: DNA
<213> ORGANISM: Homo sapiens

<400> SEQUENCE: 127
tgacatcaat tattatacat cgg                                              23

<210> SEQ ID NO 128
<211> LENGTH: 23
<212> TYPE: DNA
<213> ORGANISM: Homo sapiens

<400> SEQUENCE: 128
tgacatcaat tattatagat gga                                              23

<210> SEQ ID NO 129
<211> LENGTH: 23
<212> TYPE: DNA
<213> ORGANISM: Homo sapiens

<400> SEQUENCE: 129
tgacatcact tattatgcat ggg                                              23

<210> SEQ ID NO 130
<211> LENGTH: 23
<212> TYPE: DNA
<213> ORGANISM: Homo sapiens

<400> SEQUENCE: 130
tgacataaat tattctacat ggg                                              23

<210> SEQ ID NO 131
<211> LENGTH: 23
<212> TYPE: DNA
<213> ORGANISM: Homo sapiens

<400> SEQUENCE: 131
tgaaatcaat tatcatagat cgg                                              23

<210> SEQ ID NO 132
<211> LENGTH: 23
<212> TYPE: DNA
<213> ORGANISM: Homo sapiens

<400> SEQUENCE: 132
```

```
ccaggctcca cccgactgga ggg                                            23

<210> SEQ ID NO 133
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 133
ggccaggcuc cacccgacug gaguuuaga gcuagaaaua gcaaguuaaa auaaggcuag      60
uccguuauca acuugaaaaa guggcaccgag ucggugcuu uuuuuu                   106

<210> SEQ ID NO 134
<211> LENGTH: 53
<212> TYPE: DNA
<213> ORGANISM: Homo sapiens

<400> SEQUENCE: 134
acttccaggc tccacccgac tggagggcga accccaaggg gacctcatgc agg           53

<210> SEQ ID NO 135
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
acttccaggc tcc                                                        13

<210> SEQ ID NO 136
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
acttccaggc tccacccgac ctcatgcagg                                      30

<210> SEQ ID NO 137
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
acttccaggc tccaccccaa ggggacctca tgcagg                               36

<210> SEQ ID NO 138
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
acttccaggc tccacccgac ttggagggcg aaccccaagg ggacctcatg cagg           54
```

<210> SEQ ID NO 139
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
acttccaggc tccacccgaa ccccaagggg acctcatgca ggg                          43

<210> SEQ ID NO 140
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
acttccaggc tccacccgac tcactatctt ctgggctcct ccatgtc                      47

<210> SEQ ID NO 141
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
acttccaggc tccacccgac gaaccccaag gggacctcat gcagg                        45

<210> SEQ ID NO 142
<211> LENGTH: 18
<212> TYPE: PRT
<213> ORGANISM: Homo sapiens

<400> SEQUENCE: 142

Leu Pro Gly Ser Thr Arg Leu Glu Gly Glu Pro Gln Gly Asp Leu Met
1               5                   10                  15

Gln Ala

<210> SEQ ID NO 143
<211> LENGTH: 57
<212> TYPE: DNA
<213> ORGANISM: Homo sapiens
<220> FEATURE:
<221> NAME/KEY: CDS
<222> LOCATION: (2)..(55)

<400> SEQUENCE: 143 a ctt cca ggc tcc acc cga ctg gag ggc gaa ccc caa ggg gac ctc atg       49
  Leu Pro Gly Ser Thr Arg Leu Glu Gly Glu Pro Gln Gly Asp Leu Met
  1               5                   10                  15 cag gct cc                                                               57
Gln Ala <210> SEQ ID NO 144
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 144
acttccaggc tccacccgaa ccccaagggg acctcatgca ggctcc                    46

<210> SEQ ID NO 145
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
acttccaggc tccacccgaa ccccaagggg acctcatgca ggc                       43

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
acttccaggc tccacccgac                                                 20

<210> SEQ ID NO 147
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
acttccaggc tccaccccaa ggggacctca tgcaggctcc                           40

<210> SEQ ID NO 148
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
acttccaggc tccacccgac ttggagggcg aaccccaagg ggacctcatg caggctcc       58

<210> SEQ ID NO 149
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
acttccaggc tccaggcgaa ccccaagggg acctcatgca ggctcc                    46

<210> SEQ ID NO 150
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
```

```
ggcgaacccc aagggggacct catgcaggct cc                                    32
```

<210> SEQ ID NO 151
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151

```
acttccaggc aagggggacct catgcaggct cc                                    32
```

<210> SEQ ID NO 152
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152

```
acttccaggc taaggggacc tcatgcaggc tcc                                    33
```

<210> SEQ ID NO 153
<211> LENGTH: 52
<212> TYPE: DNA
<213> ORGANISM: Homo sapiens

<400> SEQUENCE: 153

```
acttccaggc tccacccgac tggagggcga accccaaggg gacctcatgc ag              52
```

<210> SEQ ID NO 154
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154

```
acttccaggc gaaccccaag gggacctcat gcag                                   34
```

<210> SEQ ID NO 155
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155

```
acttccaggc tccacaaggg gacctcatgc ag                                     32
```

<210> SEQ ID NO 156
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156

```
acttccaggc tccacccaag gggacctcat gccc                                   34
```

```
<210> SEQ ID NO 157
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
acttccaggc tccaccccaa ggggacctca tgcag                                 35

<210> SEQ ID NO 158
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
acttccaggc tccacccgaa ccccaagggg acctcatgca g                          41

<210> SEQ ID NO 159
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
acttccaggc tccacccgaa ggagggcgaa ccccaagggg acctcatgca                 50

<210> SEQ ID NO 160
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
acttccaggc tccacccgac tagggcgaac cccaagggga cctcatgcag                 50

<210> SEQ ID NO 161
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
acttccaggc tccacccgac tgggagggcg aaccccaagg ggacctcatg ca              52

<210> SEQ ID NO 162
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
acttccaggc tccacccgac ttggagggcg aaccccaagg ggacctcatg ca              52

<210> SEQ ID NO 163
```

```
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
acttccaggc tccacccgag gcgaaccca aggggacctc atgcag            46

<210> SEQ ID NO 164
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
acttccaggc tccacccgag ggcgaacccc aagggacct catgcag           47

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
acttccaggc tccacctcat gcag                                   24

<210> SEQ ID NO 166
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
agggcgaacc ccaaggggac ctcatgcag                              29

<210> SEQ ID NO 167
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
caatctatga catcaattat tatcggagcc ctgccaaaaa atcaa            45

<210> SEQ ID NO 168
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
caatctatga catcaattat catcggagcc ctgccaaaaa atcaa            45

<210> SEQ ID NO 169
<211> LENGTH: 42
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
caatctatga catcaattat cggagccctg ccaaaaaatc aa                              42

<210> SEQ ID NO 170
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
caatctatga catcaattat tatcatcgga gccctgccaa aaatcaa                        48

<210> SEQ ID NO 171
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
caatctatga caagagccct gccaaaaaat caa                                        33

<210> SEQ ID NO 172
<211> LENGTH: 52
<212> TYPE: DNA
<213> ORGANISM: Homo sapiens

<400> SEQUENCE: 172
ttctcaaggc agcatcatac ttcccccacg gtgggacagc tgccctccct gg                  52

<210> SEQ ID NO 173
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ttctcaaggc agcatcatac ttccctggga cagctgccct ccctgg                          46

<210> SEQ ID NO 174
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
ttctcaaggc agcatcatac ttccacggtg ggacagctgc cctccctgg                       49

<210> SEQ ID NO 175
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 175
ttctcaaggc agctgccctc cctgg                                    25

<210> SEQ ID NO 176
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
ttctcaaggc agcatcatac ttccctccct gg                            32

<210> SEQ ID NO 177
<211> LENGTH: 264
<212> TYPE: DNA
<213> ORGANISM: Homo sapiens
<220> FEATURE:
<221> NAME/KEY: modified_base
<222> LOCATION: (38)..(227)
<223> OTHER INFORMATION: a, c, t, g, unknown or other

<400> SEQUENCE: 177
acaaagcgat tttgaaagat ggaagcgcgg tggctatnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnggg gtgaaactaa      240 actggtccac acggcggaag attg                                            264

<210> SEQ ID NO 178
<211> LENGTH: 257
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (38)..(227)
<223> OTHER INFORMATION: a, c, t, g, unknown or other

<400> SEQUENCE: 178
acaaagcgat tttgaaagat ggaagcgcgg tggctatnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnggg gtgaaactaa     240
aacacggcgg aagattg                                                    257

<210> SEQ ID NO 179
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
acaaagcgat tttgaaagat ggaagcgaca cggcggaaga ttg                 43

<210> SEQ ID NO 180
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
acaaagcgat tttgaaagat ggaagcgcac acggcggaag attg          44

<210> SEQ ID NO 181
<211> LENGTH: 106
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181
acaaagcgat tttgaaagat ggaagcgaaa tagcaagtta aaataaggct agtccgttat    60
caacttgaaa aagtggcacc gagtcggtgc acacggcgga agattg                  106

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
gggtgggggg agtttgctcc tgg                                            23

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
ggatggaggg agtttgctcc tgg                                            23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ggggagggga agtttgctcc tgg                                            23

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
gaccccctcc accccgcctc cgg                                            23

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gacccccccc accccgcccc cgg                                           23

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gcccccaccc accccgcctc tgg                                           23

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ctccccaccc accccgcctc agg                                           23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ggtgagtgag tgtgtgcgtg tgg                                           23

<210> SEQ ID NO 190
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tgtgggtgag tgtgtgcgtg agg                                           23

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
gagtccgagc agaagaagaa ggg                                           23

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gagttagagc agaagaagaa agg                                           23

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
gaacctgagc tgctctgacg cgg                                           23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ttggcagggg gtgggaggga agg                                           23

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gggagggaga gcttggcagg ggg                                           23

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
gatggagcca gagaggatcc tgg                                           23

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cctgccaagc tctccctccc agg                                           23

```
<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ctccctccca ggatcctctc tgg                                              23

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
cctctaaggt ttgcttacga tgg                                              23

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
ggttctggca aggagagaga tgg                                              23

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
tctaaccccc acctcctgtt agg                                              23

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
ttggcagggg gtgggaggga tgg                                              23

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ttggtagggg gtgggaggga tgg                                              23

<210> SEQ ID NO 204
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
gggaagggga gcttggcagg tgg                                          23

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ggtagtgaga gcttggcagg tgg                                          23

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
ctccctccca ggatcctccc agg                                          23

<210> SEQ ID NO 207
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
gtccatggca ggatcctctc agg                                          23

<210> SEQ ID NO 208
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208 ctcccccca gtatcctctc agg                                           23

<210> SEQ ID NO 209
<211> LENGTH: 108
<212> TYPE: DNA
<213> ORGANISM: Homo sapiens

<400> SEQUENCE: 209
ccaatctatg acatcaatta ttatacatcg gagccctgcc aaaaaatcaa tgtgaagcaa   60
atcgcagccc gcctcctgcc tccgctctac tcactggtgt tcatctttt             108

<210> SEQ ID NO 210
<211> LENGTH: 138
<212> TYPE: DNA
```

<213> ORGANISM: Homo sapiens

<400> SEQUENCE: 210
ccaccctata attctgaacc tgcagaagaa tctgaacata aaaacaacaa ttacgaacca    60
aacctattta aaactccaca aaggaaacca tcttataatc agctggcttc aactccaata   120
atattcaaag agcaaggg                                                 138

<210> SEQ ID NO 211
<211> LENGTH: 121
<212> TYPE: DNA
<213> ORGANISM: Homo sapiens
<220> FEATURE:
<221> NAME/KEY: misc_feature
<222> LOCATION: (49)..(50)
<223> OTHER INFORMATION: Nucleotides at these positions are non-
      consecutive and are separated by a non-disclosed sequence

<400> SEQUENCE: 211
ggccgggaat caagagtcac ccagagacag tgaccaacca tccctgttta gctctccctc    60
ccaggatcct ctctggctcc atcgtaagca aaccttagag gttctggcaa ggagagagat   120
g                                                                   121

<210> SEQ ID NO 212
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
ggccgggaat caagagtcac ccagtgacca accatccctg taagcaaacc ttagaggttc    60
tggcaaggag agagatg                                                   77

<210> SEQ ID NO 213
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
ggccgggaat caagagtcac ccaggaa                                        27

<210> SEQ ID NO 214
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
ggccgggaat caagagtcac ccagacctct ctggctccat cgtaagcaaa ccttagaggt    60
tctggcaagg agagagatg                                                 79

<210> SEQ ID NO 215
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 215
ggccgggaat caagagtcac cctaacag                                      28

<210> SEQ ID NO 216
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
ggccgggaat caagacgctg gctccatcgt aagcaaacct tagaggttct ggcaaggaga    60
gagatg                                                              66

<210> SEQ ID NO 217
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
ggctccatcg taagcaaacc ttagaggttc tggcaaggag agagatg                  47

<210> SEQ ID NO 218
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
ggccgggaat caagagtcac ccagactctc tggctccatc gtaagcaaac cttagaggtt    60
ctggcaagga gagagatg                                                 78

<210> SEQ ID NO 219
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
ggccgggaat caagagtcac ccagagacag tgaccaacca tcgtaagcaa accttagagg    60
ttctggcaag gagagagatg                                               80

<210> SEQ ID NO 220
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
ggtccatcgt aagcaaacct tagaggttct ggcaaggaga gagatg                  46

<210> SEQ ID NO 221

```
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
ggccgggaat caagagtcac ccatctccat cgtaagcaaa ccttagaggt tctggcaagg    60
agagagatg                                                            69

<210> SEQ ID NO 222
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
ggccgggaat caagagtcac ccagactctg gctccatcgt aagcaaacct tagaggttct    60
ggcaaggaga gagatg                                                    76

<210> SEQ ID NO 223
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
ggccgggaat caagagtcac ccagagacag tgaccaacca tcccatatca               50

<210> SEQ ID NO 224
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
ggccgggaat caagagtcat cgtaagcaaa ccttagaggt tctggcaagg agagagatg     59

<210> SEQ ID NO 225
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
aatgaccact acatccttca aggg                                           24

<210> SEQ ID NO 226
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
aatgaccact acatcctttc aaggg                                          25
```

<210> SEQ ID NO 227
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
aatgaccact acatccttt caagggg                                          26

<210> SEQ ID NO 228
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
aatgaccact acatcctaag gg                                              22

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
aatgaccact acatcctagg g                                               21

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
aatgaccact acatcctggg                                                 20

<210> SEQ ID NO 231
<211> LENGTH: 42
<212> TYPE: DNA
<213> ORGANISM: Homo sapiens

<400> SEQUENCE: 231
tatgtgcaat gaccactaca tcctcaaggg cagcaatcgg ag                         42

<210> SEQ ID NO 232
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
tatgtgcaat gaccactaca tcctcctcaa gggcagcaat cggag                      45

<210> SEQ ID NO 233
<211> LENGTH: 30

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
tatgtgcaat gaccactaca tcaatcggag                                      30

<210> SEQ ID NO 234
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
tatgtgcaat gaccactaca tcagcaatcg gag                                  33

<210> SEQ ID NO 235
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tatgtgcaat gaccactaca tccagcaatc ggag                                 34

<210> SEQ ID NO 236
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
cagcaatcgg                                                            10

<210> SEQ ID NO 237
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
tatgtgcaat gaccactaca tccttcaagg gcagcaatcg g                         41

<210> SEQ ID NO 238
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
tatgtgcaat gaccactaca tcctccaagg gcagcaatcg g                         41

<210> SEQ ID NO 239
<211> LENGTH: 41
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 239
tatgtgcaat gaccactaca tcctbcaagg gcagcaatcg g         41

<210> SEQ ID NO 240
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
tatgtgcaat gaccactaca ttggcagcaa tcgg                 34

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
tatgtgcaat gaccactaca t                               21

<210> SEQ ID NO 242
<211> LENGTH: 53
<212> TYPE: DNA
<213> ORGANISM: Homo sapiens

<400> SEQUENCE: 242
tcatacagat gatgtctcat catcagagga gcgagaaggt aaagtcaaaa tca    53

<210> SEQ ID NO 243
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
tcatacagat gatacaggta aagtcaaaat ca                   32

<210> SEQ ID NO 244
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
tcatacaggt gatgaaggta aagtcaaaat ca                   32

<210> SEQ ID NO 245
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 245
tcatacagat gatgtctcat catcagagcg agaaggtaaa gtcaaaatca          50

<210> SEQ ID NO 246
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
tcatacagat gatgtctcat catcagcgag aaggtaaagt caaaatca            48

<210> SEQ ID NO 247
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
tcatacagat gatgtctcat catcagggag cgagaaggta aagtcaaaat ca       52

<210> SEQ ID NO 248
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
tcatacagat gatgtctcgc gagaaggtaa agtcaaaatc a                   41

<210> SEQ ID NO 249
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
tcatacagat gatgaaggta aagtcaaaat ca                             32

<210> SEQ ID NO 250
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tcatacagat gaaggtaaag tcaaaatca                                 29

<210> SEQ ID NO 251
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 251
tcatacagat gatgtctaca gatgaaggta aagtcaaaat ca          42

<210> SEQ ID NO 252
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
tcatacagat gatgtctcat catcaggagc gagaaggtaa agtcaaaatc a          51

<210> SEQ ID NO 253
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
gtcatcctca tcctgataaa ctgcaaaagg ctga          34

<210> SEQ ID NO 254
<211> LENGTH: 606
<212> TYPE: DNA
<213> ORGANISM: Homo sapiens

<400> SEQUENCE: 254
gctggtgtct gggttctgtg cccccttcccc acccccagccc accccaggtg tcctgtccat     60
tctcaggctg gtcacatggg tggtcctagg gtgtcccatg agagatgcaa agcgcctgaa     120
ttttctgact cttcccatca gacccccccaa agacacatgt gacccaccac cccatctctg    180
accatgaggc caccctgagg tgctgggccc tgggcttcta ccctgcggag atcacactga     240
cctggcagcg ggatggcgag gaccaaactc aggacaccga gcttgtggag accagaccag     300
caggagatag aaccttccag aagtgggcag ctgtggtggt gccttctgga gaagagcaga     360
gatacacatg ccatgtacag catgagggggc tgccgaagcc cctcaccctg agatggggta     420
aggaggggga tgaggggtca tatctgttca tatctgttct cagggaaagc aggagcccctt    480 ctggagccct tcagcagggt cagggcccct catcttcccc tcctttccca gagccatctt    540
cccagtccac catccccatc gtgggcattg ttgctggcct ggctgtccta gcagttgtgg    600
tcatcg                                                                606

<210> SEQ ID NO 255
<211> LENGTH: 26
<212> TYPE: DNA
<213> ORGANISM: Homo sapiens

<400> SEQUENCE: 255
actaccacag ctccttctct gagtgg          26

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 256
actaccacag ctcctctgag tgg                                              23

<210> SEQ ID NO 257
<211> LENGTH: 23
<212> TYPE: DNA
<213> ORGANISM: Homo sapiens

<400> SEQUENCE: 257
gtagttggag ctggcggcgt agg                                              23

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
gtagttggag ctagcggcgt agg                                              23

<210> SEQ ID NO 259
<211> LENGTH: 23
<212> TYPE: DNA
<213> ORGANISM: Homo sapiens

<400> SEQUENCE: 259
gtagttggag ctggtggcgt agg                                              23

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gtagttggag ctagtggcgt agg                                              23

<210> SEQ ID NO 261
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
ccatacatta aagatagtca tcttgggg                                         28

<210> SEQ ID NO 262
<211> LENGTH: 60
<212> TYPE: DNA
<213> ORGANISM: Homo sapiens

<400> SEQUENCE: 262
ccatacagtc agtatcaatt ctggaagaat ttccagacat taaagatagt catcttgggg      60

<210> SEQ ID NO 263
<211> LENGTH: 55
<212> TYPE: DNA
<213> ORGANISM: Homo sapiens
```

```
<400> SEQUENCE: 263
ccatacagtc agtatcaatt ctggaagaat ttccagacat taaagatagt catct      55

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
ccatacatta aagatagtca tct                                         23

<210> SEQ ID NO 265
<211> LENGTH: 23
<212> TYPE: DNA
<213> ORGANISM: Homo sapiens

<400> SEQUENCE: 265
agatgactat ctttaatgtc tgg                                         23

<210> SEQ ID NO 266
<211> LENGTH: 23
<212> TYPE: DNA
<213> ORGANISM: Homo sapiens

<400> SEQUENCE: 266
agatgactat ctttaatgta tgg                                         23

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
gtagttggag ctgatggcgt agg                                         23

<210> SEQ ID NO 268
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
gtagttggag ctggtagcgt agg                                         23

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gtagttggag ctggtgacgt agg                                         23

<210> SEQ ID NO 270
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
gtagttggag ctaatggcgt agg                                            23

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
gtagttggag ctagtagcgt agg                                            23

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gtagttggag ctagtgacgt agg                                            23

<210> SEQ ID NO 273
<211> LENGTH: 23
<212> TYPE: DNA
<213> ORGANISM: Homo sapiens

<400> SEQUENCE: 273
caaatgaatg atgcacatca tgg                                            23

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
caaatgaatg atgcacgtca tgg                                            23

<210> SEQ ID NO 275
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
caaatgaatg atgcatatca tgg                                            23

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 276
caaatgaatg atgcgcatca tgg                                           23

<210> SEQ ID NO 277
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
caaatgaatg atgtacatca tgg                                           23

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
caaatgaatg gtgcacatca tgg                                           23

<210> SEQ ID NO 279
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
caaatgagtg atgcacatca tgg                                           23

<210> SEQ ID NO 280
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
caaaagaatg atgcacatca tgg                                           23

<210> SEQ ID NO 281
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
cgaatgaatg atgcacatca tgg                                           23

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide <210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 283
caaatgaatg atgcgcgtca tgg                                              23

<210> SEQ ID NO 284
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 284
caaatgaatg atgtacgtca tgg                                              23

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 285
caaatgaatg gtgcacgtca tgg                                              23

<210> SEQ ID NO 286
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 286
caaatgagtg atgcacgtca tgg                                              23

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 287
caaaagaatg atgcacgtca tgg                                              23

<210> SEQ ID NO 288
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 288
cgaatgaatg atgcacgtca tgg                                              23

<210> SEQ ID NO 289
<211> LENGTH: 23
<212> TYPE: DNA
<213> ORGANISM: Homo sapiens

<400> SEQUENCE: 289
atcataggtc gtcatgctta tgg                                              23

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
atcataggtt gtcatgctta tgg                                              23

<210> SEQ ID NO 291
<211> LENGTH: 23
<212> TYPE: DNA
<213> ORGANISM: Homo sapiens

<400> SEQUENCE: 291
atcataggtc gtcctgctta tgg                                              23

<210> SEQ ID NO 292
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
atcataggtt gtcctgctta tgg                                              23

<210> SEQ ID NO 293
<211> LENGTH: 23
<212> TYPE: DNA
<213> ORGANISM: Homo sapiens

<400> SEQUENCE: 293
ctggacaaga agagtacagt gcc                                              23

<210> SEQ ID NO 294
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 294
ctggaaaaga agagtacagt gcc                                              23

<210> SEQ ID NO 295
<211> LENGTH: 23
<212> TYPE: DNA
<213> ORGANISM: Homo sapiens
```

```
<400> SEQUENCE: 295
actccatcga gatttcactg tag                                              23

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
actccatcga gatttctctg tag                                              23
```